United States Patent
Yamada et al.

(10) Patent No.: US 7,402,688 B2
(45) Date of Patent: Jul. 22, 2008

(54) 2,2-DI-SUBSTITUTED 1ALPHA,25-DIHYDROXY-19-NORVITAMIN D DERIVATIVE

(75) Inventors: Sachiko Yamada, Hachioji (JP); Masato Shimizu, Shinagawa-ku (JP); Yukiko Miyamoto, Matsudo (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 100 days.

(21) Appl. No.: 10/530,903

(22) PCT Filed: Oct. 10, 2003

(86) PCT No.: PCT/JP03/13053

§ 371 (c)(1),
(2), (4) Date: Sep. 30, 2005

(87) PCT Pub. No.: WO2004/033420

PCT Pub. Date: Apr. 22, 2004

(65) Prior Publication Data

US 2006/0160779 A1    Jul. 20, 2006

(30) Foreign Application Priority Data

Oct. 10, 2002 (JP) .............................. 2002-297366
Jan. 31, 2003 (JP) .............................. 2003-024183

(51) Int. Cl.
*C07C 401/00* (2006.01)
*A01K 31/59* (2006.01)
*C07D 321/00* (2006.01)

(52) U.S. Cl. ................... 552/653; 514/167; 549/200
(58) Field of Classification Search .............. 552/653; 514/167; 549/200
See application file for complete search history.

(56) References Cited

U.S. PATENT DOCUMENTS 6,566,352 B1 * 5/2003 DeLuca et al. ............... 514/167
6,627,622 B2 * 9/2003 DeLuca et al. ............... 514/167

FOREIGN PATENT DOCUMENTS

| EP | 0619306 | 10/1994 |
|----|---------|---------|
| WO | WO 01/07405 | 2/2001 |
| WO | WO 01/74765 | 10/2001 |
| WO | WO 01/74766 | 10/2001 |
| WO | WO 01/92221 | 12/2001 |

OTHER PUBLICATIONS

Shimizu, Masato et al. (DN 142:392562, CAPLUS, abstract of Bioorganic & Medicinal Chemistry Letters (2005), 15(5), 1451-1455).*

* cited by examiner

*Primary Examiner*—Sabiha N. Qazi
(74) *Attorney, Agent, or Firm*—Andrus, Sceales, Starke & Sawall, LLP

(57) ABSTRACT

A novel 2,2-di-substituted 19-norvitamin D derivative. It is a compound represented by the general formula (I) wherein R1 and R2 are the same or different and each represents hydroxy and A represents hydrogen, or an unsubstituted linear or branched alkyl.

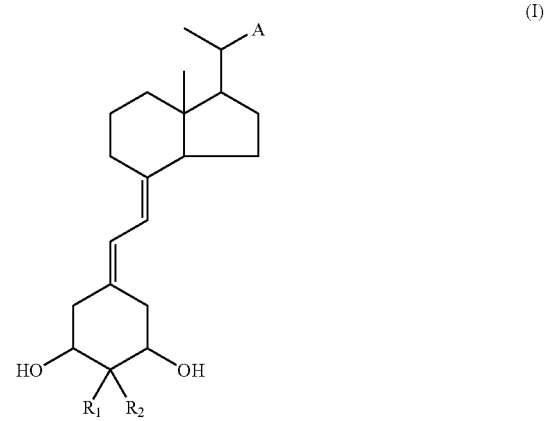

4 Claims, No Drawings

2,2-DI-SUBSTITUTED 1ALPHA,25-DIHYDROXY-19-NORVITAMIN D DERIVATIVE

CROSS-REFERENCE TO RELATED APPLICATIONS

This application is the U.S. national stage application of International Application PCT/JP2003/013053, filed Oct. 10, 2003, which international application was published on Apr. 22, 2004, as International Publication WO2004/033420 in the Japanese language. The International Application claims priority of Japanese Patent Applications No. 2002-297366 filed Oct. 10, 2002 and No. 2003-024183 filed Jan. 31, 2003.

TECHNICAL FIELD

The present invention relates to novel vitamin D derivatives, and more particularly to novel 2,2-disubstituted-19-norvitamin D derivatives and novel 20-epi-19-norvitamin D derivatives.

BACKGROUND ART

Activated form of vitamin $D_3$ (1α,25-dihydroxyvitamin $D_3$, 1,25-$(OH)_2D_3$) is known as a metabolic regulatory hormone of calcium and phosphorus, and it exhibits various biological activities such as cellular induced differentiation, suppression of proliferation, and immunomodulation. These activities are expressed by transcription control of target gene mediated by the vitamin D receptor (VDR) that exists in the nucleus. 1,25-$(OH)_2D_3$ is applied to treatment of renal osteodystrophy, D-resistant rickets, hypoparathyroidism, osteoporosis, and psoriasis. It is also expected as a candidate of therapeutic agent against cancers and immune diseases. However, administration of effective amounts as therapeutic agent against cancers and immune diseases causes harmful hypercalcemia. Thus, it has been desired to develop vitamin D derivatives that dissociate an increasing activity of serum calcium from a cellular induced differentiation activity. In the study of synthesis of the derivatives have selectivity of cellular induced differentiation activity, attention has been focused mostly on modification of the side chain of the derivatives. However, DeLuca et al. have been prepared the A-ring modified by removing the 19-exomethylene group from 1,25-$(OH)_2$ $D_3$, that is, 19-nor-1α,25-dihydroxyvitamin $D_3$ (hereinafter referred to as 19-nor-1,25-$(OH)_2D_3$)(Perlman K. L., Swenson R. E., Paaren H. E., Schnoes H. K., DeLuca H. F., Tetrahedron Lett., 1991, 32, 7663-7666.). Comparing the biological activities of 19-nor-1,25-$(OH)2D_3$ with one of the activated 1,25-$(OH)2D_3$, it was shown that VDR affinity was reduced to approximately one-third and the bone resorption activity was reduced to one-tenth or less of 1,25-$(OH)_2D_3$, but 19-nor-1,25-$(OH)_2D_3$ still retained the cellular effects equivalent to 1,25-$(OH)_2D_3$. 19-nor-1,25-$(OH)_2D_3$ revealed a selective activity profile with potent cellular differentiation and very low calcium mobilizing activity. In addition, 19-norvitamin D derivatives with a variety of substituents at C-2 position on the A-ring have been synthesized and literature data concerning interesting biological potency of 2-substituted 19-norvitamin D derivatives have been accumulated (Sicinski R. R., Perlman K. L., DeLuca H. F., J. Med. Chem., 1994, 37, 3730-3738; Sicinski R. R., Prahl J. M., Smith C. M., DeLuca H. F., J. Med. Chem., 1998, 41, 4662-4674; Sicinski R. R., Rotkiewicz P., Kolinski A., Sicinska W., Prahl J. M., Smith C. M., DeLuca H. F., J. Med. Chem., 2002, 45, 3366-3380; Yukiko Iwasaki et al., The 121$^{st}$ Annual Meeting of the Pharmaceutical Society of Japan, Abstract 3, p 17, 29[PB]II-011, 2001 (Sapporo); Akihiro Yoshida et al, The 121$^{st}$ Annual Meeting of the Pharmaceutical Society of Japan, Abstract 3, p 17, 29[PB]II-014, 2001 (Sapporo); Yukiko Iwasaki et al., The 122$^{nd}$ Annual Meeting of the Pharmaceutical Society of Japan, Abstract 3, p 180, 28[P]I-184, 2002 (Chiba); Masato Shimizu et al, The 56$^{th}$ Annual Meeting of the Vitamin Society of Japan, Abstract, Vitamin, 76, 155-156, 2002 (Tokyo); Masato Shimizu et al, 28$^{th}$ Symposium on Progress in Organic Reactions and Syntheses—Applications in the Life Sciences-, Abstract, pp 234-235, 2002 (Tokyo)). Introduction of an alkyl or alkylidene moiety at C-2 position of 19-nor-1,25-$(OH)_2D_3$ causes increased activity of serum calcium as well as cellular induced differentiation (Sicinski R. R., Prahl J. M., Smith C. M., DeLuca H. F., J. Med. Chem., 1998, 41, 4662-4674; Sicinski R. R., Rotkiewicz P., Kolinski A., Sicinska W., Prahl J. M., Smith C. M., DeLuca H. F., J. Med. Chem., 2002, 45, 3366-3380.).

However, in the conventional synthetic studies of 2-substituted 19-norvitamin D derivatives, most of the derivatives have a single substituent at C-2 position. Concerning 20-epi-19-norvitamin D derivatives, 19-norvitamin D derivatives bearing 2-methyl, 2-ethyl or 2-hydroxymethyl moiety have been synthesized so far. (Sicinski R. R., Prahl J. M., Smith C. M., DeLuca H. F., J. Med. Chem., 1998, 41, 4662-4674; Sicinski R. R., Rotkiewicz P., Kolinski A., Sicinska W, Prahl J. M., Smith C. M., DeLuca H. F., J. Med. Chem., 2002, 45, 3366-3380.). It has been desired to develop derivatives having more excellent biological activities.

DISCLOSURE OF THE INVENTION

An object of the present invention is to synthesize and provide a novel 2,2-disubsututed-19-norvitamin D derivative and a novel 20-epi-19-norvitamin D derivative. A further object of the present invention is to evaluate biological activities of the synthesized novel 2,2-disubsututed-19-norvitamin D derivative and novel 20-epi-19-norvitamin D derivative.

Extensive studies have been made by the inventors to solve the problems described above. As a result, we have succeeded in synthesis of a novel 2,2-disubsututed-19-norvitamin D derivative and a novel 20-epi-19-norvitamin D derivative and have completed the present invention.

According to the present invention, there is provided a compound represented by the general formula (I):

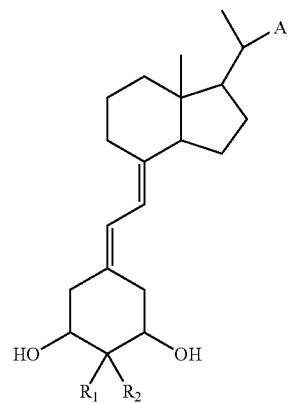

Formula (I)

(wherein, R1 and R2 may be the same or different each other and they represent a halogen atom or a hydroxyl group or an unsubstituted straight chain or branched chain alkyl group having 1-10 carbon atoms, or a substituted straight chain or branched chain alkyl group having 1-10 carbon atoms, or an unsubstituted straight chain or branched chain alkenyl group having 2-15 carbon atoms, or a substituted straight chain or branched chain alkenyl group having 2-15 carbon atoms, or R1 may form together with R2 an unsubstituted spiro-cyclic alkyl group having 3-6 carbon atoms, or a substituted spiro-cyclic alkyl group having 3-6 carbon atoms, or an unsubstituted spiro-hetero-cyclic containing an oxygen atom as a hetero atom having 3-6 carbon atoms, or a substituted spiro-hetero-cyclic containing an oxygen atom as a hetero atom having 3-6 carbon atoms;

A represents a hydrogen or an unsubstituted straight chain or branched chain alkyl group having 1-12 carbon atoms, or a substituted straight chain or branched chain alkyl group having 1-12 carbon atoms, or an unsubstituted straight chain or branched chain alkyloxy group having 1-12 carbon atoms, or a substituted straight chain or branched chain alkyloxy group having 1-12 carbon atoms, or an unsubstituted straight chain or branched chain alkenyl group having 2-14 carbon atoms, or a substituted straight chain or branched chain alkenyl group having 2-14 carbon atoms.)

Preferably, in the general formula (I), R1 and R2 may be the same or different each other and they represent a halogen atom or a hydroxyl group or an unsubstituted straight chain or branched chain alkyl group having 1-8 carbon atoms, or a straight chain or branched chain alkyl group having 1-8 carbon atoms having at least one substituent selected from the group consisting of a halogen atom, an unsubstituted straight chain or branched chain alkyloxy group having 1-4 carbon atoms, and aryl group, amino group and azido group, or an unsubstituted straight chain or branched chain alkenyl group having 2-8 carbon atoms, or a straight chain or branched chain alkenyl group having 2-8 carbon atoms having at least one substituent selected from the group consisting of a halogen atom, an unsubstituted straight chain or branched chain alkyloxy group having 1-4 carbon atoms, and aryl group, amino group and azido group; or R1 may form together with R2 an unsubstituted spiro-cyclopropyl group or a spiro-cyclopropyl group substituted by at least one unsubstituted straight or branched hydroxyalkyl group having 1-4 carbon atoms, or an unsubstituted spiro-oxirane, or a spiro-oxirane group substituted by an unsubstituted straight or branched hydroxyalkyl group having 1-4 carbon atoms; A represents a straight chain or branched chain alkyl group having 1-12 carbon atoms substituted by at least one hydroxy group, or a straight chain or branched chain alkyloxy group having 1-12 carbon atoms substituted by at least one hydroxy group, or a straight chain or branched chain alkenyl group having 2-14 carbon atoms substituted by at least one hydroxy group.

Further preferably, in the general formula (I), R1 and R2 may be the same or different each other and they represent a halogen atom, or a hydroxyl group, or an unsubstituted straight chain or branched chain alkyl group having 1-6 carbon atoms, or a straight chain or branched chain alkyl group having 1-6 carbon atoms having at least one substituent selected from the group consisting of a halogen atom, an unsubstituted straight chain or branched chain alkyloxy group having 1-3 carbon atoms, phenyl group, amino group and azido group, or an unsubstituted straight chain or branched chain alkenyl group having 2-4 carbon atoms; or R1 may form together with R2 an unsubstituted spiro-cyclopropyl group, or spiro-cyclopropyl group substituted by at least one unsubstituted straight chain or branched chain hydroxyalkyl group having 1-3 carbon atoms, or unsubstituted spiro-oxirane; A represents a hydrogen, or a straight chain or branched chain alkyl group having 3-10 carbon atoms substituted by at least one hydroxy group, or a straight chain or branched chain alkyloxy group having 3-8 carbon atoms substituted by at least one hydroxyl group, or a straight chain or branched chain alkenyl group having 4-12 carbon atoms substituted by at least one hydroxy group.

Further preferably, in the general formula (I), R1 and R2 may be the same or different each other and they represent a hydroxyl group, or an unsubstituted straight or branched chain alkyl group having 1-6 carbon atoms, or a straight or branched chain alkyl group having 1-6 carbon atoms having at least one substituent selected from the group consisting of a fluorine atom and an unsubstituted straight chain or branched chain alkyloxy group having 1-3 atoms; or R1 may form together with R2 an unsubstituted spiro-oxirane; A represents a hydrogen atom, or a straight or branched chain alkyl group having 5-7 carbon atoms substituted by at least one hydroxy group.

In the general formula (I), the configuration at 20-position may be S-configuration or R-configuration.

According to another aspect of the present invention, there is provided a compound represented by the general formula (IV);

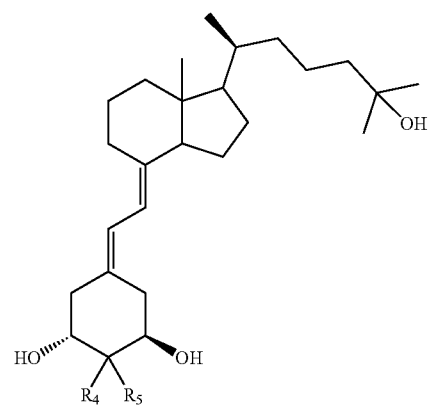

Formula (IV)

(wherein, one of R4 and R5 represents a hydrogen atom and the other represents a straight chain or branched chain alkyl group having 1-4 carbon atoms substituted by a hydroxy group or —OR6 (wherein, R6 represents a straight chain or branched chain alkyl group having 1-4 carbon atoms substituted by a hydroxy group); or R4 may form =CR7 together with R5 (wherein, R7 represents a straight chain or branched chain alkyl group having 1-4 carbon atoms substituted by a hydroxy group).)

According to further aspect of the present invention, there is provided a pharmaceutical composition comprising a compound represented by the general formula (I) or the general formula (IV) described above and a pharmaceutically allowable carrier or a diluent.

According to still further aspect of the present invention, there is provided a method of therapy or prevention of disease accompanying abnormality in cell differentiation comprising a step of administrating a compound illustrated by the general formulae (I) or (IV) in therapeutic effective amount to an object demanding such therapy or prevention.

According to still further aspect of the present invention, there is provided use of a compound illustrated by the general formulae (I) or (IV) described above for a pharmaceutical composition for therapy of disease accompanying abnormality in cell differentiation.

According to still further aspect of the present invention, there is provided a method of preparing a compound represented by the general formulae (I) described above comprising a step of obtaining a compound represented by the general formula (III);

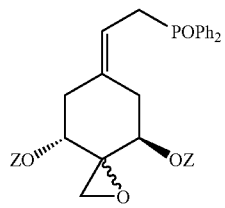

Formula (III)

(wherein, Z may be the same or different each other and it represents a hydrogen atom or a protective group; Ph is a phenyl group), from a compound represented by the general formula (II);

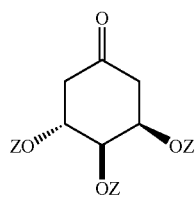

Formula (II)

(wherein, Z may be the same or different each other and it represents a hydrogen atom or a protective group.)

PREFERRED MODE OF CARRYING OUT THE INVENTION

The contents of the specification of Japanese Patent Application No. 2002-297366 and Japanese Patent Application No. 2003-024183 on which the priority right for the present application is claimed are incorporated in their entirety by reference.

Detailed modes and methods with respect to vitamin D derivatives represented by the general formulae (I) and (IV) of the present invention are described below.

In this invention, "vitamin D derivative" is defined as a compound having 9,10-seco-5,7,10 (19)-cholestatriene structure. In this invention, "19-nor-1,25-dihydroxyvitamin D derivative" is defined as a compound in which a 10 (19)-exo-methylene group is removed from a compound having 9,10-seco-5,7,10 (19)-cholestatriene structure.

A "halogen atom" for R1 and R2 in the general formula (I) is fluorine, chlorine, bromine and iodine, but fluorine may be preferable.

An "unsubstituted straight chain or branched chain alkyl group" for R1 and R2 in the general formula (I) is preferably an unsubstituted straight chain or branched chain alkyl group having 1-10 carbon atoms, more preferably that-having 1-8 carbon atoms, more further preferably that having 1-6, and still more further preferably that having 1-4. The non-limiting examples thereof includes a methyl group, ethyl group, n-propyl group, i-propyl group, n-butyl group, s-butyl group, i-butyl group, t-butyl group, and a straight chain and branched chain pentyl group, hexyl group, heptyl group, octyl group, nonyl group, decanyl group.

A "substituted straight chain or branched chain alkyl group" for R1 and R2 in the general formula (I) means a group obtained by substituting one or more hydrogen atoms of the "unsubstituted straight chain or branched chain alkyl group" described above. A substituent in this case may be, for example, a halogen atom such as a fluorine atom, substituted straight chain or branched chain alkyloxy group (1-4 carbon atoms preferable, and 1-3 carbon atoms specifically preferable), unsubstituted straight chain or branched chain alkyloxy group (1-4 carbon atoms preferable, and 1-3 carbon atoms specifically preferable), unsubstituted aryl group such as phenyl group, an aryl group (such as tolyl group) substituted by a halogen atom or an unsubstituted straight chain or branched chain alkyl group having 1-4 carbon atoms, an amino group, an azido group, and the like. Further a substituent in this case may be specifically preferably a fluorine atom, a methoxy group, an ethoxy group, a phenyl group, an amino group, an azido group, and the like.

An "unsubstituted straight chain or branched chain alkenyl group" for R1 and R2 is preferably a straight chain or branched chain alkenyl group having 2-15 carbon atoms having at least one double bond. Number of carbon atoms in this case is preferably 2-8, more preferably 2-6, and still more preferably 2-4. Number of double bond in this case is preferably 1-3, more preferably 1 or 2, and still more preferably 1.

A "substituted straight chain or branched chain alkenyl group" means a group obtained by substituting one or more hydrogen atoms of the "unsubstituted straight chain or branched chain alkyl group" described above. A substituent in this case may be, for example, a halogen atom or unsubstituted straight chain or branched chain alkyl group having 1-4 carbon atoms.

The configuration at 2-position may be R-configuration or S-configuration.

An "unsubstituted spiro-cyclic alkyl group" which R1 forms together with R2 may preferably have 3-6 carbon atoms, more preferably 3-4 carbon atoms, and a spiro-cyclopropyl group specifically preferable.

A "substituted spiro-cyclic alkyl group" means a group obtained by substituting one or more hydrogen atoms of the above-described "unsubstituted spiro-cyclic alkyl group". A substituent in this case is preferably an unsubstituted straight chain or branched chain hydroxyalkyl. Number of carbon atoms in this case is preferably 1-4, more preferably 1-3. Such a substituent may be, for example, a hydroxymethyl group, hydroxyethyl group, hydroxypropyl group, and the like.

An "unsubstituted spiro-hetero-cyclic containing an oxygen atom as a hetero atom" which R1 forms together with R2 may preferably have 3-6 carbon atoms, more preferably 3-4 carbon atoms. It may preferably have one oxygen atom as a hetero atom. Spiro-oxirane may be specifically preferable.

A "substituted spiro-hetero cyclic containing an oxygen atom as a hetero atom" means a group obtained by substituting one or more hydrogen atoms of the "unsubstituted spirohetero cyclic containing an oxygen atom as a hetero atom" described above.

An "unsubstituted straight chain or branched chain alkyl group" for A of the general formula (I) is preferably unsubstituted straight chain or branched chain alkyl group having 1-12 carbon atoms. Number of carbon atom in this case is preferably 3-10, more preferably 5-7, still more preferably 6. The non-limiting example thereof may be a methyl group, ethyl group, n-propyl group, i-propyl group, n-butyl group, s-butyl group, i-butyl group, t-butyl group, and a straight chain and branched chain pentyl group, hexyl group, heptyl group, octyl group, nonyl group, decanyl group.

A "substituted straight chain or branched chain alkyl group" for A means a group obtained by substituting one or more hydrogen atoms of the "unsubstituted straight chain or branched chain alkyl group" described above. A substituent in this case is preferably a hydroxy group. Non-limiting number of the substituent is preferably 1-3, more preferably 1 or 2. Such a substituent may be, for example, a hydroxymethyl group, hydroxyethyl group, hydroxybutyl group, hydroxypropyl group, hydroxypentyl group, hydroxyhexyl group, hydroxyheptyl group, hydroxyoctyl group, hydroxynonyl group, hydroxydecanyl group, 4-hydroxy-4-methylpentyl group, 1,4-dihydroxy-4-methylpentyl group, 4-ethyl-4-hydroxyhexyl group, 6-hydroxy-6-methyl-2-heptyl group, 7-hydroxy-7-methyl-2-octyl group, 5,6-dihydroxy-6-methyl-2-heptyl group, and the like.

An "unsubstituted straight chain or branched chain alkyloxy group" for A of the general formula (I) is preferably an unsubstituted straight chain or branched chain alkyloxy group having 1-12 carbon atoms. Number of carbon atom in this case is preferably 3-8, more preferably 4-6, still more preferably 5. The non-limiting example thereof is preferably a methoxy group, an ethoxy group, a propoxy group, a butoxy group, a pentyloxy group, a hexyloxy group, and the like.

A "substituted straight chain or branched chain alkyloxy group" for A means a group obtained by substituting one or more hydrogen atoms of the "unsubstituted straight chain or branched chain alkyloxy group" described above. A substituent in this case is preferably a hydroxy group. Non-limiting number of the substituent is preferably 1-3, and more preferably 1 or 2. For example, —$OC_2H_4C(CH_3)_2OH$, —$OCH_2CHOHC(CH_3)_2OH$, and the like.

An "unsubstituted straight chain or branched chain alkenyl group" for A of the general formula (I) is preferably an unsubstituted straight chain or branched chain alkenyl group having 2-14 carbon atoms. Number of carbon atom in this case is preferably 4-12, more preferably 5-10 and most preferably 6-9. As a double bond may be cis- or trans-. Number of the double bond may be preferably 1-3 and more preferably 1 or 2. The non-limiting examples thereof may be preferably a vinyl group, propenyl group, butenyl group, hexenyl group, heptenyl group, octenyl group, nonenyl group, decanenyl group, 4-methyl-penta-1-ene-1-yl group, 5-ethyl-1,3-hepta-1,3-diene-1-yl group, and the like.

A "substituted straight chain or branched chain alkenyl group" for A means a group obtained by substituting one or more hydrogen atom of the "unsubstituted straight chain or branched chain alkenyl group" described above. As a substituent in this case is preferably a hydroxy group. Non-limiting number of the substituent is preferably 1-3, and more preferably 1 or 2. For example, 4-hydroxy-4-methyl-penta-1-ene-1-yl group (—$C_2H_2CH_2C(CH_3)_2OH$), 5-hydroxy-5-ethyl-hepta-1,3-diene-1-yl group (—$C_4H_4C(C_2H_5)_2OH$), and the like.

The configuration of the hydroxy groups at the 1- and 3-positions in the compound of formula (I) of the present invention can occur in α or β conformation, and the respective compounds are all included within the scope of the present invention. Furthermore, cis- and trans-geometrical isomers of the compound of formula (I) wherein A is alkenyl group resulting from the double bond, and other optical and geometrical isomers are all included within the scope of the present invention.

Examples of the compound of the general formula (I) of the present invention are as follows:

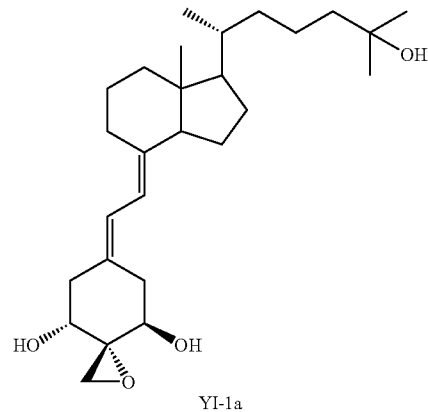

YI-1a

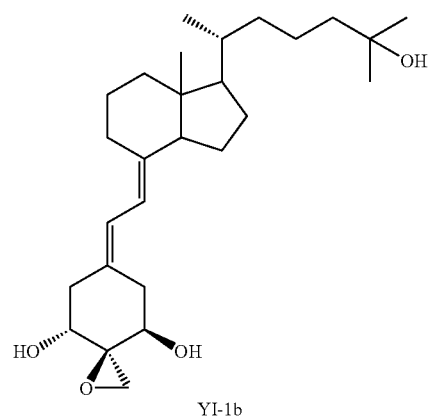

YI-1b

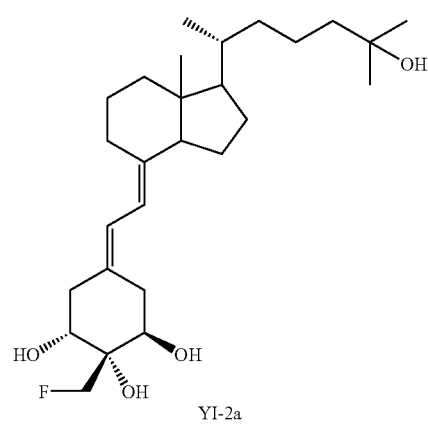

YI-2a

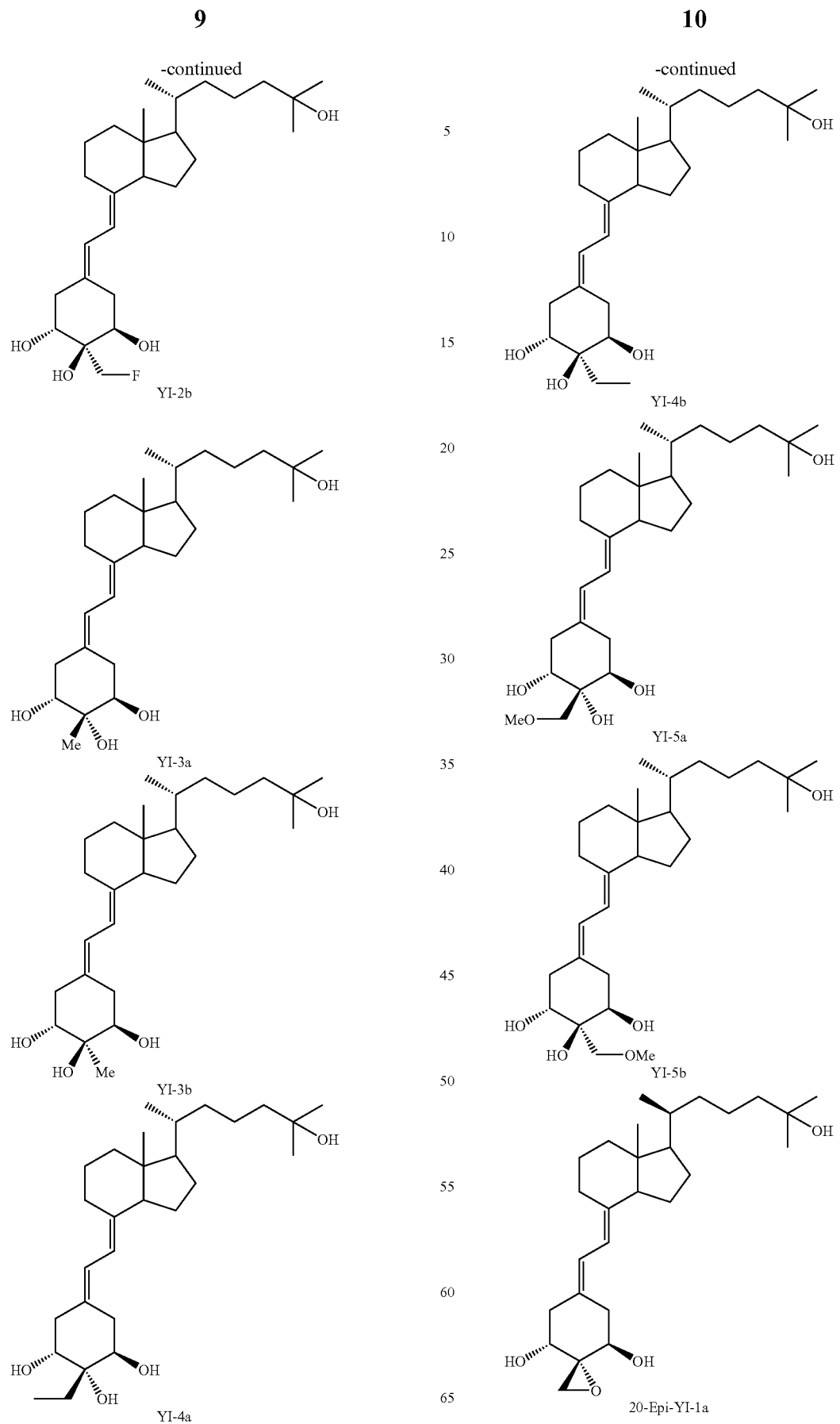

-continued
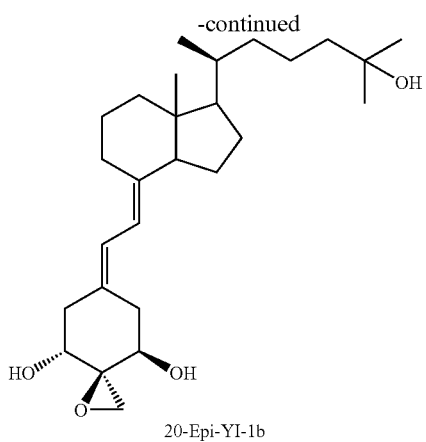
20-Epi-YI-1b
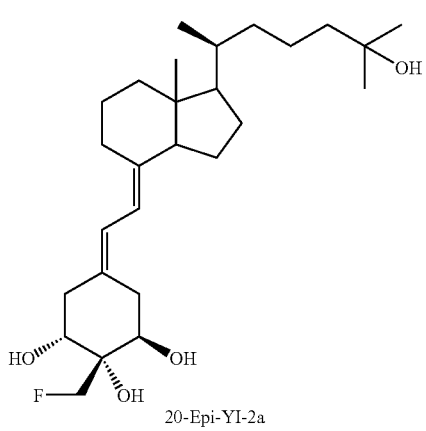
20-Epi-YI-2a
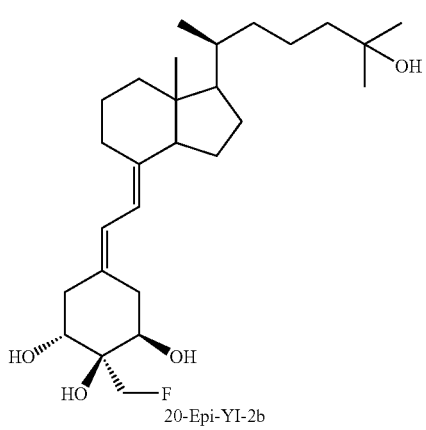
20-Epi-YI-2b
-continued
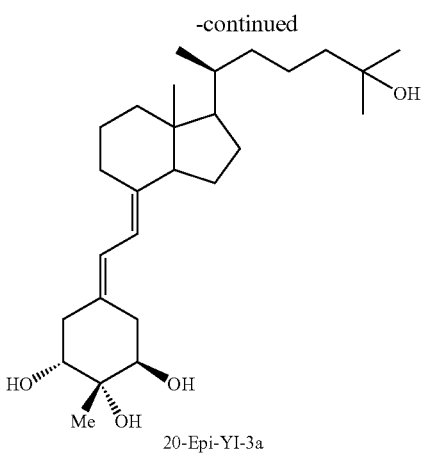
20-Epi-YI-3a
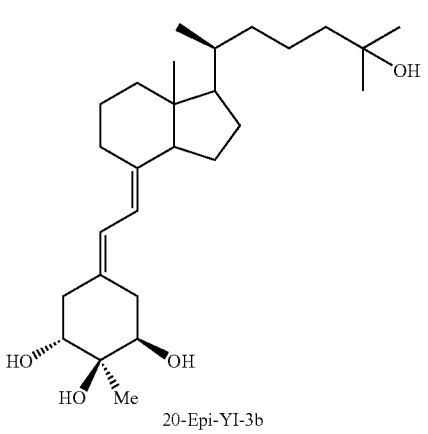
20-Epi-YI-3b
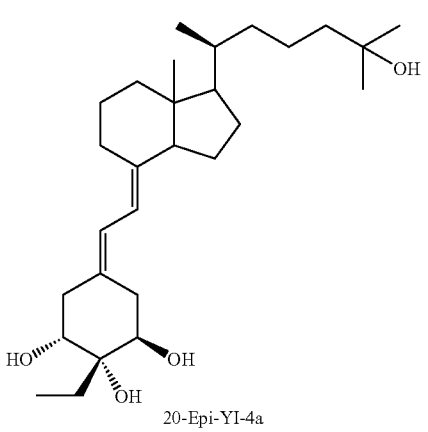
20-Epi-YI-4a

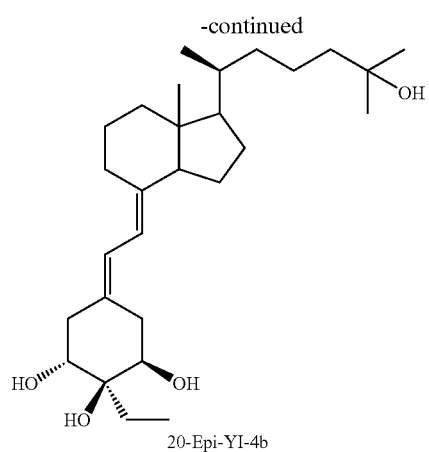
20-Epi-YI-4b
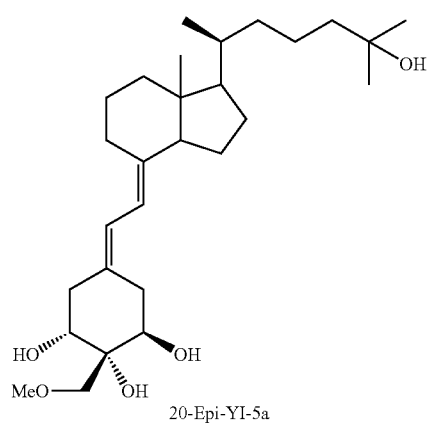
20-Epi-YI-5a
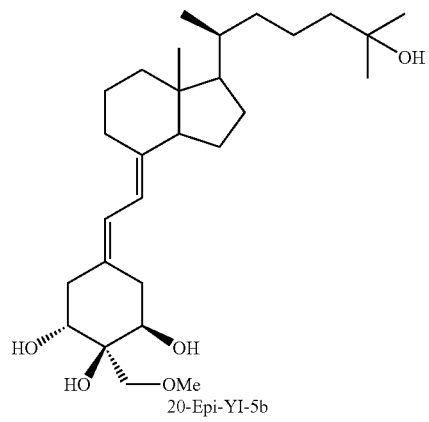
20-Epi-YI-5b
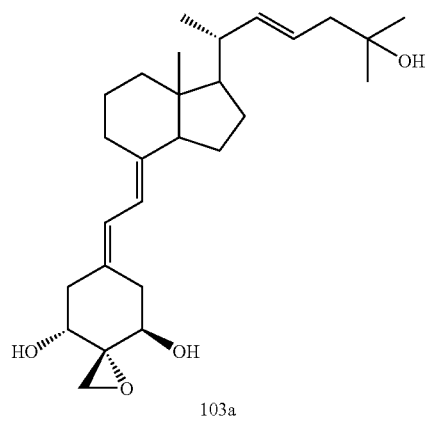
103a
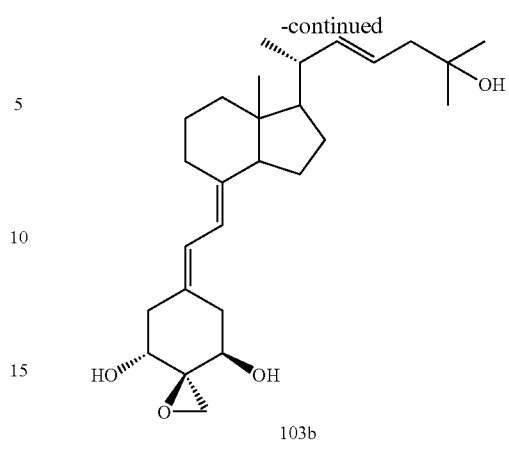
103b
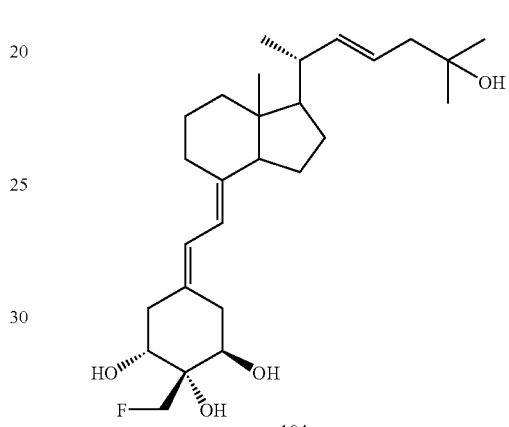
104a
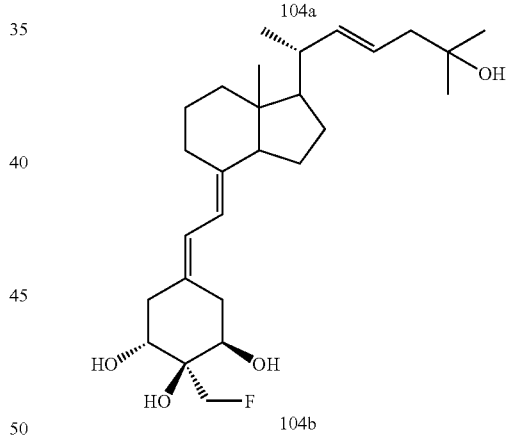
104b
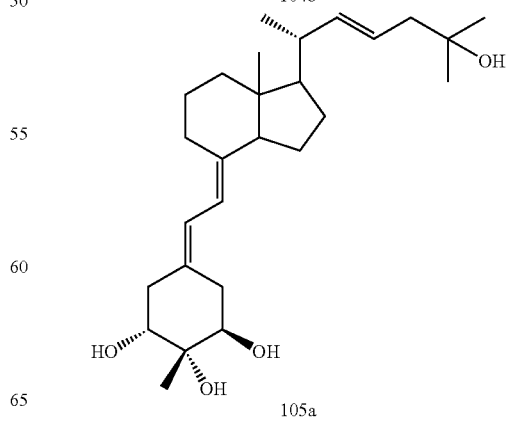
105a -continued
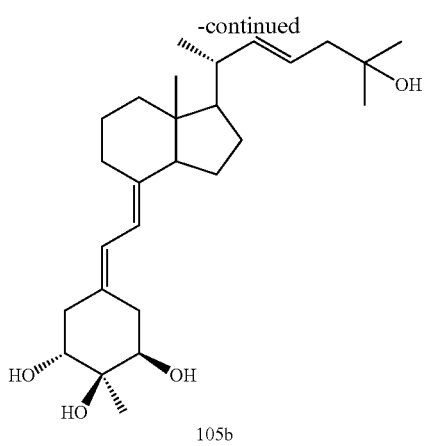
105b
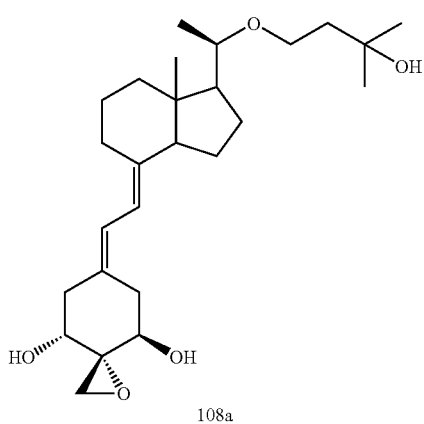
108a
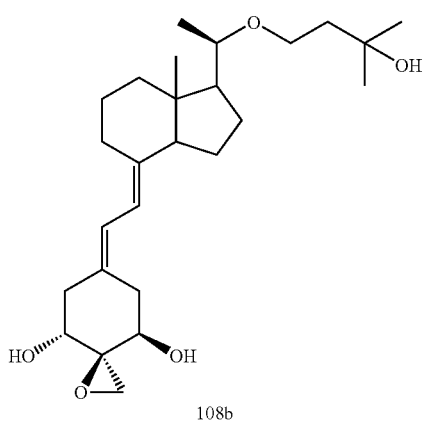
108b
-continued
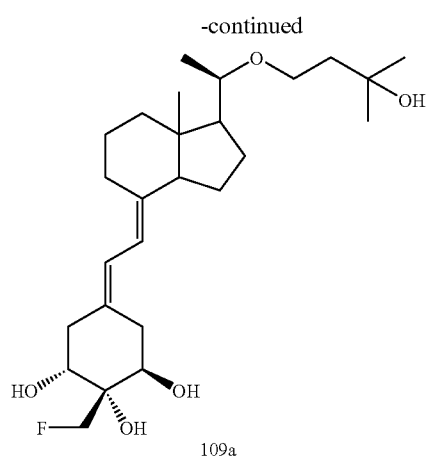
109a
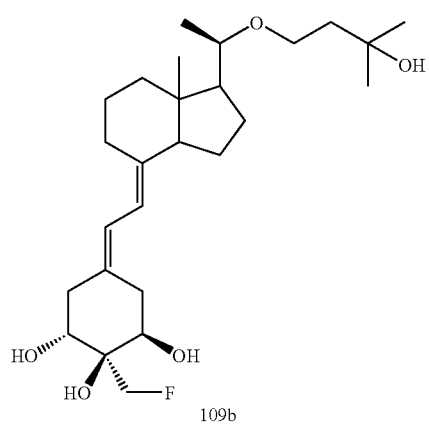
109b
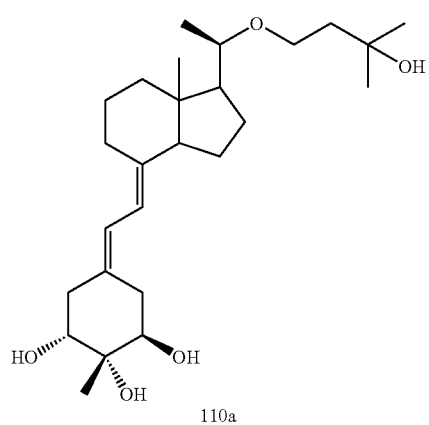
110a -continued

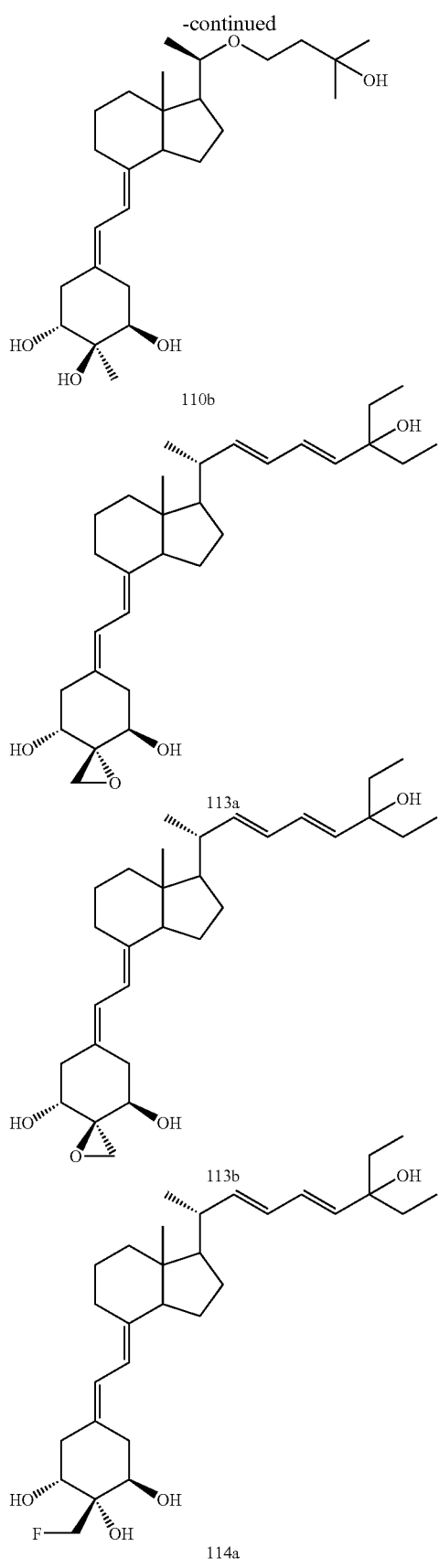

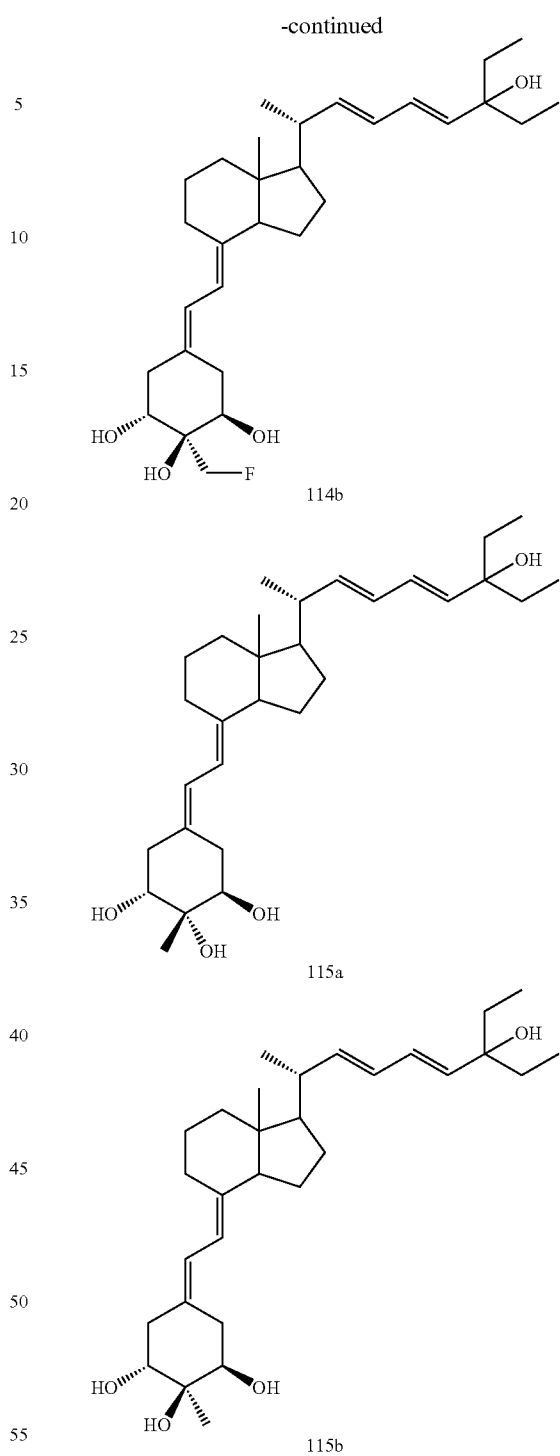

As a "straight chain or branched chain alkyl group having 1-4 carbon atoms" of "straight chain or branched chain alkyl group having 1-4 carbon atoms substituted by a hydroxy group" of the definition on R4 or R5 of the general formula (IV) is preferably a methyl group, ethyl group, n-propyl group, i-propyl group, n-butyl group, s-butyl group, i-butyl group, t-butyl group, and the like, more preferably a straight chain or branched chain alkyl group having 2-3 carbon atoms, and more preferably an ethyl group, n-propyl group. Number of a hydroxy group to be substituted is preferably 1 or 2, and more preferably 1.

As a "straight chain or branched chain alkyl group having 1-4 carbon atoms" of "straight chain or branched chain alkyl group having 1-4 carbon atoms substituted by a hydroxy group" of the definition on R6 of the general formula (IV) is preferably a methyl group, ethyl group, n-propyl group, i-propyl group, n-butyl group, s-butyl group, i-butyl group, t-butyl group, and the like, more preferably a straight chain or branched chain alkyl group having 1-3 carbon atoms, and more preferably a methyl group, ethyl group, n-propyl group, still more preferably an ethyl group. Number of a hydroxy group to be substituted is preferably 1 or 2, and more preferably 1.

As a "straight chain or branched chain alkyl group having 1-4 carbon atoms" of "straight chain or branched chain alkyl group having 1-4 carbon atoms substituted by a hydroxy group" of the definition on R7 of the general formula (IV) is preferably a methyl group, ethyl group, n-propyl group, i-propyl group, n-butyl group, s-butyl group, i-butyl group, t-butyl group, and the like, and more preferably a straight chain or branched chain alkyl group having 1-3 carbon atoms, and more preferably a methyl group, ethyl group, ethyl group-and still more preferably a methyl group. Number of a hydroxy group to be substituted is preferably 1 or 2, and more preferably 1.

In the case where one of $R_4$ and $R_5$ of the general formula (IV) is a hydrogen atom and the other of the two is a straight chain or branched chain alkyl group having 1-4 carbon atoms substituted by a hydroxy group or —$OR_6$, the straight chain or branched chain alkyl group having 1-4 carbon atoms substituted by a hydroxy group and —$OR_6$ may be situated at 2α-position or 2β-position.

In the case where $R_4$ forms =$CR_7$ together with $R_5$, each of (Z) form or (E) form produced by this double bond may be preferable.

Examples of the compound of the general formula (IV) are as follows:

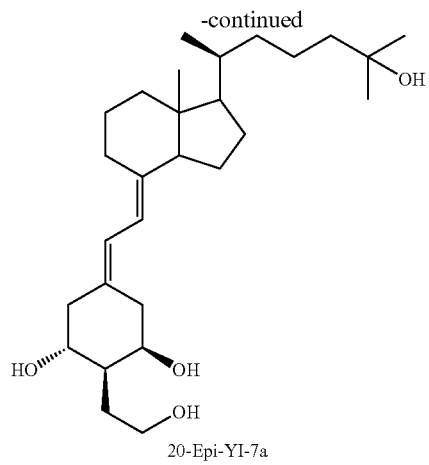
20-Epi-YI-7a

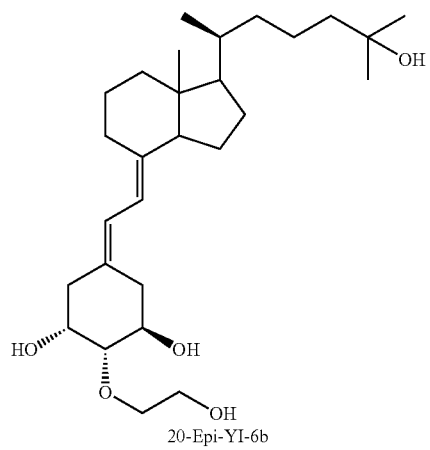
20-Epi-YI-6b

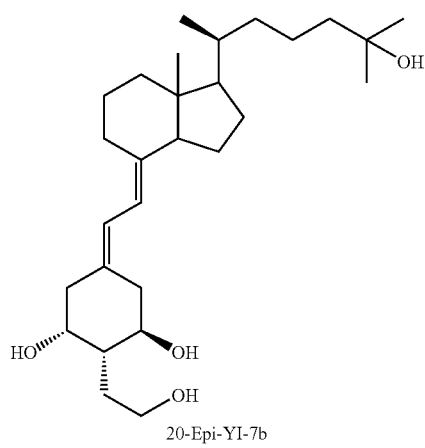
20-Epi-YI-7b

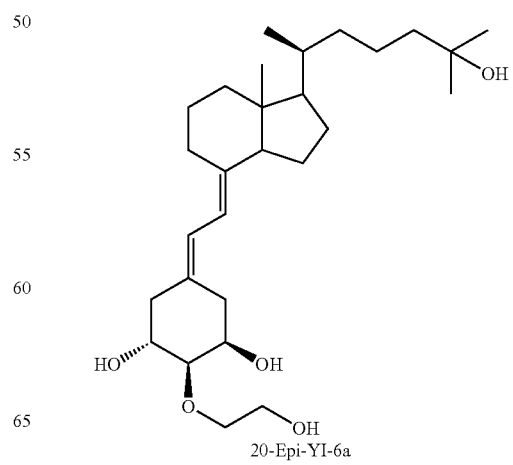
20-Epi-YI-6a

-continued
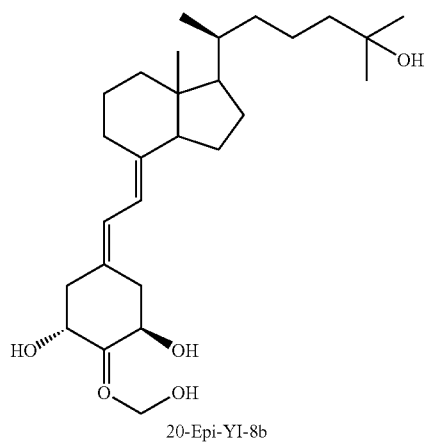
20-Epi-YI-8b
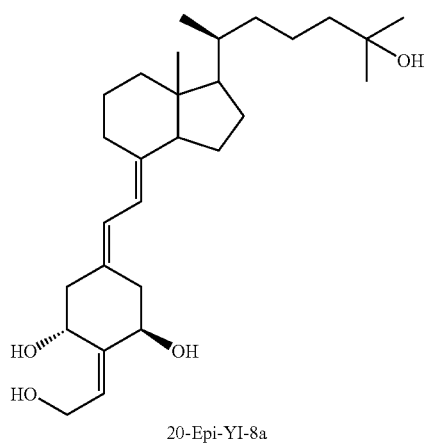
20-Epi-YI-8a
-continued
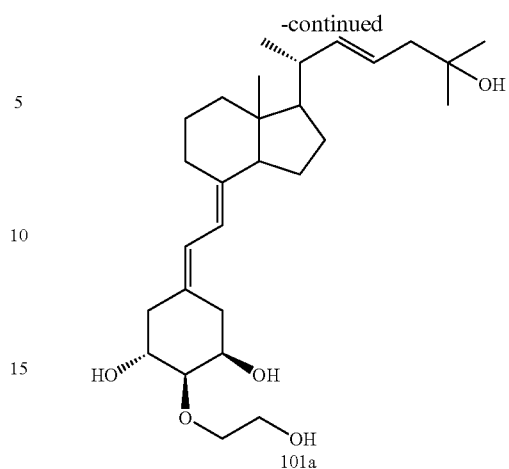
101a
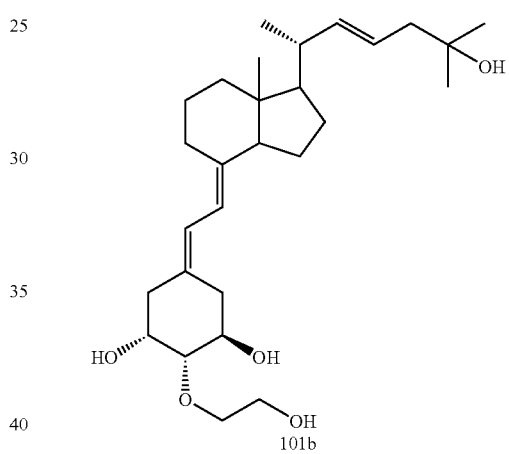
101b
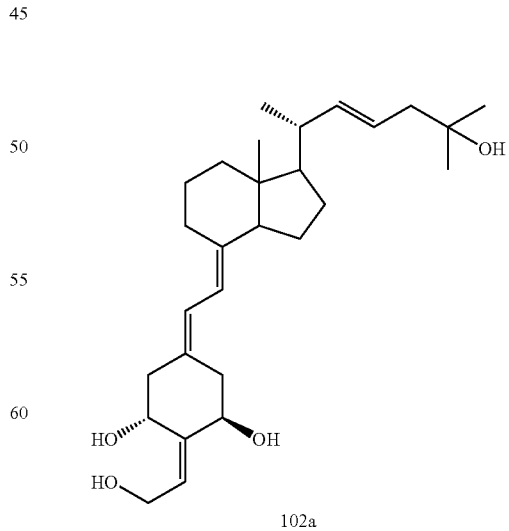
102a -continued
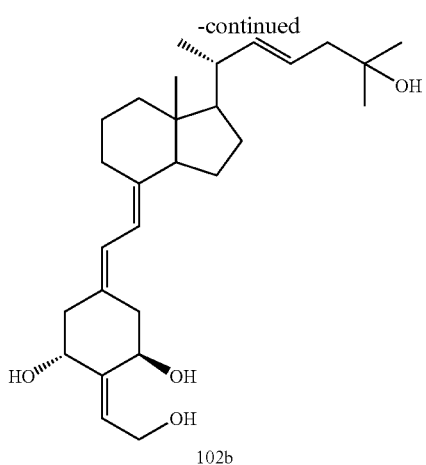
102b
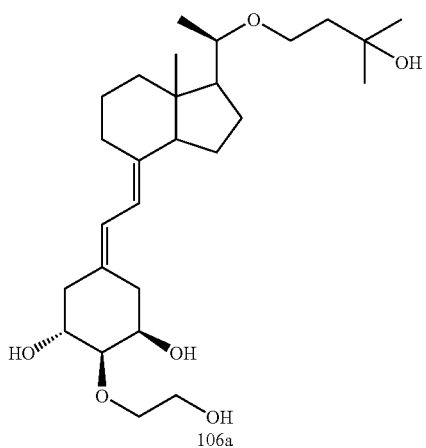
106a
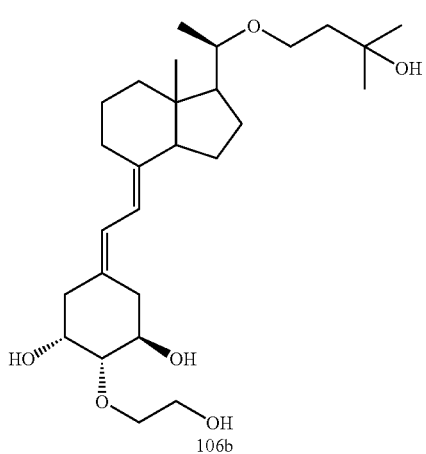
106b
-continued
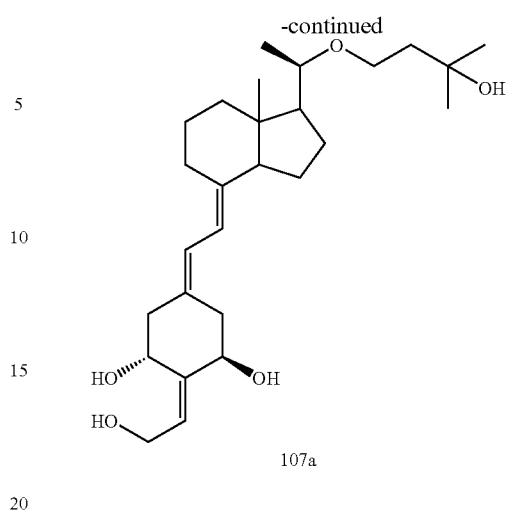
107a
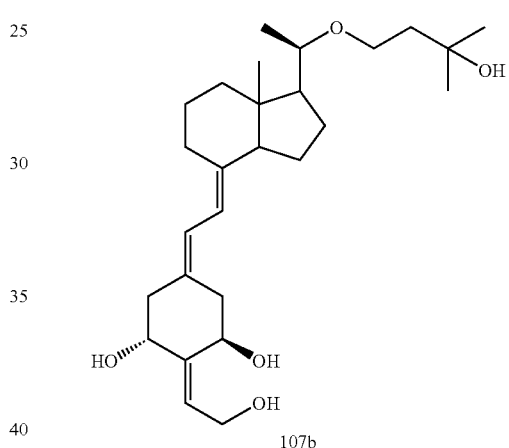
107b
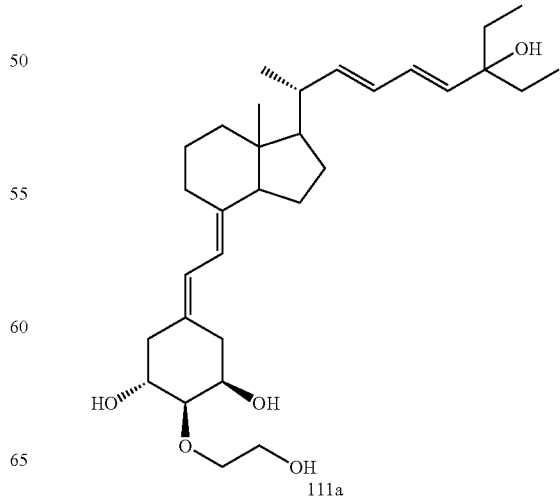
111a -continued

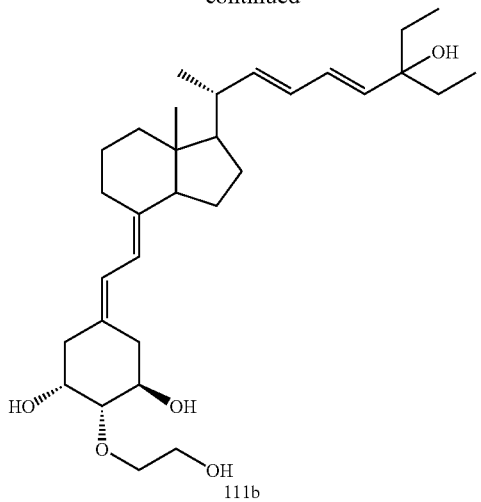
111b

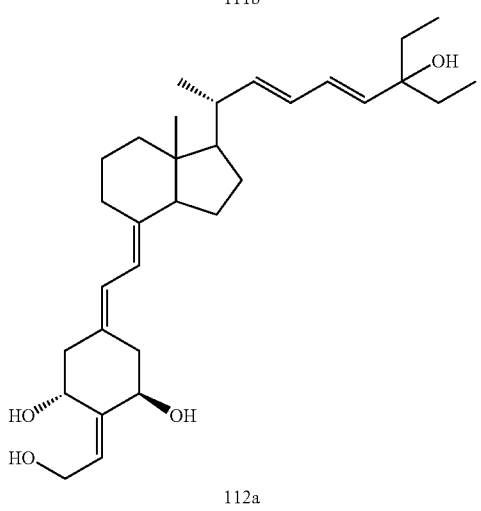
112a

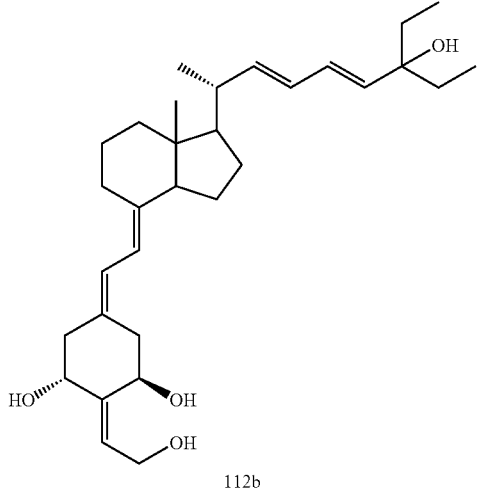
112b

The vitamin D derivatives represented by the general formula (I) or (IV) of the present invention can be used as active ingredients of pharmaceutical compositions (such as a cell differentiation regulating agent).

The compounds of the present invention are preferably formulated into appropriate dosage forms with pharmaceutically acceptable carriers, excipients, disintegrants, lubricants, binders, flavors, colorants, and the like. Examples of the dosage forms include tablets, granules, fine granules, capsules, powder, injections, solutions, suspensions, emulsions, percutaneous administration formulations, suppositories and the like.

There is no restriction for routes of administration for the compounds of the present invention. The compounds may be administered orally or parenterally (intravenously,. intramuscularly, intraperitoneally, percutaneously and the like).

Dosage of compounds of the present invention can be appropriately chosen depending on target disease, conditions, body type, constitution, age and sex of the patient, administration route, dosage form and other factors. Typically, the lower limit of the dosage for an adult ranges from 0.001 μg to 0.1 μg and preferably around 0.01 μg daily, and the upper limit of the dosage for an adult ranges from 100 μg to 10000 μg and preferably from 200 μg to 1000 μg, which may be administered in divided portion once to three times a day.

The vitamin D derivative of the general formula (I) is a novel compound, and there is no limitation with respect to methods of synthesis of the compound. It can be synthesized by a method comprising a step of obtaining a compound represented by the general formula (III):

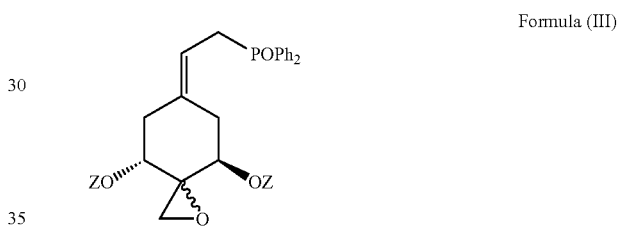

Formula (III)

(wherein, Z may be the same or different each other and hydrogen or a protective group, Ph is a phenyl group) from a compound represented by the general formula (II):

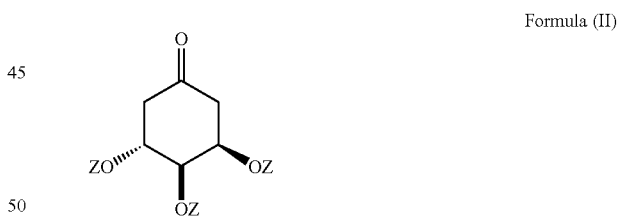

Formula (II)

(wherein, Z may be the same or different each other and hydrogen or a protective group.)

A protective group as Z may be the same or different each other and may be a substituted silyl group, an acyl group, an alkyl group which may be possibly substituted, more preferably a benzyl group, trimethylsilyl group, t-butyldimethylsilyl group, and the like.

The protective group can be removed by a conventional process well-known to a chemical field at a proper step in the synthesis.

The vitamin D derivatives of the general formula (I) can be synthesized by, for example, a method described below:

A general synthesis scheme of A-ring phosphine oxide of the present invention is as follows:

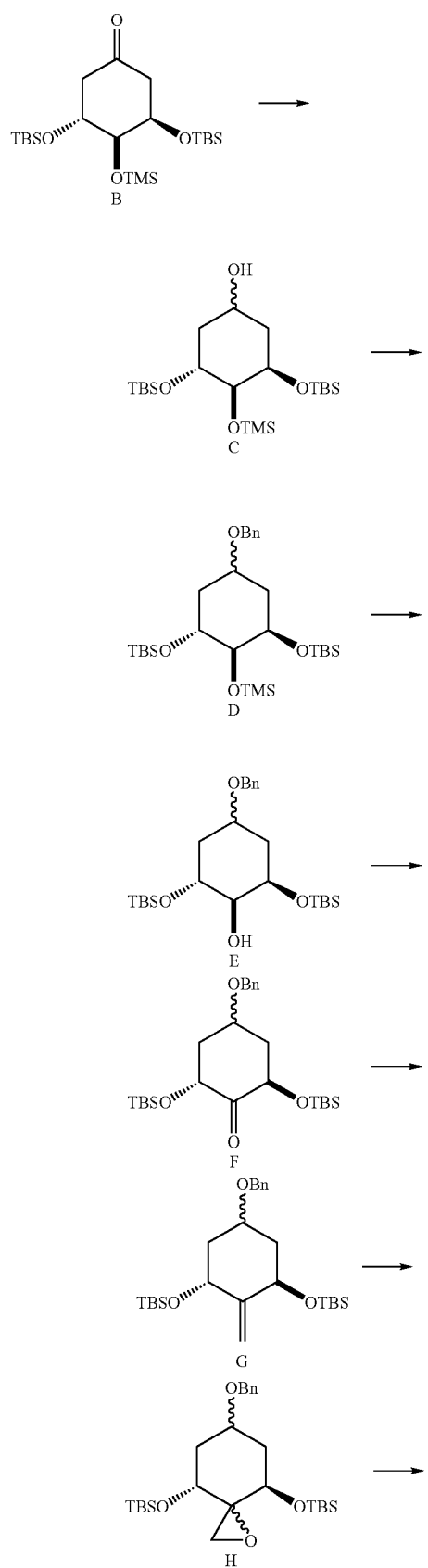
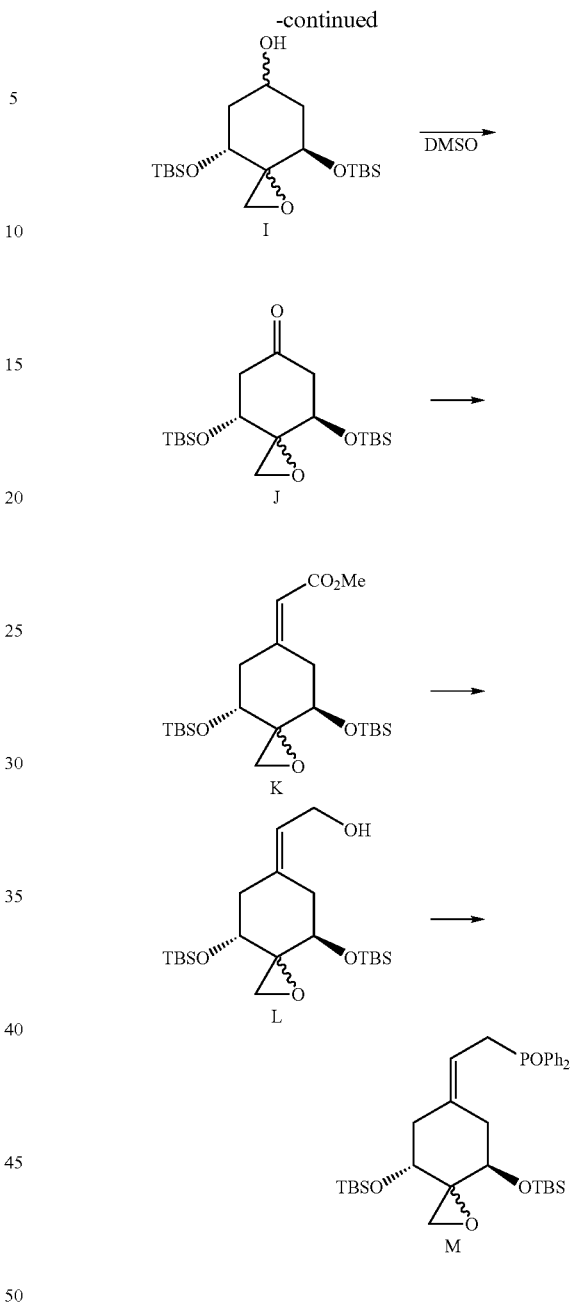

A cyclohexanone derivative (compound B) having a hydroxy group protect by a silyl group as a starting material can be synthesized from (−)-quinic acid by a well-known method (Perlman, K. L., Sewnson, R. E., Paaren, H. E., Schnoes, H. K., DeLuca, H. F., Tetrahedron Lett., 1991, 32, 7663-7666). The cyclohexanone derivative B is once changed to an alcoholic form C by a reducing agent such as sodium boron hydride. Then, a hydroxy group of the alcoholic form C is protected by a protective group and to form a compound D. It is preferable to from an ether linkage by the use of a benzyl group as a protective group. Next, only a protect of a trimethylsilyl group at 4-position of the compound D is removed by acid treatment using such as acetic acid, and changed to a ketone group by oxidation-reaction using such as dimethylsulfoxide and oxalyl dichloride, to obtain a compound F. A ketone group of the compound F is changed to methylene by Wittig reagent to obtain a compound G. Compound G thus obtained is changed to a spiro-epoxy compound H by a peroxidizing agent such as m-chloroperbenzoic acid. A benzyl protective group at 6-position is removed by hydrogenation reaction by palladium catalyst to form a compound I. A hydroxy group formed is oxidized to a ketone group to form a compound J. Thereafter, the compound J thus formed is changed to an alcoholic form L by carbon-addition and reduction-reaction by (trimethylsilyl) acetic ester. The alcoholic form L is diphenylphosphinized and oxidized by hydrogen peroxide to obtain an objective A-ring phosphine oxide compound M.

CD-ring 25-hydroxy Grundmann's ketone can be synthesized by ozonolysis of vitamin D derivative having desired CD-ring known by reference (Sandina, F. J., Mourino, S., Castedo, L., J. Org. Chem., 1986, 51, 1264-1269.: Kiegiel, J., Wovkulich, P. M., Uskokovic, M. R., Tetrahedron Lett., 1991, 32, 6057-6060.: Fernadez, B., Perez, J. A., Granja, J. R., Castefo, L., Mourino, A., J. Org. Chem., 1992, 57,3173-3178.: Fujishima, T., Konno, K., Nakagawa, K., Kurobe, M., Okano, T., Takayama, H., Bioogr. Med. Chem., 2000, 8, 123-134.)

Synthesis of desired vitamin D derivative can be carried out by bonding A-ring phosphine oxide compound with CD-ring 25-hydroxy Grundmann's ketone which is synthesized in such a manner as described above. Generally, when the coupling reaction is carried out without protecting a hydroxy group at 25-position, yield is lowered. It is, therefore, preferable to protect a hydroxy group at 25-position of 25-hydroxy Grundmann's ketone by a proper protective group such as acyl group, substituted silyl group, substituted alkyl group, and the like (for example, triethylsilyl group, methoxymethyl group, and the like). A-ring phosphine oxide compound is treated with strong base such as butyl lithium to form phosphinoxycarbanion which is reacted with a ketone group of CD-ring Grundmann's ketone.

Spiro-oxirane at 2-position is optionally subjected to ring cleavage to form 2,2-disubstituted one. For example, when a fluorinating agent such as tetrabutylammonium fluoride is used, a derivative having a fluoromethyl group and a hydroxy group at 2-position can be synthesized. When a metal hydrogenating agent such lithium aluminum hydride is used, a derivative having a methyl group and a hydroxy group at 2-position can be synthesized. When a metylating agent or methoxizating agent is used, a derivative having a methyl group and a hydroxy group, or a derivative having a methoxymethyl group and a hydroxy group can be synthesized, respectively.

The vitamin D derivative represented by the general formula (IV) of the present invention is a novel compound and there is no limitation with respect to methods of synthesis thereof. It can be synthesized by a method described in the general synthesis scheme described below:

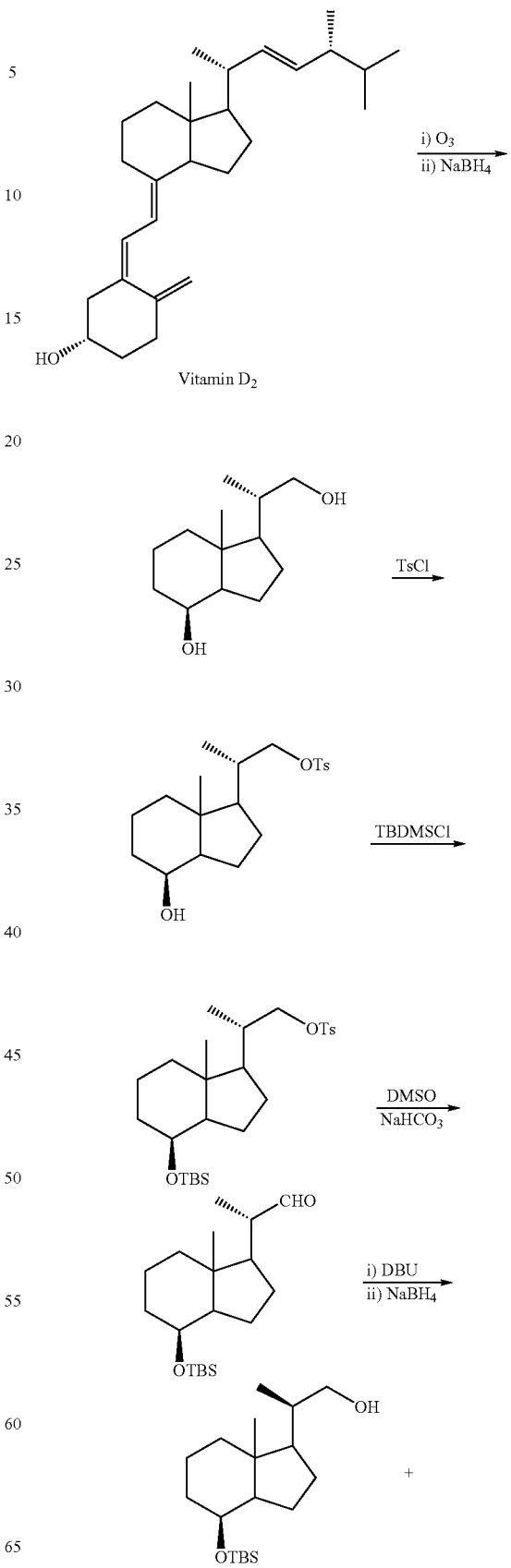

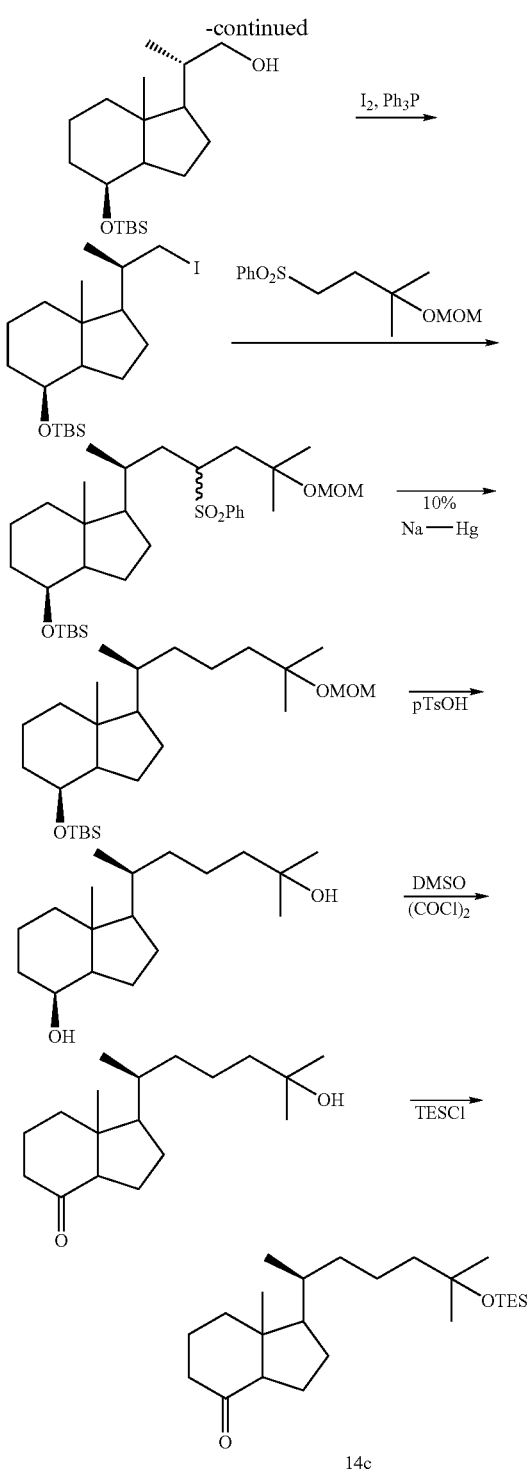

A., Granja, J. R., Castefo, L., Mourino, A., J. Org. Chem., 1992, 57, 3173-3178.: Fujishima, T., Konno, K., Nakagawa, K., Kurobe, M., Okano, T., Takayama, H., Bioogr. Med. Chem., 2000, 8, 123-134.).

EXAMPLES

The present invention will be described specifically by way of the following Examples, which is no way limit the invention.

(Conditions for Instrumental Analysis)

$^1$H NMR and $^{19}$F MHR were measured with a Bruker ARX-400 spectrometer. Chemical shifts were shown in terms of δ value using tetramethylsilane (TMS) as an internal standard, and trifluorotoluene as an external standard (δ=−63 ppm) for $^{19}$F NMR. NMR spectra were described using the following abbreviations: s=singlet, d=doublet, t=triplet, m=multiplet, arom=aromatic, br=broad signal.

MS spectra were measured by electronic ionization (EI) method with JEOL JMS-AX505HA spectrometer. In the specification, "no M$^+$" means that no M$^+$ was observed. "HR-MS" stands for High Resolution MS spectrum.

UV spectra were obtained on a Beckmann DU-7500 spectrophotometer.

Mixtures of some isomers were separated and refined with HPLC system equipped with JASCO MD-910 multiwave-length UV detector.

All reactions, unless specifically mentioned, were conducted under an atmosphere of argon gas.

Wakogel C-200 was used as a silica gel.

In following experiments, the numbering of the compounds 2-13, 30-38, 118, 119, 125-135 corresponding to the A-ring of the 19-norvitamin D were expressed based on the IUPAC nomenclature of organic chemistry. The nomenclature of the compounds having 19-norvitamin D structure after being bonded with CD-ring grundmann keton was expressed on the basis of the steroidal numbering.

Example 1

(1,4-cis)- and (1,4-trans)-3,5-bis-[(t-butyldimethylsilyl)oxy]-4-[(trimethylsilyl)oxy]-cyclohexanols (Compound 3)

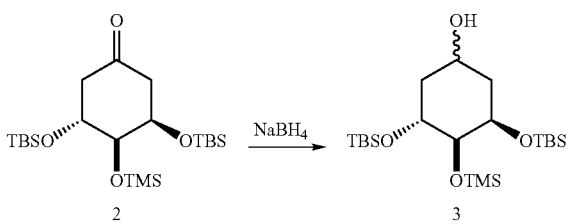

Sodium borohydride (NaBH$_4$, 217.5 mg, 5.75 mmol) was added over a period of about 10 min to a solution of (3R,5R)-3,5-bis-[(t-butyldimethylsilyl)oxy]-4-[(trimethylsilyl)oxy]-cyclohexanone (Compound 2) (5.13 g, 11.5 mmol) in ethanol (EtOH, 50 mL) cooled to 0° C. Stirring was continued for 1.5 h, and then ice water was added to the reaction mixture. After extraction with ethyl acetate (AcOEt), the organic layer was washed with saturated brine and dried over anhydrous magnesium sulfate (MgSO$_4$), and the solvent was distilled off. The residue was purified by silica gel column chromatography (60 g; 5% AcOEt/hexane), to yield Compound 3 (5.15 g, As shown in the scheme described above, the known vitamin D derivative having a desired CD-ring is subjected to ozonolysis, 20-position of 20-aldehyde is epimerized by DBU, and then immediately reducing by NaBH$_4$ to obtain CD-ring 20-epi-25-hydroxy Grundmann's ketone as a main product (non-natural type-22-alcoholic form) (Sandina, F. J., Mourino, S., Castedo, L., J. Org. Chem., 1986, 51, 1264-1269.: Kiegiel, J., Wovkulich, P. M., Uskokovic, M. R., Tetrahedron Lett., 1991, 32, 6057-6060.: Fernadez, B., Perez, J.

99%) as a mixture of 1,4-cis isomer and 1,4-trans isomer. The ratio of the stereoisomers constituting the mixture was ca. 2:1. It was impossible to know whether the major product was 1,4-cis isomer or 1,4-trans isomer. In this connection, the C-1 position is pseudoasymmetric, and 1,4-cis isomer and 1,4-trans isomer are achiral diastereoisomers to each other.

2: $^1$H NMR (CDCl$_3$) δ: 0.05 (6H, Si-Me×2), 0.06, 0.07 (each 3H, s, Si-Me×2), 0.16 (9H, s, SiMe$_3$), 0.86, 0.89 (each 9H, s, Si-tBu×2), 2.17 (1H, m), 2.36 (1H, dd, J=13.7, 4.5 Hz), 2.73 (2H, m), 3.80 (1H, m, H-4), 4.03 (1H, dd, J=8.3, 2.3 Hz, H-5), 4.24 (1H, ddd, J=10.6, 4.5, 2.3 Hz, H-3). MS m/z (%): no M$^+$, 431 (3), 389 (68), 299 (69), 257 (44), 73 (100).

3: $^1$H NMR (CDCl$_3$) δ: 0.06-0.11 (12H, Si-Me×4), 0.11, 0.12 (9H, s, SiMe$_3$), 0.89-0.91 (18H, s, Si-tBu×2), 1.52-1.92 (4H, m), 3.43, 3.68 (ca. 2:1) (1H, m), 3.94-4.22 (3H, m). MS m/z (%): no M$^+$, 391 (3), 373 (15), 301 (19), 259 (23), 73 (100).

Example 2

(1,4-cis)- and (1,4-trans)-3,5-bis-[(t-butyldimethylsilyl)oxy]-4-[(trimethylsilyl)oxy]-cyclohexanol benzyl ethers (Compound 4)

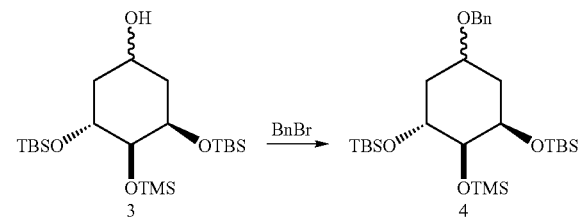

To a solution of Compound 3 (a mixture of ca. 2:1 of the major product and the minor product; 4.57 g, 10.2 mmol) in dry dimethylformamide (DMF, 30 mL) cooled to 0° C. were added sodium hydride (NaH, 1.22 g, 30.5 mmol, 60% paraffin liquid) and benzyl bromide (3.483 g, 20.4 mmol), and stirred for 8 h. Ice water was added to the reaction mixture, and then the reaction mixture was extracted with AcOEt/hexane (1:1). The organic layer was washed with saturated brine and dried over anhydrous MgSO$_4$, and the solvent was distilled off. The residue was purified by silica gel column chromatography (150 g; 3% AcOEt/hexane), to yield Compound 4 (4.66 g, 85%) as a mixture of 1,4-cis isomer and 1,4-trans isomer. The ratio of the stereoisomers constituting the mixture was ca. 2:1. It was impossible to know whether the major product was 1,4-cis isomer or 1,4-trans isomer. In this connection, the C-1 position is pseudoasymmetric, and 1,4-cis isomer and 1,4-trans isomer are achiral diastereoisomers to each other.

4a (major product): $^1$H NMR (CDCl$_3$) δ: 0.03, 0.06 (each 6 EL Si-Me×4), 0.10 (9H, s, SiMe$_3$), 0.85, 0.90 (each 9H, s, Si-tBu×2), 1.70-1.93 (4H, m), 3.57 (1H, m), 3.64 (1H, tt, J=11.0, 5.0 Hz), 3.80 (1H, m), 3.91 (1H, ddd, J=9.5, 4.3, 2.4 Hz), 4.51, 4.55 (each 1H, d, J=11.7 Hz, PhCH$_2$), 7.30-7.37 (5H, m, arom-H).

4b (minor product): $^1$H NMR (CDCl$_3$) δ: 0.01, 0.046 (each 3H, Si-Me×2), 0.055 (6H, s, Si-Me×2), 0.11 (9H, s, SiMe$_3$), 0.84, 0.88 (each 9H, s, Si-tBu×2), 1.37 (2H, m), 2.07 (1H, m), 2.19 (1H, m), 3.28 (1H, dd, J=8.5, 2.3 Hz), 3.80 (2H, m), 3.93 (1H, m), 4.50, 4.52 (each 1H, d, J=12.1 Hz, PhCH$_2$), 7.30-7.37 (5H, m, arom-H). MS m/z (%) of the mixture: no M$^+$, 481 (5), 391 (9), 373 (20), 349 (6), 259 (6), 91 (100).

Example 3

(1,4-cis)- and (1,4-trans)-2,6-bis-[(t-butyldimethylsilyl)oxy]-4-[(benzyl)oxy]-cyclohexanols (Compound 5)

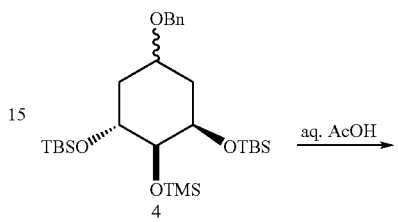

Compound 4 (a mixture of ca. 2:1 of Compound 4a and Compound 4b; 269 mg, 0.499 mmol) was dissolved in a mixture of tetrahydrofuran (THF), acetic acid (AcOH) and water (8.5 mL; 8:8: 1, v/v/v), and stirred for 20 h at room temperature. The reaction mixture was diluted with AcOEt, and successively washed with 5% sodium hydrogencarbonate (NaHCO$_3$) aqueous solution and saturated brine. The organic layer was dried over anhydrous sodium sulfate (Na$_2$SO$_4$). The solvent was distilled off, and the residue was purified by silica gel column chromatography (15 g; 4% AcOEt/hexane), to give Compound 5 (187 mg, 80%) as a mixture of 1,4-cis isomer and 1,4-trans isomer. The ratio of the stereoisomers constituting the mixture was ca. 2:1. It was impossible to know whether the major product was 1,4-cis isomer or 1,4-trans isomer. In this connection, the. C-1 position is pseudoasymmetric, and 1,4-cis isomer and 1,4-trans isomer are achiral diastereoisomers to each other.

5a (major product, more polar): $^1$H NMR (CDCl$_3$) δ: 0.04 (6H, s, Si-Me×2), 0.07, 0.08 (each 3H, Si-Me×2), 0.84, 0.90 (each 9H, s, Si-tBu×2), 1.60-1.73 (2H, m), 1.89 (1H, m), 1.98 (1H, m), 2.43 (1H, s, OH), 3.57 (1H, t, J=3.2 Hz, H-4), 3.69 (1H, tt, J=11.4, 4.1 Hz, H-1), 3.96 (1H, ddd, J=11.6, 4.8, 3.2 Hz), 4.10 (1H, m), 4.54 (2H, s, PhCH$_2$), 7.30-7.35 (5H, m, arom-H).

5b (minor product, less polar): $^1$H NMR (CDCl$_3$) δ: 0.057, 0.076, 0.077, 0.091 (each 3H, Si-Me×4), 0.86, 0.90 (each 9H, s, Si-tBu×2), 1.36-1.47 (2H, m), 2.01 (1H, d, J=5.7 Hz, OH), 2.13 (1H, m), 2.22 (1H, m), 3.28 (1H, ddd, J=8.7, 5.7, 2.9 Hz, H-4), 3.75 (2H, m, H-1, 5), 4.13 (1H, m, H-3), 4.50, 4.54 (each 1H, d, J=11.8 Hz, PhCH$_2$), 7.30-7.35 (5H, m, arom-H). MS m/z (%) of the mixture: no M$^+$, 409 (6), 319 (2), 301 (17), 277 (6), 259 (4), 211 (9), 1.69 (31), 91 (100).

Example 4

(2R,6R)-2,6-bis-[(t-butyldimethylsilyl)oxy]-4-[(benzyl)oxy]-cyclohexanone (Compound 6)

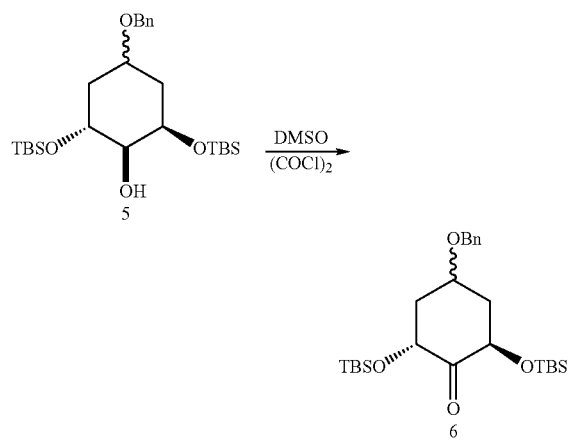

To a solution of oxalyl chloride (384 μL, 4.40 mmol) in dry methylene chloride (CH$_2$Cl$_2$, 5 mL) cooled to −78° C. was added a solution of dimethyl sulfoxide (DMSO, 621 μL, 8.75 mmol) in dry CH$_2$Cl$_2$ (2.5 mL), and stirred for 5 min. To this cooled stirring solution, a solution of Compound 5 (1.71 g, 3.66 mmol, a mixture of isomers 5a:5b=ca. 2:1) in dry CH$_2$Cl$_2$ (10 mL) was added. The reaction mixture was stirred for 15 min, and triethylamine (Et$_3$N, 2.55 mL, 18.3 mmol) was added to the reaction mixture. The mixture was stirred while gradually raising the reaction temperature from −78° C. to room temperature, over a period of ca. 1.5 h. Then the reaction solution was poured into ice water, and then extracted with CH$_2$Cl$_2$. The organic layer was washed with saturated brine, and dried over anhydrous MgSO$_4$. The solvent was removed by evaporation. The residue was purified by silica gel column chromatography (30 g; 5% AcOEt/hexane), to yield Compound 6 (1.69 g, 99%) as a single compound.

$^1$H NMR (CDCl$_3$) δ: 0.02, 0.03, 0.06, 0.12 (each 3H, Si-Me×4), 0.86, 0.90 (each 9H, s, Si-tBu×2), 1.74 (2H, m), 2.31 (1H, m), 2.51 (1H, m), 4.12 (2H, m), 4.55, 4.60 (each 1H, d, J=11.7 Hz, PhCH$_2$), 4.73 (1H, dd, J=12.1, 6.4 Hz), 7.27-7.35 (5H, m, arom-H). MS m/z (%): no M$^+$, 449 (2), 407 (27), 299 (21), 275 (5), 91 (100).

Example 5

(3R,5R)-3,5-bis-[(t-butyldimethylsilyl)oxy]-4-methylene-cyclohexanol benzyl ether (Compound 7)

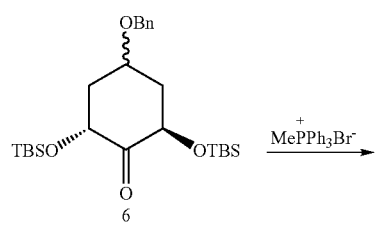

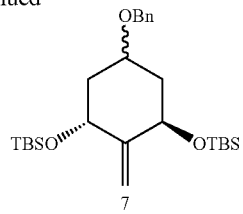

To a suspension of methyltriphenylphosphonium bromide (1.55 g, 4.34 mmol) in dry THF (10 mL) cooled to 0° C. was added n-butyl lithium (n-BuLi, 2.71 mL, 4.34 mmol, 1.6 M solution in hexane), and the mixture was stirred for 10 min, and further stirred for 1 h at room temperature. To the resulting orange mixture was added over ca. 20 min period a solution of Compound 6 (1.0 g, 2.15 mmol) dissolved in dry THF (10 mL). After being stirred for 1 h at 0° C. and for 17 h at room temperature, the reaction mixture was poured into ice water, and extracted with AcOEt. The organic layer was rinsed with saturated brine, and dried over anhydrous MgSO$_4$. The solvent was removed by evaporation. The residue was purified by silica gel column chromatography (5 g; 2% AcOEt/hexane), to yield Compound 7 (978.5 mg, 98%, single compound).

$^1$H NMR (CDCl$_3$) δ: −0.01, 0.04, 0.06, 0.07 (each 3H, Si-Me×4), 0.84, 0.92 (each 9H, s, Si-tBu×2), 1.35-1.46 (2H, m), 2.18 (1H, m), 2.35 (1H, m), 3.94 (1H, tt, J=11.2, 4.2 Hz, H-1), 4.40-4.46 (2H, m, H-1, 3), 4.54, 4.56 (each 1H, d, J=11.9 Hz, PhCH$_2$), 4.84 (1H, m, C=CH), 5.03 (1H, t, J=2.0 Hz, C=CH), 7.27-7.35 (5H, m, arom-H). MS m/z (%): no M$^+$, 405 (84), 355 (2), 313 (35), 297 (15), 273 (20), 223 (18), 165 (22), 91 (100).

Example 6

(3,6-cis)- and (3,6-trans)-6-benzyloxy-4,8-bis-[(t-butyldimethylsilyl)oxy]-1-oxa-spiro[2.5]octanes (Compound 8)

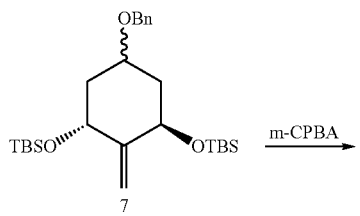

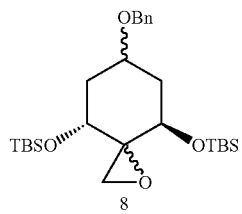

To a solution of Compound 7 (191.4 mg, 0.414 mmol) in CH$_2$Cl$_2$ (2 mL) cooled to 0° C. was added m-chloroperbenzoic acid (106.8 mg, 0.619 mmol). The reaction mixture was stirred for 2 h at 0° C. and for 16 h at room temperature, and then CH$_2$Cl$_2$ was added thereto. The CH$_2$Cl$_2$ layer was successively washed with 5% NaHCO$_3$ and saturated brine, and dried over anhydrous MgSO₄. The solvent was removed by evaporation, and the residue was purified by silica gel column chromatography (8 g; 2%→5% AcOEt/hexane), to yield Compound 8b (19.0 mg) from 2% AcOEt-containing hexane eluate and Compound 8a (178.0 mg) from 5% AcOEt-containing hexane eluate. The total yield was 99%. It was impossible to know whether the major product was 3,6-cis isomer or 3,6-trans isomer.

8a (more polar isomer): $^1$H NMR (CDCl$_3$) δ: 0.01, 0.02, 0.05, 0.06 (each 3H, s, Si-Me×4), 0.85, 0.88 (each 9H, s, Si-tBu×2), 1.66-1.75 (2H, m), 2.05 (1H, m), 2.24 (1H, m), 2.62, 3.03 (each 1H, d, J=5.3 Hz, CH$_2$O), 3.53 (1H, t, J=3.0 Hz), 3.84 (1H, tt, J=11.1, 4.1 Hz, H-1), 4.21 (1H, dd, J=11.6, 4.4 Hz), 4.56 (2H, s, PhCH$_2$), 7.27-7.35 (5H, m, arom-H). MS m/z (%): no M⁺, 421 (3), 391 (2), 313 (18), 91 (100), 75 (74).

8b (less polar isomer): $^1$H NMR (CDCl$_3$) δ: 0.02 (6H, s, Si-Me×2), 0.04, 0.07 (each 3H, s, Si-Me×4), 0.856, 0.863 (each 9H, s, Si-tBu×2), 1.44-1.55 (2H, m), 2.18 (1H, m), 2.35-2.41 (1H, m), 2.38, 2.96 (each 1H, d, J=5.6 Hz, CH$_2$O), 3.55 (1H, m), 3.93 (1H, tt, J=11.2, 4.2 Hz, H-1), 4.18 (1H, dd, J=11.5, 4.8 Hz), 4.54, 4.57 (each 1H, d, J=11.8 Hz, PhCH$_2$), 7.27-7.35 (5H, m, arom. H). MS m/z (%): no M⁺, 421 (7), 391 (3), 313 (11), 91 (96), 75 (100).

Example 7

(3,6-cis)- and (3,6-trans)-4,8-bis-[(t-butyldimethylsilyl)oxy]-1-oxa-spiro[2.5]octane-6-oles (Compound 9)

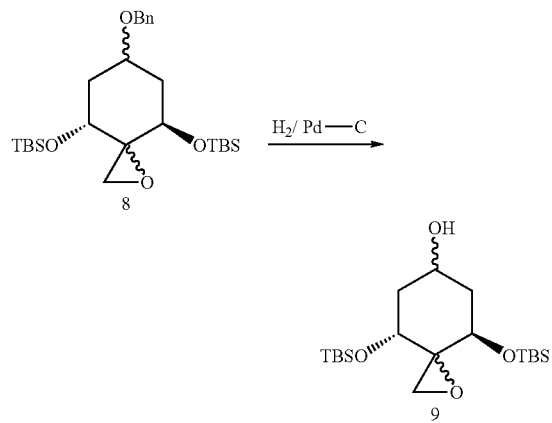

To a solution of Compound 8a (216.8 mg, 0.453 mmol), which was an epoxy compound, in AcOEt (2 mL), was added 10% palladium on activated carbon (43.4 mg), and then the mixture was vigorously stirred with H$_2$ gas for 1 h, under an atmospheric pressure, at room temperature. The reaction mixture was filtered through Celite, washed with ethanol and AcOEt, and the combined filtrate was subjected to evaporation to remove the solvent. The residue was purified by silica gel column chromatography (8 g; 8% AcOEt/hexane), to obtain Compound 9a (176.0 mg, quantitative).

Catalytic hydrogenation and column purification of Compound 8b (24.6 mg, 0.0514 mmol) were carried out in the same manner as described above, to obtain Compound 9b (17.2 mg, 86%), which was a debenzylated compound.

9a: $^1$H NMR (CDCl$_3$) δ: 0.05, 0.07, 0.10, 0.15 (each 3H, s, Si-Me×4), 0.87, 0.91 (each 9H, s, Si-tBu×2), 1.62 (1H, m), 1.80 (1H, t, J=14.1, 2.9 Hz), 2.08, 2.27 (each 1H, m), 2.50, 2.95 (each 1H, d, J=5.5 Hz, CH$_2$O), 3.80 (1H, m), 4.14 (1H, m), 4.40 (1H, m). MS m/z (%): no M⁺, 331 (25), 313 (52), 301 (16), 199 (63), 181 (46), 75 (100).

9b: $^1$H NMR (CDCl$_3$) δ: 0.05, 0.07, 0.08, 0.09 (each 3H, s, Si-Me×4), 0.88, 0.89 (each 9H), s, Si-tBu×2), 1.68, 1.82, 1.98, 2.14 (each 1H, m, H-2, 6), 2.71 (1H, m, CH$_2$O), 2.82 (1H, d, J=5.4 Hz, CH$_2$O), 4.00 (2H, m), 4.21 (1H, m). MS m/z (%): no M⁺, 331 (20), 313 (42), 301 (14), 199 (72), 181 (39), 73 (100).

Example 8

(4R,8R)-4,8-bis-[(t-butyldimethylsilyl)oxy]-1-oxa-spiro[2.5]octane-6-one (Compound 10)

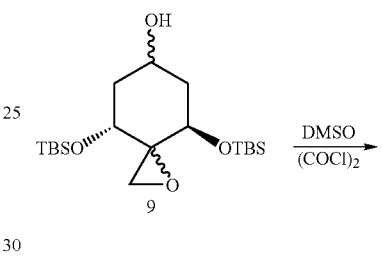

To a solution of oxalyl chloride (51 µL, 0.585 mmol) in dry methylene chloride (CH$_2$Cl$_2$, 0.5 mL) cooled to −78° C. was added a solution of DMSO (83 µL, 1.170 mmol) in dry CH$_2$Cl$_2$ (0.2 mL). After 5 min of stirring, a solution of Compound 9 (a mixture of Compounds 9a:9b=ca. 10:1) (190.6 mg, 0.490 mmol) in dry CH$_2$Cl$_2$ (1.3 mL) was added.

The reaction mixture was stirred for 15 min at −78° C., and Et$_3$N (341 µL, 2.445 mmol) was added. The whole mixture was stirred over a period of about 1.5 h) until the reaction temperature was raised from −78° C. to room temperature. Ice water was added to the reaction mixture, and the mixture was extracted with CH$_2$Cl$_2$. The organic layer was washed with saturated brine, and dried over anhydrous MgSO$_4$. The solvent was distilled off. The residue was purified by silica gel column chromatography (8 g; 5% AcOEt/hexane), to yield Compound 10 (188.5 mg, 99%) as a single compound.

$^1$H NMR (CDCl$_3$) δ: 0.047, 0.055, 0.061, 0.086 (each 3H, s, Si-Me×4), 0.86, 0.88 (each 9H, s, Si-tBu×2), 2.45 (1H, ddd, J=14.4, 7.9, 1.1 Hz), 2.57 (1H) ddd, J=14.2, 6.2, 1.9 Hz), 2.67 (1H, ddd, J=14.2, 3.9, 1.1 Hz), 2.79 (1H ddd, J=14.4, 4.9, 1.1 Hz), 2.80, 3.02 (each 1H, d, J=5.3 Hz, CH$_2$O), 4.03 (1H, d, J=6.2, 3.9 Hz), 4.21 (1H, dd, J=7.9, 4.9 Hz), 4.40 (1H, m). MS m/z (%): no M⁺, 329 (31), 313 (10), 299 (9), 197 (20), 75 (100).

Example 9

[(aS*,4R,8R)- and [(aR*,4R,8R)-[4,8-bis-[(t-butyldimethylsilyl)oxy]-1-oxa-spiro[2.5]octy-6-ylidene]-methyl acetate esters (Compound 11)

Example 10

[(aS*,4R,8R)- and [(aR*,4R,8R)-2-[4,8-bis-[(t-butyldimethylsilyl)oxy]-1-oxa-spiro[2.5]octy-6-ylidene]-ethanols (Compound 12)

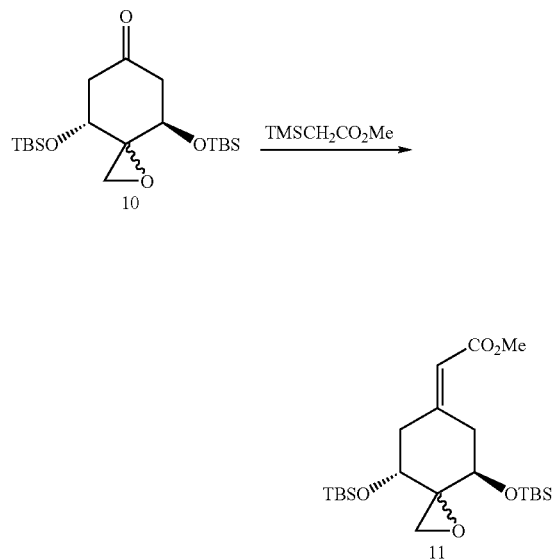

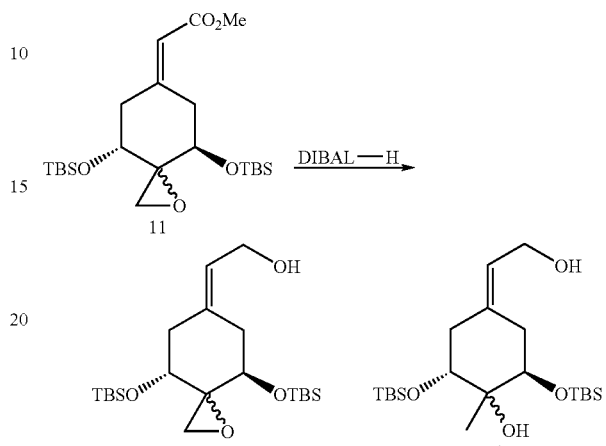

To a solution of diisopropylamine (115 μL, 0.82 mmol) in dry THF (1 mL) cooled to −78° C. was added n-BuLi (513 μL, 0.82 mmol, 1.6 M solution in hexane) and stirred for 15 min. Then, methyl (trimethylsilyl)acetate (135 μL, 0.82 mmol) was added thereto. After 10 min of stirring, a solution of Compound 10 (158.8 mg, 0.41 mmol) dissolved in dry THF (1.2 mL) was slowly added, and stirring was continued for 1 h at −78° C. To the reaction mixture was added saturated ammonium chloride ($NH_4Cl$) aqueous solution, and the mixture was extracted with AcOEt. The organic layer was washed with saturated brine, dried over anhydrous $MgSO_4$, and evaporated to remove the solvent. The residue was purified by silica gel column chromatography (8 g; 2% AcOEt/hexane), to give Compound 11 (172.1 mg, 95%) as a mixture of two stereoisomers. The ratio of the stereoisomers constituting the mixture was ca. 3:1. It was impossible to know whether the major product was aS*,4R,8R isomer or aR*,4R,8R isomer.

NMR Data of the Mixture 11a (major product): $^1$H NMR ($CDCl_3$) δ: 0.03-0.08 (12H, Si-Me×4), 0.86, 0.88 (each 9H, s, Si-tBu×2), 2.41 (1H, d, J=13.2, 6.7 Hz), 2.47 (1H, m), 2.74 (1H, d, J=5.4 Hz, $CH_2O$), 2.80 (1H, dd, J=13.7, 7.6 Hz), 2.90 (1H, d, J=5.4 Hz, $CH_2O$), 3.40 (1H, dd, J=13.7, 4.0 Hz), 3.70 (3H, s, OMe), 3.91 (2H, m, H-3, 5), 5.76 (1H, s, C=CHCO).

11b (minor product): $^1$H NMR ($CDCl_3$) δ: 0.03-0.08 (12H, Si-Me×4), 0.86, 0.88 (each 9H, s, Si-tBu×2), 2.28 (1H, m), 2.60 (1H, dd, J=13.2, 4.6 Hz), 2.67 (1H, d, J=5.4 Hz, $CH_2O$), 2.72 (1H, m), 2.92 (1H, d, J=5.4 Hz, $CH_2O$), 3.48 (1H, m), 3.69 (3H, s, OMe), 3.80 (1H, dd, J=5.9, 3.2 Hz), 4.04 (1H, dd, J=8.6, 4.6 Hz), 5.81 (1H, s, C=CHCO). MS m/z (%) of the mixture: no M$^+$, 411 (3), 385 (86), 355 (14), 353 (47), 325 (8), 293 (30), 280 (24), 253 (65), 223 (13), 221 (20), 73 (100).

To a solution of Compound 11 (190.3 mg, 0.43 mmol, a mixture of 11a:11b=ca. 3:1), which was allylester compound, in dry toluene (2 mL) cooled to −78° C. was added di-isobutylaluminum hydride (1.07 mL, 1.07 mmol, 1.0 M solution in toluene), and the mixture was stirred for 1 h. The reducing agent was decomposed by adding an aqueous solution of saturated potassium sodium tartrate, the reaction mixture was poured into ice water, and then extracted with AcOEt. The organic layer was successively washed with water and saturated brine, and dried over anhydrous $MgSO_4$, and then the solvent was distilled off. The residue was purified by silica gel column chromatography (8 g; 10%→15% AcOEt/hexane), to yield Compound 12 (167.6 mg, 94%) as a mixture of two stereoisomers, from. 10% AcOEt-containing hexane eluate. The ratio of the isomers constituting the mixture was ca. 3:1. It was impossible to know whether the major product was aS*,4R,8R isomer or aR*,4R,8R isomer. Compound 12', which had an open-ring, was obtained from 15% AcOEt-containing hexane eluate (11 mg, 6%; obtained only for one of the stereoisomers)

12a (major product): $^1$H NMR ($CDCl_3$) δ: 0.034 (3H, s, Si-Me), 0.056 (6H, s, Si-Me×2), 0.068 (3H, s, Si-Me), 0.87, 0.88 (each 9H, s, Si-tBu×2), 1.15 (1H, t, J=5.6 Hz, OH), 2.22 (1H, dd, J=13.6, 6.9 Hz), 2.32 (1H, dd, J=13.1, 6.9 Hz), 2.39 (1H, dd, J=13.1, 3.8 Hz), 2.61 (1H, dd, J=13.6, 4.1 Hz), 2.74, 2.84 (each 1H, d, J=5.4 Hz, $CH_2O$), 3.83-3.86 (2H, m, H-3, 5), 4.13-4.20 (2H, m, C$\underline{H}_2$OH), 5.59 (1H, t, J=7.0 Hz, C=CHCO).

12b (minor product): $^1$H NMR ($CDCl_3$) δ: 0.026, 0.056, 0.063, 0.09 (each 3H, s, Si-Me×4), 0.86, 0.88 (each 9H, s, Si-tBu×2), 1.22 (1H, dd, J=6.5, 4.7 Hz, OH), 2.16, 2.21, 2.53 (each 1H, m), 2.57 (1H, d, J=5.5 Hz, $CH_2O$), 2.60 (1H, m), 2.93 (1H, d, J=5.5 Hz, $CH_2O$), 3.71 (1H, dd, J=5.1, 3.1 Hz), 4.00 (1H, dd, J=9.5, 4.6 Hz), 4.08-4.20 (2H, m, $CH_2OH$), 5.67 (1H, t, J=6.9 Hz, C=CHCO). MS m/z (%) of the mixture: no M$^+$, 357 (13), 339 (100), 327 (4), 309 (14), 265 (20), 235 (26), 225 (20), 207 (38), 195 (15), 177 (37), 75 (100).

12': $^1$H NMR ($CDCl_3$) δ: 0.07 (6H, s, Si-Me×2), 0.08, 0.10 (each 3H, Si-Me×2), 0.87, 0.91 (each 9H, s, Si-tBu×2), 1.18 (3H, s, Me), 2.19-2.38 (4H, m), 2.46 (1H, d, J=13.6 Hz), 3.71

(1H, dd, J=9.6, 4.9 Hz), 3.78 (1H, dd, J=4.3, 3.4 Hz), 4.09-4.16 (2H, m, CH₂OH), 5.50 (1H, t, J=7.0 Hz, C═CHCO).

Example 11

[(aS*,4R,8R)- and [(aR*,4R,8R)-2-[4,8-bis-[(t-butyldimethylsilyl)oxy]-6-[2-(diphenyl-phosphinoyl)-ethylidene]-1-oxa-spiro[2.5]octane (Compound 13)

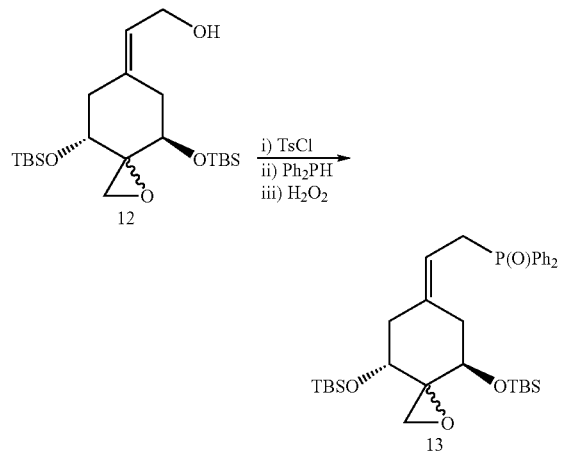

To a solution of Compound 12 (167.6 mg, 0.404 mmol, a mixture of 12a:12b =ca. 3:1), which was an allylalcohol compound, in dry THF (2 mL) cooled to 0° C. were subsequently added n-BuLi (278 μL, 0.445 mmol, 1.6 M solution in hexane) and a solution of p-toluenesulfonyl chloride (84.7 mg, 0.445 mmol) in dry THF (0.3 mL), and the mixture was stirred for 5 min. In a separate vessel, a solution of diphenylphosphine (141 μL, 0.810 mmol) in THF (1 mL) was prepared; and when n-BuLi (505 μL, 0.808 mmol, 1.6 M solution in hexane) was added while stirring at 0° C., the solution turned dark red. The dark red solution cooled to 0° C. was slowly added dropwise to the above tosyl compound solution, until the reaction mixture turned red. The entire mixture was further stirred for 30 min at 0° C., and water (100 μL) was added to stop the reaction. The solvent was evaporated from the reaction mixture, and the residue was dissolved in CH₂Cl₂ (4 mL). To this mixture was added 10% hydrogen peroxide (6 mL). The mixture was stirred for 1 h at 0° C. To the reaction solution was added 2N sodium sulfite (Na₂SO₃), and the reaction solution was extracted with CH₂Cl₂. The organic layer was successively washed with water and saturated brine, and then dried over anhydrous MgSO₄. After evaporation of the solvent, the residue was purified by silica gel column chromatography (8 g; 30% AcOEt/hexane), to yield Compound 13 (187.9 mg, 77%) as a mixture of two stereoisomers. The ratio of the isomers constituting the mixture was ca. 3:1. It was impossible to know whether the major product was aS*,4R,8R isomer or aR*,4R,8R isomer.

NMR Data of the Mixture 13a (major product): ¹H NMR (CDCl₃) δ: −0.01-0.06 (12H, Si-Me×4), 0.83, 0.84 (each 9H, s, Si-tBu×2), 1.83 (1H, m), 2.25-2.40 (3H, m), 2.60, 2.82 (each 1H, d, J=5.5 Hz, CH₂O), 3.05-3.24 (2H, m, CH₂PO), 3.70 (1H, dd, J=5.8, 3.6 Hz), 3.83 (1H, dd, J=8.5, 4.4 Hz), 5.36 (1H, m, C═CHCO), 7.44-7.77 (10H, m, arom H).

13b (minor product): ¹H NMR (CDCl₃) δ: −0.01-0.06 (12H, Si-Me×4), 0.82, 0.86 (each 9H, s, Si-tBu×2), 1.93, 2.10, 2.25, 2.46 (each 1H, m, H-2, 6), 2.55, 2.84 (each 1H, d, J=5.5 Hz, CH₂O), 3.05-3.24 (2H, m, CH₂PO), 3.65 (1H, dd, J=5.6, 3.2 Hz), 3.89 (1H, dd, J=8.7, 4.6 Hz), 5.36 (1H, m, C═CHCO), 7.44-7.77 (10H, m, arom H). MS m/z (%) of the mixture: no M⁺, 541 (100), 511 (8), 449 (39), 409 (86), 201 (26), 75 (44).

Example 12

1α-[(t-butyldimethylsilyl)oxy]-2β,2'-epoxy-25-[(triethylsilyl)oxy]-19-norvitamin D₃ t-butyldimethylsilyl ether and 1α-[(t-butyldimethylsilyl)oxy]-2α,2'-epoxy-25-[(triethylsilyl)oxy]-19-norvitamin D₃ t-butyldimethylsilyl ether (Compounds 15a, b)

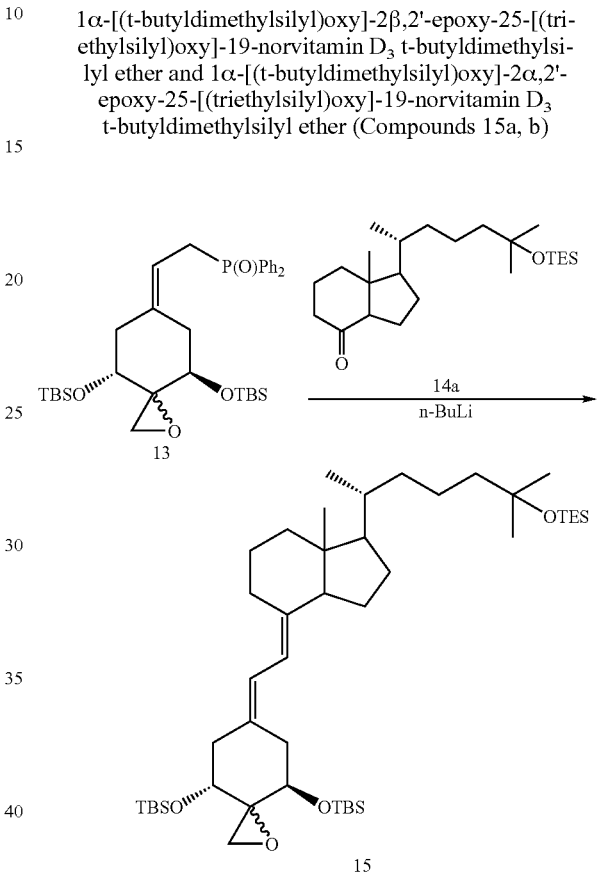

To a solution of Compound 13 (100.1 mg, 0.167 mmol, a mixture of 13a:13b =ca. 3:1) in dry THF (1.5 mL) cooled to −78° C. was added slowly n-BuLi (104 μL, 0.167 mmol, 1.6 M solution in hexane), to obtain dark orange solution. After stirring for 15 min, to this colored solution was added a solution of Compound 14a (44.0 mg, 0.114 mmol), which was a Grundmann's keton, in dry THF (0.5 mL), and the reaction mixture was stirred for 2 h at −78° C. To the reaction solution was added saturated NH₄Cl aqueous solution, and the reaction solution was extracted with AcOEt. The organic layer was washed with saturated brine, dried over anhydrous MgSO₄, and evaporated to remove the solvent. The residue was purified by silica gel column chromatography (7 g; 2%→10%→40% AcOEt/hexane), to yield Compound 15 (58.4 mg, 68%) as a mixture of two stereoisomers, from 2% AcOEt-containing hexane eluate. The ratio of the isomers constituting the mixture was ca. 3:1. From the results of Example 13, it was considered that 2β,2'-epoxy compound (15a) was the major product. Unreacted Compound 14a (14.0 mg, 32%) and Compound 13 (34.0 mg, 34%) were recovered from 10% AcOEt-containing hexane eluate and 40% AcOEt-containing hexane eluate, respectively.

NMR Data of the Mixture 15a (major product): $^1$H NMR (CDCl$_3$) δ: 0.02 (3H, s, Si-Me), 0.055 (3H, s, Si-Me×2), 0.065 (6H, s, Si-Me), 0.55 (3H, s, H-18), 0.56 (6H, q, SiCH$_2$×3), 0.86, 0.88 (each 9H, s, Si-tBu×2), 0.95 (12H, t, J=7.9 Hz, SiCH$_2$C$\underline{H}_3$×3, overlapped with H-21), 1.19 (6H, s, H-26, 27), 2.27-2.38 (2H, m), 2.42 (1H, dd, J=13.1, 3.6 Hz), 2.66 (1H, dd, J=13.3, 3.4 Hz), 2.74, 2.82 (each 1H, d, J=5.5 Hz, CH$_2$O), 3.81 (1H, dd, J=7.7, 3.9 Hz), 3.88 (1H, dd, J=7.0, 3.8 Hz), 5.82 (1H, d, J=11.1 Hz, H-7), 6.21 (1H, d, J=11.1 Hz, H-6).

15b (minor product): $^1$H NMR (CDCl$_3$) δ: 0.02 (3H, s, Si-Me), 0.064 (6H, s, Si-Me×2), 0.08 (3H, Si-Me), 0.55 (3H, s, H-18), 0.56 (6H, q, SiCH$_2$×3), 0.86, 0.88 (each 9H, s, Si-tBu×2), 0.95 (12H, t, J=7.9 Hz, SiCH$_2$C$\underline{H}_3$×3, overlapped with H-21), 1.19 (6H, s, H-26, 27), 2.57, 2.92 (each 1H, d, J=5.5 Hz, CH$_2$O), 3.68 (1H, m), 4.04 (1H, dd, J=9.5, 4.5 Hz, H-1), 5.82 (1H, d, J=12.1 Hz, H-7), 6.27 (1H, d, J=12.1 Hz, H-6).

Example 13

1α,25-dihydroxy-2β,2'-epoxy-19-norvitamin D$_3$ (Compound YI-1a), and 1α,25-dihydroxy-2α,2'-epoxy-19-norvitamin D$_3$ (Compound YI-1b), and 1α,2β,25-trihydroxy-2α-fluoromethyl-19-norvitamin D$_3$ (Compound YI-2a), and 1α,2α,25-trihydroxy-2β-fluoromethyl-19-norvitamin D$_3$ (Compound YI-2b)

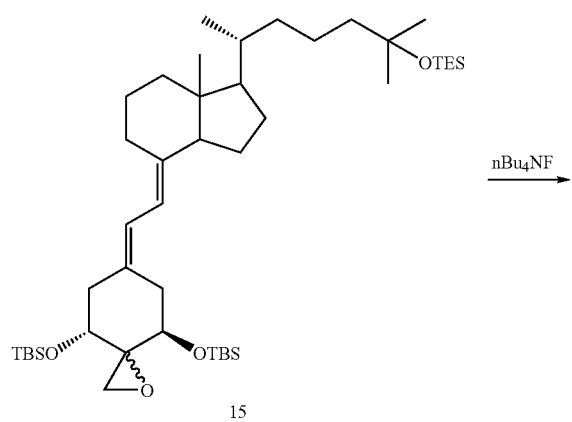

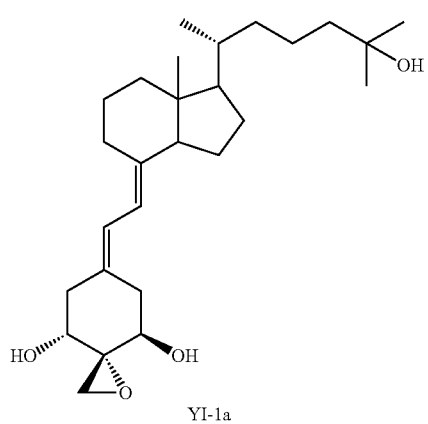

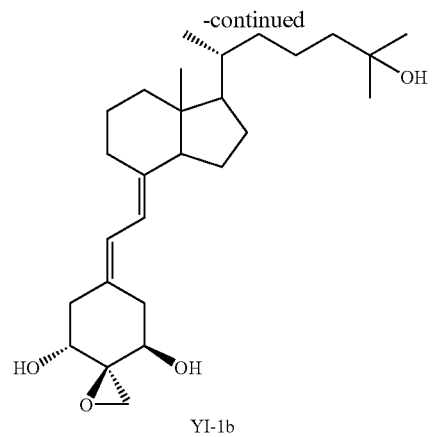

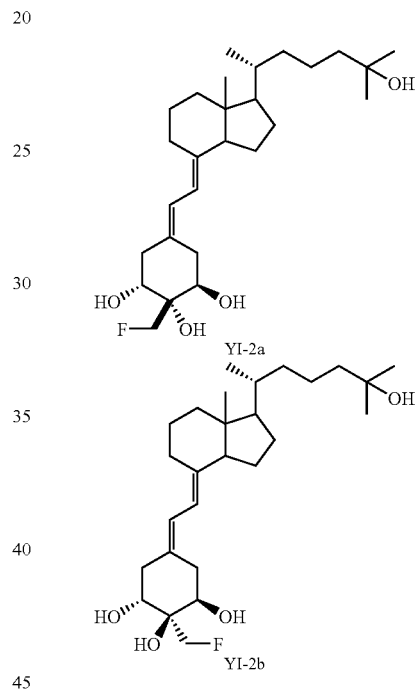

To a solution of Compound 15 (58.4 mg, 0.075 mmol, a mixture of 15a:15b=ca. 3:1), which was a trisilylether compound, in dry THF (1 mL), was added tetrabutylammonium fluoride (301 μL, 0.301 mmol, 1.0 M solution in THF), and stirred for 30 min at 0° C. and then for 7 h at room temperature. To the reaction solution was added ice water, and the reaction solution was extracted with AcOEt. The organic layer was washed with saturated brine, and dried over anhydrous MgSO$_4$. After removal of the solvent, the residue was subjected to silica gel column chromatography (5 g; 60%→70% AcOEt/hexane), to yield a mixture (2.6 mg, 8%) of Compounds YI-2a and YI-2b from the 60% AcOEt-containing hexane eluate and a mixture (19.7 mg, 60%) of Compounds YI-1a and YI-1b from the 70% AcOEt-containing hexane eluate.

The mixture containing YI-1a and YI-1b was separated and purified by HPLC (LiChrosorb Si 60, 250×10 mm, hexane: CH$_2$Cl$_2$:2-propanol=50:50:8), to yield Compound YI-1a (11.0 mg) and Compound YI-1b (2.6 mg). The mixture containing YI-2a and YI-2b was separated and purified by HPLC (YMC-Pack ODS-AM SH-342-5, 150×20 mm, 20% H$_2$O/methanol (MeOH)), to yield Compound YI-2a (0.9 mg) and Compound YI-2b (0.3 mg).

YI-1a (major product): $^1$H NMR (CDCl$_3$) δ: 0.55 (3H, s, H-18), 0.94 (3H, d, J=6.4 Hz, H-21), 1.22 (6H, s, H-26, 27), 2.30 (1H, dd, J=13.5, 8.7 Hz, H-10), 2.40 (1H, dd, J=13.7, 6.1 Hz, H-4), 2.60 (1H, dd, J=13.7, 3.5 Hz, H-4), 2.81 (1H, m, H-9), 2.84 (1H, d, J=4.7 Hz, CH$_2$O), 2.96 (1H, dd, J=13.5, 4.3 Hz, H-10), 3.08 (1H, d, J=4.7 Hz, CH$_2$O), 3.80 (1H, m, H-3), 3.99 (1H, m, H-1), 5.86 (1H, d, J=11.2 Hz, H-7), 6.39 (1H, d, J=11.2 Hz, H-6).

YI-1b (minor product): $^1$H NMR (CDCl$_3$) δ: 0.56 (3H, s, H-18), 0.94 (3H, d, J=6.4 Hz, H-21), 1.22 (6H, s, H-26, 27), 2.30 (1H, dd, J=13.7, 6.2 Hz, H-4), 2.36 (1H, dd, J=13.3, 8.6 Hz, H-10), 2.71 (1H, dd, J=13.7, 3.6 Hz, H-4), 2.81 (1H, m, H-9), 2.86 (1H, dd, J=13.3, 4.3 Hz, H-10), 2.94, 2.99 (each 1H, d, J=4.7 Hz, CH$_2$O), 3.81 (1H, m, H-3W/2≈12 Hz), 3.91 (1H, m, H-1W/2≈20 Hz), 5.87 (1H, d, J=11.2 Hz, H-7), 6.37 (1H, d, J=11.2 Hz, H-6). MS m/z (%): 432 (23, M$^+$), 414 (20), 396 (23), 378 (52), 303 (12), 267 (68), 135 (100).

YI-2a (major product): $^1$H NMR (CDCl$_3$) δ: 0.53 (3H, s, H-18), 0.94 (3H, d, J=6.4 Hz, H-21), 1.22 (6H, s, H-26, 27), 2.45 (1H, dd, J=13.5, 8.9 Hz, H-4), 2.49 (1H, dd, J=13.5, 54 Hz, H-4), 2.55 (1H, dd, J=14.1, 5.8 Hz, H-10), 2.63 (1H, br. s, OH), 2.69 (1H, dd, J=14.1, 2.9 Hz, H-10), 2.80 (1H, m, H-9), 3.86 (1H, m, H-3), 3.97 (1H, m, H-1), 4.77 (each 1H, dd, J=47.6, 9.7 Hz, CH$_2$F), 5.80 (1H, d, J=11.2 Hz, H-7), 6.41 (1H, d, J=11.2 Hz, H-6).

$^{19}$F NMR (CDCl$_3$) δ: −240.6 (t, J=47.6 Hz). MS m/z (%): 452 (75, M$^+$), 434 (100), 414 (34), 396 (19), 378 (38), 323 (54), 305 (19), 303 (21), 287 (17), 285 (18), 267 (22), 228 (24), 133 (82).

YI-2b (minor product): $^1$H NMR (CDCl$_3$) δ: 0.55 (3H, s, H-18), 0.94 (3H, d, J=6.4 Hz, H-21), 1.22 (6H, s, H-26, 27), 2.16 (1H, dd, J=14.1, 4.0 Hz, H-4), 2.27 (1H, br, t, J=≦12 Hz, H-10), 2.57 (1H, br. s, OH), 2.79 (1H, m, H-9), 2.84 (1H, m, H-4), 2.88 (1H, dd, J=13.2, 4.9 Hz, H-10), 3.77 (1H, m, H-1W/2≈20 Hz), 3.95 (1H, m, H-3W/2≈12 Hz), 4.69, 4.77 (each 1H, dd, J=47.6, 9.6 Hz, CH$_2$F), 5.86 (1H, d, J=11.3 Hz, H-7), 6.29 (1H, d, J=11.2 Hz, H-6).

$^{19}$F NMR (CDCl$_3$) δ: −240.2 (t, J=47.6 Hz). MS m/z (%): 452 (74, M$^+$), 434 (100), 414 (35), 396 (16), 378 (33), 323 (50), 3.5 (17), 303 (20), 287 (15), 285 (16), 267 (18), 228 (24), 133 (74).

Example 14

1α-[(t-butyldimethylsilyl)oxy]-2β,2'-epoxy-25-[(methoxymethyl)oxy]-19-norvitamin D$_3$ t-butyldimethylsilyl ether and 1α-[(t-butyldimethylsilyl)oxy]-2α,2'-epoxy-25-[(methoxymethyl)oxy]-19-norvitamin D$_3$ t-butyldimethylsilyl ether (Compounds 16a, b)

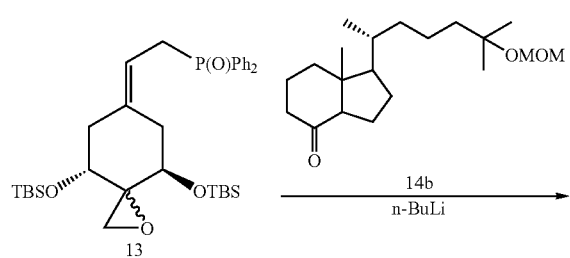

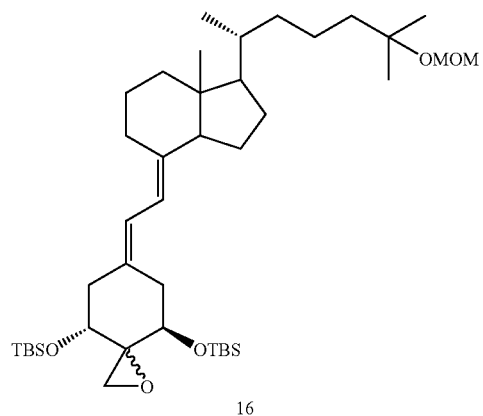

To a solution of Compound 13 (185.1 mg, 0.31 mmol, a mixture of 13a:13b =ca. 3:1) in dry THF (1 mL) cooled to −78° C. was added n-BuLi (193 μL, 0.31 mmol, 1.6 M solution in hexane), and the resulting orange solution was stirred for 30 min. To this colored solution was added a solution of Compound 14b (66:8 mg, 0.206 mmol), which was a Grundmann's keton, in dry THF (1.2 mL), and the reaction mixture was stirred for 2 h at −78° C. An aqueous solution of saturated NH$_4$Cl was added to the reaction solution, and then the reaction solution was extracted with AcOEt. The organic layer was washed with saturated brine and dried over anhydrous MgSO$_4$, and the solvent was evaporated. The residue was purified by silica gel column chromatography (9 g; 3%→12%→40% AcOEt/hexane), to afford Compound 16 (96.6 mg, 67%) as a mixture of two stereoisomers, from 3% AcOEt-containing hexane eluate. The ratio of the isomers constituting the mixture was ca. 5:1. Unreacted Compound 14b (22.0 mg, 33%) and Compound 13 (43.4 mg, 23%) were recovered from 12% AcOEt-containing hexane eluate and 40% AcOEt-containing hexane eluate, respectively.

NMR Data of the Mixture 16a (major product): $^1$H NMR (CDCl$_3$) δ: 0.02, 0.055 (each 3H, s, Si-Me), 0.065 (6H, Si-Me×2), 0.55 (3H, s, H-18), 0.86, 0.87 (each 9H, s, Si-tBu×2), 0.94 (3H, d, J=6.4 Hz, H-21), 1.22 (6H, s, H-26, 27), 2.28-2.37 (2H, m), 2.42 (1H, dd, J=13.1, 3.7 Hz), 2.65 (1H, dd, J=13.7, 3.7 Hz), 2.74 (1H, d, J=5.5 Hz, CH$_2$O), 2.80 (1H, m, H-9), 2.82 (1H, d, J=5.5 Hz, CH$_2$O), 3.37 (3H, s, OMe), 3.81 (1H, dd, J=7.1, 3.9 Hz, H-3), 3.88 (1H, dd, J=7.0, 3.9 Hz, H-1), 4.71 (2H, s, OCH$_2$O), 5.82 (1H, d, J=11.0 Hz, H-7), 6.21 (1H, d, J=11.0 Hz, H-6).

16b (minor product): $^1$H NMR (CDCl$_3$) δ: 0.02-0.08 (12H, Si-Me×4), 0.55 (3H, s, H-18), 0.86, 0.87 (each 9H, s, Si-tBu× 2), 0.94 (3H, d, J=6.4 Hz, H-21), 1.22 (6H, s, H-26, 27), 2.57 (1H, d, J=5.5 Hz, CH$_2$O), 2.80 (1H, m, H-9), 2.92 (1H, d, J=5.5 Hz, CH$_2$O), 3.37 (3H, s, OMe), 3.68 (1H, m, H-3), 4.04 (1H, dd, J=9.1, 4.9 Hz, H-1), 4.71 (2H, s, OCH$_2$O), 5.82 (1H, d, J=11.2 Hz, H-7), 6.28 (1H, d, J=11.0 Hz, H-6).

Example 15

1α-hydroxy-2β,2'-epoxy-25-[(methoxymethyl)oxy]-19-norvitamin $D_3$ and 1α-hydroxy-2α,2'-epoxy-25-[(methoxymethyl)oxy]-19-norvitamin $D_3$ (Compounds 17a, b)

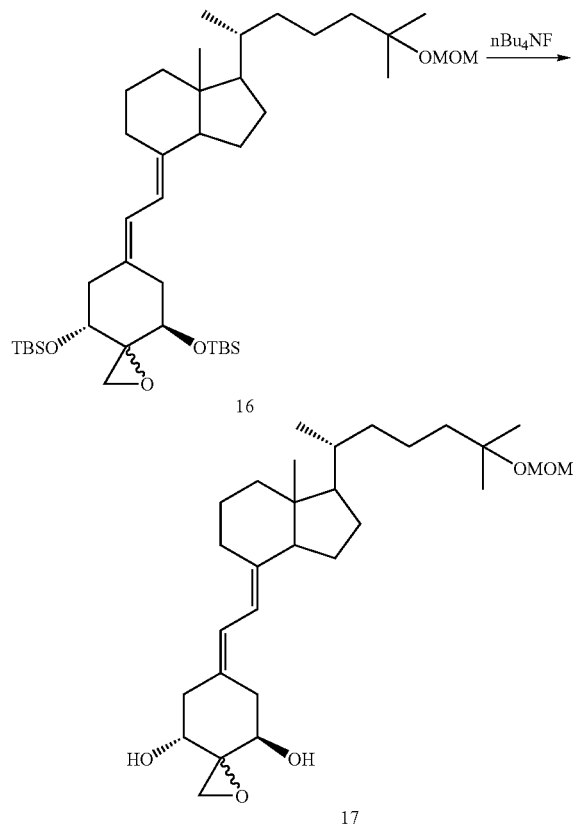

To a solution of Compound 16 (34.4 mg, 0.049 mmol, a mixture of 16a:16b ca. 5:1) in dry THF (1 mL) was added tetrabutylammonium fluoride (122.41, 0.122 mmol, 1.0 M solution in THF), and stirred for 30 min at 0° C. and then for 5 h at room temperature. Ice water was added to the reaction solution, and the reaction solution was extracted with AcOEt. The organic layer was washed with saturated brine, and dried over anhydrous $MgSO_4$. The solvent was distilled off. The residue was purified by silica gel column chromatography (5 g; 50% AcOEt/hexane), to yield Compound 17 (21.5 mg, 92%) as a mixture of two stereoisomers. The ratio of the isomers constituting the mixture was ca. 4:1.

NMR Data of the Mixture 17a (major product): $^1$H NMR ($CDCl_3$) δ: 0.55 (3H, s, H-18), 0.93 (3H, d, J=6.4 Hz, H-21), 1.22 (6H, s, H-26, 27), 2.32 (1H, dd, J=13.5, 8.9 Hz), 2.40 (1H, dd, J=13.8, 6.1 Hz), 2.62 (1H, dd, J=13.8, 3.5 Hz), 2.80 (1H, m, H-9), 2.85 (1H, d, J=4.7 Hz, $CH_2O$), 2.95 (1H, dd, J=13.5, 4.5 Hz), 3.07 (1H, d, J=4.7 Hz, $CH_2O$), 3.37 (3H, s, OMe), 3.82 (1H, m), 3.98 (1H, m), 4.71 (2H, s, $OCH_2O$), 5.86 (1H, d, J=11.1 Hz, H-7), 6.40 (1H, d, J=11.1 Hz, H-6).

17b (minor product): $^1$H NMR ($CDCl_3$) δ: 0.55 (3H, s, H-18), 0.93 (3H, d, J=6.4 Hz, H-21), 1.22 (6H, s, H-26, 27), 2.72 (1H, m), 2.94, 2.99 (each 1H, d, J=4.7 Hz, $CH_2O$), 3.37 (3H, s, OMe), 3.82 (1H, m), 3.91 (1H, m), 4.71 (2H, s, $OCH_2O$), 5.86 (1H, d, J=11.1 Hz, H-7), 6.37 (1H, d, J=11.1 Hz, H-6).

Example 16

1α,2β-dihydroxy-2α-methyl- and 1α,2α-dihydroxy-2β-methyl-25-[(methoxymethyl)oxy]-19-norvitamin $D_3$ (Compounds 18a, b)

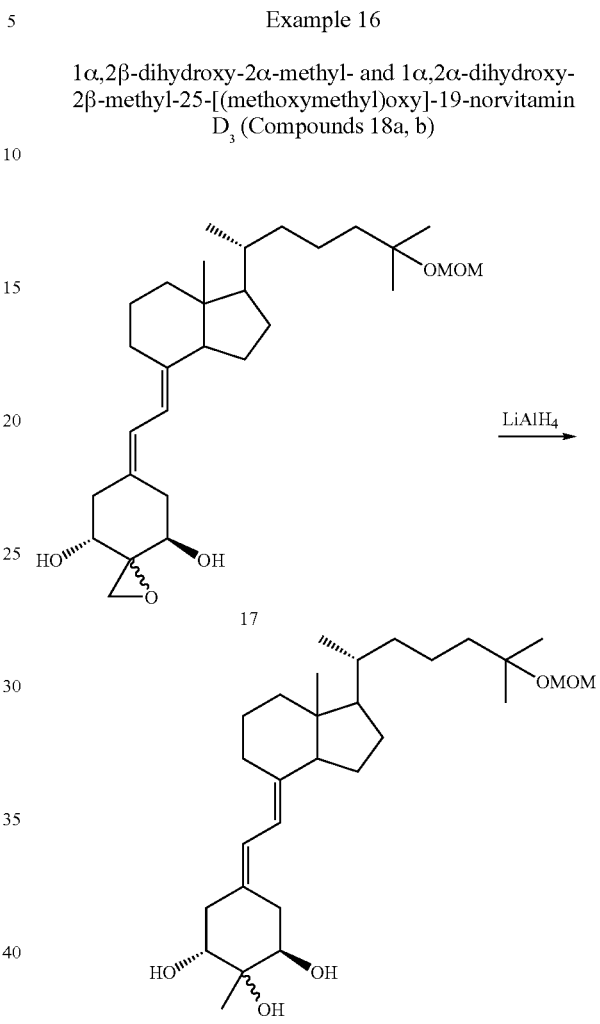

To a suspension of lithium aluminum hydride ($LiAlH_4$, 0.5 mg, 0.014 mmol) in dry diethyl ether (0.25 mL) was added a solution of Compound 17 (6.8 mg, 0.014 mmol, a mixture of 17a:17b=ca. 4:1) in dry diethyl ether (0.25 mL), and the suspension was stirred for 1 h at room temperature. A potassium sodium tartrate water was added to the reaction mixture, and the mixture was extracted with AcOEt. The organic layer was washed with saturated brine and dried over anhydrous $MgSO_4$, and the solvent was distilled off. The residue was purified by silica gel column chromatography (3 g; 60% AcOEt/hexane), to afford Compound 18 (4.7 mg, 69%) as a mixture of two stereoisomers. The ratio of the isomers constituting the mixture was ca. 4:1.

NMR Data of the Mixture 18a (major product): $^1$H NMR ($CDCl_3$) δ: 0.54 (3H, s, H-18), 0.93 (3H, d, J=6.4 Hz, H-21), 1.22 (6H, s, H-26, 27), 1.27 (3H, s, 2-Me), 2.37 (1H, dd, J=14.4, 4.6 Hz), 2.53 (1H, m), 2.79 (1H, m), 2.94 (1H, dd, J=13.6, 4.3 Hz), 3.37 (3H, s, OMe), 3.74 (2H, m, H-1, 3), 4.71 (2H, s, $OCH_2O$), 5.84 (1H, d, J=11.2 Hz, H-7), 6.30 (1H, d, J=11.2 Hz, H-6).

18b (minor product): $^1$H NMR ($CDCl_3$) δ: 0.54 (3H, s, H-18), 0.93 (3H, d, J=6.4 Hz, H-21), 1.22 (6H, s, H-26, 27), 1.30 (3H, s, 2-Me), 2.17 (1H, m), 2.67 (1H, m), 3.37 (3H, s, OMe), 3.74 (2H, m, H-1, 3), 4.71 (2H, s, OCH$_2$O), 5.82 (1H, d, J=≦11 Hz, H-7), 6.34 (1H, d, J=≦11 Hz, H-6).

Example 17

1α,2β,25-trihydroxy-2α-methyl-19-norvitamin D$_3$ (Compound YI-3a) and 1α,2α,25-trihydroxy-2β-methyl-19-norvitamin D$_3$ (Compound YI-3b)

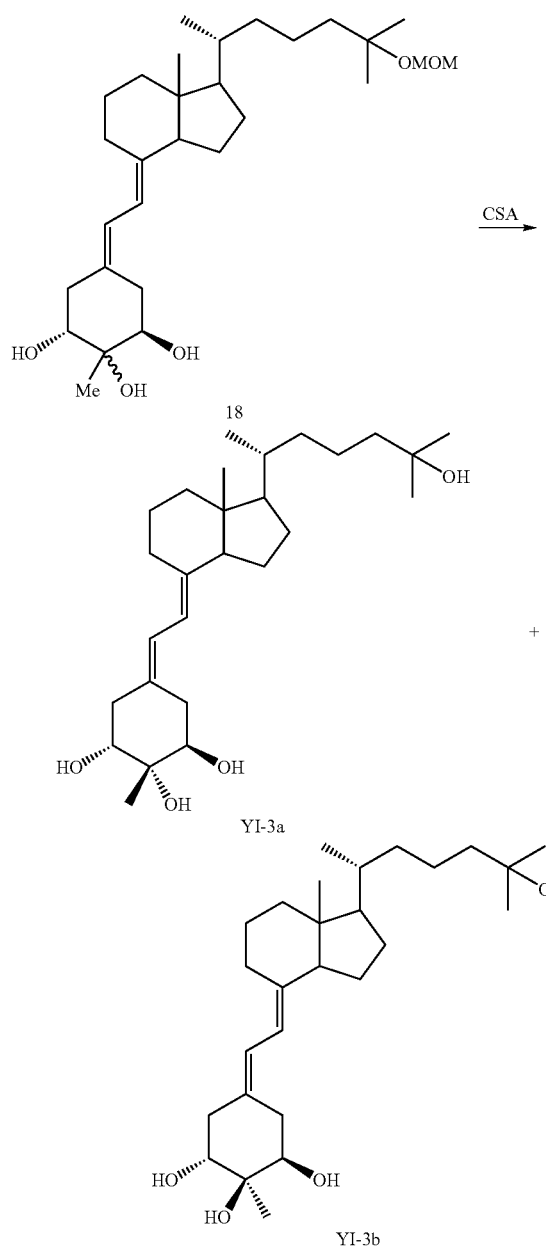

To a solution of Compound 18 (10.5 mg, 0.022 mmol, a mixture of 18a:18b =ca. 4:1) in dry MeOH (0.5 mL), was added camphor sulfonic acid (10.1 mg, 0.044 mmol) and stirred for 30 min at 0° C. and then for 2 h at room temperature, and the reaction mixture was diluted with AcOEt. The organic layer was successively washed with 5% NaHCO$_3$ aqueous solution and saturated brine, and dried over anhydrous MgSO$_4$. Solvents were distilled off, and the residue was purified by silica gel column chromatography (3 g; 70% AcOEt/hexane), to yield a mixture (8.8 mg, 93%) of Compounds YI-3a and YI-3b.

The mixture of Compounds YI-3a and YI-3b was separated and purified by HPLC (YMC-Pack ODS-AM SH-342-5, 150×20 mm, 20% H$_2$O/MeOH), to afford Compound YI-3a (5.2 mg) and Compound YI-3b (0.7 mg).

YI-3a: $^1$H NMR (CDCl$_3$) δ: 0.54 (3H, s, H-18), 0.94 (3H, d, J=6.4 Hz, H-21), 1.22 (6H, s, H-26, 27), 1.27 (3H, s, 2-Me), 2.05 (1H, m, H-10), 2.36 (1H, dd, J=14.4, 4.5 Hz, H-4), 2.55 (2H, m, H-4, OH), 2.79 (1H, m, H-9), 2.94 (1H, dd, J=13.5, 4.4 Hz, H-10), 3.74 (2H, m, H-1, 3), 5.84 (1H, d, J=11.2 Hz, H-7), 6.30 (1H, d, J=11.2 Hz, H-6).

YI-3b: $^1$H NMR (CDCl$_3$) δ: 0.55 (3H, s, H-18), 0.94 (3H, d, J=6.4 Hz, H-21), 1.22 (6H, s, H-26, 27), 1.30 (3H, s, 2-Me), 2.17 (1H, dd, J=13.6, 8.4 Hz, H-4), 2.30 (1H, br s, OH), 2.49 (1H, dd, J=14.2, 3.3 Hz, H-10), 2.62 (1H, dd, J=14.2, 6.5 Hz, H-10), 2.67 (1H, dd, J=13.6, 4.1 Hz, H-4), 2.79 (1H, m, H-9), 3.73 (1H, m, H-1, W/2≈12 Hz), 3,78 (1H, m, H-3, W/2≈18 Hz), 5.82 (1H, d, J=11.2 Hz, H-7), 6.34 (1H, d, J=11.2 Hz, H-6). MS m/z (%): 434 (75, M$^+$), 416 (100), 401 (16), 398 (31), 380 (21), 362 (20), 3.05 (29), 287 (27), 269 (29), 251 (25), 135 (74).

Example 18

1α-[(t-butyldimethylsilyl)oxy]-2β-hydroxy-2α-ethyl- and 1α-[(t-butyldimethylsilyl)oxy]-2α-hydroxy-2β-ethyl-25-[(methoxymethyl)oxy]-19-norvitamin D$_3$ t-butyldimethylsilyl ethers (Compounds 19a, b)

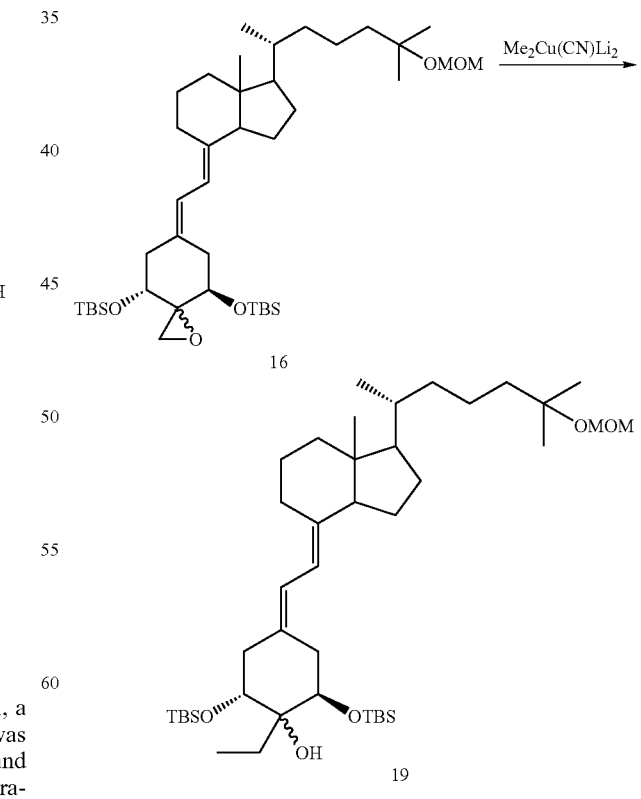

To a suspension of copper (1) cyanide (CuCN, 114.6 mg, 1.280 mmol) in dry Et$_2$O (1.5 mL) cooled to −40° C. was added a solution of methyl lithium (MeLi, 2.25 mL, 2.565 mmol, 1.14 M solution in Et$_2$O), and the mixture was stirred for 30 min. To this solution was added a solution of Compound 16 (113.1 mg, 0.160 mmol, 16a:16b=ca. 3:1 mixture was used in this working example) dissolved in dry Et$_2$O (3 mL). The reaction mixture was stirred for 1 h at −40° C., the temperature was gradually raised to 0° C., and then the mixture was further stirred for 2 h. A solution of saturated NH$_4$Cl was added to the reaction mixture to stop the reaction, and then the mixture was poured into ice water and extracted with AcOEt. The organic layer was rinsed with saturated brine, dried over anhydrous MgSO$_4$, and the solvent was evaporated. The residue was purified by silica gel column chromatography (Wacogel C-300, 10 g; 2% AcOEt/hexane), to yield Compound 19 (90.3 mg, 78%) as a mixture of 2β hydroxyl product and 2α hydroxyl product, and unreacted Compound 16 (18.5 mg, 16%). The ratio of the isomers constituting Compounds 19a, b was ca. 3:1. In this separation step by chromatography, a fraction containing only Compound 19a and a fraction containing only Compound 19b were obtained, and these fractions were separated.

19a (major product): $^1$H NMR (CDCl$_3$) δ: 0.06, 0.07, 0.09, 0.11 (each 3H, s, Si-Me), 0.55 (3H, s, H-18), 0.83 (9H, s, Si-tBu), 0.90 (9H, s, Si-tBu, overlapped with CH$_2$C$\underline{H}_3$), 0.93 (3H, d, J=6.5 Hz, H-21), 1.21 (6H, s, H-26, 27), 1.62 (2H, m, C$\underline{H}_2$CH$_3$), 2.26 (1H, dd, J=13.6, 5.0 Hz), 2.43 (2H, m), 2.52 (1H, dd, J=14.4, 4.0 Hz), 2.80 (1H, m, H-9), 3.37 (3H, s, OMe), 3.78 (1H, dd, J=9.7, 5.0 Hz), 3.96 (1H, t, J=3.0 Hz), 4.71 (2H, s, OCH$_2$O), 5.79 (1H, d, J=11.3 Hz, H-7), 6.16 (1H, d, J=11.3 Hz, H-6).

19b (minor product): $^1$H NMR (CDCl$_3$) δ: 0.06, 0.07, 0.99, 0.11 (each 3H, s, Si-Me), 0.55 (3H, s, H-18), 0.85 (9H, s, Si-tBu), 0.91 (9H, s, Si-tBu, overlapped with CH$_2$C$\underline{H}_3$), 0.93 (3H, d, J=6.5 Hz, H-21), 1.21 (6H, s, H-26, 27), 1.62 (m, C$\underline{H}_2$CH$_3$), 2.09 (1H, dd, J=13.8, 5.0 Hz), 2.30 (1H, dd, J=12.8, 9.6 Hz), 2.59 (2H, m), 2.79 (1H, m, H-9), 3.37 (3H, s, OMe), 3.70 (1H, dd, J=9.2, 4.4 Hz), 3.92 (1H, dd, J=4.8, 3.2 Hz), 4.71 (2H, s, OCH$_2$O), 5.80 (1H, d, J=11.0 Hz, H-7), 6.10 (1H, d, J=11.0 Hz, H-6).

Example 19

1α,2β,25-trihydroxy-2α-ethyl-19-norvitamin D$_3$ (Compound YI-4a) and 1α,2α,25-trihydroxy-2β-ethyl-19-norvitamin D$_3$ (Compound YI-4b)

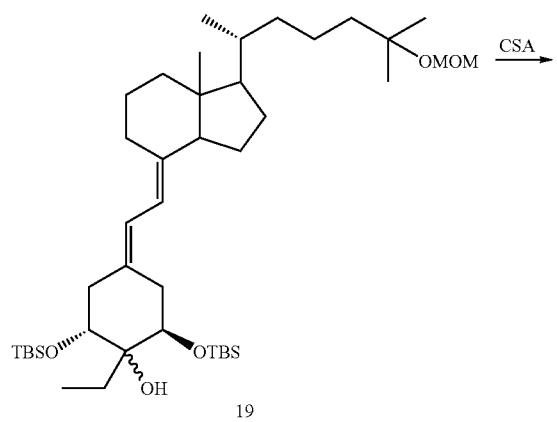

19

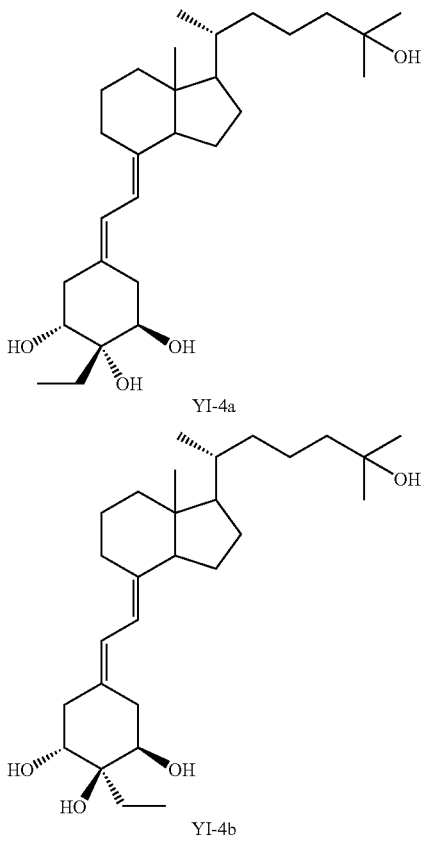

YI-4a

YI-4b

To a solution of Compound 19b (17.8 mg, 0.025 mmol) in dry MeOH (1 mL) was added camphor sulfonic acid (48.1 mg, 0.207 mmol), and the reaction mixture was stirred for 8 h at room temperature. 5% NaHCO$_3$ aqueous solution was added to the reaction mixture. The reaction mixture was extracted with AcOEt, and the organic layer was washed with saturated brine, and dried over anhydrous MgSO$_4$. The solvent was evaporated. The residue was purified by silica gel column chromatography (3 g; 50% AcOEt/hexane), to yield Compound YI-4b (11.0 mg, 99%).

The major product 19a (6.2 mg, 0.009 mmol) was reacted and after-treated in the same manner as described above, to give Compound YI-4a (2.3 mg, 60%).

YI-4a (major product): $^1$H NMR (CDCl$_3$) δ: 0.54 (3H, s, H-18), 0.94 (3H, d, J=6.4 Hz, H-21), 0.98 (3H, t, J=7.5 Hz, CH$_2$C$\underline{H}_3$), 1.22 (6H, s, H-26, 27), 1.68, 1.85 (each 1H, m, C$\underline{H}_2$CH$_3$), 2.26 (1H, dd, J=13.5, 9.2 Hz), 2.38 (1H, dd, J=13.8, 6.4 Hz), 2.47 (1H, dd, J=13.8, 3.5 Hz), 2.80 (2H, m, H-9, 10), 3.83 (2H, m, H-1, 3), 5.84 (1H, d, J=11.0 Hz, H-7), 6.33 (1H, d, J=11.0 Hz, H-6). UV λmax (EtOH): 244, 252, 261 nm.

YI-4b (minor product): $^1$H NMR (CDCl$_3$) δ: 0.55 (3H, s, H-18), 0.94 (3H, d, J=6.4 Hz, H-21), 0.99 (3H, t, J=7.5 Hz, CH$_2$C$\underline{H}_3$), 1.22 (6H, s, H-26, 27), 1.72, 1.81 (each 1H, m, C$\underline{H}_2$CH$_3$), 2.18 (1H, dd, J=13.8, 6.5 Hz, H-4), 2.44 (1H, dd, J=13.5, 8.5 Hz, H-10), 2.63 (1H, dd, J=13.5, 4.2 Hz, H-10), 2.72 (1H, dd, J=13.8, 3.3 Hz, H-4), 2.79 (1H, m, H-9 (, 3.73 (1H, m, W/2-17 Hz, H-1), 3.88 (1H, m, W/2-13 Hz, H-3), 5.84 (1H, d, J=11.2 Hz, H-7), 6.31 (1H, d, J=11.2 Hz, H-6).

Example 20

1α,2β,25-trihydroxy-2α-methoxymethyl-19-norvitamin D$_3$ (Compound YI-5a) and 1α,2α,25-trihydroxy-2β-methoxymethyl-19-norvitamin D$_3$ (Compound YI-5b)

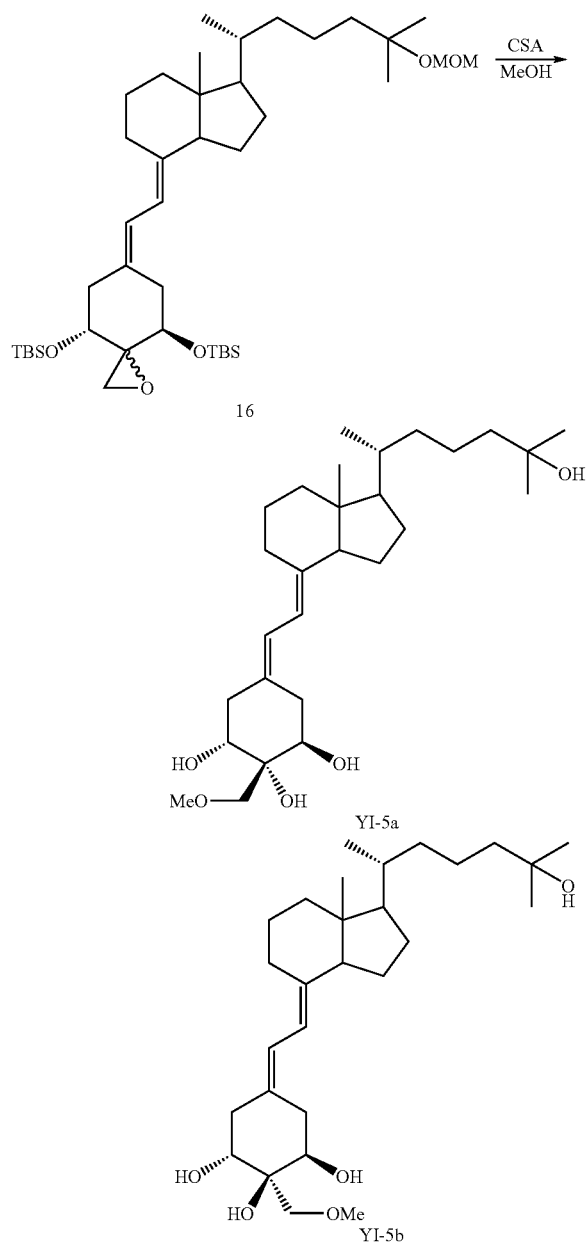

To a solution of Compound 16 (49.7 mg, 0.070 mmol, a mixture of 16a:16b=ca. 5:1) in dry MeOH (1 mL), was added camphor sulfonic acid (98.2 mg, 0.423 mmol), and the reaction mixture was stirred for 1 h at 0° C. and then for 4 h at room temperature.

To the reaction mixture, 5% NaHCO$_3$ aqueous solution was added. The whole mixture was extracted with AcOEt, and the organic layer was washed with saturated brine, dried over anhydrous MgSO$_4$, and the solvent was distilled off The residue was purified by silica gel column chromatography (5 g; 70% AcOEt/hexane), to give a mixture (28.5 mg, 87%) of Compounds YI-5a and YI-5b. The mixture of YI-5a and YI-5b was separated and purified by HPLC (YMC-Pack ODS-AM SH-342-5, 150×20 mm, 15% H$_2$O/MeOH), to obtain Compound YI-5a (8.2 mg) and Compound YI-5b (1.6 mg).

YI-5a: $^1$H NMR (CDCl$_3$) δ: 0.53 (3H, s, H-18), 0.93 (3H, d, J=6.4 Hz, H-21), 1.22 (6H, s, H-26, 27), 2.41 (2H, m, H-4), 2.53 (1H, dd, J=14.1, 5.7 Hz, H-10), 2.68 (2H, m, H-10, OH), 2.79 (1H, m, H-9), 2.97 (1H, br s, OH), 3.43 (3H, s, OMe), 3.69, 3.73 (each 1H, d, J=9.5 Hz, OCH$_2$O), 3.88 (2H, m, H-1, 3), 5.81 (1H, d, J=11.2 Hz, H-7), 6.39 (1H, d, J=11.2 Hz, H-6).

YI-5b (minor product): $^1$H NMR (CDCl$_3$) δ: 0.55 (3H, s, H-18), 0.94 (3H, d, J=6.4 Hz, H-21), 1.22 (6H, s, H-26, 27), 2.13 (1H, dd, J=13.8, 3.6 Hz, H-4), 2.21 (1H, br t, J=≦12 Hz, H-10), 2.77-2.89 (4H, m, H-4, 9, 10, OH), 3.43 (3H, s, OMe), 3.65, 3.77 (each 1H, d, J=9.4 Hz, OCH$_2$O), 3.80 (1H, m, H-1), 3.85 (1H, m, H-3), 5.88 (1H, d, J=11.2 Hz, H-7), 6.27 (1H, d, J=11.2 Hz, H-6). MS m/z (%): 464 (52, M$^+$), 446 (74), 428 (23), 410 (10), 401 (65), 383 (100), 335 (13), 317 (10), 299 (12), 281 (13), 222 (12).

Example 21

(20S)-1α-[(t-butyldimethylsilyl)oxy]-2β,2'-epoxy- and (20S)-1α-[(t-butyldimethylsilyl)oxy]-2α,2'-epoxy-25-[(triethylsilyl)oxy]-19-norvitamin D$_3$ t-butyldimethylsilyl ethers (Compounds 20a, b)

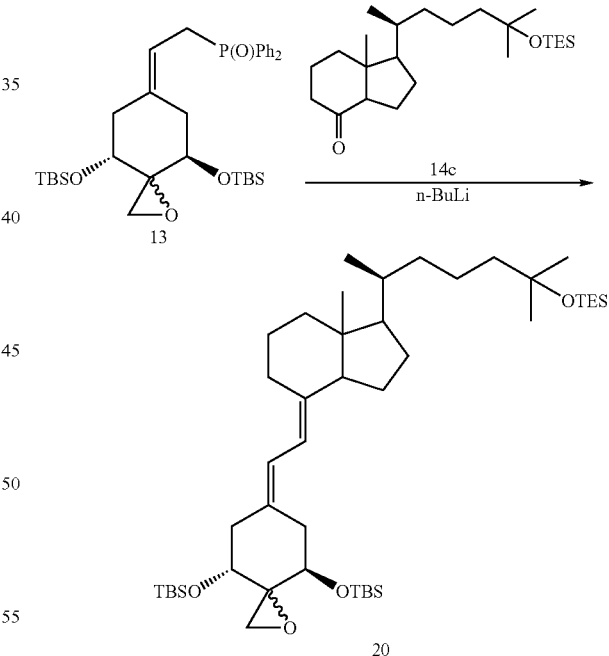

To a solution of Compound 13 (351.0 mg, 0.586 mmol, 13a:13b=ca. 2:1 mixture was used in this working example) in dry THF (3 mL) cooled to −78° C. was slowly added n-BuLi (371 μL, 0.586 mmol, 1.58 M solution in hexane), and a dark orange solution was obtained. After stirring for 15 min, to this colored solution was added a solution of Compound 14c (154.2 mg, 0.391 mmol), which was a Grundmann's keton, in dry THF (2.3 mL), and the whole mixture was stirred for 2 h at −78° C. A solution of saturated NH$_4$Cl was added to the reaction solution, and the reaction solution was extracted with AcOEt. The organic layer was rinsed with saturated brine, and dried over anhydrous MgSO$_4$. The solvent was distilled off. The residue was purified by silica gel column chromatography (15 g; 2%→10%→60% AcOEt/hexane), to yield Compound 20 (227.0 mg, 75%) as a mixture of two stereoisomers, from 2% AcOEt-containing hexane eluate. The ratio of the isomers constituting the mixture was ca. 3:1. Unreacted Compound 14c (35.8 mg) and Compound 13 (99.0 mg) were recovered from 10% AcOEt-containing hexane eluate and 60% AcOEt-containing hexane eluate, respectively.

NMR Data of the Mixture 20a (major product): $^1$H NMR (CDCl$_3$) δ: 0.02 (3H, s, Si-Me), 0.05 (3H, s, Si-Me×2), 0.06 (6H, s, Si-Me), 0.55 (3H, s, H-18), 0.56 (6H, q, SiCH$_2$×3), 0.86, 0.88 (each 9H, s, Si-Btu×2, overlapped with H-21), 0.95 (9H, t, J=7.9 Hz, SiCH$_2$C$\underline{H}_3$×3), 1.19 (6H, s, H-26, 27), 2.42 (1H, dd, J=13.2, 3.6 Hz), 2.68 (1H, dd, J=13.5, 3.8 Hz), 2.79, 2.82 (each 1H, d, J=5.5 Hz, CH$_2$O), 3.81 (1H, dd, J=7.2, 3.9 Hz, H-3), 3.87 (1H, dd, J=7.0, 3.9 Hz, H-1), 5.82 (1H, d, J=11.1 Hz, H-7), 6.21 (1H, d, J=11.1 Hz, H-6).

20b (minor product): $^1$H NMR (CDCl$_3$) δ: 0.02-0.07 (12H, Si-Me×4), 0.55 (3H, s, H-18), 0.56 (9H, m, SiCH$_2$×3, overlapped with H-18), 0.86, 0.88 (each 9H, s, Si-tBu×2, overlapped with H-21), 0:95 (9H, t, J=7.9 Hz, SiCH$_2$C$\underline{H}_3$×3), 1.19 (6H, s, H-26, 27), 2.57, 2.92 (each 1H, d, J=5.5 Hz, CH$_2$O), 3.69 (1H, m, H-3), 4.03 (1H, d, J=9.3, 4.7 Hz, H-1), 5.82 (1H, d, J=0.7 Hz, H-7), 6.28 (1H, d, J=10.7 Hz, H-6).

Example 22

(20S)-1α,25-dihydroxy-2β,2'-epoxy- and (20S)-1α, 25-dihydroxy-2α,2'-epoxy-19-norvitamin D$_3$ (20-Epi-YI-1a, 1b), and (20S)-1α,2β,25-trihydroxy-2α-fluoromethyl-19-norvitamin D$_3$ (Compound 20-Epi-YI-2a), and (20S)-1α,2α,25-trihydroxy-2β-fluoromethyl-19-norvitamin D$_3$ (Compound 20-Epi-YI-2b)

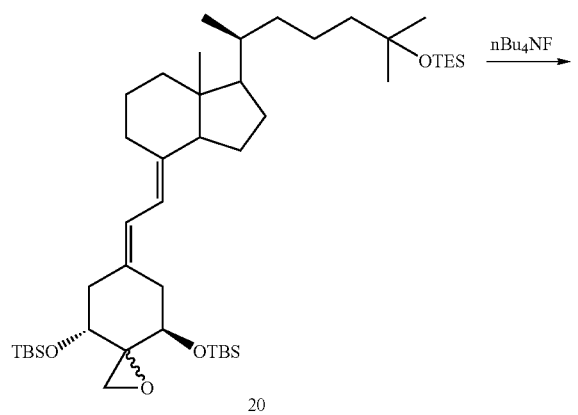

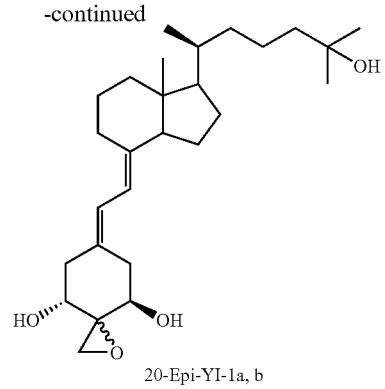

20-Epi-YI-1a, b

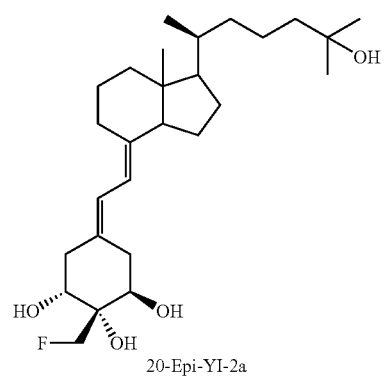

20-Epi-YI-2a

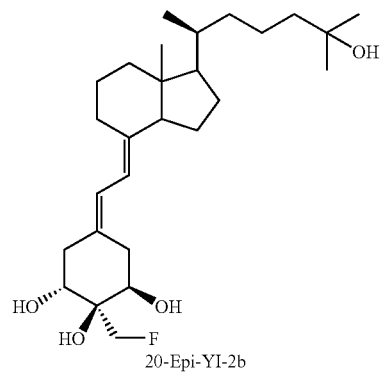

20-Epi-YI-2b

To a solution of Compound 20 (50.0 mg, 0.0645 mmol, a mixture of 20a:20b=ca. 3:1), which was a tolylsilylether compound, in dry THF (1 mL), was added tetrabutylammonium fluoride (387 μL, 0.387 mmol, 1.0 M solution in THF), and the reaction solution was stirred for 7 h at room temperature. Ice water was added to the reaction solution, and the reaction solution was extracted with AcOEt. The organic layer was washed with saturated brine and dried over anhydrous MgSO$_4$, and the solvent was distilled off. The residue was purified by silica gel column chromatography (5 g; 50%→70% AcOEt/hexane), to yield a mixture of Compounds 20-Epi-YI-2a and 20-Epi-YI-2b (3.5 mg, 12%; 20-Epi-YI-2a:20-Epi-YI-2b=ca.4:1) from 50% AcOEt-containing hexane eluate, and a mixture of Compounds 20-Epi- YI-1a and 20-Epi-YI-1b (23.0 mg, 82%; 20-Epi-YI-1a:20-Epi-YI-1b=ca.3:1) from 70% AcOEt-containing hexane eluate.

The mixture of Compounds 20-Epi-YI-2a and 20-Epi-YI-2b was separated and purified by HPLC (YMC-Pack ODS-AM SH-342-5, 150×20 mm, 20% H$_2$O/MeOH), to give Compound 20-Epi-YI-2a (2.1 mg) and Compound 20-Epi-YI-2b (0.5 mg), respectively.

The mixture of Compounds 20-Epi-YI-1a and 1b was separated and purified by HPLC (LiChrosorb Si 60, Hibar, 250×4 mm, hexane:CH$_2$Cl$_2$:MeOH=50:50:8), to afford Compound YI-20-Epi-1a (15.8 mg) and Compound YI-20-Epi-1b (6.1 mg; Z-isomer), respectively.

YI-20-Epi-1a: $^1$H NMR (CDCl$_3$) δ: 0.55 (3H, s, H-18), 0.86 (3H, d, J=6.5 Hz, H-21), 1.22 (6H, s, H-26, 27), 2.30 (1H, dd, J=13.4, 8.8 Hz, H-10), 2.40 (1H, dd, J=13.7, 6.1 Hz, H-4), 2.61 (H, dd, J=13.7, 3.5 Hz, H-4), 2.80 (1H, m, H-90, 2.84 (1H, d, J=4.7 Hz, CH$_2$O), 2.95 (1H, dd, J=13.4, 4.3 Hz, H-10), 3.08 (1H, d, J=4.7 Hz, CH$_2$O), 3.81 (1H, m, H-3), 3.98 (1H, m, H-1), 5.86 (1H, d, J=11.2 Hz, H-7), 6.39 (1H, d, J=11.2 Hz, H-6). MS m/z (%): 432 (M$^+$, 29), 414 (29), 396 (18), 378 (56), 303 (18), 267 (48), 138 (100).

YI-20-Epi-1b: $^1$H NMR (CDCl$_3$) δ: 0.56 (3H, s, H-18), 0.86 (3H, d, J=6.5 Hz, H-21), 1.22 (6H, s, H-26, 27), 2.30 (1H, dd, J=13.7, 6.2 Hz, H-4), 2.36 (1H, dd, J=13.5, 8.7 Hz, H-10), 2.72 (1H, dd, J=13.7, 3.7 Hz, H-4), 2.81 (1H, m, H-9β), 2.86 (1H, dd, J=13.5, 4.4 Hz, H-10), 2.94, 2.99 (each 1H, d, J=4.7 Hz, CH$_2$O), 3.82 (1H, m, H-3), 3.90 (1H, m, H-1), 5.88 (1H, d, J=11.2 Hz, H-7), 6.38 (1H, d, J=11.2 Hz, H-6). MS m/z (%): 432 (M$^+$, 68), 414 (77), 396 (35), 378 (50), 303 (35), 267 (42), 133 (100).

20-Epi-YI-2a (major product): $^1$H NMR (CDCl$_3$) δ: 0.53 (3H, s, H-18), 0.85 (3H, d, J=6.5 Hz, H-21), 1.21 (6H, s, H-26, 27), 2.45 (1H, dd, J=13.3, 8.7 Hz, H-4), 2.49 (1H, dd, J=13.3, 5.5 Hz, H-4), 2.56 (1H, dd, J=14.2, 5.8 Hz, H-10), 2.62 (1H, d, J=1.5 Hz, OH), 2.69 (1H, dd, J=14.2, 2.9 Hz, H-10), 2.79 (1H, m, H-9), 3.87 (1H, m, H-3), 3.97 (1H, m, H-1), 4.71, 4.76 (each 1H, dd, J=47.8, 9.7 Hz, CH$_2$F), 5.81 (1H, d, J=11.2 Hz, H-7), 6.40 (1H, d, J=11.2 Hz, H-6). $^{19}$F NMR (CDCl$_3$) δ: −240.3 (t, J=47.8 Hz).

20-Epi-YI-2b (minor product): $^1$H NMR (CDCl$_3$) δ: 0.55 (3H, s, H-18), 0.86 (3H, d, J=6.5 Hz, H-21), 1.22 (6H, s, H-26, 27), 2.17 (1H, dd, J=14.0, 4.0 Hz, H-4), 2.27 (1H, br. t, J=≦11 Hz, H-10), 2.57 (1H, d, J=1.8 Hz, OH), 2.79 (1H, m, H-9), 2.84 (1H, m, H-4), 2.89 (1H, dd, J=13.2, 5.0 Hz, H-10), 3.76 (1H, m, H-1), 3.95 (1H, m, H-3), 4.70, 4.76 (each 1H, dd, J=47.6, 9.5 Hz, CH$_2$F), 5.86 (1H, d, J=11.2 Hz, H-7), 6.29 (1H, d, J=11.2 Hz, H-6). $^{19}$F NMR (CDCl$_3$) δ: −240.2 (t, J=47.6 Hz).

Example 23

(20S)-1α,2β,25-trihydroxy-2α-methyl-19-norvitamin D$_3$ (Compound 20-Epi-YI-3a), and (20S)-1α,2α,25-trihydroxy-2β-methyl-19-norvitamin D$_3$ (Compound 20-Epi-YI-3b)

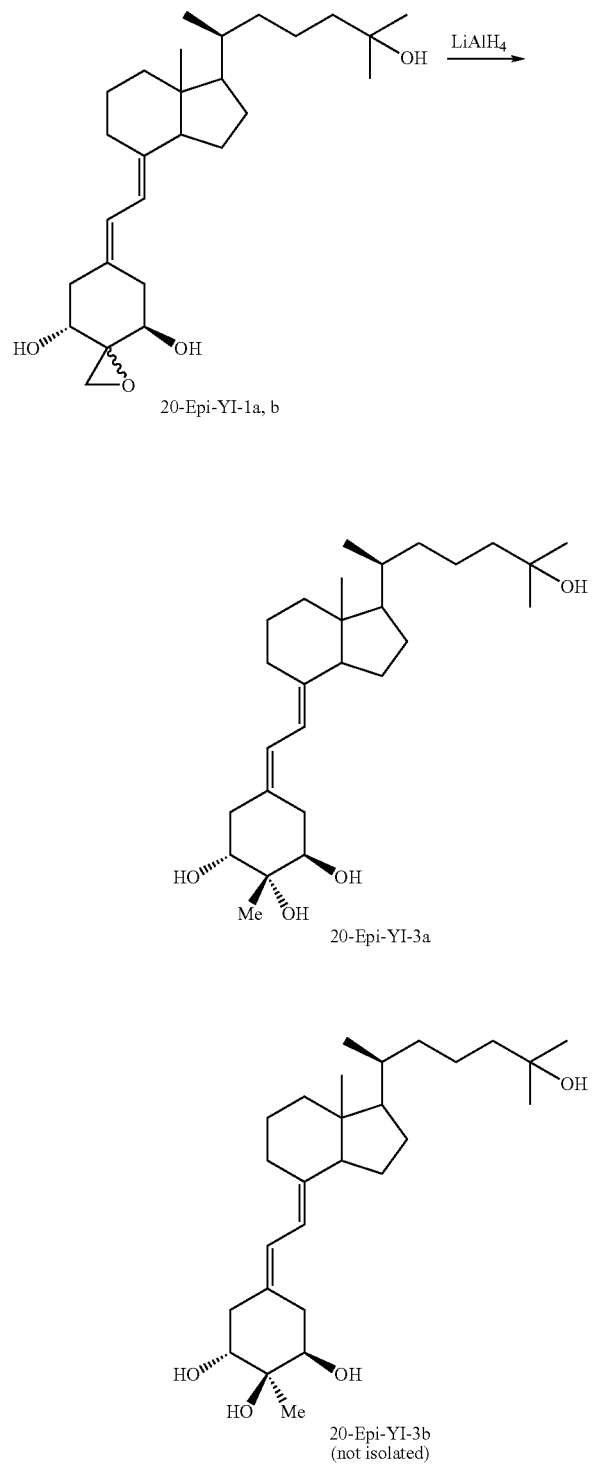

20-Epi-YI-1a, b

20-Epi-YI-3a

20-Epi-YI-3b
(not isolated)

To a solution of Compounds 20-Epi-YI-1a and 20-Epi-YI-1b (23.0 mg, 0.053 mmol, 20-Epi-YI-1a: 20-Epi-YI-1b=ca. 3:1), which were epoxy compounds, in dry THF (0.25 mL) was added LiAlH$_4$ (2 mg, 0.053 mmol), and the mixture was stirred for 7 h at room temperature. After 2 h and 6 h from the reaction, additional LiAlH$_4$ (2 mg) was added, respectively. Potassium sodium tartrate water was added to the reaction mixture, and the mixture was extracted with AcOEt. The organic layer was washed with saturated brine, and dried over anhydrous MgSO$_4$. The solvent was distilled off. The residue was purified by silica gel column chromatography (3 g; 60% AcOEt/hexane), to give a mixture of Compounds 20-Epi-YI-3a and 20-Epi-YI-3b (15.5 mg, 67%; the ratio was unknown).

The mixture of 20-Epi-YI-3a and 20-Epi-YI-3b was separated and purified by HPLC (YMC-Pack ODS-AM SH-342-5, 150×20 mm, 20% H$_2$O/MeOH), to give Compound 20-Epi-YI-3a (6.3 mg). It was impossible to isolate Compound 20-Epi-YI-3b as a pure compound.

20-Epi-YI-3a (major product): $^1$H NMR (CDCl$_3$) δ: 0.54 (3H, s, H-18), 0.86 (3H, d, J=6.5 Hz, H-21), 1.22 (6H, s, H-26, 27), 1.27 (3H, s, 2-Me), 2.07 (1H, m, H-10), 2.36 (1H, dd, J=14.4, 4.6 Hz, H-4), 2.54.(2H, m, H-4, OH), 2.79 (1H, m, H-9), 2.94 (1H, dd, J=13.5, 4.4 Hz), 3.74 (2H, m, H-1, 3), 5.85 (1H, d, J=11.3 Hz, H-7), 6.30 (1H, d, J=11.3 Hz, H-6).

Example 24

(20S)-1α-[(t-butyldimethylsilyl)oxy]-2β-hydroxy-2α-ethyl- and (20S)-1α-[(t-butyldimethylsilyl)oxy]-2α-hydroxy-2β-ethyl-25-[(triethylsilyl)oxy]-19-nor-vitamin D$_3$ t-butyldimethylsilyl ethers (Compounds 21a, b)

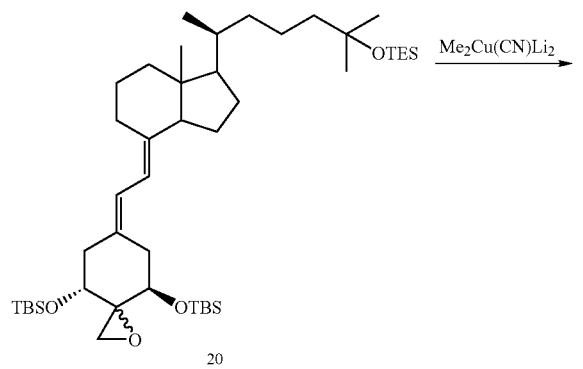

20

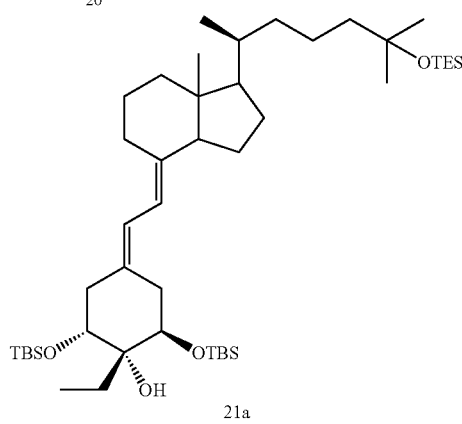

21a

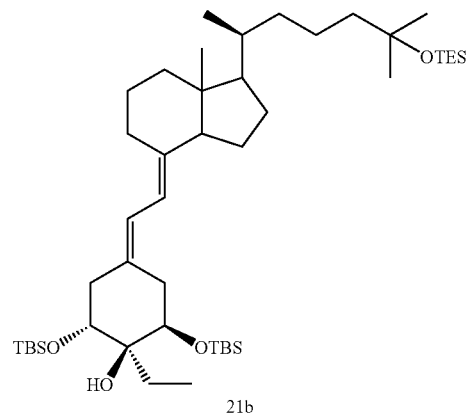

21b

To a suspension of CuCN (101.9 mg, 1.138 mmol) in dry Et$_2$O (1 mL) cooled to −40° C. was gradually added MeLi (2.0 mL, 2.272 mmol, 1.14 M solution in hexane), and the mixture was stirred for 30 min at −40° C. To this solution was added slowly a solution of Compound 20 (110.3 mg, 0.142 mmol, a mixture of ca. 3:1 was used in this working example), which was an epoxy compound, in dry Et$_2$O (1.5 mL), and the reaction mixture was stirred for 1 h at −40° C., the temperature was gradually raised to 0° C., and then the mixture was further stirred for 2 h. Saturated NH$_4$Cl aqueous solution was added to the reaction mixture, and the reaction mixture was extracted with AcOEt. The organic layer was rinsed with saturated brine, and dried over anhydrous MgSO$_4$. The solvent was distilled off, and the residue was purified by silica gel column chromatography (10 g; 2% AcOEt/hexane), to afford Compound 21 (98.5 mg, 88%) as a mixture of two stereoisomers. The ratio of the isomers constituting the mixture was 21a:21b=ca. 3:1.

21: $^1$H NMR (CDCl$_3$) δ: 0.06, 0.07, 0.09, 0.10 (each 3H, s, Si-Me×4), 0.54 (3H, s, H-18), 0.56 (6H, q, J=7.9 Hz, Si—CH$_2$×3), 0.84, 0.91 (each 9H, s, Si-tBu×2, overlapped with H-21), 0.94 (9H, t, J=7.9 Hz, Si—CH$_2$CH$_3$×3, overlapped with CH$_2$CH$_3$), 1.19 (6H, s, H-26, 27), 2.80 (1H, m, H-9), 3.78, 3.92 (ca. 3:1) (1H, m, H-3), 3.70, 3.95 (ca. 1:3) (1H, m, H-1), 5.79 (1H, d, J=11.3 Hz, H-7), 6.10, 6.16 (ca. 1:3) (1H, d, J=11.3 Hz, H-6).

Example 25

(20S)-1α,2β,25-trihydroxy-2α-ethyl-19-norvitamin D₃ (Compound 20-epi-YI-4a), and (20S)-1α,2α,25-trihydroxy-2β-ethyl-19-norvitamin D₃ (Compound 20-epi-YI-4b)

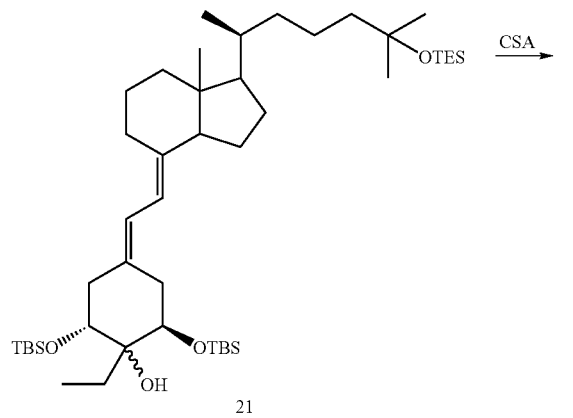

To a solution of Compound 21 (98.5 mg, 0.124 mmol, a mixture of 21a:21b=ca. 3:1) in dry MeOH (2 mL), was added camphor sulfonic acid (173.5 mg, 0.747 mmol), and the mixture was stirred for 6 h at room temperature. To the reaction mixture, 5% NaHCO₃ aqueous solution was added, and the solution was extracted with AcOEt. The organic layer was washed with saturated brine, dried over anhydrous MgSO₄, and the solvent was distilled off. The residue was purified by silica gel column chromatography (6 g; 50% AcOEt/hexane), to obtain a mixture (45.0 mg, 81%) containing Compounds 20-epi-YI-4a and 20-epi-YI-4b in a ratio of ca. 3:1.

The mixture containing Compounds 20-epi-YI-4a and 20-epi-YI-4b in a ratio of ca. 3:1 was separated and purified by HPLC (YMC-Pack ODS-AM SH-342-5, 20% H₂O/MeOH, 8 ml/min), to yield Compound 20-epi-YI-4a (27.4 mg) and Compound 20-epi-YI-4b (7.3 mg), respectively.

20-epi-YI-4a: ¹H NMR (CDCl₃) δ: 0.53 (3H, s, H-18), 0.85 (3H, d, J=6.5 Hz, H-21), 0.98 (3H, t, J=7.5 Hz, CH₂C$\underline{H}$₃), 1.21 (6H, s, H-26, 27), 2.25 (1H, dd, J=13.7, 8.9 Hz, H-10), 2.37 (1H, dd, J=14.0, 6.2 Hz, H-4), 2.45 (2H, m, H-4, OH), 2.80 (2H, m, H-9₁), 3.85 (2H, m, H-1, 3), 5.83 (1H, d, J=11.2 Hz, H-7), 6.31 (1H, d, J=11.2 Hz H-6). UV λmax (EtOH): 244, 252, 261 nm.

20-epi-YI-4b: ¹H NMR (CDCl₃) δ: 0.55 (3H, s, H-18), 0.85 (3H, d, J=6.5 Hz, H-21), 0.99 (3H, t, J=7.5 Hz, CH₂C$\underline{H}$₃), 1.22 (6H, s, H-26, 27), 2.18 (1H, dd, J=13.8, 6.6 Hz, H-4), 2.45 (1H, dd, J=13.6, 8.5 Hz, H-10), 2.62 (1H, dd, J=13.6, 4.3 Hz, H-10), 2.71 (1H, dd, J=13.8, 3.4 Hz, H-4), 2.80 (1H, m, H-9), 3.74 (1H, dd, J=8.5, 4.3 Hz, H-1), 3.88 (1H, dd, J=6.6, 3.4 Hz, H-3), 5.84 (1H, d, J=11.2 Hz, H-7), 6.31 (1H, d, J=11.2 Hz, H-6). UV λmax (EtOH): 244, 252, 261 nm.

Example 26

(20S)-1α,2β,25-trihydroxy-2α-methoxymethyl-19-norvitamin D₃ (Compound 20-epi-YI-5a), and (20S)-1α,2α,25-trihydroxy-2β-methoxymethyl-19-norvitamin D₃ (Compound 20-epi-YI-5b)

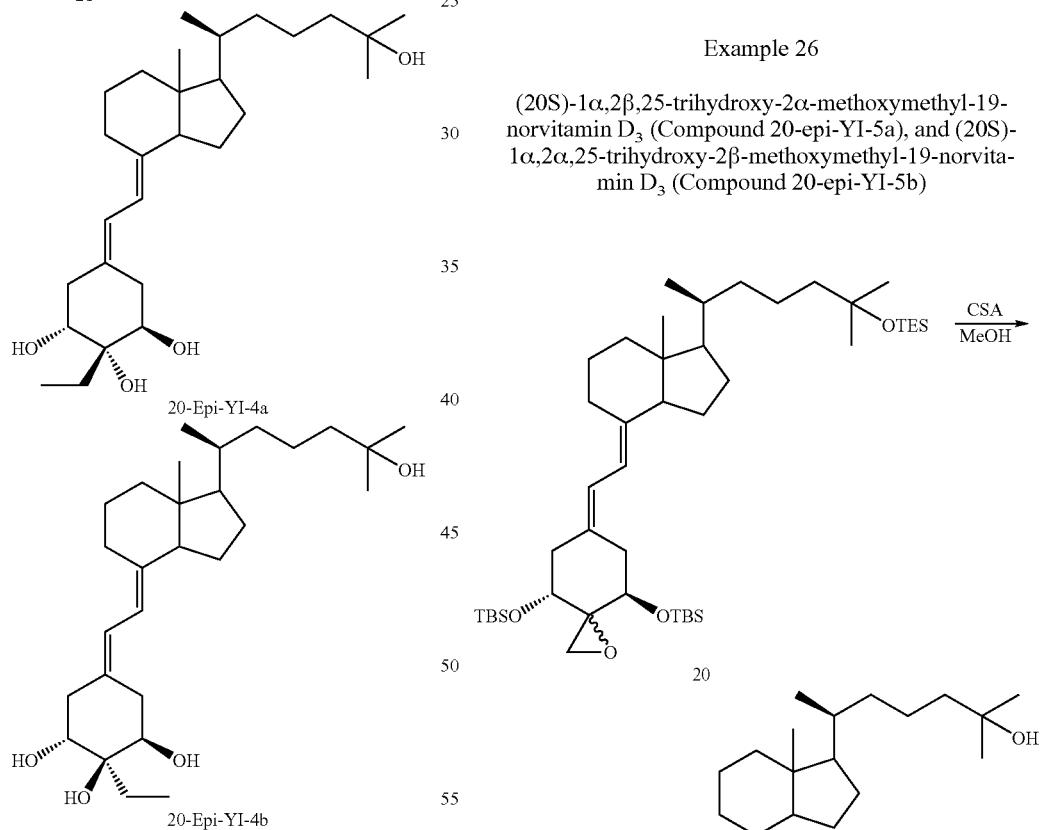

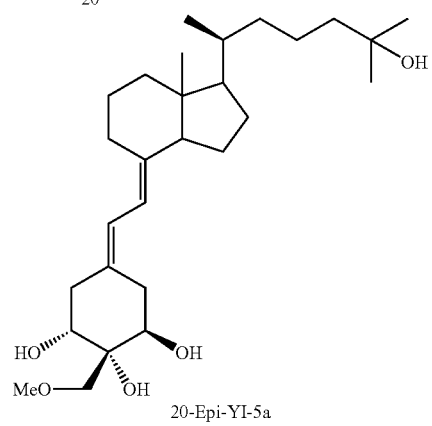

-continued

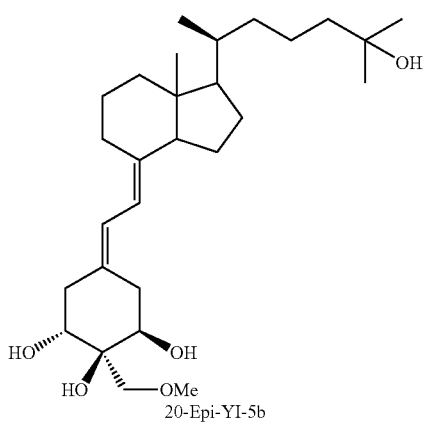

20-Epi-YI-5b

To a solution of Compound 20 (10.4 mg, 0.013 mmol, a mixture of 20a:20b=ca. 3:1) in dry MeOH (0.5 mL), was added camphor sulfonic acid (18.7 mg, 0.080 mmol), and the mixture was stirred for 1 h at 0° C. and then for 4 h at room temperature. 5% NaHCO$_3$ aqueous solution was added to the reaction mixture, and the mixture was extracted with AcOEt. The organic layer was washed with saturated brine, and dried over anhydrous MgSO$_4$. The solvent was distilled off. The residue was purified by silica gel column chromatography (5 g; 70% AcOEt/hexane), to give a mixture (5.0 mg, 81%) containing Compounds 20-epi-YI-5a and 20-epi-YI-5b in a ratio of ca. 3:1. The mixture containing 20-epi-YI-5a and 20-epi-YI-5b in a ratio of ca. 3:1 was separated and purified by HPLC (YMC-Pack ODS-AM SH-342-5, 150×20 mm, 15% H$_2$O/MeOH); to yield Compounds 20-epi-YI-5a (2.0 mg) and 20-epi-YI-5b (0.8 mg), respectively.

20-epi-YI-5a: $^1$H NMR (CDCl$_3$) δ: 0.53 (3H, s, H-18), 0.85 (3H, d, J=6.5 Hz, H-21), 1.21 (6H, s, H-26, 27), 2.41 (2H, m, H-4, OH), 2.53 (1H, dd, J=14.1, 5.6 Hz, H-10), 2.68 (2H, m, H-10, OH), 2.80 (1H, m, H-9), 2.94 (1H, s, OH), 3.44 (3H, s, OMe), 3.69, 3.74 (each 1H, d, J=9.5 Hz, OCH$_2$O), 3.89 (2H, m, H-1, 3), 5.82 (1H, d, J=11.2 Hz, H-7), 6.39 (1H, d, J=11.2 Hz, H-6). UV λmax (EtOH): 244, 252, 261 nm.

20-epi-YI-5b: $^1$H NMR (CDCl$_3$) δ: 0.55 (3H, s, H-18), 0.85 (3H, d, J=6.4 Hz, H-21), 1.21 (6H, s, H-26, 27), 2.12 (1H, dd, J=13.9, 3.4 Hz, H-4), 2.21 (1H, br. t, J≦12 Hz, H-10), 2.77-2.89 (4H, m, H-4, 9, 10), 2.89 (1H, s, OH), 3.43 (3H, s, OMe), 3.65, 3.77 (each 1H, d, J=9.5 Hz, OCH$_2$O), 3.79 (1H, m, H-1), 3.84 (1H, m, H-3), 5.88 (1H, d, J=11.2 Hz, H-7), 6.27 (1H, d, J=11.2 Hz, H-6). UV λmax (EtOH): 244, 252, 261 nm.

Example 27

(20S)-1α-[(t-butyldimethylsilyl)oxy]-2α-[(trimethylsilyl)oxy]- and (20S)-1α-[(t-butyldimethylsilyl)oxy]-2β-[(trimethylsilyl)oxy]-25-[(triethylsilyl)oxy]-19-norvitamin D$_3$ t-butyldimethylsilyl ethers (Compounds 23a, 23b)

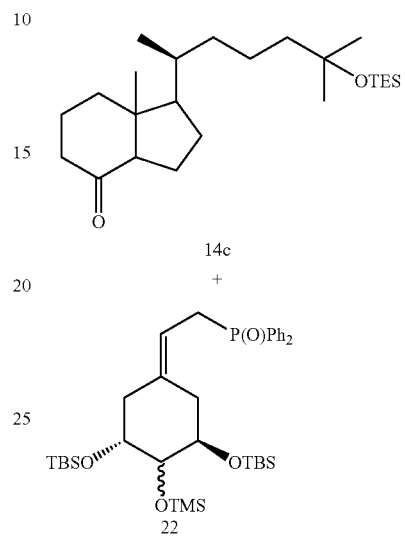

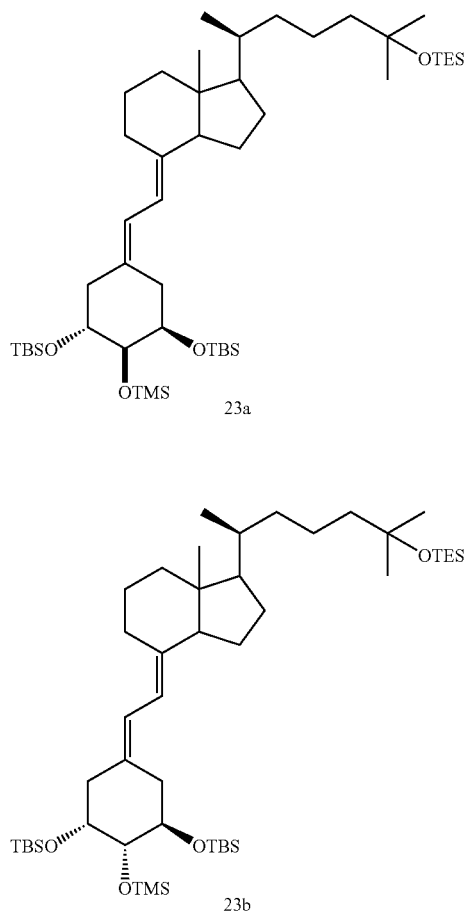

To solution of Compound 22 (435.2 mg, 0.660 mmol, a mixture of 22a:22b=ca. 2:1) in dry THF (5 mL) cooled to −78° C. was added n-BuLi (412 μL, 0.660 mmol, 1.6 M solution in hexane), and the resulting solution was stirred for 15 min. To this solution was added a solution of Compound 14c (173.8 mg, 0.440 mmol), which was a Grundmann's keton, in dry THF (3 mL), and the mixture was stirred for 2 h at −78° C. Saturated NH$_4$Cl aqueous solution was added to the reaction solution, and the solution was extracted with AcOEt. The organic layer was rinsed with saturated brine, dried over anhydrous MgSO$_4$, and the solvent was distilled off. The residue was purified by silica gel column chromatography (20 g; 2% AcOEt/hexane), to give Compound 23 (243.4 mg, 66%) as a mixture of two stereoisomers. The ratio of the isomers 23a and 23b constituting the mixture was ca. 3:2. Unreacted Compound 14c (30.0 mg, 17%) and Compound 22 (157.6 mg) were recovered from 5% AcOEt/hexane eluate and 5% AcOEt/hexane eluate, respectively.

NMR Data of the Mixture 23a (major product): $^1$H NMR (CDCl$_3$) δ: 0.04, 0.055, 0.058, 0.063 (each 3H, s, Si-Me×4), 0.12 (9H, Si-Me×3), 0.54 (3H, s, H-18), 0.56 (6H, q, J=7.9 Hz, SiCH$_2$×3), 0.85 (3H, d, J=6.5 Hz, H-21), 0.87, 0.88 (each 9H, s, Si-tBu×2), 0.94 (9H, t, J=7.9 Hz, SiCH$_2$CH$_3$×3), 1.19 (6H, s, H-26, 27), 2.30 (1H, m), 2.50 (2H, m), 2.79 (1H, m, H-9), 3.54 (1H, m, H-2), 3.80 (1H, m, H-3), 3.88 (1H, m, H-1), 5.81 (1H, d, J=11.1 Hz, H-7), 6.10 (1H, d, J=11.1 Hz, H-6).

23b (minor product): $^1$H NMR (CDCl$_3$) δ: 0.04, 0.06 (each 3H, s, Si-Me×2), 0.07 (6H, s, Si-Me×2), 0.12 (9H, Si-Me×3), 0.53 (3H, s, H-18), 0.56 (6H, q, J=7.8 Hz, SiCH$_2$×3), 0.84 (3H, d, J=6.6 Hz, H-21), 0.86, 0.89 (each 9H, s, Si-tBu×2), 0.94 (9H, t, J=7.8 Hz, SiCH$_2$CH$_3$×3), 1.19 (6H, s, H-26, 27), 2.10 (1H, m), 2.44 (2H, m), 2.79 (1H, m, H-9), 3.6 (1H, m, H-2), 3.80 (1H, dd, J=8.7, 4.5 Hz, H-1), 3.94 (1H, m, H-3), 5.79 (1H, d, J=11.2 Hz, H-7), 6.13 (1H, d, J=11.2 Hz, H-6).

Example 28

(20S)-1α-(t-butyldimethylsilyloxy)-2α,25-dihydroxy- and (20S)-1α-(t-butyldimethylsilyloxy)-2β, 25-dihydroxy-19-norvitamin D$_3$ t-butyldimethylsilyl ethers (Compounds 24a, 24b)

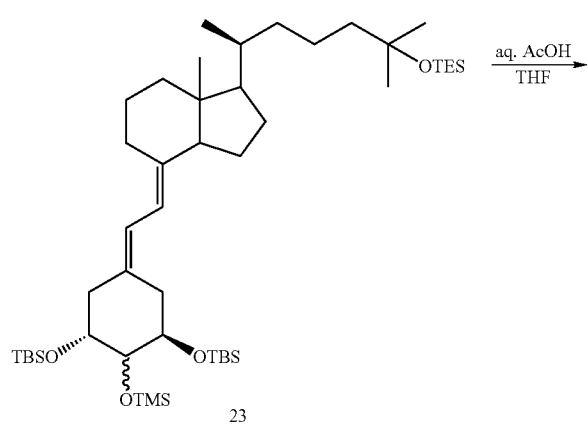

23

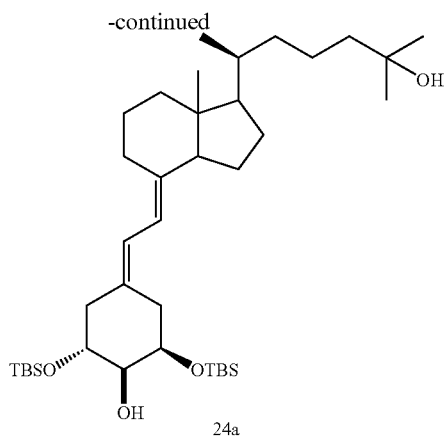

24a

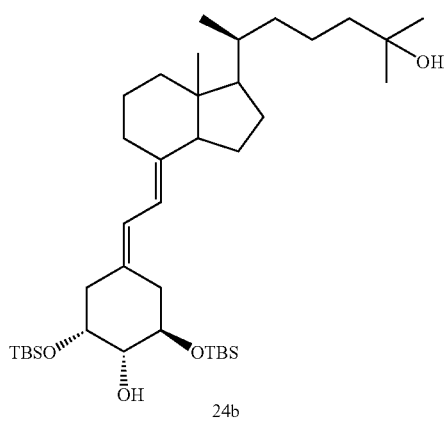

24b

Compound 23 (182.5 mg, 0.218 mmol, a mixture of 23a: 23b=ca. 3:2) was dissolved in a mixture of THF, AcOH, and water (9.5 mL, 8:8:1, v/v/v), and the resulting solution was stirred for 2 h at 0° C. and then for 2.5 h at room temperature. The reaction solution was diluted with AcOE, and then was successively washed with 5% NaHCO$_3$ aqueous solution and saturated brine. The organic layer was dried over anhydrous Na$_2$SO$_4$. The solvent was distilled off, and the residue was purified by silica gel column chromatography (10 g; 2% AcOEt/hexane), to give Compound 24a (39.1 mg, 28%) and Compound 24b (26.0 mg, 18%). The total yield was 46%.

24a: $^1$H NMR (CDCl$_3$) δ: 0.067, 0.077, 0.083, 0.10 (each 3H, s, Si-Me×4), 0.54 (3H, s, H-18), 0.86 (3H, d, J=6.6 Hz, H-21), 0.87, 0.88 (each 9H, s, Si-tBu×2), 1.22 (6H, s, H-26, 27), 2.27 (1H, d, J=3.2 Hz, OH), 2.31 (1H, dd, J=12.6, 3.7 Hz), 2.48 (2H, m), 2.79 (1H, m, H-9), 3.51 (1H, m, H-2), 3.91 (1H, m, H-3), 4.00 (1H, m, H-1), 5.80 (1H, d, J=11.1 Hz, H-7), 6.15 (1H, d, J=11.1 Hz, H-6).

24b: $^1$H NMR (CDCl$_3$) δ: 0.06, 0.07, 0.08, 0.10 (each 3H, s, Si-Me×4), 0.53 (3H, s, H-18), 0.86, 0.90 (each 9H, s, Si-tBu×2, overlapped with H-21), 1.21 (6H, s, H-26, 27), 2.18 (1H), dd, J=13.0, 4.5 Hz), 2.39 (3H, m), 2.80 (1H, m, H-9), 3.59 (1H, m, H-2), 4.00 (2H, m, H-1, 3), 5.80 (1H, d, J=11.2 Hz, H-7), 6.18 (1H, d, J=11.2 Hz, H-6).

Example 29

(20S)-1α-[(t-butyldimethylsilyl)oxy]-2α-{2-[(t-butyldimethylsilyl)oxy]-ethoxy}-25-hydroxy-19-norvitamin $D_3$ t-butyldimethylsilyl ether (Compound 25a)

Example 30

(20S)-1α-[(t-butyldimethylsilyl)oxy]-2β-{2-[(t-butyldimethylsilyl)oxy]-ethoxy}-25-hydroxy-19-norvitamin $D_3$ t-butyldimethylsilyl ether (Compound 25b)

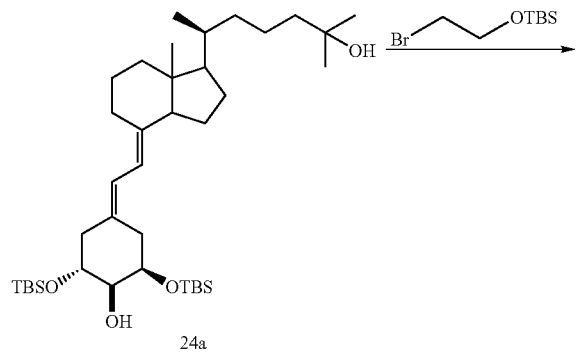

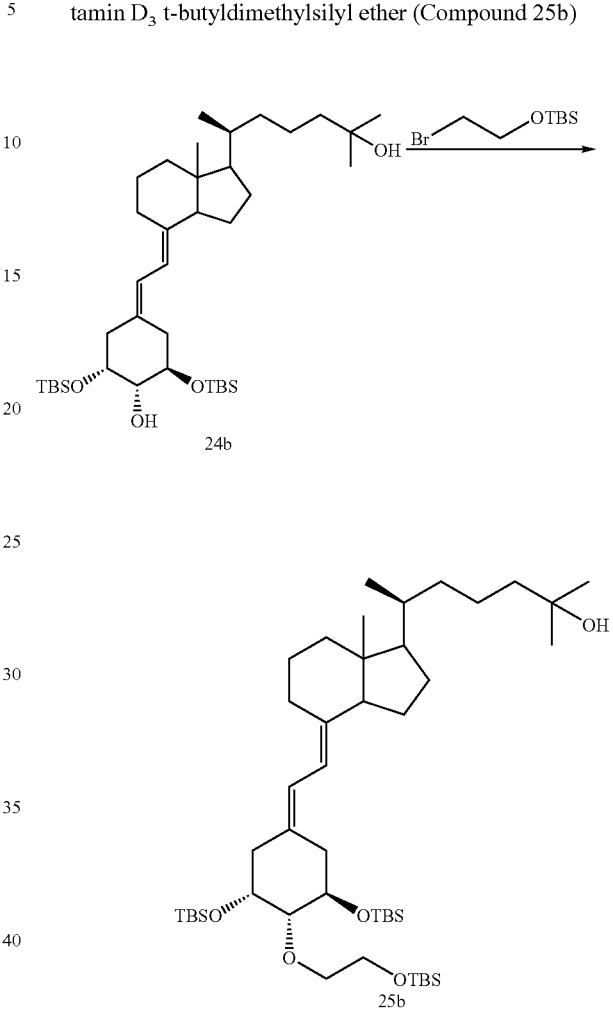

To a mixed solution of Compound 24a (17.0 mg, 0.026 mmol) in dry DMF and dry THF (9:1, 1 mL, v/v) cooled to 0° C., were added NaH (31.4 mg, 0.786 mmol, 60% paraffin liquid) and (2-bromoethoxy)-tert-butyldimethylsilane (27 μL, 0.126 mmol), and the mixture was vigorously stirred. After 22 h, ice water was added to the reaction solution, and then the solution was extracted with a mixed solution of AcOEt and hexane (1:1, v/v). The organic layer was washed with saturated brine, and dried over anhydrous $MgSO_4$. Following evaporation of the solvent, the residue was purified by silica gel column chromatography (5 g; 7% AcOEt/hexane), to afford Compound 25a (15.4 mg, 73%), and Compound 24a (2.8 mg, 16%), which was the unreacted starting material, was recovered from 20% AcOEt/hexane eluate.

25a: $^1$H NMR (CDCl$_3$) δ: 0.04-0.08 (18H, Si-Me×6), 0.54 (3H, s, H-18), 0.87, 0.89, 0.91 (each 9H, s, Si-tBu×3 overlapped with H-21), 1.21 (6H, s, H-26, 27), 2.79 (1H, m, H-9), 3.21 (1H, m, H-2), 3.7-3.9 (4H, m, OCH$_2$CH$_2$O), 3.96 (1H, m, H-3), 4.14 (1H, m, H-1), 5.81 (1H, d, J=11.2 Hz, H-7), 6.15 (1H, d, J=11.2 Hz, H-6).

To Compound 24b (15.3 mg, 0.024 mmol) in dry DMF (1 mL) cooled to 0° C., were added NaH (18.9 mg, 0.471 mmol, 60% paraffin liquid) and (2-bromoethoxy)-tert-butyldimethylsilane (20 μL, 0.093 mmol), and the mixture was vigorously stirred. After 22 h, ice water was added to the reaction solution, and then the solution was extracted with a mixed solution of AcOEt and hexane (1:1, v/v). The organic layer was washed with saturated brine and dried over anhydrous $MgSO_4$, and the solvent was distilled off. The residue was purified by silica gel column chromatography (5 g; 7% AcOEt/hexane), to afford Compound 25b (12.0 mg, 63%), and Compound 24b (3.4 mg, 22%), which was the unreacted starting material, was recovered from 20% AcOEt/hexane eluate.

25b: $^1$H NMR (CDCl$_3$) δ: 0.05-0.07 (18H, Si-Me×6), 0.53 (3H, s, H-18), 0.86, 0.88, 0.89 (each 9H, s, Si-tBu×3, overlapped with H-21), 1.21 (6H, s, H-26, 27), 2.13 (1H, dd, J=12.8, 4.0 Hz, H-10), 2.35 (2H, m, H-4), 2.46 (1H, m, H-10), 2.80 (1H, m, H-9), 3.28 (1H, m, H-2), 3.61 (1H, m), 3.73 (2H, m), 3.83 (1H, m), 3.96 (1H, dd, J=8.8, 4.3 Hz, H-1), 4.04 (1H, m, H-3), 5.79 (1H, d, J=11.1 Hz, H-7), 6.14 (1H, d, J=11.1 Hz, H-6).

Example 31

(20S)-1α,25-dihydroxy-2α-(2-hydroxy-ethoxy)-19-norvitamin D₃ (Compound 20-epi-YI-6a)

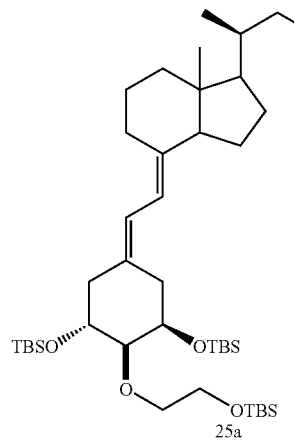

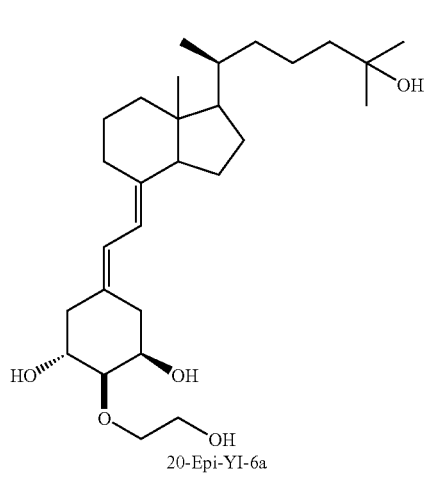

To a solution of Compound 25a (15.4 mg, 0.019 mmol) in dry MeOH (0.5 mL), was added camphor sulfonic acid (26.6 mg, 0.114 mmol), and the reaction mixture was stirred for 2 h at room temperature. 5% NaHCO₃ aqueous solution was added to the reaction mixture, and the mixture was extracted with AcOEt. The organic layer was washed with saturated brine, dried over anhydrous MgSO₄, and the solvent was distilled off. The residue was purified by silica gel column chromatography (3 g; 2% MeOH/AcOEt), and further purified by HPLC (YMC-Pack ODS-AM SH-342-5, 150×20 mm, 20% H₂O/MeOH, 8 mL/min), to yield Compound 20-epi-YI-6a (6.4-mg, 72%).

20-Epi-YI-6a: $^1$H NMR (CDCl₃) δ: 0.55 (3H, s, H-18), 0.85 (3H, d, J=6.5 Hz, H-21 (6H, s, H-26, 27), 2.19 (2H, m, H-4, 10), 2.33, 2.41, 2.56 (each 1H, br. s, OH×3), 2.63 (1H, dd, J=13.2, 4.3 Hz, H-4), 2.80 (1H, m, H-9), 2.84 (1H, dd, J=14.4, 5.4 Hz, H-10), 3.37 (1H, dd, J=7.8, 2.8 Hz, H-2), 3.72-3.83 (4H, m, OCH₂CH₂O), 3.96 (1H, m, H-3), 4.14 (1H, m, H-1), 5.83 (1H, d, J=11.2 Hz, H-7), 6.34 (1H, d, J=1.2 Hz, H-6). UV λmax (EtOH): 243, 252, 261 nm.

Example 32

(20S)-1α,25-dihydroxy-2β-(2-hydroxy-ethoxy)-19-norvitamin D₃ (Compound 20-epi-YI-6b)

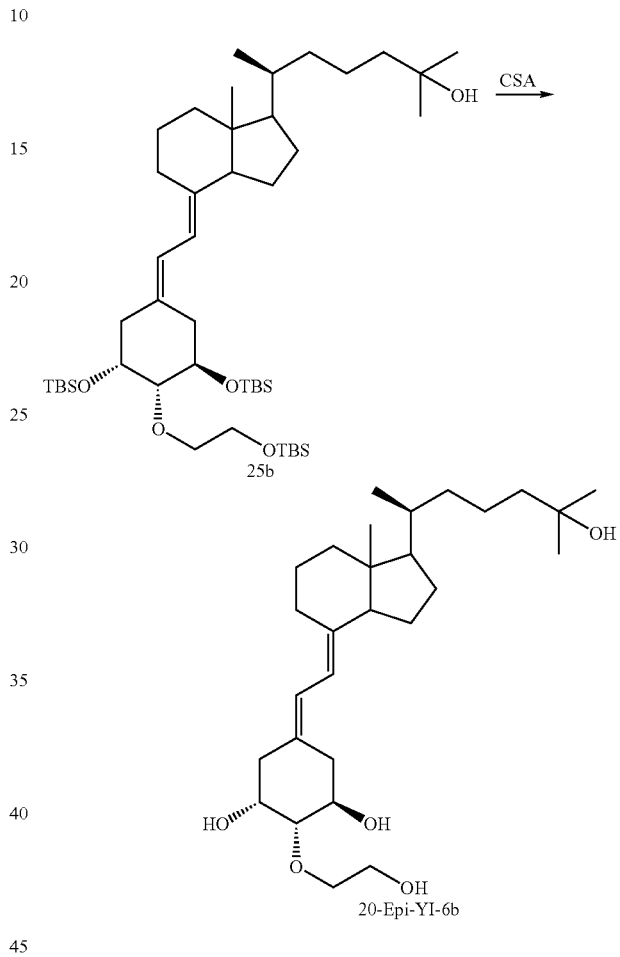

To a solution of Compound 25b (12.0 mg, 0.015 mmol) in dry MeOH (0.5 mL), was added camphor sulfonic acid (20.7 mg, 0.089 mmol), and the reaction mixture was stirred for 2 h at room temperature. 5% NaHCO₃ aqueous solution was added to the reaction mixture. The mixture was extracted with AcOEt. The organic layer was washed with saturated brine, and dried over anhydrous MgSO₄. The solvent was distilled off. The residue was purified by silica gel column chromatography (3 g; 2% MeOH/AcOEt), and further purified by HPLC (YMC-Pack ODS-AM SH-342-5, 150×20 mm, 20% H₂O/MeOH, 8 mL/min), to yield Compound 20-epi-YI-6b (5.6 mg, 81%).

20-epi-YI-6b: $^1$H NMR (CDCl₃) δ: 0.54 (3H, s, H-18), 0.85 (3H, d, J=6.5 Hz, H-21), 1.21 (6H, s, H-26, 27), 2.35 (1H, br. d, J=14.2 Hz, H-4), 2.48 (1H, dm, J=14.2 Hz, H-4), 2.79 (1H, m, H-9), 3.09 (1H, dd, J=13.5, 3.7 Hz, H-10), 3.29 (1H, dd, J=8.7, 2.7 Hz, H-2), 3.67 (1H, m), 3.76-3.89 (4H, m, H-1, OCH₂CH₂O), 4.17 (1H, m, H-3), 5.84 (1H, d, J=11.2 Hz, H-7), 6.28 (1H, d, J=11.2 Hz, H-6). UV λmax (EtOH): 243, 252, 261 nm.

Example 33

(20S)-1α-[(t-butyldimethylsilyl)oxy]-2-oxo-25-hydroxy-19-norvitamin D₃ t-butyldimethylsilyl ether (Compound 26)

Example 34

E-isomer and Z-isomer of (20S)-1α-[(t-butyldimethylsilyl)oxy]-2-cyanomethylene-25-hydroxy-19-norvitamin D₃ t-butyldimethylsilyl ether (Compounds 27a, 27b)

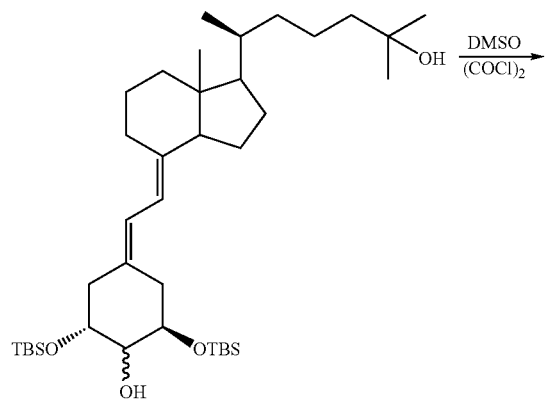

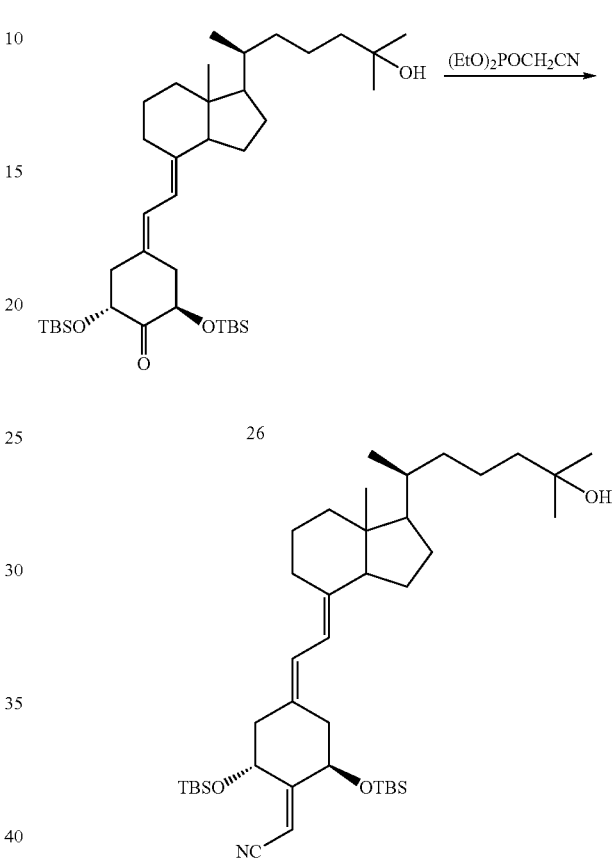

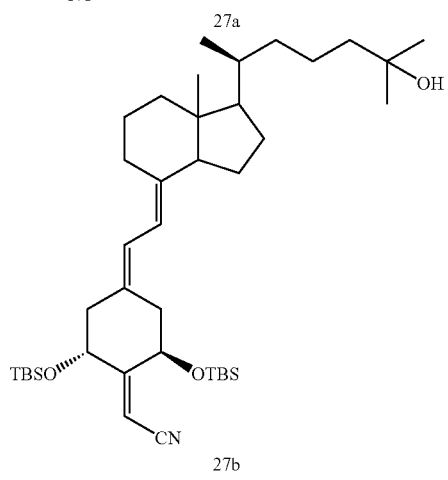

To a solution of oxalyl chloride (18 μL, 0.206 mmol) in dry CH₂Cl₂ (1 mL) cooled to −78° C. was added a solution of DMSO (29 μL, 0.414 mmol) in dry CH₂Cl₂ (0.2 mL), and the solution was stirred for 5 min. To the cooled stirred solution, a solution of Compound 24 (61.0 mg, 0.094 mmol, a mixture of isomers 24a:24b=ca. 3:2) in dry CH₂Cl₂ (1.2 mL) was added. The reaction mixture was stirred for 15 min at −78° C., and Et₃N (131 μL, 0.940 mmol) was added. The mixture was stirred for 30 min at −78° C. and then for 10 min at 0° C., followed by addition of ice water. The solution was extracted with CH₂Cl₂. The organic layer was washed with saturated brine, dried over anhydrous MgSO₄, and the solvent was distilled off. The residue was purified by silica gel column chromatography (5 g; 20% AcOEt/hexane), to afford Compound 26 (52.0 mg, 86%) as a single compound.

26: $^1$H NMR (CDCl₃) δ: 0.055, 0.065, 0.069, 0.10 (each 3H, s, Si-Me×4), 0.55 (3H, s, H-18), 0.87, 0.89 (each 9H, s, Si-tBu×2, overlapped with H-21), 1.22 (6H, s, H-26, 27), 2.45 (1H, dd, J=13.5, 8.7 Hz), 2.52 (1H, dd, J=14.2, 4.1 Hz), 2.66 (1H, dd, J=13.5, 5.5 Hz), 2,72 (1H, dd, J=14.2, 6.3 Hz), 2.83 (1H, m, H-9), 4.35 (1H, dd, J=6.3, 4.1 Hz), 4.55 (1H, dd, J=8.7, 5.5 Hz), 5.81 (1H, d, J=11.2 Hz, H-7), 6.35 (1H, d, J=11.2 Hz, H-6).

To a solution of diethyl cyanomethyl phosphonate (24 μL, 0.148 mmol) in dry THF (1 mL) cooled to −40° C., was added n-BuLi (95 μL, 0.151 mmol, 1.58 M solution in hexane), and the mixture was stirred for 15 min. To the mixture, a solution of Compound 26 (48.7 mg, 0.075 mmol) in dry THF (1.2 mL) was gradually added. Stirring was continued for 1.5 h at −40° C., then saturated NH₄Cl aqueous solution was added to the reaction mixture, and the mixture was extracted with AcOEt. The organic layer was washed with saturated brine, and dried over anhydrous MgSO$_4$. The solvent was distilled off. The residue was purified by silica gel column chromatography (5 g; 10% AcOEt/hexane), to afford Compound 27 (50.0 mg, 99%) as a mixture of two stereoisomers. The ratio of Isomer 27a (E-isomer) and Isomer 27b (Z-isomer) constituting the mixture was ca. 1:1.

27a: $^1$H NMR (CDCl$_3$) δ: 0.054, 0.067, 0.099, 0.121 (each 3H, s, Si-Me×4), 0.55 (3H, s, H-18), 0.83, 0.92 (each 9H, s, Si-tBu×2), 0.86 (3H, d, J=6.5 Hz, H-21), 1.22 (6H, s, H-26, 27), 2.80 (1H, m, H-9), 3.12 (1H, m, H-10), 4.46 (1H, m, H-1), 4.99 (1H, t, J=2.8 Hz, H-3), 5.47 (1H, d, J=1.8 Hz, C=CHCN), 5.82 (1H, d, J=11.1 Hz, H-7), 6.19 (1H, d, J=11.1 Hz, H-6).

27b: $^1$H NMR (CDCl$_3$) δ: 0.063, 0.075, 0.112, 0.132 (each 3H, s, Si-Me×4), 0.54 (3H, s, H-18), 0.83, 0.92 (each 9H, s, Si-tBu×2), 0.86 (3H, d, J=6.5 Hz, H-21), 1.22 (6H, s, H-26, 27), 2.80 (1H, m, H-9), 2.99 (1H, m, H-10), 4.57 (1H, m, H-3), 5.04 (1H, t, J=2.8 Hz, H-1), 5.47 (1H, d, J=1.8 Hz, C=CHCN), 5.79, (1H, d, J=11.1 Hz, H-7), 6.32 (1H, d, J=11.2 Hz, H-6, 7).

Example 35

E-isomer and Z-isomer of (20S)-1α-[(t-butyldimethylsilyl)oxy]-2-[2-(hydroxy)-ethylidene]-25-hydroxy-19-norvitamin D$_3$ t-butyldimethylsilyl ether (Compounds 29a, 29b)

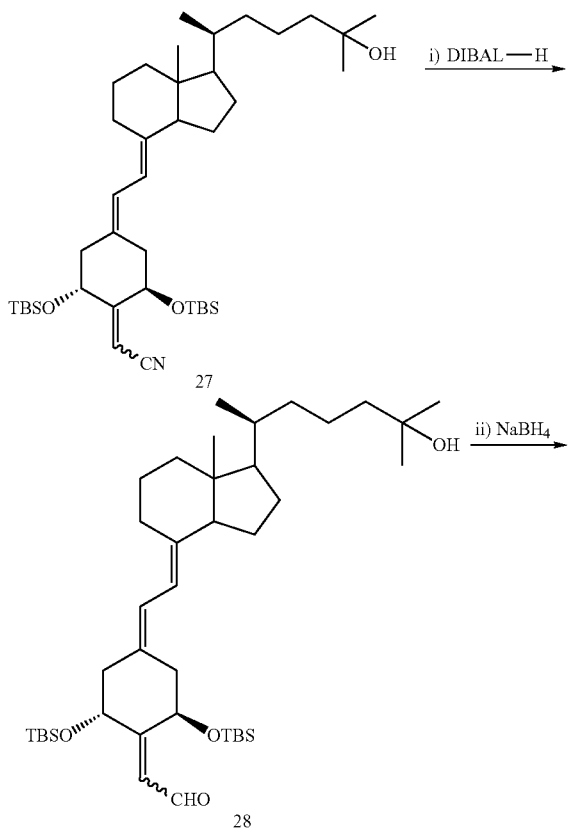

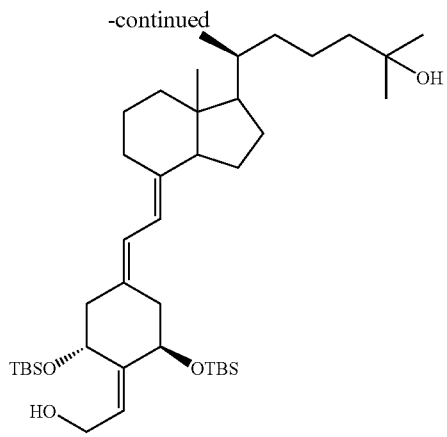

29a

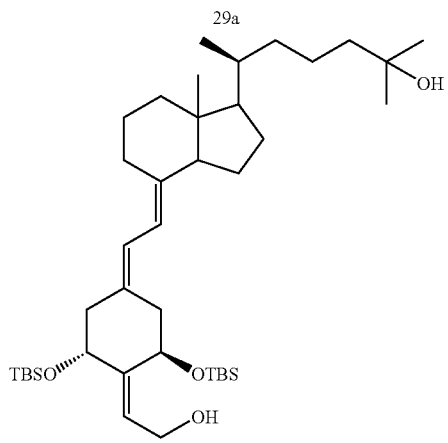

29b

To a solution of Compound 27 (20.0 mg, 0.030 mmol, a mixture of 27a:27b=ca. 1:1) in dry toluene (1 mL) cooled to −78° C. was added diisobutylaluminum hydride (60 μL, 0.060 mmol, 1.0 M solution in hexane). After 3 h, the reaction temperature was raised to −20° C. After stirring for 1 h, additional diusobutylaluminum hydride (30 AL, 0.030 mmol, 1.0 M solution in hexane) was added, and stirring was further continued for 5.5 h. The reducing agent was decomposed by adding an aqueous solution of saturated potassium sodium tartrate, thereafter the reaction mixture was poured into ice water, and extracted with AcOEt. The organic layer was washed with saturated brine, dried over anhydrous MgSO$_4$, and the solvent was distilled off. The residue was dissolved in EtOH (1 mL), and NaBH$_4$ (1.1 mg, 0.030 mmol) was added. The mixture was stirred for 1 h at 0° C. Ice water was added to the reaction solution, and the solution was extracted with AcOEt. The organic extract was washed with saturated brine, and dried over anhydrous MgSO$_4$. Solvent was removed by evaporation, and the residue was purified by silica gel column chromatography (4 g; 15% AcOEt/hexane), to give Compound 29a (5.5 mg) and Compound 29b (5.0 mg). The total yield was 52%. The unreacted starting material, Compound 27, was recovered (7.5 mg, 38%).

29a: $^1$H NMR (CDCl$_3$) δ: 0.02, 0.07, 0.08 (3H, 3H, 6H, s, Si-Me×4), 0.55 (3H, s, H-18), 0.85, 0.92 (each 9H, s, Si-tBu× 2, overlapped with H-21), 1.22 (6H, s, H-26, 27), 2.29 (2H, m, H-4), 2.79 (1H, m, H-9), 2.88 (1H, dd, J=12.7, 4.3 Hz, H-10), 4.19 (1H, dd, J=12.7, 6.8 Hz, CH$_2$OH), 4.31 (1H, dd, J=12.7, 6.7 Hz, CH$_2$OH), 4.37 (1H, dd, J=9.7, 4.3 Hz, H-1), 4.81 (1H, t, J=3.8 Hz, H-3), 5.72 (1H, t, J=6.8 Hz, C=CH), 5.85 (1H, d, J=11.2 Hz, H-7), 6.15 (1H, d, J=11.2 Hz, H-6).

29b: $^1$H NMR (CDCl$_3$) δ: 0.01, 0.07, 0.08, 0.09 (each 3H, s, Si-Me×4), 0.54 (3H, s, H-18), 0.83, 0.93 (each 9H, s, Si-tBu×2), 0.85 (3H, d, J=6.5 Hz, H-21), 1.22 (6H, s, H-26, 27), 2.14 (1H, br. t, J=≦11.5 Hz, H-4), 2.55 (1H, dd, J=12.3, 5.0 Hz, H-4), 2.82 (2H, m, H-9, 10), 4.22 (1H, dd, J=12.3, 7.1 Hz, CH$_2$OH), 4.30 (each 1H, dd, J=12.7, 7.0 Hz, CH$_2$OH), 4.47 (1H, m, H-3), 4.86 (1H, t, J=3.1 Hz, H-1), 5.72 (1H, m, C=CH), 5.81 (1H, d, J=11.1 Hz, H-7), 6.25 (1H, d, J=11.1 Hz, H-6).

Example 36

(20S)-1α,25-dihydroxy-2-[2-(hydroxy)-ethylidene-19-norvitamin D$_3$ (E-isomer) (Compound 20-epi-YI-8a)

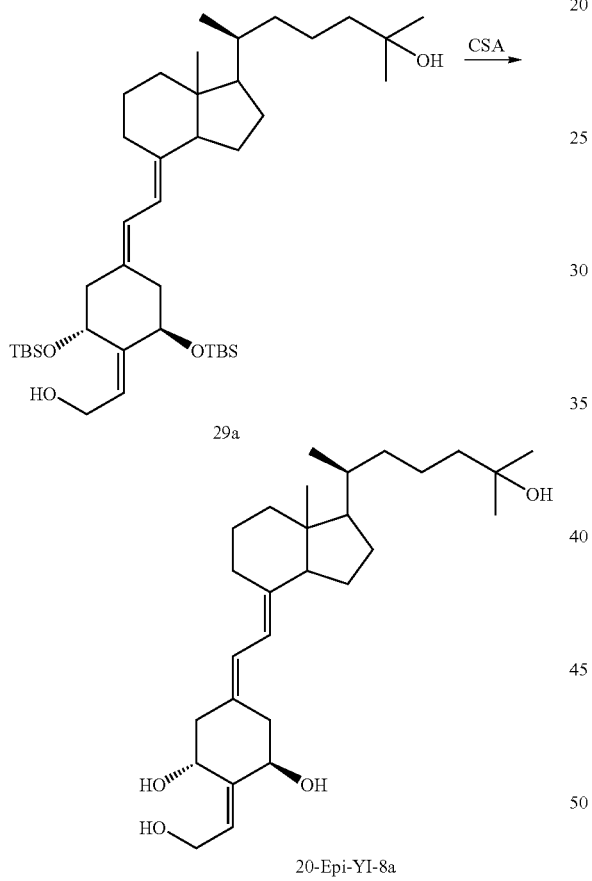

To a solution of Compound 29a (11.0 mg, 0.016 mmol) in dry MeOH (0.5 mL), was added camphor sulfonic acid (11.4 mg, 0.049 mmol) and the reaction mixture was stirred for 2 h at room temperature. 5% NaHCO$_3$ aqueous solution was added to the reaction mixture, and the mixture was extracted with AcOEt. The organic layer was washed with saturated brine, dried over anhydrous MgSO$_4$, and the solvent was distilled off. The residue was purified by silica gel column chromatography (3 g; 3% MeOH/AcOEt), to afford Compound 20-epi-YI-8a (6.4 mg, 88%).

20-epi-YI-8a: $^1$H NMR (CDCl$_3$) δ: 0.54 (3H, s, H-18), 0.86 (3H, d, J=6.5 Hz, H-21), 1.21 (6H, s, H-26, 27), 2.42 (2H, m, H-4), 2.81 (1H, m, H-9), 3.15 (1H, d, J=12.8, 4.9 Hz, H-10), 4.15 (1H, dd, J=12.4, 5.9 Hz, CH$_2$OH), 4.39 (2H, m, H-1, CH$_2$OH), 4.84 (1H, m, H-3), 5.80 (1H, m, C=CH), 5.88 (1H, d, J=11.1 Hz, H-7), 6.29 (1H, d, J=11.1 Hz, H-6). UV λmax (EtOH): 246, 254, 263 nm.

Example 37

(20S)-1α,25-dihydroxy-2-[2-(hydroxyl)-ethylidene]-19-norvitamin D$_3$ (Z-isomer) (Compound 20-Epi-YI-8b)

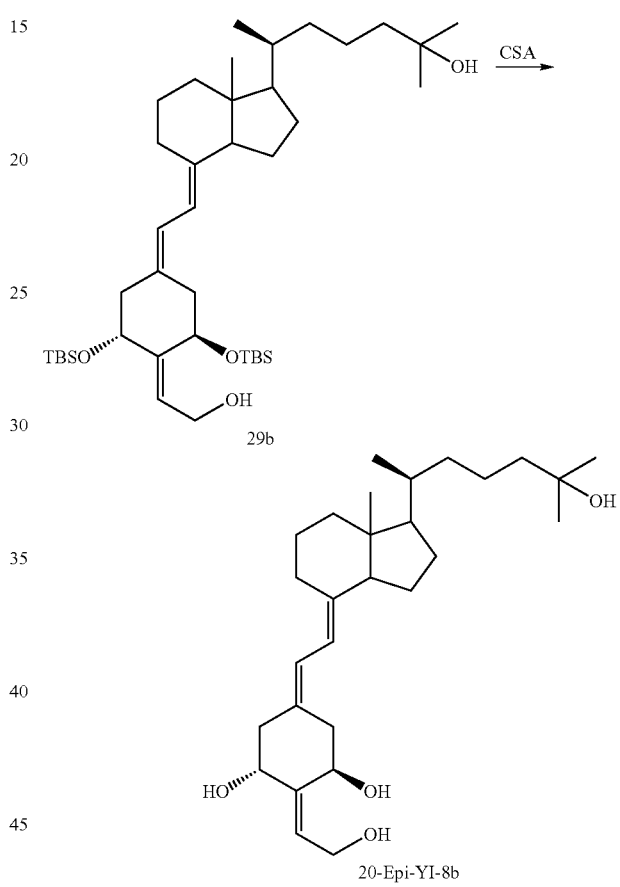

A mixture of Compound 29b (11.0 mg, 0.016 mmol) and camphor sulfonic acid (11.4 mg, 0.049 mmol) in dry MeOH (0.5 mL) was stirred for 2 h at room temperature. A 5% NaHCO$_3$ aqueous solution was added, and the mixture was extracted with AcOEt. The organic phase was washed with saturated brine, and dried over anhydrous MgSO$_4$. Evaporation of the solvent in vacuo left the residue, which was purified by silica gel column chromatography (3 g; 3% MeOH/AcOEt) to afford Compound 20-Epi-YI-8b (4.8 mg, 66%).

20-Epi-YI-8b: $^1$H NMR (CDCl$_3$) δ: 0.55 (3H, s, H-18), 0.85 (3H, d, J=6.5 Hz, H-21), 1.21 (6H, s, H-26, 27), 2.21 (1H, br. t. J=≦13 Hz, H-4), 2.33 (1H, dm, H-10), 2.70 (1H, d, J=12.8, 4.7 Hz, H-4), 2.82 (2H, m, H-9,10), 4.24 (1H, dd, J=12.6, 6.4 Hz, CH$_2$OH), 4.38 (1H, dd, J=12.6, 7.4 Hz, CH$_2$OH), 4.46 (1H, m, H-3), 4.87 (1H, t, J=4.2 Hz, H-1), 5.83 (2H, m, H-7, C=CH), 6.40 (1H, d, J=11.1 Hz, H-6). UV λmax (EtOH): 246, 254, 263 nm.

Example 38

(aS*,2R,6R)-and (aR*,2R,6R)-{[4-benzyloxy-2,6-bis-[(t-butyldimethylsilyl)oxy]-cyclohexylidene}-acetonitrile (Compound 30)

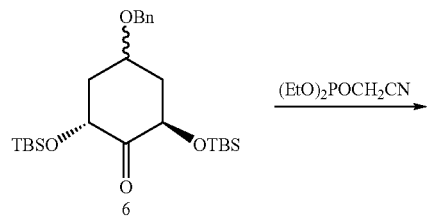

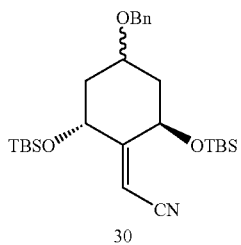

To a solution of diethyl(cyanomethyl)phosphonate (112 μL, 0.69 mmol) in dry THF (1 mL) cooled to −78° C. was added n-BuLi (493 μL, 0.69 mmol, 1.4 M solution in hexane). The mixture was stirred for 15 min, and a solution of 6 (160 mg, 0.345 mmol) prepared in Example 4 in dry THF (1.2 mL) was added slowly. Stirring was continued for 1.5 h at 0° C. after which time the reaction mixture was quenched with a saturated NH$_4$Cl aqueous solution, and extracted with AcOEt. The AcOEt layer was washed with saturated brine, and dried over anhydrous MgSO$_4$. Solvent was evaporated in vacuo, and the residue was purified by silica gel column chromatography (5 g; 2% AcOEt/hexane) to afford Compound 30 (162 mg, 96%) as a mixture of two stereoisomers. The ratio of the stereoisomers constituting the mixture was ca. 1:2. It was impossible to know whether the major product was aS*,2R,6R isomer or aR*,2R,6R isomer.

NMR Data of the Mixture 30a (minor product, less polar isomer): $^1$H NMR (CDCl$_3$) δ: 0.05, 0.06, 0.08, 0.11 (each 3H, Si-Me×4), 0.85, 0.91 (each 9H, s, Si-tBu×2), 1.32-1.48 (2H, m), 2.28 (1H, m), 2.39 (1H, m), 3.96 (1H, m, H-1), 4.54 (2H, s, PhCH$_2$), 4.56 (1H, m), 4.98 (1H, m), 5.41 (1H, d, J=2.0 Hz, C=CH), 7.25-7.35 (5H, m, arom. H).

30b (major product, more polar isomer): $^1$H NMR (CDCl$_3$) δ: 0.07, 0.08, 0.09, 0.11 (each 3H, Si-Me×4), 0.84, 0.91 (each 9H, s, Si-tBu×2), 1.60-1.73 (2H, m), 2.22 (2H, m), 3.85 (1H, m, H-1), 4.57, 4.61 (each 1H, d, J=12.1 Hz, PhCH$_2$), 4.94- 5.00 (2H, m, H-3, 5), 5.43 (1H, d, J=1.5 Hz, C=CH), 7.25-7.33 (5H, m, arom. H). MS m/z (%) of the mixture: no M$^+$, 403 (47), 91 (100).

Example 39

(aS*,2R,6R)-and (aR*,2R,6R)-{[4-benzyloxy-2,6-bis-[(t-butyldimethylsilyl)oxy]-cyclohexylidene}-acetaldehyde (Compound 31)

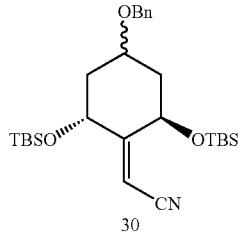

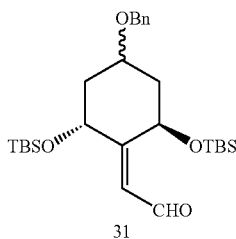

To a solution of Compound 30 (310 mg, 0.635 mmol, 30a:30b=ca. 1:2) in dry toluene (3 mL) cooled to −78° C. was slowly added diisobutylaluminum hydride (763 μL, 0.763 mmol, 1.0 M solution in toluene), and the mixture was stirred for 1.5 h. Excess reagent was decomposed by adding an aqueous solution of saturated potassium sodium tartrate, thereby quenching reaction, and into the mixture was poured ice water, and then extracted with AcOEt. The organic layer was washed with saturated brine, dried over anhydrous MgSO$_4$, and evaporated in vacuo. The residue was purified by silica gel column chromatography (13 g; 5% AcOEt/hexane) to afford Compound 31 (288.5 mg, 93%) as a mixture of two stereoisomers. The ratio of the stereoisomers constituting the mixture was ca. 1:2. It was impossible to know whether the major product was aS*,2R,6R isomer or aR*,2R,6R isomer.

NMR Data of the Mixture 31a (minor product, less polar isomer): $^1$H NMR (CDCl$_3$) δ: 0.03-0.07 (12 lEt Si-Me×4), 0.85, 0.92 (each 9H, s, Si-tBu× 2), 1.47 (2H, m), 2.33, 2.44 (each 1H, m), 3.97 (1H, m, H-1), 4.56 (2H, s, PhCH$_2$), 4.69 (1H, ddd, J=11.8, 5.3, 1.7 Hz), 5.53 (1H, m), 6.16 (1H, dd, J=7.9, 1.6 Hz, C=CH), 7.26-7.36 (5H, m, arom. H), 10.09 (1H, d, J=7.8 Hz, CHO).

31b (major product, more polar isomer): $^1$H NMR (CDCl$_3$) δ: 0.03-0.07 (12H, Si-Me×4), 0.88 (18H, s, Si-tBu×2), 1.78, 1.90, 2.04, 2.17 (each 1H, m), 3.93 (1H, m, H-1), 4.53, 4.58 (each 1H, d, J=11.8 Hz, PhCH$_2$), 4.61 (1H, m), 5.12 (1H, dd, J=8.9, 4.3 Hz), 5.88 (1H, d, J=7.7 Hz, C=CH), 7.25-7.36 (5H, m, arom. H), 10.49 (1H, d, J=7.7 Hz, CHO). MS m/z (%) of the mixture: no M$^+$, 449 (32), 433 (3), 358 (4), 341 (13), 325 (7), 317 (5), 209 (10), 91 (100).

Example 40

(aS*,2R,6R)- and (aR*,2R,6R)-{[4-benzyloxy-2,6-bis-[(t-butyldimethylsilyl)oxy]-cyclohexylidene}-ethanol (Compound 32)

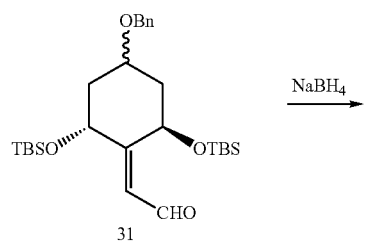

To a solution of Compound 31 (288 mg, 0.587 mmol, 31a:31b=ca. 1:2) in EtOH (1 mL) cooled to 0° C. was added NaBH$_4$ (26.6 mg, 0.704 mmol). After, the reaction mixture was stirred for 1 h at 0° C., into the reaction mixture was poured ice water, and extracted with AcOEt. The organic layer was washed with saturated brine, and dried over anhydrous MgSO$_4$. Solvents were removed in vacuo, and the residue was purified by silica gel column chromatography (10 g; 15% AcOEt/hexane) to yield Compound 32 (283.3 mg, 98%) as a mixture of two stereoisomers. The ratio of the stereoisomers constituting the mixture was ca. 2:1. It was impossible to know whether the major product was aS*,2R,6R isomer or aR*,2R,6R isomer.

NMR Data of the Mixture 32a (major product, less polar isomer): $^1$H NMR (CDCl$_3$) δ: 0.008, 0.04, 0.10, 0.11 (each 3H, s, Si-Me×4), 0.85, 0.92 (each 9H, s, Si-tBu×2), 1.55 (1H, m), 1.68 (1H, q, J=10.8 Hz), 2.08 (1H, m), 2.20 (1H, m), 2.94 (1H, dd, J=10.0, 4.3 Hz, H-1), 3.90 (1H, tt, J=10.0, 4.3 Hz, H-1), 4.02 (1H, ddd, J=13.5, 9.2, 7.0 Hz, CH$_2$OH), 4.34 (1H, m, H-3, 5), 4.40 (1H, m, CH$_2$OH), 4.54 (2H, s, PhCH$_2$), 4.69 (1H, dd, J=10.8, 4.0 Hz, H-3, 5), 5.62 (1H, t, J=5.8 Hz, C=CH), 7.24-7.35 (5H, m, arom. H).

32b (minor product, more polar isomer): $^1$H NMR (CDCl$_3$) δ: -0.01, 0.05 (each 3H, s, Si-Me×2), 0.07 (6H, s, Si-Me×2), 0.83, 0.92 (each 9H, s, Si-tBu×2), 1.30-1.41 (2H, m), 2.21 (1H, m), 2.38 (1H, m), 3.94 (1H, tt, J=11.3, 4.3 Hz, H-1), 4.23 (2H, m, CH$_2$OH), 4.48 (1H, m, H-3, 5), 4.53, 4.57 (each H, d, J=11.8 Hz, PhCH$_2$), 4.86 (1H, m, H-3, 5), 5.70 (1H, dt, J=7.1, 1.8 Hz, C=CH), 7.24-7.35 (5H, m, arom. H). MS m/z (%) of the mixture: no M$^+$, 474 (8), 435 (3), 360 (1), 327 (25), 303 (8), 91 (100).

Example 41

(aS*,3R,5R)- and (aR*,3R, 5R)-{3,5-bis-[(t-butyldimethylsilyl)oxy]-4-[2-(t-butyldimethylsilyl)oxy]-ethylidene}-cyclohexyloxymethyl}-benzene (Compound 33)

A mixture of Compound 32 (55 mg, 0.112 mmol, 32a:32b=ca. 2:1), imidazole (18.3 mg, 0.269 mmol), and tert-butyldimethylsilyl chloride (20.2 mg, 0.134 mmol) in dry DMF (1 mL) cooled to 0° C. was stirred for 1.5 h. Into the reaction mixture was poured ice water, and extracted with AcOEt-hexane (v/v. 1:1). The organic phase was washed with saturated brine, and dried over anhydrous MgSO$_4$. Solvents were removed in vacuo, and the residue was purified by silica gel column chromatography (5 g, 2% AcOEt/hexane) to yield Compound 33 (62 mg, 91%) as a mixture of two stereoisomers. The ratio of the stereoisomers constituting the mixture was ca. 2:1. It was impossible to know whether the major product was aS*,2R,6R isomer or aR*,2R,6R isomer.

NMR Data of the Mixture 33a (major product, less polar isomer): $^1$H NMR (CDCl$_3$) δ: 0.02, 0.04, 0.051, 0.06 (each 3H, s, Si-Me×4), 0.048 (6H, s, Si-Me×2), 0.86, 0.88, 0.91 (each 9H, s, Si-tBu×3), 1.57-1.68 (2H, m), 2.02 (1H, m), 2.10 (1H, m), 3.86 (1H, m, H-1), 4.36 (1H, m), 4.38 (1H, m, CH$_2$OTBS), 4.52, 4.55 (each 1H, d, J=11.9 Hz, PhCH$_2$), 4.63 (1H, m), 4.65 (1H, m, CH$_2$OTBS), 5.35 (1H, m, C=CH), 7.24-7.35 (5H, m, arom. H).

33b (minor product, more polar isomer): $^1$H NMR (CDCl$_3$) δ: -0.01, 0.04, 0.053, 0.054 (each 3H, s, Si-Me×4), 0.06 (6H, s, Si-Me×2), 0.83, 0.88, 0.92 (each 9H, s, Si-tBu×3), 1.30-1.40 (2H, m), 2.19 (1H, m), 2.36 (1H, m), 3.93 (1H, tt, J=6.9, 4.3 Hz, H-1), 4.24 (2H, m, CH$_2$OTBS), 4.45 (1H, m, H-3 or 5), 4.53, 4.56 (each 1H, d, J=11.8 Hz, PhCH$_2$), 4.83 (1H, m), 5.60 (1H, td, J=6.5, 1.8 Hz, C=CH), 7.24-7.35 (5H, m, arom. H). MS m/z (%) of the mixture: no M$^+$, 591 (1), 549 (23), 474 (8), 441 (27), 417 (29), 285 (13), 91 (100).

Example 42

3,5-bis-[(t-butyldimethylsilyl)oxy]-4-{[2-(t-butyldimethylsilyl)oxy]-ethyl}-cyclohexanone (Compound 35)

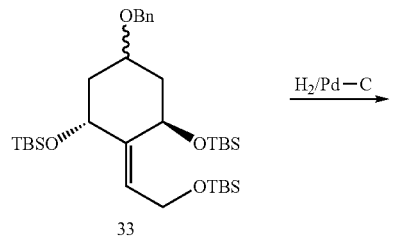

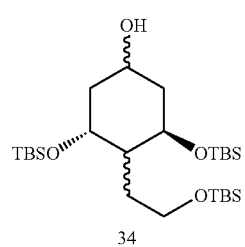

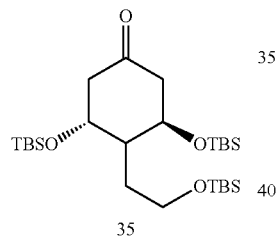

A mixture of Compound 33 (116.5 mg, 0.192 mmol, 33a: 33b=ca. 2:1) and palladium, 10 wt % on carbon (11.7 mg) in EtOH (5 mL) was hydrogenated under an atmospheric pressure of H₂ at room temperature. After vigorous stirring for 21 h, the reaction mixture was filtered through a pad of Celite. The pad was washed with AcOEt, and the combined filtrate was evaporated in vacuo. The residue was purified by silica gel column chromatography (15 g; 5% AcOEt/hexane) to afford Compound 34 (42.7 mg, 43%).

To a solution of oxalyl chloride (9 μL, 0.099 mmol) in dry CH₂Cl₂ (0.3 mL) cooled to −78° C. was added a solution of DMSO (14 μL, 0.197 mmol) in dry CH₂Cl₂ (0.3 mL). After being stirred for 5 min, a solution of Compound 34 (42.7 mg, 0.082 mmol) in dry CH₂Cl₂ (0.5 mL) was added. The reaction mixture was stirred for 15 min, and Et₃N (57 μL, 0.358 mmol) was added. The mixture was stirred for 30 min at −78° C. and for 1 h at room temperature, after which time it was quenched with ice water, and extracted with CH₂Cl₂. The CH₂Cl₂ extract was washed with saturated brine, and dried over anhydrous MgSO₄. The solvent was evaporated to give the residue, which was purified by silica gel column chromatography (4 g, 2% AcOEt/hexane) to afford Compound 35 (38.0 mg, 89% based on coumpound 34) as a single compound.

35: ¹H NMR (CDCl₃) δ: 0.04-0.06 (18H, Si-Me×6), 0.86, 0.87, 0.90 (each 9H, s, Si-tBu×3), 1.69, 1.78 (each 1H, m, C$\underline{H}_2$CH₂OTBS), 1.96 (1H, ddd, J=13.1, 6.9, 3.1 Hz, H-4), 2.30 (1H, dd, J=14.5, 6.9 Hz), 2.45 (2H, m), 2.62 (1H, dd, J=14.5, 4.0 Hz), 3.67-3.80 (2H, m, C$\underline{H}_2$OTBS), 4.14, 4.38 (each 1H, m, H-3, 5). MS m/z (%): no M⁺, 459 (31), 327 (41), 195 (100).

Example 43

(aS*,3R,5R)-and (aR*,3R,5R)-{3,5-bis-[(t-butyldimethylsilyl)oxy]-4-{[2-(t-butyldimethylsilyl)oxy]-ethyl}-cyclohexylidene}-methyl acetate (Compound 36)

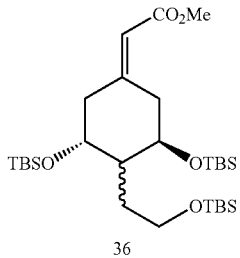

To a solution of diisopropylamine (90 μL, 0.641 mmol) in dry THF (1 mL) cooled to −78° C. was added n-BuLi (458 μL, 0.641 mmol, 1.4 M solution in hexane). After stirring for 15 min, to the solution was added methyl (trimethylsilyl)acetate (105 μL, 0.641 mmol). After stirring for 10 min, to this solution was added slowly a solution of Compound 35 (165.7 mg, 0.321 mmol) dissolved in dry THF (1.3 mL), and stirring was continued for 2 h at −78° C. The mixture was quenched with a saturated NH₄Cl aqueous solution, and extracted with AcOEt. The organic phase was washed with saturated brine, dried over anhydrous MgSO₄, and evaporated in vacuo. The residue was purified by silica gel column chromatography (6 g; 2% AcOEt/hexane) to give Compound 36 (163.0 mg, 89%) as a mixture of two stereoisomers. The ratio of the stereoisomers constituting the mixture was ca. 1:1.

36 (mixture of isomers): ¹H NMR (CDCl₃) δ: 0.03-0.08 (18H, s, Si-Me×6), 0.84-0.89 (27H, s, Si-tBu×3), 1.58-1.77 (3H, m, H-4, C$\underline{H}_2$CH₂OTBS), 2.14 (1H, m), 2.26 (1H, m), 2.47 (1H, dd, J=13.4, 3.8 Hz), 2.62, 2.70 (1:1) (1H, m), 3.22 (1H, m), 3.62-3.73 (2H, m, C$\underline{H}_2$OTBS), 3.668, 3.674 (1:1) (3H, s, COOMe), 3.90, 4.16 (each 1H, H-3, 5), 5.65, 5.69

(1:1) (1H, s, C=CH). MS m/z (%): no M+, 557 (2), 515 (49). 483 (5), 425 (3), 383 (52), 351 (22), 309 (33), 277 (23), 251 (20), 177 (82), 73 (100).

Example 44

(aS*,3R,5R)-and (aR*,3R,5R)-{3,5-bis-[(t-butyldimethylsilyl)oxy]-4-[2-(t-butyldimethylsilyl)oxy]-ethyl]-cyclohexylidene}-ethanol (Compound 37)

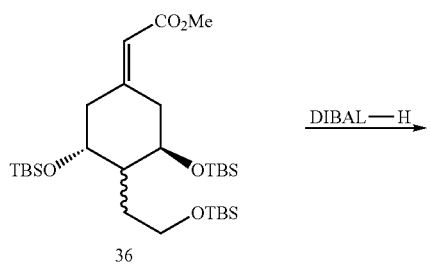

To a solution of Compound 36 (163.0 mg, 0.284 mmol, 36a:36b=ca. 1:1) in dry toluene (1.5 mL) cooled to −78° C. was added diisobutylaluminum hydride (853 μL, 0.853 mmol, 1.0 M solution in toluene), and the mixture was stirred for 1 h. Excess of reagents were decomposed by adding an aqueous solution of saturated potassium sodium tartrate. The mixture was poured into ice water, and extracted with AcOEt. The organic layer was successively washed with water and saturated brine, and dried over anhydrous MgSO$_4$. Evaporation of the solvent in vacuo gave the residue, which was purified by silica gel column chromatography (6 g; 5% AcOEt/hexane) to afford Compound 37 (143.0 mg, 92%) as a mixture of two stereoisomers in ca. 1:1 ratio.

37 (mixture of isomers): $^1$H NMR (CDCl$_3$) δ: 0.03-0.06 (18H, s, Si-Me×6), 0.86-0.89 (27H, s, Si-tBu×3), 1.6-1.8 (3H, m, H-4, CH$_2$CH$_2$OTBS), 2.00-2.24 (4H, m, H-2, 6), 3.60-3.74 (2H, m, CH$_2$OTBS), 3.78-3.91 (1H, m), 4.02-4.18 (3H, m, CH$_2$OH), 5.47, 5.51 (1:1) (1H, t, J=7.1 Hz, C=CH). MS m/z (%): no M+, 487 (3), 469 (9), 459 (9), 394 (11), 355 (17), 337 (19), 263 (57), 211 (74), 171 (86), 131 (100), 73 (100).

Example 45

(aS*,3R,5R)-and (aR*,3R,5R)-{3,5-bis-[(t-butyldimethylsilyl)oxy]-4-[2-(t-butyldimethylsilyl)oxy]-ethyl]-cyclohexylidene}ethyldiphenylphosphine oxide (Compound 38)

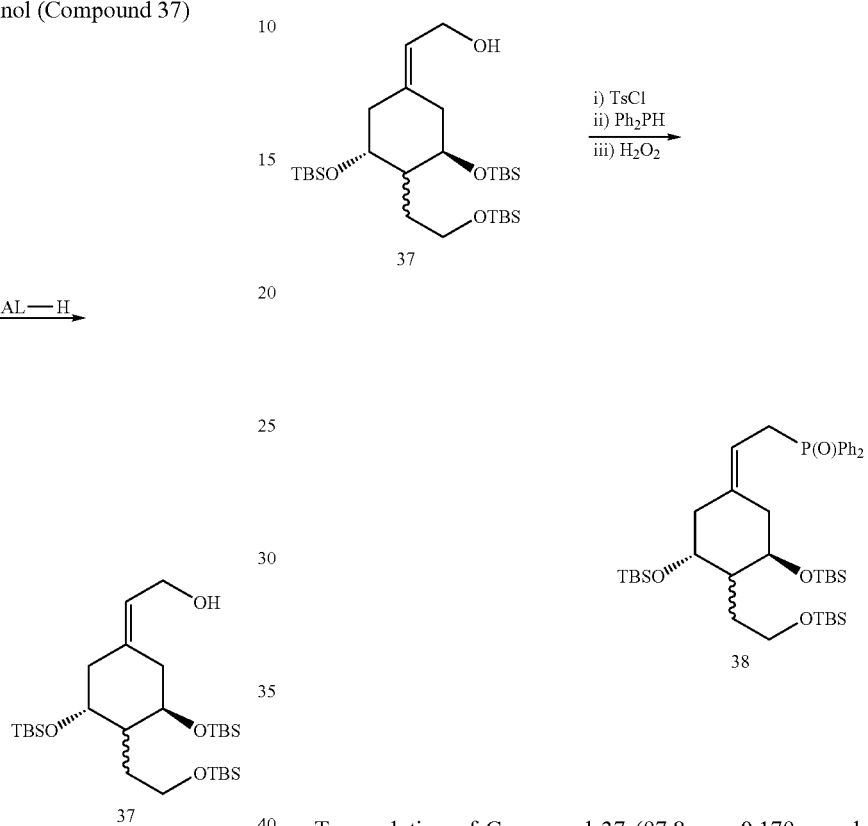

To a solution of Compound 37 (97.8 mg, 0.179 mmol, 37a:37b ca. 1:1) in dry THF (1 mL) cooled to 0° C. was added n-BuLi (141 μL, 0.197 mmol, 1.4 M solution in hexane), a solution of p-toluenesulfonyl chloride (37.6 mg, 0.197 mmol) in dry THF (0.3 mL) was added in this order, and the mixture was stirred for 5 min. To this solution of the tosylate was added slowly a red solution freshly prepared from diphenylphosphine (62 μL, 0.358 mmol) in THF (0.5 mL) and n-BuLi (255 μL, 0.358 mmol, 1.4 M solution in hexane) at 0° C. until the orange color persisted. The entire mixture was stirred for 30 min at 0° C., and quenched by adding water (50 μL). The solvent was evaporated in vacuo, and the crude product was dissolved in CH$_2$Cl$_2$ (3 mL). To this mixture was added 10% hydrogen peroxide (4.5 mL). The mixture was stirred for 1 h at 0° C., and CH$_2$Cl$_2$ phase was separated. The organic layer was successively washed with cold 2N Na$_2$SO$_3$, water and saturated brine, and dried over anhydrous MgSO$_4$. After evaporation of the solvent, the residue was purified by silica gel column chromatography (6 g; 50% AcOEt/hexane) to afford Compound 38 (110.5 mg, 84%) as a mixture of two stereoisomers in a ratio of ca. 1:1.

38 (mixture of isomers): $^1$H NMR (CDCl$_3$) δ: −0.01-0.02 (18H, s, Si-Me×6), 0.82-0.86 (27H, s, Si-tBu×3), 3.00-3.20 (2H, m, CH$_2$PO), 3.56-3.75, 3.99 (3H, m, CH$_2$OTBS, H-3 or 5), 3.77, 3.99 (ca. 1:1) (1H, m, H-3 or 5), 5.24 (1H, m, C=CH), 7.43-7.75 (10H, m, arom. H). MS m/z (%): no M+, 671 (100), 539 (63), 464 (15), 407 (21), 202 (53).

Example 46

(20S)-1α-[(t-butyldimethylsilyl)oxy]-2α-{[2-(t-butyldimethylsilyl)oxy]-ethyl}-and (20S)-1α-[(t-butyldimethylsilyl)oxy]-2β-{[2-(t-butyldimethylsilyl)oxy]-ethyl}-25-[(triethylsilyl)oxy]-19-norvitamin D₃ t-butyldimethylsilyl ether (Compounds 39a, 39b)

Example 47

(20S)-1α,25-dihydroxy-2α-(2-(hydroxyethyl)-and (20S)-1α,25-dihydroxy-2β-(2-(hydroxyethyl)-19-norvitamin D₃ (Compounds 20-Epi-YI-7a and 20-Epi-YI-7b)

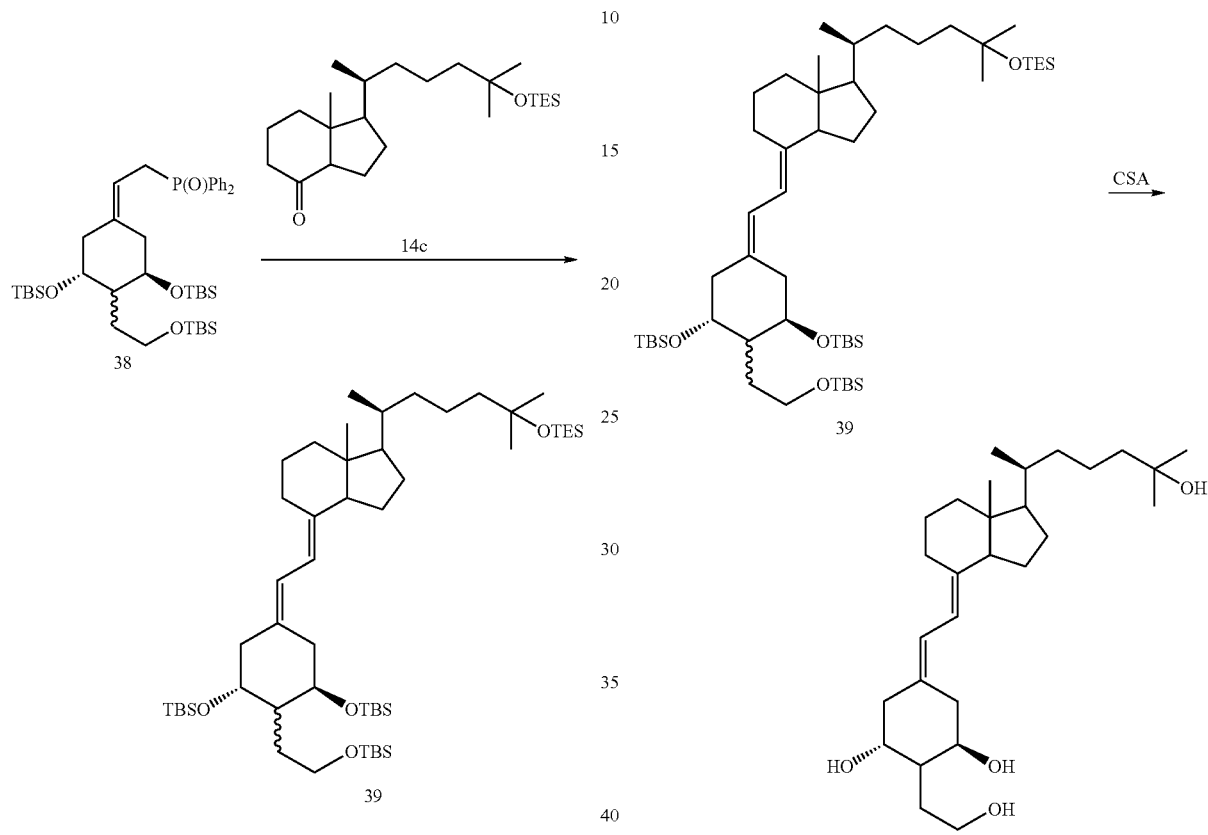

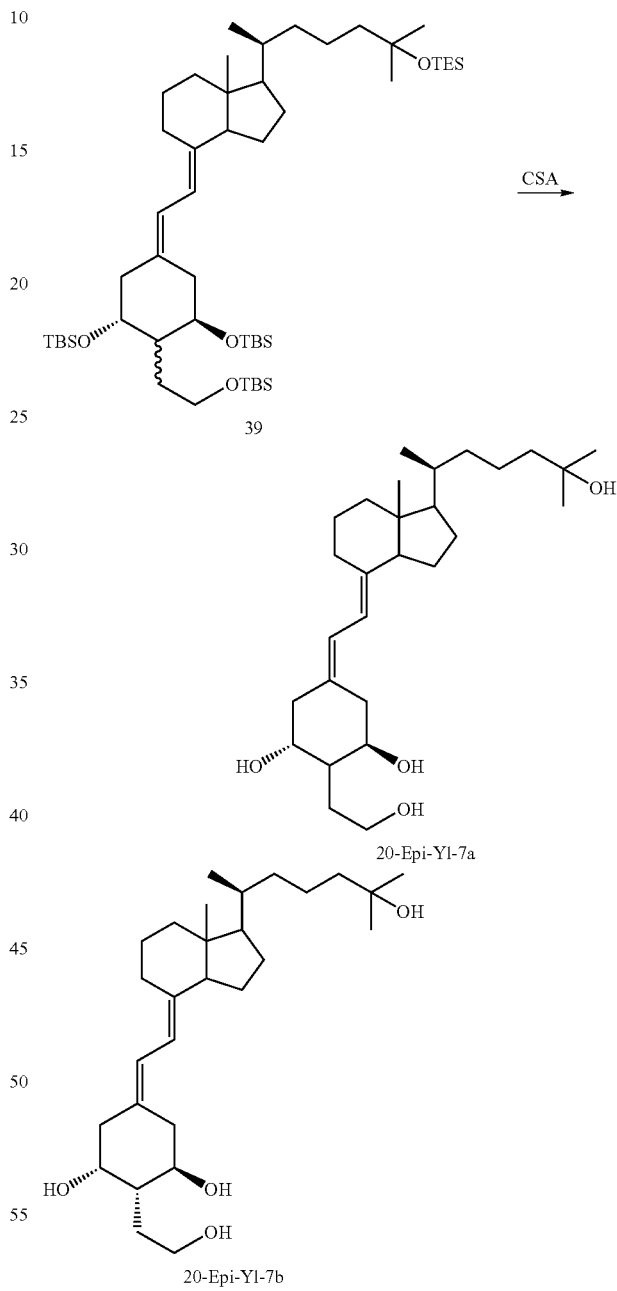

To a solution of Compound 38 (100.3 mg, 0.138 mmol, 38a:38b ca. 1:1) in dry THF (1 mL) cooled to −78° C. was added slowly n-BuLi (87 μL, 0.138 mmol, 1.58 M solution in hexane), and the resulting dark orange solution was stirred for 15 min. To this colored solution was added a solution of Grundmann's ketone 14c (36.2 mg, 0.092 mmol) in dry THF (1.2 mL), and the reaction mixture was stirred for 2 h at −78° C., quenched with a saturated NH₄Cl aqueous solution, and extracted with AcOEt. The AcOEt layer was washed with saturated brine, dried over anhydrous MgSO₄, and evaporated in vacuo. The residue was purified by silica gel column chromatography (10 g; 2% AcOEt/hexane) to afford Compound 39 (53.5 mg, 64%) as a mixture of 39a (2α-isomer): 39b (2β-isomer) =ca. 1:2 ratio. The unreacted starting material 14c (10.3 mg, 28%) and Compound 38 (23.4 mg) were recovered.

39: ¹H NMR (CDCl₃) δ: 0.03-0.07 (18H, s, Si-Me×6), 0.54 (3H, s, H-18), 0.56 (6H, q, J=7.9 Hz, SiCH₂×3), 0.84-0.90 (30H, Si-tBu×3, overlapped with H-21), 0.94 (9H, t, J=7.9 Hz, SiCH₂CH₃×3), 1.19 (6H, s, H-26, 27), 2.45, 2.58 (ca. 1:2) (1H, m, H-4), 2.79 (1H, m, H-9), 3.60-3.73 (2H, m, CH₂CH₂O), 3.79, 4.09 (each 1H, m, H-1, 3), 5.81 (1H, m, H-7), 6.12 (1H, m, H-6).

A mixture of Compound 39 (53.5 mg, 0.059 mmol, 39a:39b=ca. 1:2) and camphor sulfonic acid (109.8 mg, 0.437 mmol) in dry MeOH (1 mL) was stirred for 2 h at room temperature. A 5% NaHCO₃ aqueous solution was added, and the solution was extracted with AcOEt. The organic phase was washed with saturated brine, and dried over anhydrous MgSO₄. After evaporation of the solvent in vacuo, the residue was purified by silica gel column chromatography (5 g; 3% MeOH/AcOEt) to afford Compounds 20-Epi-YI-7a and 7b (21.2 mg, 80%).

The mixture of Compounds 20-Epi-YI-7a and 7b was separated by HPLC (YMC-Pack ODS-AM SH-342-5, 20% H$_2$O/MeOH to give Compounds 20-Epi-YI-7a (6.3 mg) and 20-Epi-YI-7b (11.5 mg), respectively.

20-Epi-YI-7a: $^1$H NMR (CDCl$_3$) δ: 0.53 (3H, s, H-18), 0.85 (3H, d, J=6.5 Hz, H-21), 1.21 (6H, s, H-26, 27), 2.17 (2H, m, H-4, 10), 2.62 (1H, dd, J=12.8, 4.4 Hz, H-4), 2.80 (1H, m, H-9), 2.85 (1H, dd, J=14.2, 4.2 Hz, H-10), 3.70-3.80 (2H, m, H-3, CH$_2$OH), 3.83 (1H, m, CH$_2$OH), 4.06 (1H, m, H-1), 5.82 (1H, d, J=11.2 Hz, H-7), 6.39 (1H, d, J=11.2 Hz, H-6). UV λmax (EtOH): 245, 253, 262 nm.

20-Epi-YI-7b: $^1$H NMR (CDCl$_3$) δ: 0.55 (3H, s, H-18), 0.85 (3H, d, J=6.4 Hz, H-21), 1.21 (6H, s, H-26, 27), 2.33 (1H, dm, J=13.5 Hz, H-4), 2.44 (1H, br. d, J=13.5 Hz, H-4), 2.79 (1H, m, H-9), 3.12 (1H, dd, J=13.0, 4.0 Hz, H-10), 3.63 (1H, m, H-1), 3.74-3.84 (2H, m, CH$_2$O H), 4.00 (1H, m, H-3), 5.88 (1H, d, J=11.2 Hz, H-7), 6.26 (1H, d, J=11.2 Hz, H-6). UV λmax (EtOH): 244, 252, 262 nm.

Example 48

(1,4-cis)-and (1,4-trans)-3,5-bis-[(t-butyldimethylsilyl)oxy]-4-hydroxy-4-methyl-cyclohexanol benzyl ether (Compound 125)

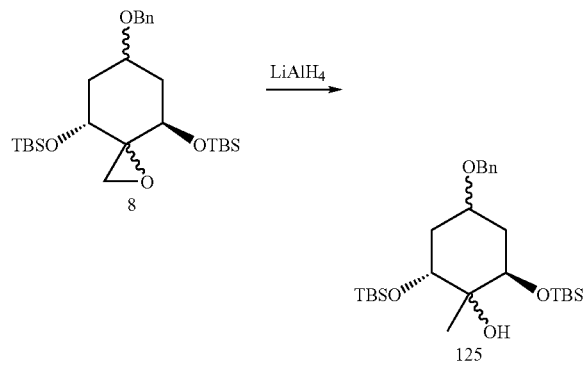

To a stirred suspension of LiAlH$_4$ (237 mg, 6.24 mmol) in dry THF (5 mL) was added a solution of Compound 8 (2.99 g, 6.24 mmol, a mixture of ca. 9:1) in dry THF (15 mL and the mixture was stirred for 2.5 h at room temperature. An additional LiAlH$_4$ (96 mg, 2.53 mmol) was added, and the whole mixture was further stirred for 3.5 h. Excess LiAlH$_4$ was destroyed by adding an aqueous solution of saturated potassium sodium tartrate, and the mixture was extracted with AcOEt. The organic layer was washed with saturated brine, dried over anhydrous MgSO$_4$, and evaporated in vacuo. The residue was purified by silica gel column chromatography (80 g; 50% AcOEt/hexane) to afford the major isomer 125 (1.81 g, 60%) in two stereoisomers, and the minor isomer was not isolated. It was impossible to know whether the major product was 1,4-cis-isomer or 1,4-trans-isomer, 125: $^1$H NMR (CDCl$_3$) δ: 0.042 (6H, s, Si-Me×2), 0.062, 0.082 (each 3H, s, Si-Me×2), 0.84, 0.90 (each 9H, s, Si-tBu× 2), 1.17 (3H, s, Me), 1.66 (1H, m), 1.88 (2H, m), 2.00 (1H, m), 2.19 (1H, s, OH), 3.70 (2H, m), 3.81 (1H, m), 4.51, 4.54 (each 1H, d, J=12.0 Hz, CH$_2$Ph), 7.26-7.35 (5H, m, arom H).

Example 49

(1,4-cis)- or (1,4-trans)-3,5-bis-[(t-butyldimethylsilyl)oxy]-4-[(trimethylsilyl)oxy]-4-methyl-cyclohexanol benzyl ether (Compound 126)

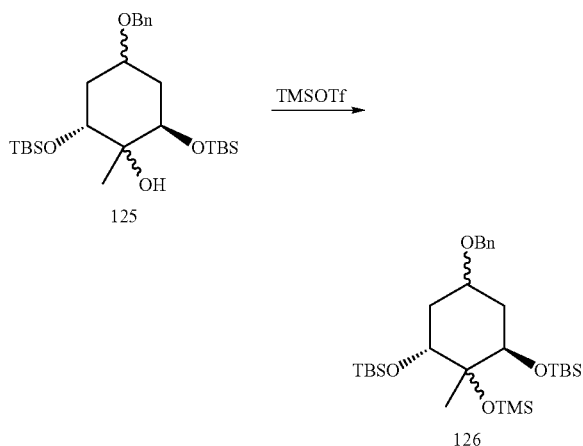

To a solution of Compound 125 (62.3 mg, 0.130 mmol, single main isomer) in dry toluene (2 mL) cooled to −78° C. were added Et$_3$N (72 μL, 0.516 mmol) and trimethylsilyl trifluoromethanesulfonate (52 μL, 0.260 mmol), and the reaction mixture was stirred, and allowed to warm to −20° C. in a period of ca. 2.5 h. The mixture was poured into a 5% NaHCO$_3$ aqueous solution, and extracted with AcOEt. The AcOEt layer was washed with saturated brine, dried over anhydrous MgSO$_4$, and evaporated in vacuo. The residue was purified by silica gel column chromatography (5 g; 5% AcOEt/hexane) to yield Compound 126 (66.7 mg, 93%).

126: $^1$H NMR (CDCl$_3$) δ: 0.018, 0.023, 0.04, 0.05 (each 3H, s, Si-Me×4), 0.11 (9H, s, Si-Me$_3$), 0.83, 0.91 (each 9H, s, Si-tBu×2), 1.20 (3H, s, Me), 1.77 (2H, m), 1.89 (2H, m), 3.56-3.66 (3H, m), 4.52 (2H, s, CH$_2$Ph), 7.26-7.35 (5H, m, arom. H). MS m/z (%): no M$^+$, 537 (1), 495 (9), 461 (3), 387 (87), 91 (100).

Example 50

(1,4-cis)- or (1,4-trans)-3,5-bis-[(t-butyldimethylsilyl)oxy]-4-[(trimethylsilyl)oxy]-4-methyl-cyclohexanol (Compound 127)

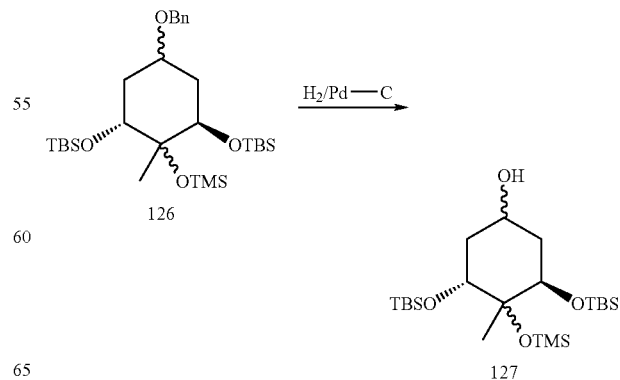

A mixture of Compound 126 (66.7 mg, 0.121 mmol, single main isomer) and palladium, 10 wt. % on carbon (6.7 mg) in AcOEt (2 mL) and EtOH (1 mL) was hydrogenated under an atmosphere pressure of $H_2$ at room temperature. After vigorous stirring for 22 h, the reaction mixture was filtered through a pad of Celite. The pad was washed with EtOH and AcOEt, and the combined filtrate was concentrated in vacuo. The residue was purified by silica gel column chromatography (6 g; 10% AcOEt/hexane) to afford Compound 127 (54.0 mg, 97%).

127: $^1$H NMR (CDCl$_3$) δ: 0.044, 0.055, 0.063, 0.070 (each 3H, s, Si-Me×4), 0.12 (9H, s, Si-Me$_3$), 0.88, 0.91 (each 9H, s, Si-tBu×2), 1.22 (3H, s, Me), 1.70-1.90 (4H, m), 3.58 (1H, t, J=2.8 Hz), 3.68 (1H, dd, J=11.5, 4.2 Hz), 3.92 (1H, m). MS m/z (%): no M$^+$, 405 (3), 387 (100), 273 (25).

Example 51

(3R,5R)-3,5-bis-[(t-butyldimethylsilyl)oxy]-4-[(trimethylsilyl)oxy]-4-methyl-cyclohexanone (Compound 128)

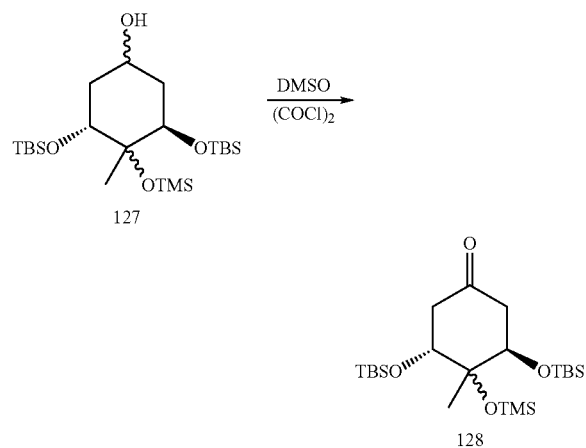

To a solution of oxalyl chloride (339 μL, 3.89 mmol, single main isomer) in dry CH$_2$Cl$_2$ (3 mL) cooled to −78° C. was added a solution of DMSO (552 μL, 7.78 mmol) in dry CH$_2$Cl$_2$ (3 mL). After being stirred for 5 min, a solution of Compound 127 (1.50 g, 3.24 mmol) in dry CH$_2$Cl$_2$ (6 mL) was added. The reaction mixture was stirred for 15 min at −78° C., and Et$_3$N (2.26 mL, 16.2 mmol) was added. The whole mixture was warmed from −78° C. to room temperature over 1.5 h after which time it was quenched with ice water, and extracted with CH$_2$Cl$_2$. The CH$_2$Cl$_2$ extract was washed with saturated brine, dried over anhydrous MgSO$_4$, and evaporated in vacuo. The residue was purified by silica gel column chromatography (30 g; 5% AcOEt/hexane) to afford Compound 128 (1.36, 91%) as a single compound.

128: $^1$H NMR (CDCl$_3$) δ: 0.045-0.058 (12H, Si-Me×4), 0.15 (9H, s, Si-Me$_3$), 0.84, 0.90 (each 9H, s, Si-tBu×2), 1.35 (3H, s, Me), 2.16 (1H, dt, J=14.6, 2.5 Hz), 2.37 (1H, ddd, J=14.0, 5.0, 2.1 Hz) 2.68 (1H, dd, J=14.0, 11.3 Hz), 2.93 (1H, dd, J=14.6, 3.1 Hz), 3.80 (1H, t, J=3.1 Hz), 3.98 (1, dd, J=11.3, 5.0 Hz). MS m/z (%): no M$^+$, 445 (5), 403 (87), 313 (19), 271 (56), 143 (100).

Example 52

(aS*,3R,5R)-and (aR*,3R,5R)-[3,5-bis-[(t-butyldimethylsilyl)oxy]-4-[(trimethylsilyl)oxy]-4-methyl-cyclohexylidene]-methyl acetate (Compound 129)

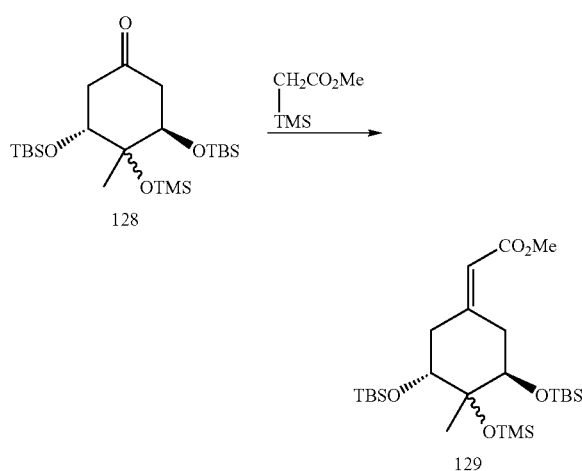

To a solution of diisopropylamine (0.827 mL, 5.90 mmol) in dry THF (5 mL) cooled to −78° C. was added n-BuLi (3.73 mL, 5.90 mmol, 1.58 M solution in hexane). After stirring for 15 min, to the solution was added methyl (trimethylsilyl) acetate (0.969 mL, 5.90 mmol). After stirring for 10 min, to this solution was slowly added a solution of Compound 128 (1.36 g, 2.95 mmol, single compound) dissolved in dry THF (6 mL), and stirring was continued for 1 h at −78° C. The mixture was quenched with a saturated NH$_4$Cl aqueous solution, and extracted with AcOEt. The organic phase was washed with saturated brine, and dried over anhydrous MgSO$_4$. Removal of the solvent in vacuo afforded the residue, which was purified by silica gel column chromatography (30 g; 2% AcOEt/hexane) to give Compound 129 (1.30 g, 85%) as a mixture of two stereoisomers. The ratio of the stereoisomers constituting the mixture was ca. 1:1.

129: $^1$H NMR (CDCl$_3$) δ: 0.02-0.073 (12H, Si-Me×4), 0.126, 0.130 (ca. 1:1) (9H, s, Si-Me$_3$), 0.81, 0.84 (ca. 1:1) (9H, s, Si-tBu), 0.91, 0.93 (ca. 1:1) (9H, s, Si-tBu), 1.25 (3H, s, Me), 1.90-2.85 (4H), 3.60-3.84 (2H, m), 3.65, 3.68 (ca. 1:1) (3H, s, CO$_2$Me), 5.56, 5.71 (ca. 1:1) (1H, s, C=CH). MS m/z (%): 516 (M$^+$, 1), 501 (4), 459 (100), 327 (46), 295 (61).

Example 53

(aS*,3R,5R)-and (aR*,3R,5R)-[3,5-bis-[(t-butyldimethylsilyl)oxy]-4-[(trimethylsilyl)oxy]-4-methyl-cyclohexylidene]-ethanol (Compound 130)

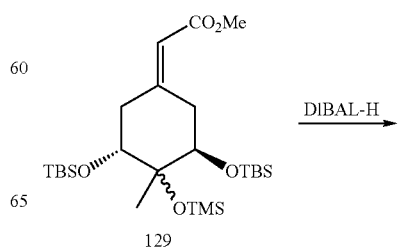

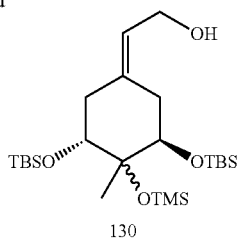

130

To a solution of Compound 129 (1.30 g, 2.51 mmol) in dry toluene (15 mL) cooled to −78° C. was added diisobutylaluminum hydride (7.53 mL, 7.53 mmol, 1.0 M solution in toluene), and the mixture was stirred for 1.5 h. Excess reducing reagents were decomposed by adding an aqueous solution of saturated potassium sodium tartrate. The mixture was poured into ice water, and extracted with AcOEt. The organic layer was successively washed with saturated brine, and dried over anhydrous MgSO$_4$. Solvents were evaporated in vacuo, and the residue was purified by silica gel column chromatography (30 g; 10% AcOEt/hexane) to afford Compound 130 (1.20 g, 98%) as a mixture of two stereoisomers in ca. 1:1 ratio.

130: $^1$H NMR (CDCl$_3$) δ: 0.03-0.07 (12H, Si-Me×4), 0.12 (9H, s, Si-Me$_3$), 0.85 (9H, s, Si-tBu), 0.91, 0.92 (ca. 1:1) (9H, s, Si-tBu), 1.23 (3H, s, Me), 1.85-2.75 (4H), 3.56-3.67 (2H, m), 4.08-4.14 (2H, m), 5.36, 5.49 (ca. 1:1) (1H, m, C=CH). MS m/z (%): 488 (M$^+$, 3), 470 (5), 455 (4), 431 (10), 413 (54), 380 (9), 341 (17), 299 (23), 73 (100).

Example 54

(aS*,3R,5R)-and (aR*,3R,5R)-[3,5-bis-[(t-butyldimethylsilyl)oxy]-4-[(trimethylsilyl)oxy]-4-methylcyclohexylidene]ethyldiphenylphosphine oxide (Compound 118)

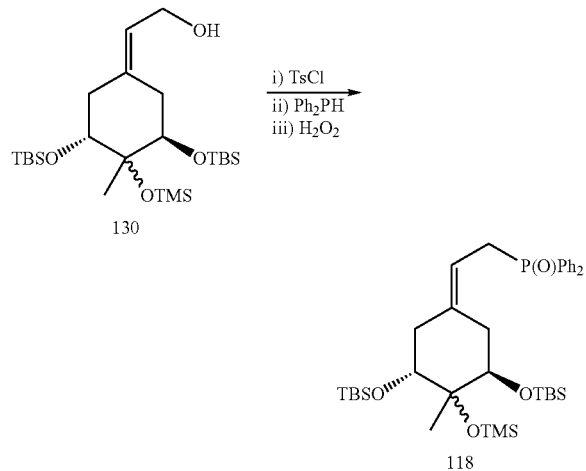

To a solution of Compound 130 (712 mg, 1.46 mmol, a mixture of ca. 1:1) in dry THF (10 mL) cooled to 0° C. were added n-BuLi (1.16 mL, 1.83 mmol, 1.58 M solution in hexane) and a solution of p-toluenesulfonyl chloride (349 mg, 1.83 mmol) in dry THF (1.5 mL) in this order, and the mixture was stirred for 5 min. To this solution of the tosylate was added a red solution freshly prepared from diphenylphosphine (0.506 mL, 2.91 mmol) in THF (3 mL) and n-BuLi (1.84 mL, 2.91 mmol, 1.58 M solution in hexane) at 0° C. until the orange color persisted. The entire mixture was stirred for 30 min at 0° C., and quenched by adding water (0.3 mL). The solvent was evaporated in vacuo, and the crude product was dissolved in CH$_2$Cl$_2$ (8 mL). To this mixture was added a 10% hydrogen peroxide aqueous solution (12 mL). The mixture was stirred for 1 h at 0° C., and CH$_2$Cl$_2$ phase was separated. The organic layer was successively washed with a 2N Na$_2$SO$_3$ aqeous solution and saturated brine, and dried over anhydrous MgSO$_4$. After evaporation of the solvent, the residue was purified by silica gel column chromatography (20 g; 30-60% AcOEt/hexane) to afford Compound 118 (717 mg, 73%) as a mixture of two stereoisomers in a ratio of ca. 1:1.

118: $^1$H NMR (CDCl$_3$) δ: −0.04-0.02 (12H, Si-Me×4), 0.07, 0.08 (ca. 1:1) (9H, s, Si-Me$_3$), 0.80, 0.83 (ca. 1:1) (9H, s, Si-tBu), 0.88, 0.89 (ca. 1:1) (9H, s, Si-tBu), 1.17, 1.18 (ca. 1:1) (3H, s, Me), 1.6-2.6 (4H, m), 2.9-3.2 (2H, m), 3.45-3.64 (2H, m), 5.17, 5.27 (ca. 1:1) (1H, m, CH=C), 7.4-7.8 (10H, m, arom. H).

Example 55

(aS*,3R, 5R)-and (aR*,3R, 5R)-[3,5-bis-[(t-butyldimethylsilyl)oxy]-4-[(t-butyldimethylsilyl)oxy]-ethylidene]-cyclohexanol (Compound 132)

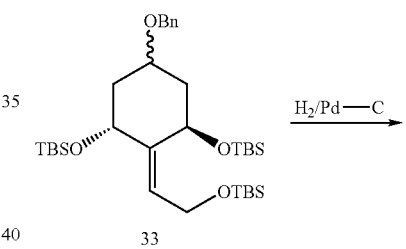

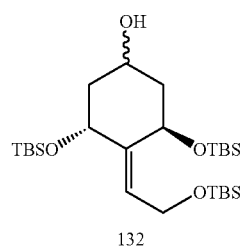

132

A mixture of Compound 33b (384 mg, 0.633 mmol, more polar isomer) and palladium, 10 wt. % on carbon (40 mg) in EtOH (5 mL) was hydrogenated under an atmospheric pressure of H$_2$ at room temperature. After vigorous stirring for 2.5 h, the reaction mixture was filtered through a pad of Celite. The pad was washed with EtOH and AcOEt, and the combined filtrate was evaporated in vacuo. The organic layer was washed with saturated brine, and dried over anhydrous MgSO$_4$. The residue was purified by silica gel column chromatography (15 g; 5% AcOEt/hexane) to afford Compound 132b (298 mg, 91%). It was impossible to know whether Compound 132b was aS*,3R,5R isomer or aR*,3R,5R isomer.

The compound 33a (800 mg, 1.32 mmol, less polar isomer) was hydrogenated by catalytic reduction to thereby gave Compound 132 (536 mg, 79%) as a mixture of 132a:

132b=ca. 2:1 ratio. It was impossible to know whether Compound 132b was aS*,3R,5R isomer or aR*,3R,5R isomer. It was impossible to know whether Compound 132a was aS*, 3R,5R isomer or aR*,3R,5R isomer. (Under catalytic reduction conditions using less polar isomer, isomerization at C-1 position occurred to give 132b.)

132a (less polar isomer): ¹H NMR (CDCl₃) δ: 0.06 (6H, s, Si-Me×2), 0.07, 0.087, 0.094, 0.12 (each 3H, s, Si-Me×4), 0.89 (18H, s, Si-tBu×2), 0.93 (9H, s, Si-tBu), 1.46-1.6 (2H, m), 2.12 (1H, m), 2.32 (1H, m), 4.11 (1H, m, H-1), 4.20 (1H, ddd, J=12.8, 6.2, 1.1 Hz, CH₂OTBS), 4.28 (1H, ddd, J=12.8, 8.0, 1.1 Hz, CH₂OTBS), 4.82 (1H, m), 5.05 (1H, m), 5.66 (1H, m, C=CH). MS m/z (%): no M⁺, 501 (1), 459 (36), 441 (18), 384 (5), 367 (24), 327 (83), 309 (4), 73 (100).

132b (more polar isomer): ¹H NMR (CDCl₃) δ: 0.02, 0.058, 0.064, 0.067, 0.073, 0.075 (each 3H, s, Si-Me×6), 0.87, 0.89, 0.92 (each 9H, s, Si-tBu×3), 1.43-1.51 (2H, m), 2.01-2.06 (1H, m), 2.12-2.18 (1H, m), 4.19 (1H, m, H-1), 4.27 (1H, ddd, J=13.1, 6.5, 0.9 Hz, CH₂OTBS), 4.37 (1H, ddd, J=13.1, 5.7, 0.9 Hz, CH₂OTBS), 4.48, 4.86 (each 1H, m, H-3, 5), 5.56 (1H, m, C=CH). MS m/z (%): no M⁺, 459 (37), 441 (22), 384 (3), 367 (8), 327 (100), 309 (5), 72 (94).

Example 56

[3,5-bis-[(t-butyldimethylsilyl)oxy]-4-[(t-butyldimethylsilyl)oxy]-ethylidene]-cyclohexanone (Compound 133)

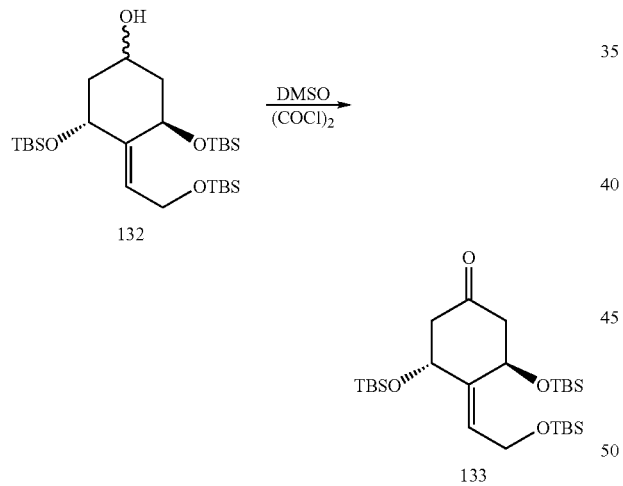

To a solution of oxalyl chloride (7.5 μL, 0.086 mmol) in dry CH₂Cl₂, (0.2 mL) cooled to −78° C. was added a solution of DMSO (12.2 μL, 0.172 mmol) in dry CH₂Cl₂ (100 μL). After being stirred for 5 min, a solution of Compound 132b (37 mg, 0.072 mmol, more polar isomer) in dry CH₂Cl₂ (0.4 mL) was added. The reaction mixture was stirred for 15 min at −78° C., and Et₃N (50 μL, 0.358 mmol) was added. The whole mixture was allowed to warm to room temperature over a period of 1 h at which point the reaction was quenched with ice water, and extracted with CH₂Cl₂. The CH₂Cl₂ extract was washed with saturated brine, and dried over anhydrous MgSO₄. Solvents were evaporated in vacuo, and the residue was purified by silica gel column chromatography (3 g; 3% AcOEt/hexane) to afford Compound 133 (36.6 mg, 99%) as a single compound.

The compound 133 (69 mg, 96%) was prepared from Compound 132a (72.5 mg, 0.140 mmol, less polar isomer) by Swern oxidation method.

133: ¹H NMR (CDCl₃) δ: 0.02, 0.06, 0.08, 0.09 (each 3H, s, Si-Me×4), 0.07 (6H, s, Si-Me×2), 0.84, 0.90, 0.91 (each 9H, s, Si-tBu×3), 2.36 (1H, dd, J=14.2, 10.2 Hz), 2.46 (1H, dd, J=14.4, 3.3 Hz), 2.51 (1H, ddd, J=14.4, 3.6, 1.9 Hz), 2.75 (1H, ddd, J=14.2, 5.6, 1.8 Hz), 4.34 (2H, m, CH₂OTBS), 4.76 (1H, m), 5.04 (1H, t, J=3.4 Hz), 5.81 (1H, m, C=CH). MS m/z (%): no M⁺, 457 (100), 325 (38), 193 (13).

Example 57

(aS*,3R,5R)-and (aR*,3R,5R)-[3,5-bis-[(t-butyldimethylsilyl)oxy]-4-[2-butyldimethylsilyl)oxy]-ethyl-cyclohexylidene]-methyl acetate (Compound 134)

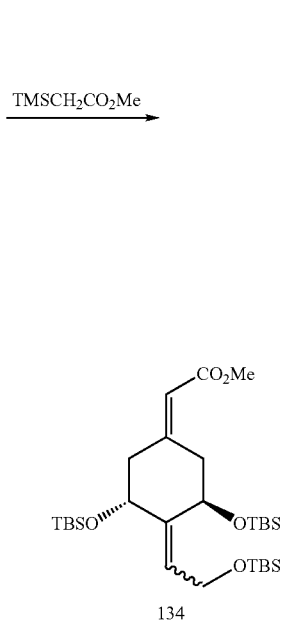

To a solution of diisopropylamine (0.385 mL, 2.64 mmol) in dry THF (4 mL) cooled to −78° C. was added n-BuLi (1.67 mL, 2.64 mmol, 1.58 M solution in hexane). After stirring for 15 min, to the solution was added methyl (trimethylsilyl) acetate (0.433 mL, 2.64 mmol). After being stirred for 10 min, to this solution was slowly added a solution of Compound 133 (680 mg, 1.32 mmol) in dry THF (8 mL), and stirring was continued for 1 h at −78° C. after which time it was quenched with a saturated NH₄Cl aqueous solution, and extracted with AcOEt. The organic phase was washed with saturated brine, dried over anhydrous MgSO₄, and evaporated in vacuo. The residue was purified by silica gel column chromatography (15 g; 2% AcOEt/hexane) to give Compound 134 (699 mg, 93%) as a mixture of two stereoisomers in ca. 3:1 ratio. It was impossible to know whether the major product was aS*,3R; 5R isomer or aR*,3R,5R isomer.

134: ¹H NMR (CDCl₃) δ: 0.04-0.12 (18H, s, Si-Me×6), 0.80-0.93 (27H, s, Si-tBu×3), 3.67, 3.70 (ca. 1:3) (3H, s,

CO₂Me), 3.90, 4.02 (ca. 1:3) (1H, m), 4.25-4.55 (4H, m), 4.87 (1H, m), 5.6-5.8 (2H, m, C=CH×2). MS m/z (%): no M⁺, 555 (3), 513 (79), 438 (33), 381 (100), 349 (8), 249 (6).

Example 58

(aS*,3R,5R)- and (aR*,3R,5R)-[3,5-bis-[(t-butyldimethylsilyl)oxy]-4-[2-butyldimethylsilyl)oxy]-ethyl-cyclohexylidene]-ethanol (Compound 135)

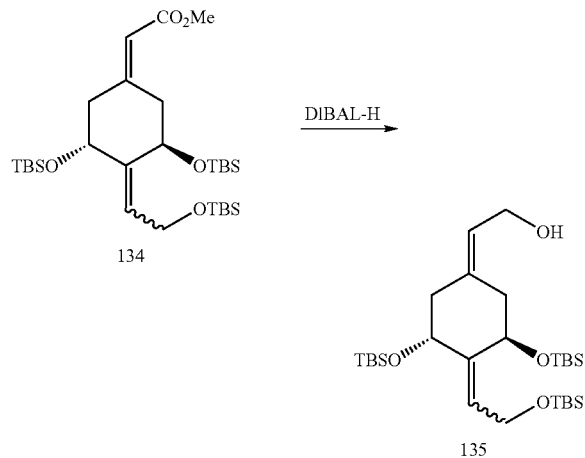

To a solution of Compound 134 (699 mg, 1.22 mmol, a mixture of ca. 3:1) in dry toluene (6 mL) cooled to −78° C. was added diisobutylaluminum hydride (3.66 mL, 3.66 mmol, 1.0 M solution in toluene), and the mixture was stirred for 1 h. Excess reagents were decomposed by adding an aqueous solution of saturated potassium sodium tartrate, and the mixture was poured into ice water, and then extracted with AcOEt. The organic layer was washed with saturated brine, and dried over anhydrous MgSO₄. Solvents were evaporated in vacuo, and the residue was purified by silica gel column chromatography (10 g; 5% AcOEt/hexane) to afford Compound 135 (567 mg, 85%) as a mixture of two stereoisomers in ca. 3:1 ratio. It was impossible to know whether the major product was aS*,3R,5R isomer or aR*,3R,5R isomer.

135: ¹H NMR (CDCl₃) δ: 0.06-0.07 (18H, Si-Me×6), 0.85-0.92 (27H, Si-tBu×3), 194-2.77 (4H, m), 4.0-4.4 (5H, m), 4.77, 4.90 (ca. 3:1) (1H, m), 5.50, 5.71 (ca. 3:1) (1H, m, C=CH), 5.60, 5.66 (ca. 3:1) (1H, m, C=CH).

Example 59

(aS*,3R,5R)- and (aR*,3R,5R)-[3,5-bis-[(t-butyldimethylsilyl)oxy]-4-[2-(t-butyldimethylsilyl)oxy]-ethyl-cyclohexylidene]ethyldiphenylphosphine oxide (Compound 119)

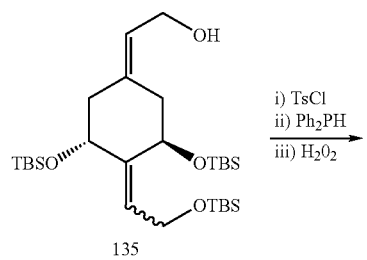

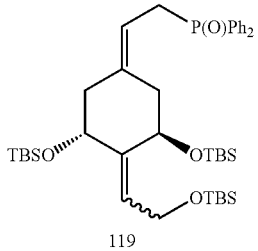

To a solution of Compound 135 (164 mg, 0.302 mmol, a mixture of ca. 3:1) in dry THF (1.5 mL) cooled to 0° C. were added n-BuLi (228 μL, 0.360 mmol, 1.58 M solution in hexane) and a solution of p-toluenesulfonyl chloride (68.6 mg, 0.360 mmol) in dry THF (0.5 mL) in this order, and the mixture was stirred for 5 min. To this solution of the tosylate was slowly added a red solution freshly prepared from diphenylphosphine (105 μL, 0.604 mmol) in THF (0.5 mL) and n-BuLi (382 μL, 0.604 mmol, 1.58 M solution in hexane) at 0° C. until the orange color persisted. The entire mixture was stirred for 30 min at 0° C., and quenched by adding water (0.1 mL). The solvent was evaporated in vacuo and the crude product was dissolved in CH₂Cl₂ (3 mL). To this mixture was added 10% hydrogen peroxide (4 mL). The mixture was stirred for 1 h at 0° C. and CH₂Cl₂ phase was separated. The organic layer was successively washed with a 2N Na₂SO₃ aqueous solution, water and saturated brine, and dried over anhydrous MgSO₄ After evaporation of the solvent, the residue was purified by silica gel column chromatography (7 g; 50% AcOEt/hexane) to afford Compound 119 (139 mg, 63%) as a mixture of two stereoisomers. Most of the ¹H NMR signals from two isomers were overlapped each other, and the ratio of the two isomers was not determined.

119: ¹H NMR (CDCl₃ δ: −0.02-0.05 (18H, Si-Me×6), 0.80-0.90 (27H, Si-tBu×3), 1.90-2.60 (4H, m), 3.15 (2H, m, CH₂PO), 4.20-4.38 (3H, m), 4.71 (H, m), 5.29 (1H, m, C=CH), 5.56 (1H, m, CH=C), 7.40-7,80 (10H, m, arom H).

Example 60

22-Ene-25-hydroxy Grundmann's ketone (Compound 120)

22-Ene-25-hydroxy Grundmann's ketones (120a, b) were synthesized as shown in the scheme.

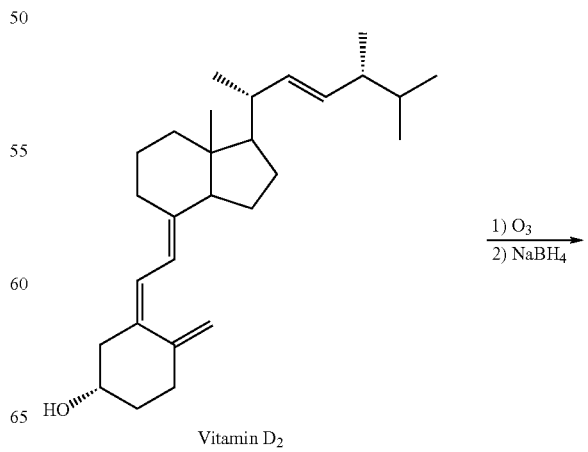

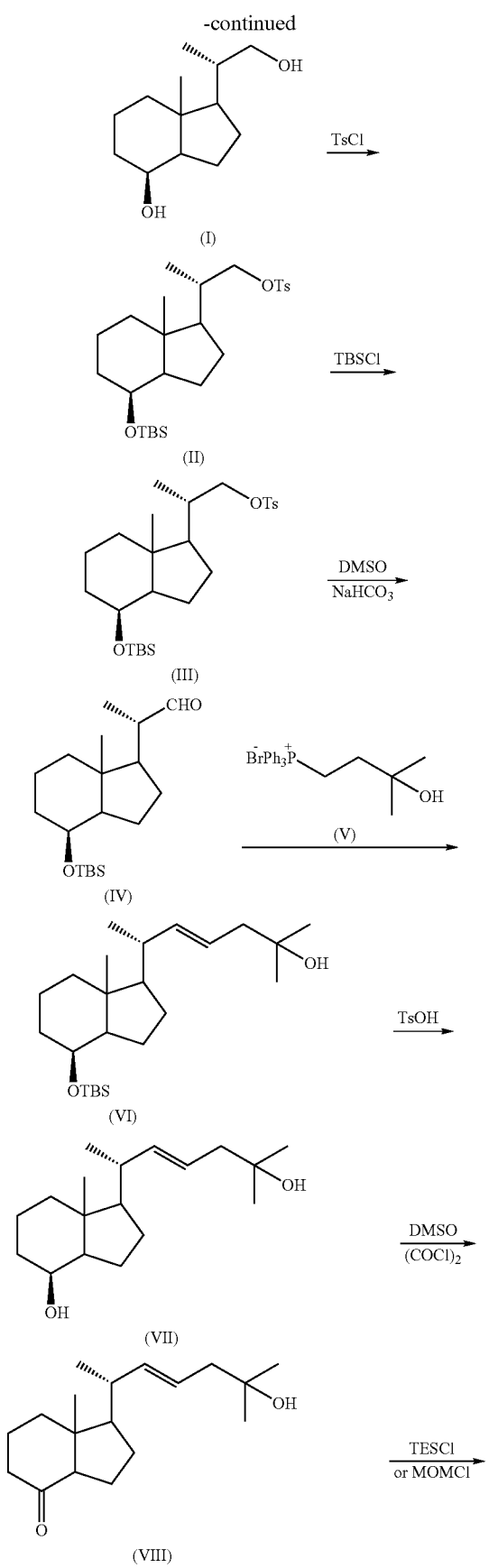

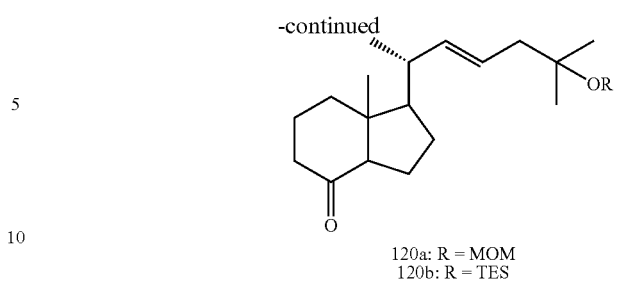

120a: R = MOM
120b: R = TES

Synthesis of 5-carbon synthon (V)

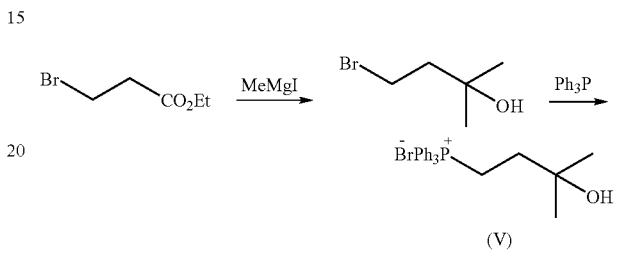

Compound (VI) was synthesized starting from commercially available vitamin $D_2$ employing the literature methods (Fernandez, B., Perez, J. A. M., Granja, J. R., Castedo, L., Mourino, A., J. Org. Chem., 1992, 57, 3173-3178 and Fall, Y., Vitale, C., Mourino, A., Tetrahedron Lett., 2000, 41, 7337-7340).

p-Toluenesulfonic acid monohydrate (1.69 g, 8.893 mmol) was added to a solution of the compound VI (1.17 g, 2.964 mmol) in MeOH (15 mL) cooled to 0° C., and the reaction mixture was stirred at 0° C. for 16 h and at room temperature for 8 h. The mixture was diluted with AcOEt, and the organic layer was successively washed with a 5% $NaHCO_3$ aqueous solution and saturated brine, and dried over anhydrous $MgSO_4$. Evaporation of the solvent gave the residue, which was purified by silica gel column chromatography (30 g; 30% AcOEt/hexane) to afford the compound VII (790.7 mg, 95%).

VII: $^1$H NMR ($CDCl_3$) δ: 0.93 (3H, s, H-18), 1.01 (3H, d, J=6.6 Hz, H-21), 1.20 (6H, s, H-26, 27), 4.08 (1H, m, H-8), 5.37 (2H, m), H-22, 23).

To a solution of oxalyl chloride (127 μL, 1.459 mmol) in dry $CH_2Cl_2$ (1 mL) cooled to −78° C. was added a solution of DMSO (206 μL, 2.917 mmol) in dry $CH_2Cl_2$ (0.5 mL). After being stirred for 10 min, a solution of the compound VII (186 mg, 0.663 mmol) in dry $CH_2Cl_2$ (2 mL) was added. The reaction mixture was stirred for 15 min at −78° C., and $Et_3N$ (924 μL, 6.63 mmol) was added. The whole mixture was warmed from −78° C. to 0° C. at which point the reaction was quenched with ice water, and extracted with $CH_2Cl_2$. The $CH_2Cl_2$ extract was washed with saturated brine, dried over anhydrous $MgSO_4$, and evaporated to dryness. The residue was purified by silica gel column chromatography (7 g; 25% AcOEt/hexane) to afford the compound VIII (178.0 mg, 96%).

VIII: $^1$H NMR ($CDCl_3$) δ: 0.67 (3H, s, H-18), 1.07 (3H, d, J=6.6 Hz, H-21), 1.20 (6H, s, H-26, 27), 5.37 (2H, m, H-22, 23).

To a solution of the compound VIII (178.0 mg, 0.639 mmol) in dry $CH_2Cl_2$ (2 mL) cooled to 0° C. was added diisopropylethylamine (557 μL, 3.196 mmol) followed by chloromethyl methyl ether (121 μL, 1.596 mmol). After stirring for 3 h at room temperature, additional diisopropylethylamine (111 μL, 0.639 mmol) and chloromethyl methyl ether (24 μL, 0.320 mmol) were added, and the whole mixture was further stirred at room temperature for 1.5 h. The mixture was poured into ice water, and extracted with CH$_2$Cl$_2$. The organic phase was successively washed with 5% NaHCO$_3$ and saturated brine, and dried over anhydrous MgSO$_4$. Evaporation of the solvent afforded a residue, which was purified by silica gel column chromatography (7 g; 10% AcOEt/hexane) to give Compound 120a (154.2 mg, 75%).

120a: $^1$H NMR (CDCl$_3$) δ: 0.65 (3H, s, H-18), 1.05 (3H, d, J=6.7 Hz, H-21), 1.19 (6H, s, H-22, 23).

To a solution of the compound VIII (710.4 mg, 2.55 mmol) in dry DMF (10 mL) cooled to 0° C. were added imidazole (520.8 mg, 7.65 mmol) followed by chlorotriethylsilane (868 μL, 5.10 mmol). After being stirred for 2.5 h, the reaction mixture was poured into ice water, and extracted with AcOEt-hexane (v/v, 1:1). The organic phase was washed with saturated brine, and dried over anhydrous MgSO$_4$. Solvents were evaporated in vacuo, and the residue was purified by silica gel column chromatography (30 g; 4% AcOEt/hexane) to give Compound 120b (887.5 mg, 89%).

120b: $^1$H NMR (CDCl$_3$) δ: 0.57 (6H, q, J=7.9 Hz, SiCH$_2$× 3), 0.66 (3H, s, H-18), 0.95 (9H, t, J=7.9 Hz, SiCH$_2$CH$_3$×3), 1.05 (3H, d, J=6.7 Hz, H-21), 1.16 (6H, s, H-26, 27), 2.45 (1H, dd, J=11.0, 7.5 Hz, H-9), 5.24, 5.40 (each 1H, m, H-22, 23).

Example 61

22-Oxa-25-hydroxy Grundmann's ketone (Compound 121)

22-Oxa-25-hydroxy Grundmann's ketone (121) was synthesized as shown in the scheme.

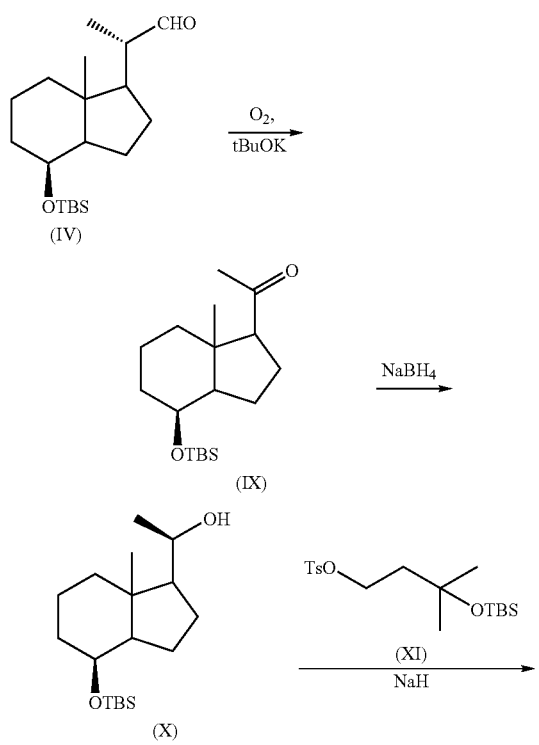

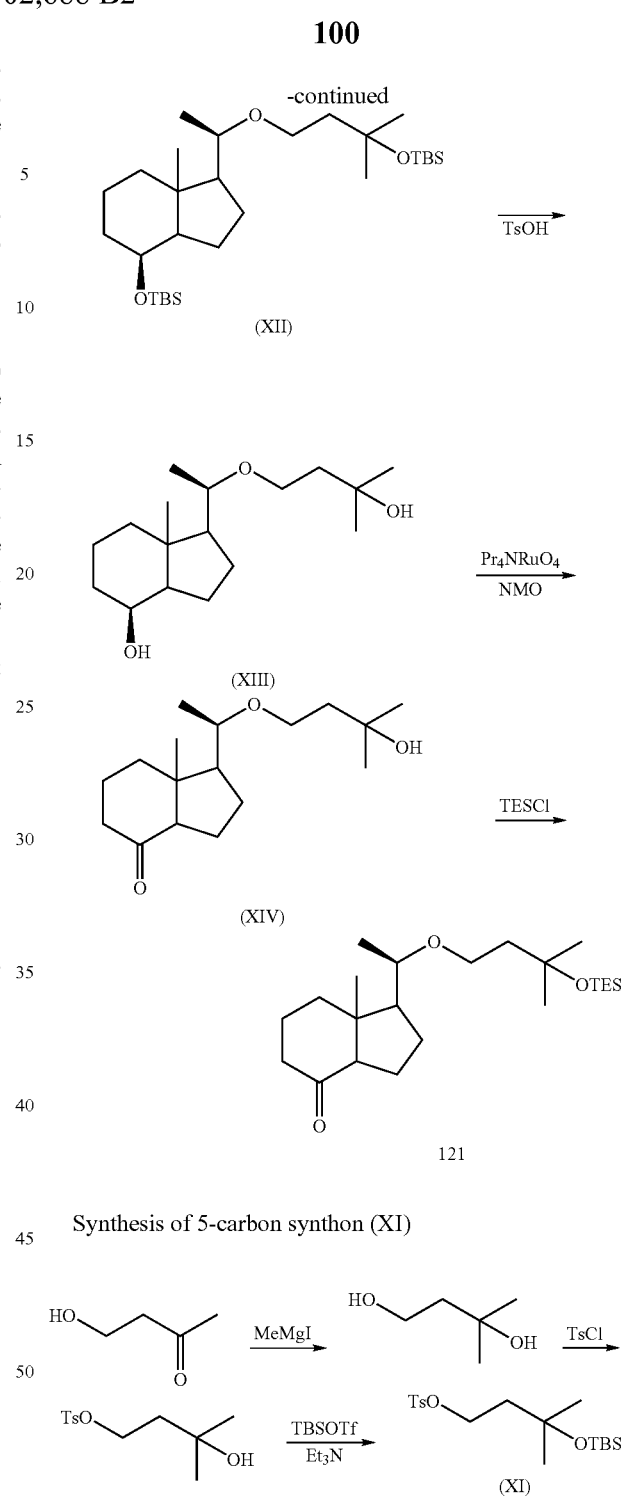

Synthesis of 5-carbon synthon (XI)

The compound X was prepared from vitamin D$_2$ according to the published methods (Posner, G. H., Lee, J. K., White, M. C., Hutchings, R. H., Dai, H., Kachinski, J. L., Dolan, P., Kensler, T. W., J. Org. Chem., 1997, 62, 3299-3314).

To a solution of the compound X (800 mg, 2.56 mmol) and the compound XI (4.77 g, 12.80 mmol) in dry DMF (30 mL) was added NaH (3.07 g, 76.77 mmol, 60% paraffin liquid), and the resulting suspension was stirred at room temperature for 16 h. The whole mixture was poured into ice water, and extracted with AcOEt-hexane. (v/v, 1:1). The organic layer was washed with saturated brine, and dried over anhydrous MgSO$_4$. After evaporation of the solvent, the residue was purified by silica gel column chromatography (85 g; 1% AcOEt/hexane) to yield the compound XII (1.135 g, 86%).

XII: $^1$H NMR (CDCl$_3$) δ: −0.01, 0.01, 0.06, 0.07 (each 3H, s, Si-Me×4), 0.85, 0.89 (each 9H, s, Si-tBu×2), 0.93 (3H, s, H-18), 1.05 (3H, d, J=6.0 Hz, H-21), 1.21, 1.22 (each 3H, s, H-26, 27), 3.27 (1H, m, H-20), 3.31, 3.68 (each 1H, m, H-23), 4.00 (1H, m, H-8). MS m/z (%): 512 (no M$^+$), 455 (1), 497 (1), 380 (1), 323 (3), 295 (20), 237 (100), 163 (89), 75 (81).

A mixture of the compound XII (1.13 g, 2.20 mmol) and p-toluenesulfonic acid monohydrate (2.10 g, 11.01 mmol) in MeOH (10 mL) was stirred at room temperature for 8 h. The mixture was diluted with AcOEt, and the organic phase was successively washed with a 5% NaHCO$_3$ aqueous solution and saturated brine, and dried over anhydrous MgSO$_4$. Evaporation of the solvent gave the residue, which was purified by silica gel column chromatography (30 g; 30% AcOEt/hexane) to afford the compound XIII (610.2 mg, 97%).

XIII: $^1$H NMR (CDCl$_3$) δ: 0.95 (3H, s, H-18), 1.11 (3H, d, J=6.0 Hz, H-21), 1.23, 1.24 (each 3H, s, H-26, 27), 3.30 (1H, m, H-20), 3.46 (1H, m, H-23), 3.59 (1H, s, OH), 3.85 (1H, dt, J=9.5, 4.1 Hz, H-23), 4.09 (1H, m, H-8). MS m/z (%): 248 (M$^+$, 2), 226 (1), 197 (6), 181 (21), 163 (84), 113 (45), 69 (100).

To a mixture of the compound XIII (742.7 mg, 2.611 mmol), 4-methylmorpholine N-oxide (2.14 g, 18.28 mmol) and Molecular sieves, 4A (450 mg) in dry CH$_2$Cl$_2$ (15 mL) was added tetrapropylammonium perruthenate (Pr$_4$NRuO$_4$, 45.9 mg, 0.131 mmol), and the whole mixture was stirred at room temperature for 1 h. The reaction mixture was directly loaded onto silica gel column (30 g). The column was eluted with 50% AcOEt/hexane to give the compound XIV (722.8 mg, 98%).

XIV: $^1$H NMR (CDCl$_3$) δ: 0.65 (3H, s, H-18), 1.15 (3H, d, J=5.9 Hz, H-21), 1.24, 1.25 (each 3H, s, H-26, 27), 2.47 (1H, m, H-9), 3.25 (1H, m, H-20), 3.45 (1H, m, H-23), 3.44 (1H, s, OH), 3.88 (1H, dt, J=9.6, 4.2 Hz, H-23). MS m/z (%): 282 (M$^+$, 1), 264 (2), 195 (23), 179 (69), 161 (41), 113 (29), 69 (100).

Imidazole (1.04 g, 15.30 mmol) followed by chlorotriethylsilane (1.3 mL, 7.65 mmol) was added to a solution of the compound XIV (720.2 mg, 2.550 mmol) in dry DMF (10 mL) cooled to 0° C. The reaction mixture was allowed to warm to room temperature, and stirred for 2 h, poured into ice water, and extracted with AcOEt-hexane (v/v, 1:1). The organic layer was washed with saturated brine, dried over anhydrous MgSO$_4$, and evaporated in vacuo. The residue was purified by silica gel column chromatography (35 g; 2% AcOEt/hexane) to yield Compound 121 (1.005 g, 99%).

121: $^1$H NMR (CDCl$_3$) δ: 0.57 (6H, q, J=7.9 Hz, SiCH$_2$×3), 0.65 (3H, s, H-18), 0.94 (9H, t, J=7.9 Hz, SiCH$_2$CH$_3$×3), 1.10 (3H, d, J=5.9 Hz, H-21), 1.22, 1.24 (each 3H, s, H-26, 27), 2.45 (1H, dd, J=11.0, 7.5 Hz, H-14), 3.24 (1H, m, H-20), 3.31, 3.73 (each 1H, m, H-23).

Example 62

24a,26a,27a-Trihomo-22,24-diene-25-hydroxy Grundmann's ketone (Compound 122)

24a,26a,27a-Trihomo-22,24-diene-25-hydroxy Grundmann's ketone (Compound 122) was synthesized according to the published methods (Posner, G. H., Lee, J. K., White, M. C., Hutchings, R. H., Dai, H., Kachinski, J. L., Dolan, P., Kensler, T. W., J. Org. Chem., 1997, 62, 3299-3314).

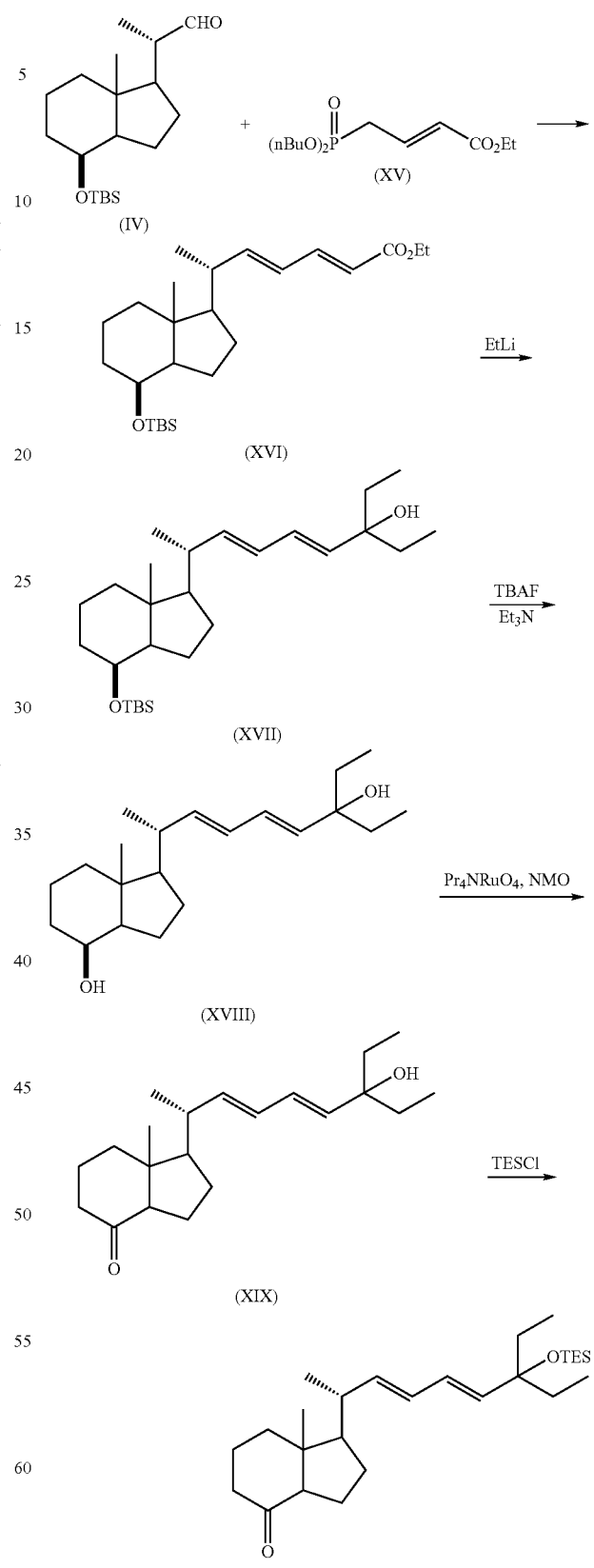

Synthesis of Wittig-Horner Reagent (XV)

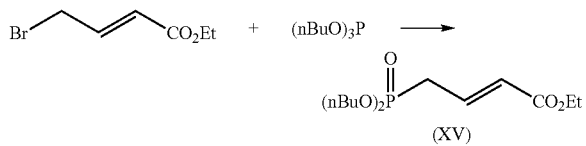

Example 63

1α-[(t-butyldimethylsilyl)oxy]-2α-[(trimethylsilyl)oxy]- and 1α-[(t-butyldimethylsilyl)oxy]-2β-[(trimethylsilyl)oxy]-22-ene-25-[(methoxymethyl)oxy]-19-norvitamin D₃ t-butyldimethylsilyl ether (Compounds 136a and 136b)

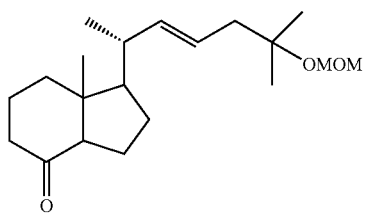

120a

+

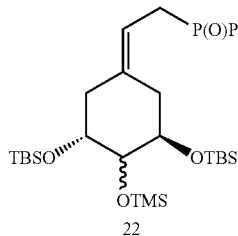

22 nBuLi →

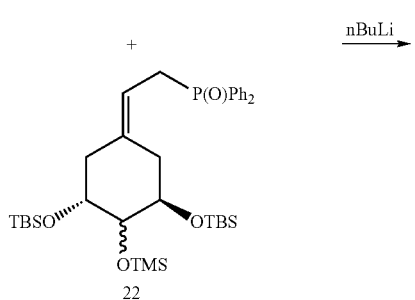

136a

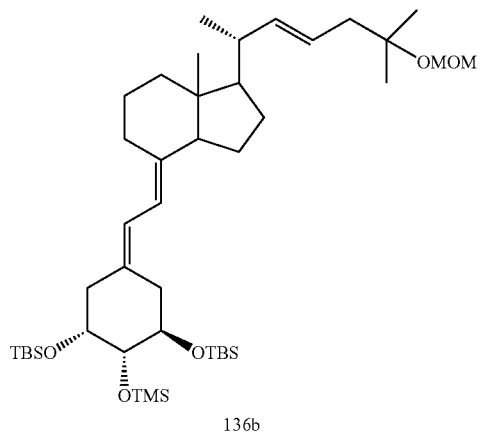

136b

To a solution of A-ring phosfine oxide 22 (268.2 mg, 0.407 mmol, a mixture of ca. 2:1) in dry THF (2 mL) cooled to −78° C. was added slowly n-BuLi (261 μL, 0.407 mmol, 1.56 M solution in hexane), and the resulting dark orange solution was stirred for 15 min. To this colored solution was added a solution of C/D-ring ketone 120a (87.5 mg, 0.271 mmol) in dry THF (1 mL), the reaction mixture was stirred for 2 h at −78° C., quenched with a saturated NH₄Cl aqueous solution, and extracted with AcOEt. The AcOEt layer was washed with saturated brine, dried over anhydrous MgSO₄, and evaporated in vacuo. The residue was purified by silica gel column chromatography (10 g; 2% AcOEt/hexane) to afford Compound 136 (116.1 mg, 56%) as a mixture of two stereoisomers. The ratio of the isomers 136a and 136b constituting the mixture was ca. 5:4. An elution of 10% AcOEt/hexane gave the unreacted starting material 120a (11.6 mg).

NMR Data of the Mixture 136a (major product): $^1$H NMR (CDCl₃) δ: 0.04-0.06 (12H, s, Si-Me×4), 0.12 (9H, s, Si-Me×3), 0.55 (3H, s, H-18), 0.87, 0.88 (each 9H, s, Si-tBu×2), 1.02 (3H, d, J=6.6 Hz, H-21), 1.20 (6H, s, H-26, 27), 2.80 (1H, m, H-9), 3.37 (3H, s, OMe), 3.54 (1H, m, H-2), 3.80 (1H, m, H-3), 3.87 (1H, m, H-1), 4.73 (2H, s, OCH₂O), 5.33 (2H, m, H-22, 23), 5.81 (1H, d, J=11.1 Hz, H-7), 6.10 (1H, d, J=11.1 Hz, H-6).

136b (minor product): $^1$H NMR (CDCl₃) δ: 0.04-0.06 (12H, s, Si-Me×4), 0.12 (9H, s, Si-Me×3), 0.54 (3H, s, H-18), 0.86, 0.89 (each 9H, s, Si-tBu×2), 1.02 (3H, d, J=6.6 Hz, H-21), 1.02 (6H, s, H-26, 27), 2.80 (1H, m, H-9), 3.37 (3H, s, OMe), 3.60 (1H, m, H-2), 3.80 (1H, m, H-3), 3.93 (1H, m, H-1), 4.73 (2H, s, OCH₂O), 5.33 (2H, m, H-22, 23), 5.79 (1H, d, J=11.2 Hz, H-7), 6.13 (1H, d, J=11.2 Hz, H-6). MS m/z (%) of the mixture: 762 (M⁺, 18), 700 (28), 630 (39), 568 (57), 511 (18), 465 (25), 309 (36), 147 (35), 109 (56), 75 (100).

Example 64

1α-[(t-butyldimethylsilyl)oxy]-2β-hydroxy-and 1α-[(t-butyldimethylsilyl)oxy]-2β-hydroxy-22-ene-25-[(methoxymethyl)oxy]-19-norvitamin D₃ t-butyldimethylsilyl ether (Compounds 137a and 137b)

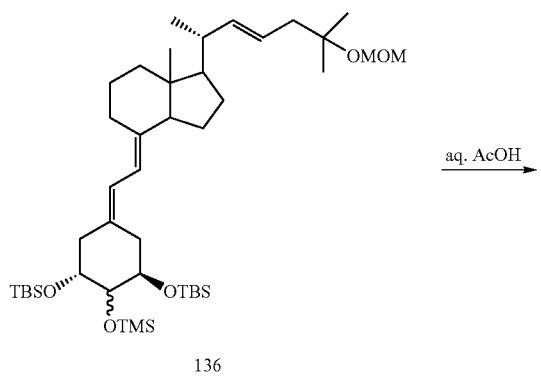

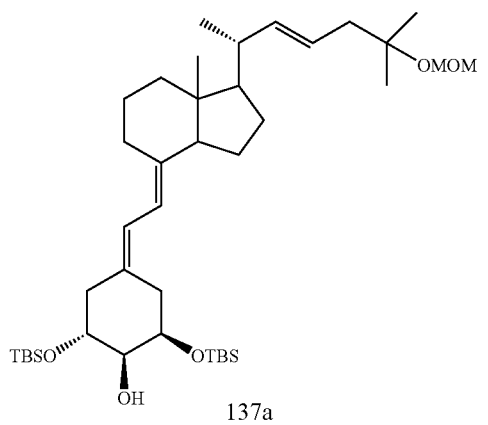

A solution of Compound 136 (60.0 mg, 0.0786 mmol, 136a:136b=ca. 5:4) in THF-AcOH—H₂O (v/v/v, 8:8:1, 4.25 mL) was stirred at room temperature for 18 h, and diluted with AcOEt. The organic phase was successively washed with a 5% NaHCO₃ aqueous solution and saturated brine, and dried over Na₂SO₄. After evaporation of the solvent, the resulting residue was purified by silica gel column chromatography (6 g;, 5% AcOEt/hexane) to afford Compound 137 (53.4 mg, 98%) as a mixture of two stereoisomers. The ratio of the isomers 137a and 137b constituting the mixture was ca. 5:4.

NMR Data of the Mixture 137a (major product): ¹H NMR (CDCl₃) δ: 0.059-0.096 (12H, Si-Me×4), 0.56 (3H, s, H-18), 0.87, 0.88 (each 9H, s, Si-tBu×2), 1.02 (3H, d, J=6.6 Hz, H-21), 1.20 (6H, s, H-26, 27), 2.80 (1H, m, H-9), 3.37 (3H, s, OMe), 3.51 (1H, m, H-2), 3.90, (1H, m, H-3), 3.99 (1H, m, H-1), 4.73 (2H, s, OCH₂O), 5.33 (2H, m, H-22, 23), 5.79 (1H, d, J=11.1 Hz, H-7), 6.15 (1H, d, J=11.1 Hz, H-6).

137b (minor product): ¹H NMR (CDCl₃) δ: 0.06-0.10 (12H, Si-Me×4), 0.54 (3H, s, H-18), 0.86, 0.90 (each 9H, s, Si-tBu×2), 1.02 (3H, d, J=6.6 Hz, H-21), 1.20 (6H, s, H-26, 27), 2.80 (1H, m, H-9), 3.37 (3H, s, OMe), 3.59 (1H, m, H-2), 3.99 (2H, m, H-1, 3), 4.73 (2H, s, OCH₂O), 5.33 (2H, m, H-22, 23), 5.80 (1H, d, J=11.2 Hz, H-7), 6.18 (1H, d, J=11.2 Hz, H-6). MS m/z (%) of the mixture: 690 (M⁺, 6), 628 (9), 571 (7), 439 (29), 309 (11), 109 (63) 75 (100).

Example 65

1α-[(t-butyldimethylsilyl)oxy]-2α-[2-(t-butyldimethylsilyl)oxy]-ethoxy]-and 1α-[(t-butyldimethylsilyl)oxy]-2β-[2-(t-butyldimethylsilyl)oxy]-ethoxy]-22-ene-25-[(methoxymethyl)oxy]-19-norvitamin D₃ t-butyldimethylsilyl ether (Compounds 138a and 138b)

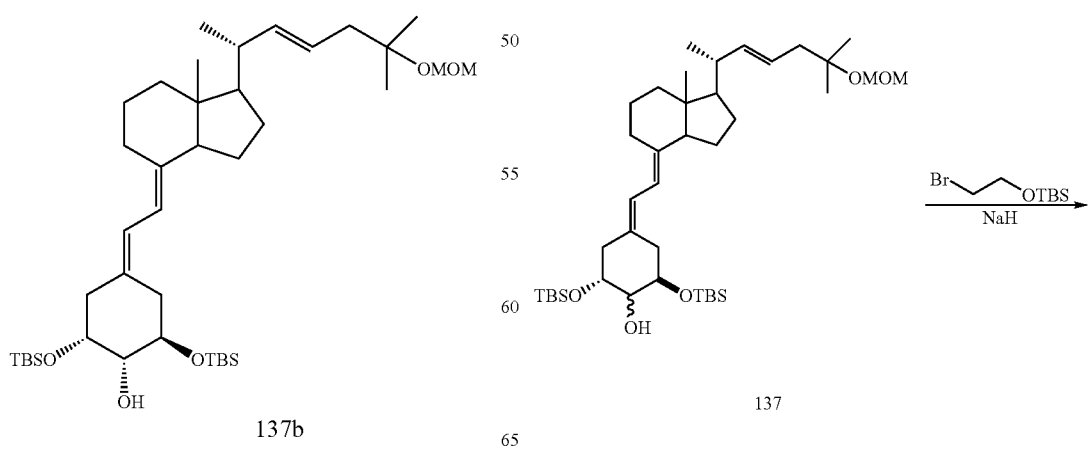

107

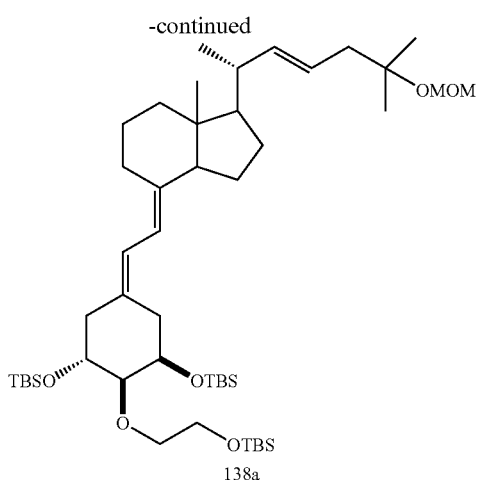

138a

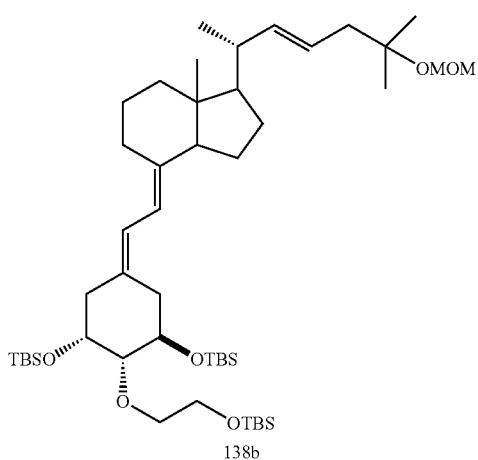

138b

A suspension of Compound 137 (44.3 mg, 0.064 mmol, 137a:137b=ca. 5:4), NaH (77.0 mg, 1.925 mmol, 60% paraffin liquid), and (2-bromoethoxy)-tert-butyldimethylsilane (69 μl, 0.320 mmol) in dry DMF (1 mL) cooled to 0° C. was stirred vigorously for 20 h, and the reaction mixture was poured into ice water, and then extracted with AcOEt-hexane (v/v, 1:1). The organic phase was washed with saturated brine, and dried over anhydrous $MgSO_4$. Following evaporation of the solvent in vacuo, the residue was purified by silica gel column chromatography (10 g; 2% AcOEt/hexane) to afford Compound 138 (45.0 mg, 83%) as a mixture of two stereoisomers. The ratio of the isomers 138a and 138b constituting the mixture was ca. 1:1.

138: $^1$H NMR ($CDCl_3$) δ: 0.05-0.09 (18H, Si-Me×6), 0.54, 0.56 (ca. 1:1) (3H, s, H-18), 0.86-0.91 (27H, Si-tBu×3), 1.02 (3H, d, J=6.6 Hz, H-21), 1.24 (6H, s, H-26, 27), 2.80 (1H, m, H-9), 3.19, 3.28 (ca. 1:1) (1H, m, H-2), 3.37 (3H, s, OMe), 3.5-4.1 (7H, m, $OCH_2CH_2O$, H-1, 3), 4.73 (2H, s, $OCH_2O$), 5.32 (2H, m, H-22, 23), 5.79 (1H, H-7), 6.13 (1H, H-6). MS m/z (%): no M$^+$, 786 (1), 716 (4), 654 (8), 610 (8), 553 (5), 522 (10), 465 (12), 233 (60), 109 (28), 75 (100).

108

Example 66

1α,25-dihydroxy-2α-(2-hydroxyethoxy)-and 1α,25-dihydroxy-2β-(2-hydroxyethoxy)-22-ene-19-norvitamin $D_3$ (Compounds 101a and 101b)

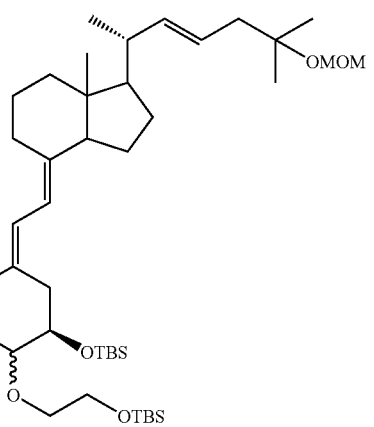

138

CSA →

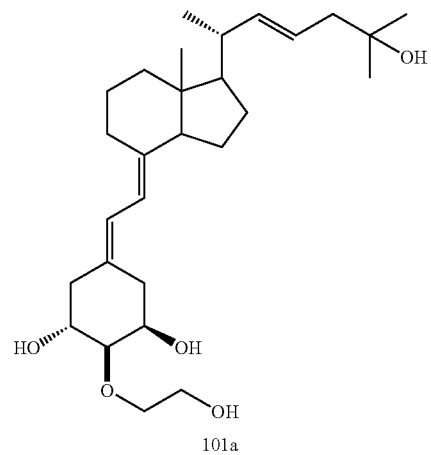

101a

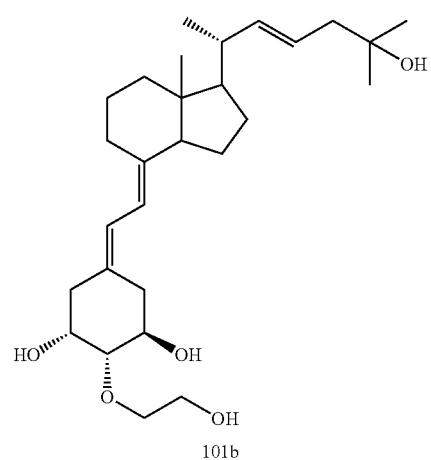

101b

A mixture of Compound 138 (45.0 mg, 0.053 mmol, 138a: 138b=ca. 1:1) and camphor sulfonic acid (73.8 mg, 0.318 mmol) in dry MeOH (1 mL) was stirred at room temperature for 2 h. The reaction mixture was poured into a 5% NaHCO$_3$ aqueous solution, and extracted with AcOEt. The organic phase was washed with saturated brine, dried over anhydrous MgSO$_4$, and evaporated in vacuo. The residue was purified by silica gel column chromatography (4 g; 2% MeOH/AcOEt) to give Compound 101 (20.3 mg, 83%) as a mixture of ca. 1:1.

The mixture of Compounds 101 a and 101 b was separated by HPLC (YMC-Pack ODS-AM SH-342-5, 150×20 mm, 25% H$_2$O in MeOH) to afford Compounds 101a (8.3 mg) and 101b (7.9 mg), respectively.

101a: $^1$H NMR (CDCl$_3$) δ: 0.57 (3H, s, H-18), 1.04 (3H, d, J=6.6 Hz, H-21), 1.20 (6H, s, H-26, 27), 2.67, 3.03, 3.33 (each 1H, br. s, OH×3), 2.62 (1H, dd, J=13.5, 4.5 Hz, H-4), 2.79 (1H, m, H-9), 2.86 (1H, dd, J=14.4, 4.9 Hz, H-10), 3.33 (1H, dd, J=8.0, 2.8 Hz, H-2), 3.68-3.83 (4H, m, OCH$_2$CH$_2$O), 3.94 (1H, m, H-3), 4.15 (1H, m, H-1), 5.38 (2H, m, H-22, 23), 5.82 (1H, d, J=11.2 Hz, H-7), 6.33 (1H, d, J=11.2 Hz, H-6). UV λmax (EtOH): 244 (ε 27,400), 252 (ε 32,000), 261 (ε 21,700) nm. MS m/z (%): 462 (M$^+$, 55), 444 (58), 426 (43), 408 (22), 346 (32), 317 (68), 299 (39), 255 (69), 237 (76), 133 (100). HR-MS m/z: 462.3348 (Calcd for C$_{28}$H$_{46}$O$_5$: 462.3345).

101b: $^1$H NMR (CDCl$_3$) δ: 0.56 (3H, s, H-18), 1.04 (3H, d, J=6.6 Hz, H-21), 1.20 (6H, s, H-26, 27), 2.34 (1H, br. d, J=14.2 Hz, H-4), 2.48 (1H, dm, J=14.2 Hz, H-4), 2.62 (1H, br. s, OH), 2.79 (1H, m, H-9), 3.07 (1H, dd, J=13.2, 3.8 Hz, H-10), 3.28 (1H, dd, J=8.7, 2.7 Hz, H-2), 3.28, 3.42 (each 1H, br. s, OH×2), 3.64-3.87 (5H, m, OCH$_2$CH$_2$O, H-1), 4.17 (1H, m, H-3), 5.39 (2H, m, H-22, 23), 5.84 (1H, d, J=11.2 Hz, H-7), 6.27 (1H, d, J=11.2 Hz, H-6). UV λmax (EtOH): 243 (ε 27,700), 251 (ε 32,300), 261 (ε 21,600) nm. MS m/z (%): 462 (M$^+$, 41), 444 (44), 426 (37), 408 (17), 346 (39), 317 (55), 299 (29), 255 (59), 237 (75), 133 (100). HR-MS m/z: 462.3362 (Calcd for C$_{28}$H$_{46}$O$_5$: 462.3345).

Example 67

1α-[(t-butyldimethylsilyl)oxy]-2-oxo-22-ene-25-[(methoxymethyl)oxy]-19-norvitamin D$_3$ t-butyldimethylsilyl ether (Compound 139)

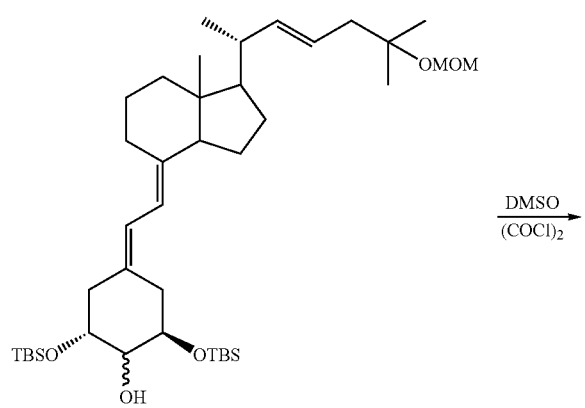

137

-continued

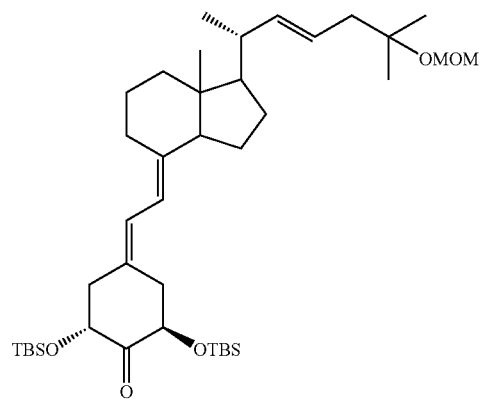

139

To a solution of oxalyl chloride (7.8 μL 0.088 mmol) in dry CH$_2$Cl$_2$ (1 mL) cooled to −78° C. was added a solution of DMSO (12.4 μL, 0.175 mmol) in dry CH$_2$Cl$_2$ (0.2 mL). After being stirred for 5 min, a solution of Compound 137 (50.4 mg, 0.073 mmol, 137a: 137b=ca. 5:4) in dry CH$_2$Cl$_2$ (1.2 mL) was added. The reaction mixture was stirred for 15 min at −78° C., and Et$_3$N (51 μL, 0.365 mmol) was added. The whole mixture was stirred at −78° C. for 40 min and at 0° C. for 20 min, quenched with ice water, and extracted with CH$_2$Cl$_2$. The CH$_2$Cl$_2$ extract was washed with saturated brine, dried over anhydrous MgSO$_4$, and concentrated in vacuo. The residue was purified by silica gel column chromatography (5 g; 5% AcOEt/hexane) to afford Compound 139 (49.0 mg, 97%) as a single compound.

139: $^1$H NMR (CDCl$_3$) δ: 0.055, 0.065, 0.069, 0.094 (each 3H, s, Si-Me×4), 0.56 (3H, s, H-18), 0.88, 0.89 (each 9H, s, Si-tBu×2), 1.03 (3H, d, J=6.6 Hz, H-21), 1.20 (6H, s, H-26, 27), 2.44 (1H, dd, J=13.3, 8.9 Hz), 2.52 (1H, dd, J=14.2, 3.8 Hz), 2.69 (2H, m), 2.81 (1H, m, H-9), 3.37 (3H, s, OMe), 4.35 (1H, dd, J=6.4, 4.2 Hz), 4.55 (1H, dd, J=8.7, 5.5 Hz), 4.73 (2H, s, OCH$_2$O), 5.34 (2H, m, H-22, 23), 5.80 (1H, d, J=11.2 Hz, H-7), 6.34 (1H, d, J=11.2 Hz, H-6). MS m/z (%): no M$^+$, 631 (5), 569 (100), 437 (22), 325 (17), 109 (81), 75 (52).

Example 68

E-isomer and Z-isomer of 1α-[(t-butyldimethylsilyl)oxy]-2-cyanomethylene-22-ene-25-[(methoxymethyl)oxy]-19-norvitamin $D_3$ t-butyldimethylsilyl ether (Compounds 140a and 140b)

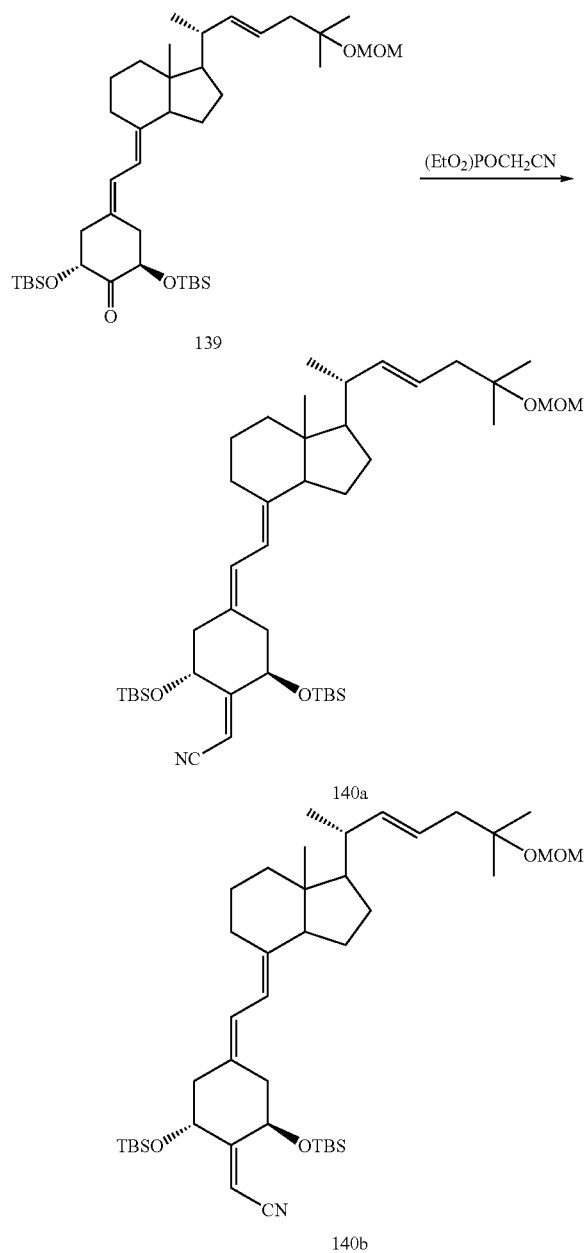

To a solution of diethyl (cyanomethyl)phosphonate (32 μL, 0.197 mmol) in dry THF (1 mL) cooled to −40° C. was added n-BuLi (126 μL, 0.197 mmol, 1.56 M solution in hexane). The mixture was stirred for 15 min, and a solution of Compound 139 (68.0 mg, 0.099 mmol) in dry THF (1.2 mL) was added slowly. Stirring was continued for 2 h at −40° C. after which time the reaction mixture was quenched with a saturated $NH_4Cl$ aqueous solution, and extracted with AcOEt. The AcOEt layer was washed with saturated brine, and dried over anhydrous $MgSO_4$. Evaporation of the solvent gave the residue, which was purified by silica gel column chromatography (5 g; 3% AcOEt/hexane) to afford Compound 140 (59.6 mg, 85%) as a mixture of two stereoisomers. The ratio of the isomers 140a (E-isomer) and 140b (Z-isomr) constituting the mixture was ca. 1:1.

NMR Data of the Mixture

140a: $^1$H NMR (CDCl$_3$) δ: 0.054, 0.065, 0.094, 0.120 (each 3H, s, Si-Me×4), 0.56 (3H, s, H-18), 0.84, 0.92 (each 9H, s, Si-tBu×2), 1.02 (3H, d, J=6.6 Hz, H-21), 1.20 (6H, s, H-26, 27), 2.80 (1H, m, H-9), 3.12 (1H, m, H-10), 3.37 (3H, s, OMe), 4.46 (1H, m, H-1), 4.73 (2H, s, OCH$_2$O), 4.99 (1H, t, J=2.8 Hz, H-3), 5.33 (2H, m, H-22, 23), 5.47 (1H, d, J=1.8 Hz, C═CHCN), 5.82 (1H, d, J=11.1 Hz, H-7), 6.18 (1H, d, J=11.1 Hz, H-6).

140b: $^1$H NMR (CDCl$_3$) δ: 0.065, 0.075, 0.111, 0.133 (each 3H, s, Si-Me×4), 0.55 (3H, s, H-18), 0.84, 0.92 (each 9H, s, Si-tBu×2), 1.02 (3H, d, J=6.6 Hz, H-21), 1.20 (6H, s, H-26, 27), 2.80 (1H, m, H-9), 2.99 (1H, m, H-10), 3.37 (3H, s, OMe), 4.57 (1H, m, H-3), 4.73 (2H, s, OCH$_2$O), 5.04 (1H, t, J=2.8 Hz, H-1), 5.33 (2H, m, H-22, 23), 5.47 (1H, d, J=1.8 Hz, C═CHCN), 5.78 (1H, d, J=11.1 Hz, H-7), 6.31 (1H, d, J=11.1 Hz, H-6). MS m/z (%) of the mixture: 711 (M$^+$, 5), 649 (18), 592 (61), 565 (76), 517 (20), 408 (26), 109 (92), 75 (99), 73 (100).

Example 69

E-isomer and Z-isomer of 1α-[(t-butyldimethylsilyl)oxy]-2-[2-(formyl)-ethylidene]-22-ene-25-[(methoxymethyl)oxy]-19-norvitamin $D_3$ t-butyldimethylsilyl ether (Compounds 141a and 141b)

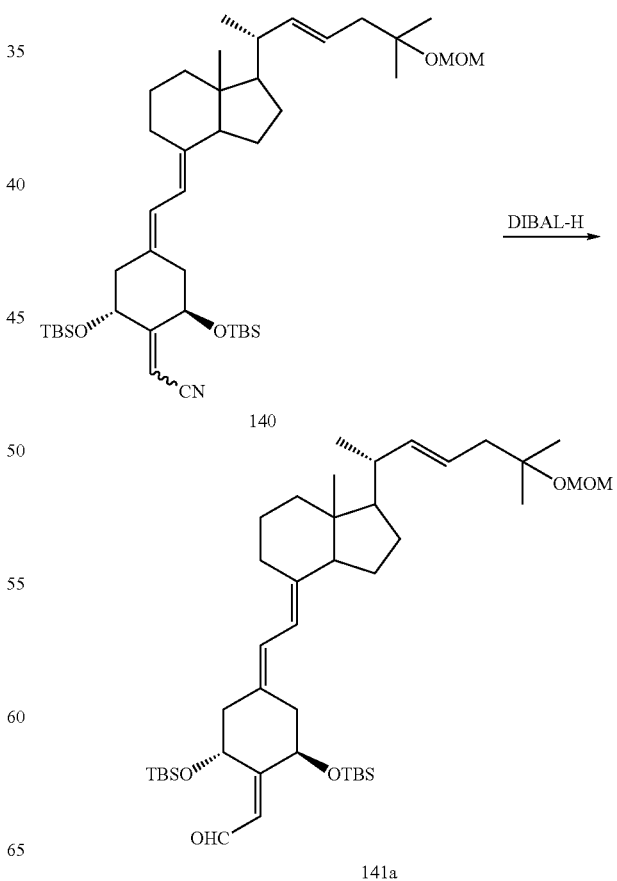

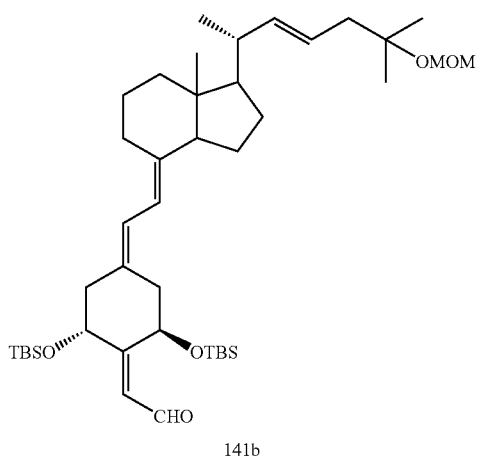

141b

Example 70

E-isomer and Z-isomer of 1α-[(t-butyldimethylsilyl)oxy]-2-[2-(hydroxy)-ethylidene]-22-ene-25-[(methoxymethyl)oxy]-19-norvitamin $D_3$ t-butyldimethylsilyl ether (Compounds 142a and 142b)

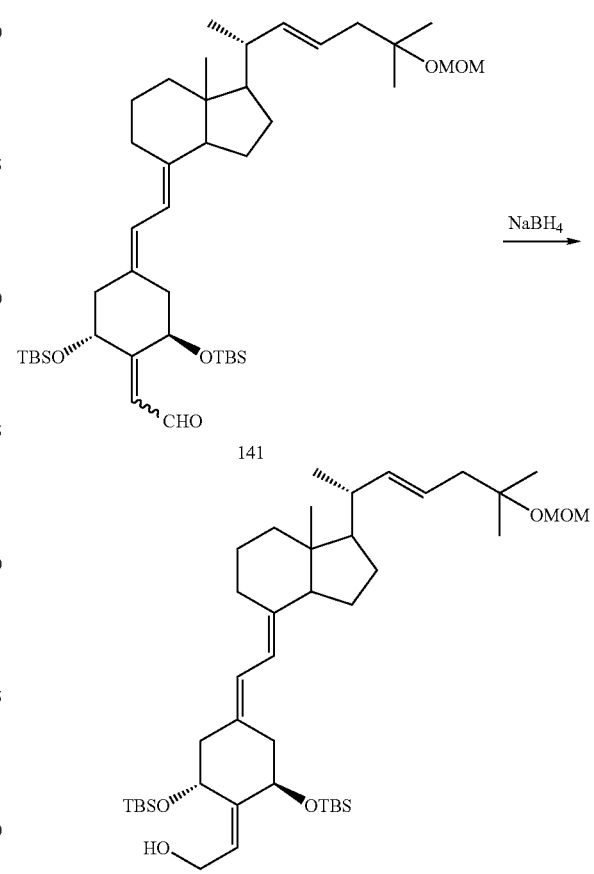

To a solution of Compound 140 (59.6 mg, 0.084 mmol, 140a:140b=ca. 1:1) in dry toluene (1 mL) cooled to −78° C. was added diisobutylaluminum hydride (126 μL, 0.126 mmol, 1.0 M solution in hexane), and the mixture was stirred for 1.5 h at the same temperature. The reaction mixture was diluted with hexane, and directly loaded onto silica gel column (5 g). The column was eluted with 5% AcOEt/hexane to afford Compound 141 (56.0 mg, 94%) as a mixture of two stereoisomers. The ratio of the isomers 141a (E-isomer) and 141b (Z-isomer)-constituting the mixture was ca. 1:1.

NMR Data of the Mixture

141a: $^1$H NMR (CDCl$_3$) δ: 0.01 -0.10 (12H, Si-Me×4), 0.57 (3H, s, H-18), 0.84, 0.92 (each 9H, s, Si-tBu'2), 1.03 (3H, d, J=6.6 Hz, H-21), 1.20 (6H, s, H-26, 27), 2.42 (2H, m, H-4), 2.80 (1H, m, H-9), 3.05 (1H, m, H-10), 3.37 (3H, s, OMe), 4.56 (1H, m, H-1), 4.73 (2H, s, OCH$_2$O), 5.35 (2H, m, H-22, 23), 5.46 (1H, t, J=3.2 Hz, H-3), 5.79 (1H, d, J=11.4 Hz, H-7), 6.16 (1H, m, C=CH), 6.19 (1H, d, J=11.4 Hz, H-6), 10.18 (1H, d, J=7.9 Hz, CHO).

141b: $^1$H NMR (CDCl$_3$) δ: 0.01 -0.10 (12H, Si-Me×4), 0.56 (3H, s, H-18), 0.84, 0.93 (each 9H, s, Si-tBu×2), 1.03 (3H, d, J=6.6 Hz, H-21), 1.20 (6H, s, H-26, 27), 2.65 (1H, m, H-4), 2.80 (1H, m, H-9), 3.00 (1H, m, H-10), 3.37 (3H, s, OMe), 4.70 (1H, m, H-3), 4.73 (2H, s, OCH$_2$O), 5.35 (2H, m, H-22, 23), 5.53 (1H, m, H-1), 5.84 (1H, d, J=11.3 Hz, H-7), 6.17 (1H, m, C=CH), 6.31 (1H, d, J=11.3 Hz, H-6), 10.16 (1H, d, J=7.9 Hz, CHO). MS m/z (%) of the mixture: 714 (M$^+$, 9), 652 (13), 595 (20), 582 (13), 520 (34), 491 (23), 463 (14), 411 (17), 109 (33), 75 (100).

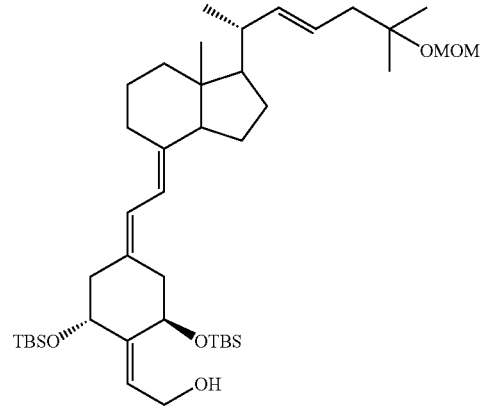

NaBH$_4$ (3.6 mg, 0.094 mmol) was added to a solution of Compound 141 (56.0 mg, 0.078 mmol, 141a:141b=ca. 1:1) in MeOH-THF (v/v, 2:1, 1.5 mL) cooled to 0° C. After being stirred for 1 h at 0° C., into the mixture was poured ice water, and extracted with AcOEt. The organic layer was washed with saturated brine, dried over anhydrous MgSO$_4$, and evaporated in vacuo. The residue was purified by silica gel column chromatography (6 g; 8% AcOEt/hexane) to give Compounds 142a (26.3 mg, E-isomer) and 142b (22.7 mg, Z-isomer). The total yield was 87%.

NMR Data of the Mixture

142a: $^1$H NMR (CDCl$_3$) δ: 0.02, 0.06, 0.08 (3H, 3H, 6H, s, Si-Me×4), 0.56 (3H, s, H-18), 0.85, 0.92 (each 9H, s, Si-tBu× 2), 1.02 (3H, d, J=6.6 Hz, H-21), 1.20 (6H, s, H-26, 27), 2.30 (2H, m, H-4), 2.80 (1H, m, H-9), 2.88 (1H, dd, J=12.7, 4.6 Hz, H-10), 3.37 (3H, s, OMe), 4.20, 4.30 (each 1H, m, CH$_2$OH), 4.37 (1H, dd, J=9.5, 4.0 Hz, H-1), 4.73 (2H, s, OCH$_2$O), 4.81 (1H, t, J=3.8 Hz, H-3), 5.33 (2H, m, H-22, 23), 5.72 (1H, m, C=CH), 5.85 (1H, d, J=11.1 Hz, H-7), 6.14 (1H, d, J=11.1 Hz, H-6).

142b: $^1$H NMR (CDCl$_3$) δ: 0.01, 0.08, 0.08, 0.09 (each 3H, s, Si-Me×4), 0.55 (3H, s, H-18), 0.84, 0.93 (each 9H, s, Si-tBu×2), 1.02 (3H, d, J=6.6 Hz, H-21), 1.20 (6H, s, H-26, 27), 2.55 (1H, dd, J=12.5, 4.9 Hz, H-4), 2.83 (2H, m, H-9, 10), 3.37 (3H, s, OMe), 4.22 (1H, dd, J=12.4, 7.0 Hz, CH$_2$OH), 4.30 (1H, dd, J=12.4, 7.0 Hz, CH$_2$OH), 4.48 (1H, m, H-3), 4.73 (2H, s, OCH$_2$O), 4.86 (1H, t, J=3.2 Hz, H-1), 5.33 (2H, m, H-22, 23), 5.72 (1H, dt, J=7.0, 1.3 Hz, C=CH), 5.80 (1H, d, J=11.1 Hz, H-7), 6.25 (1H, d, J=11.1 Hz, H-6).

142a and 142b MS m/z (%) of the mixture: 716 (M$^+$, 1), 584 (39), 522 (14), 491 (9), 147 (8), 109 (19), 75 (100).

Example 71

1α,25-dihydroxy-2-[2-(hydroxy)-ethylidene]-22-ene-19-norvitamin D$_3$ (E-isomer) (Compound 102a)

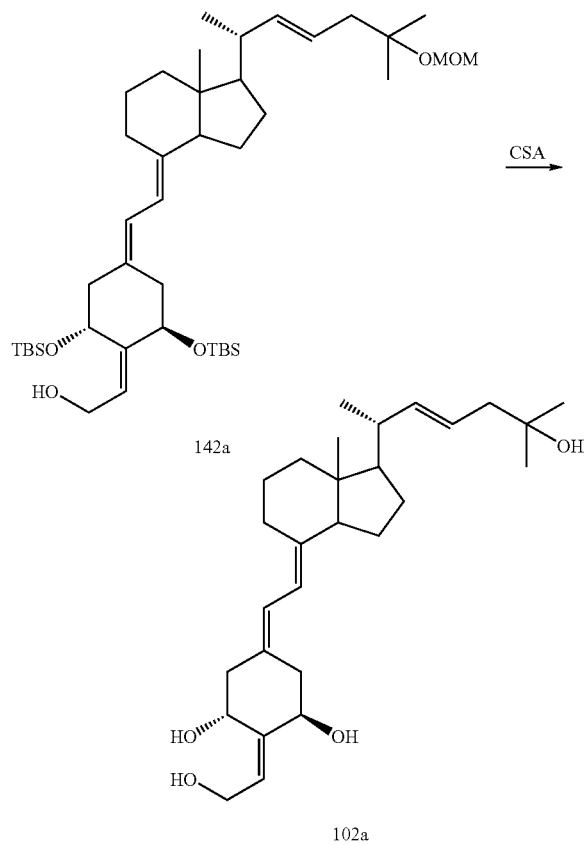

A mixture of Compound 142a (26.3 mg, 0.037 mmol) and camphor sulfonic acid (51.2 mg, 0.220 mmol) in dry MeOH (1 mL) was stirred at room temperature for 2 h. A 5% NaHCO$_3$ aqueous solution was added, and the mixture was extracted with AcOEt. The organic phase was washed with saturated brine, and dried over anhydrous MgSO$_4$. Solvents were evaporated in vacuo, and the residue was purified by silica gel column chromatography (5 g; 2% MeOH/AcOEt) to afford Compound 102a (15.6 mg, 96%). The desired product was further purified by HPLC (YMC-Pack ODS-AM SH-342-5, 150×20 mm, 20% H$_2$O in MeOH) to give pure Compound 102a (12.5 mg).

102a: $^1$H NMR (CD$_3$OD) δ: 0.59 (3H, s, H-18), 1.05 (3H, d, J=6.6 Hz, H-21), 1.16 (6H, s, H-26, 27), 2.35 (1H, br, d, J=13.9 Hz, H-4), 2.43 (1H, dd, J=13.9, 2.9 Hz, H-4), 2.86 (1H, m, H-9), 3.11 (1H, d, J=12.8, 5.0 Hz, H-10), 4.24 (2H, m, CH$_2$OH), 4.30 (1H, m, H-1), 4.83 (1H, m, H-3), 5.31, 5.42 (each 1H, m, H-22, 23), 5.79 (1H, dt, J=6.9, 1.8 Hz, C=CH), 5.91 (1H, d, J=11.1 Hz, H-7), 6.23 (1H, d, J=11.1 Hz, H-6). UV λmax (EtOH): 246 (ε 37,000), 254 (ε 42,000), 263 (ε 27,800) nm. MS m/z (%): 444 (M$^+$, 7), 426 (5), 408 (22), 390 (9), 372 (14), 281 (4), 263 (11), 252 (100), 147 (9), 109 (12). HR-MS m/z: 444.3246 (Calcd for C$_{28}$H$_{44}$O$_4$: 444.3240).

Example 72

1α,25-dihydroxy-2-[2-(hydroxy)-ethylidene]-22-ene-19-norvitamin D$_3$ (Z-isomer) (Compound 102b)

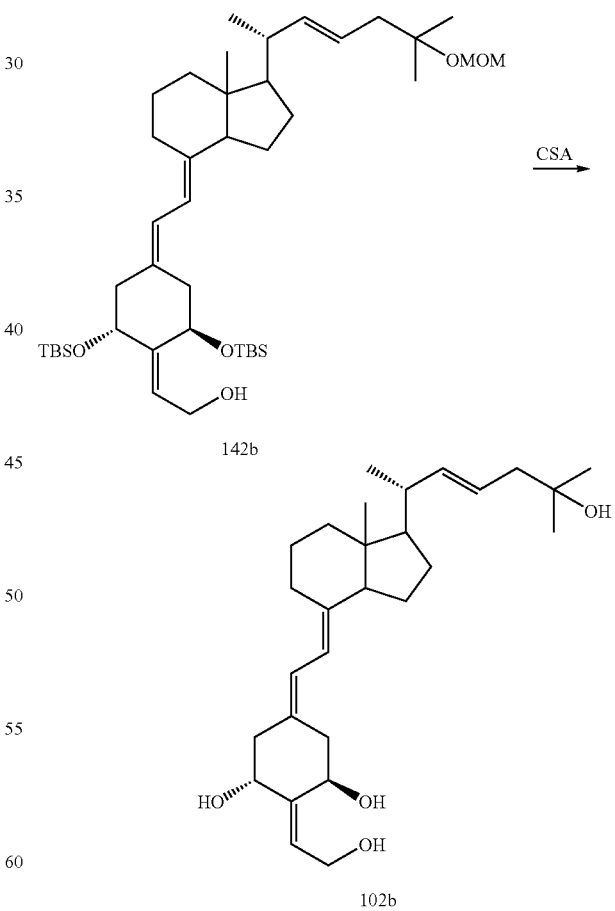

A mixture of Compound 142b (22.7 mg, 0.032 mmol) and camphor sulfonic acid (44.1 mg, 0.190 mmol) in dry MeOH (1 mL) was stirred at room temperature for 2.5 h. A 5% NaHCO$_3$ aqueous solution was added, and the solution was extracted with AcOEt. The organic phase was washed with saturated brine, and dried over anhydrous MgSO₄. Evaporation of the solvent in vacuo gave the residue, which was purified by silica gel column chromatography (5 g; 2% MeOH/AcOEt) to afford Compound 102b (13.5 mg, 96%). The desired product was further purified by HPLC (YMC-Pack ODS-AM SH-342-5, 150×20 mm, 20% H₂O in MeOH) to give pure Compound 102b (12.6 mg).

102b: $^1$H NMR (CD$_3$OD) δ: 0.61 (3H, s, H-18), 1.04 (3H, d, J=6.6 Hz, H-21), 1.16 (6H, s, H-26, 27), 2.65 (1H, dd, J=12.4, 5.0 Hz, H-4), 2.85 (1H, m, H-9), 2.93 (1H, d, J=14.4, 3.0 Hz, H-10), 4.25 (2H, m, CH₂OH), 4.39 (1H, m, H-3), 4.87 (1H, t, J=3.0 Hz, H-1), 5.31, 5.42 (each 1H, m, H-22, 23), 5.77 (1H, dt, J=6.9, 1.7 Hz, C=CH), 5.89 (1H, d, J=11.1 Hz, H-7), 6.32 (1H, d, J=11.1 Hz, H-6). UV λmax (EtOH): 246 (ε 32,500), 254 (ε 37,200), 263 (ε 24,500) nm. MS m/z (%): 444 (M⁺, 10), 426 (5), 408 (23), 390 (27), 372 (91), 281 (54), 263 (79), 252 (57), 147 (86), 109 (100). HR-MS m/z: 444.3227 (Calcd for C₂₈H₄₄O₄: 444.3240).

Example 73

1α-[(t-butyldimethylsilyl)oxy]-2β,2'-epoxy-and 1α-[(t-butyldimethylsilyl)oxy]-2α,2'-epoxy-22-ene-25-[(triethylsilyl)oxy]-19-norvitamin D₃ t-butyldimethylsilyl ether (Compounds 143a and 143b)

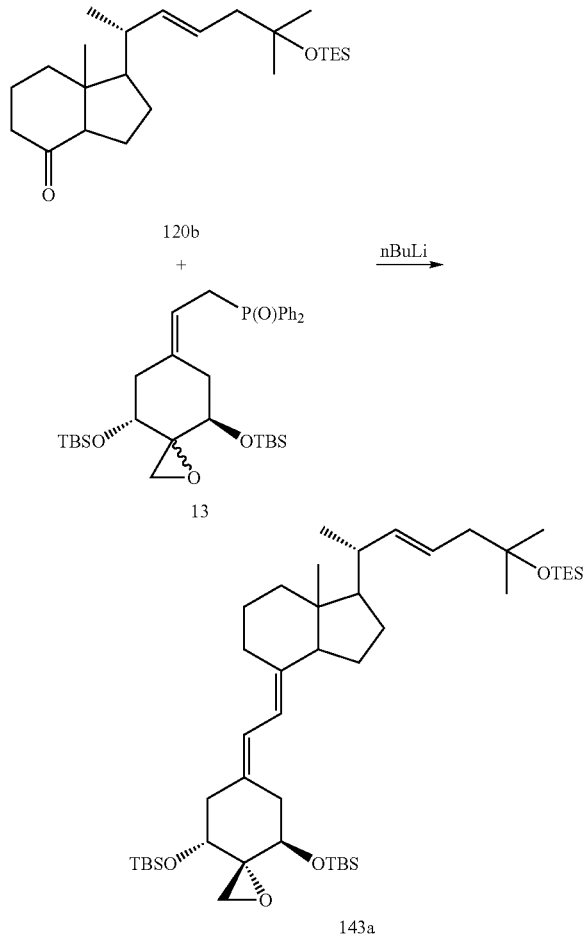

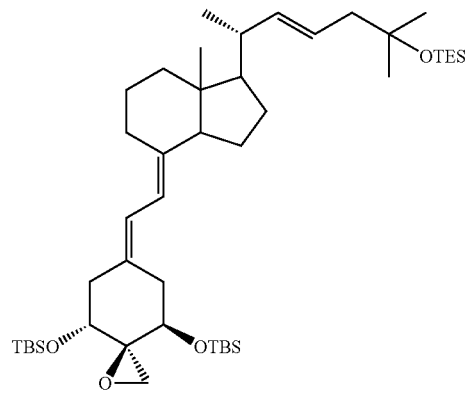

To a solution of A-ring phosfine oxide 13 (106.0 mg, 0.177 mmol, a mixture of ca. 3:1) in dry THF (1 mL) cooled to −78° C. was added n-BuLi (112 μL, 0.177 mmol, 1.58 M solution in hexane), and the resulting solution was stirred for 15 min. To this solution was added a solution of C/D-ring ketone 120b (46.4 mg, 0.118 mmol) in dry THF (1.3 mL), and the reaction mixture was warmed from −78° C. to 0° C. over 3 h, at which point the reaction mixture was quenched with a saturated NH₄Cl aqueous solution, and extracted with AcOEt. The AcOEt layer was washed with saturated brine, dried over anhydrous MgSO₄, and evaporated in vacuo. The residue was purified by silica gel column chromatography (10 g; 2% AcOEt/hexane) to afford Compound 143 (44.4 mg, 49% based on 120b) as a mixture of two stereoisomers 143a:143b=ca. 3:1 ratio, and 15% AcOEt in hexane to give the unreacted starting material 120b (22.6 mg).

NMR Data of the Mixture 143a (major product): $^1$H NMR (CDCl₃) δ: 0.02-0.06 (12H, Si-Me×4), 0.56 (3H, s, H-18), 0.57 (6H, q, J=7.9 Hz, Si—CH₂CH₃×3), 0.86, 0.88 (each 9H, s, Si-tBu×2), 0.95 (9H, t, J=7.9 Hz, Si—CH₂CH₃×3), 1.02 (3H, d, J=6.6 Hz, H-21), 1.17 (6H, s, H-26, 27), 2.73, 2.82 (each 1H, d, J=5.5 Hz, CH₂O), 3.81, 3.87 (each 1H, m), 5.23-5.42 (2H, m), 5.82 (1H, d, J=11.0 Hz, H-7), 6.21 (1H, d, J=11.0 Hz, H-6).

143b (minor product): $^1$H NMR (CDCl₃) δ: 0.02-0.06 (12H, Si-Me×4), 0.56 (3H, s, H-18), 0.57 (6H, q, J=7.9 Hz, Si—CH₂CH₃×3), 0.86, 0.88 (each 9H, s, Si-tBu×2), 0.95 (9H, t, J=7.9 Hz, Si—CH₂CH₃×3), 1.02 (3H, d, J=6.6 Hz, H-21), 1.17 (6H, s, H-26, 27), 2.57, 2.92 (each 1H, d, J=5.5 Hz, CH₂—O), 3.68, 4.03 (each 1H, m), 5.23-5.42 (2H, m), 5.82 (1H, d, J=11.0 Hz, H-7), 6.27 (1H, d, J=11.0 Hz, H-6). MS m/z (%) of the mixture: 772 (M⁺, 4), 715 (10), 583 (6), 451 (3), 173 (100).

Example 74

1α,25-dihydroxy-2β,2'-epoxy-22-ene-19-norvitamin D$_3$ (Compound 103 a), 1α,25-dihydroxy-2α,2'-epoxy-22-ene-19-norvitamin D$_3$ (Compound 103b), 1α,2β,25-trihydroxy-2α-fluoromethyl-22-ene-19-norvitamin D$_3$ (Compound 104a) and 1α,2α,25-trihydroxy-2β-fluoromethyl-22-ene-19-norvitamin D$_3$ (Compound 104b)

A mixture of Compound 143 (75.1 mg, 0.097 mmol, 143a:143b=ca. 3:1) and tetrabutylammonium fluoride (0.583 mL, 0.583 mmol, 1.0 M solution in THF) in dry THF (1 mL) was stirred at room temperature for 4 h. The mixture was poured into ice water, and extracted with AcOEt. The organic phase was washed with saturated brine, and dried over anhydrous MgSO$_4$. Removal of the solvent in vacuo afforded the residue, which was purified by silica gel column chromatography (5 g; 70% AcOEt/hexane) to yield Compound 103 (31.1 mg, 74%) as a mixture of two stereoisomers. The ratio of the

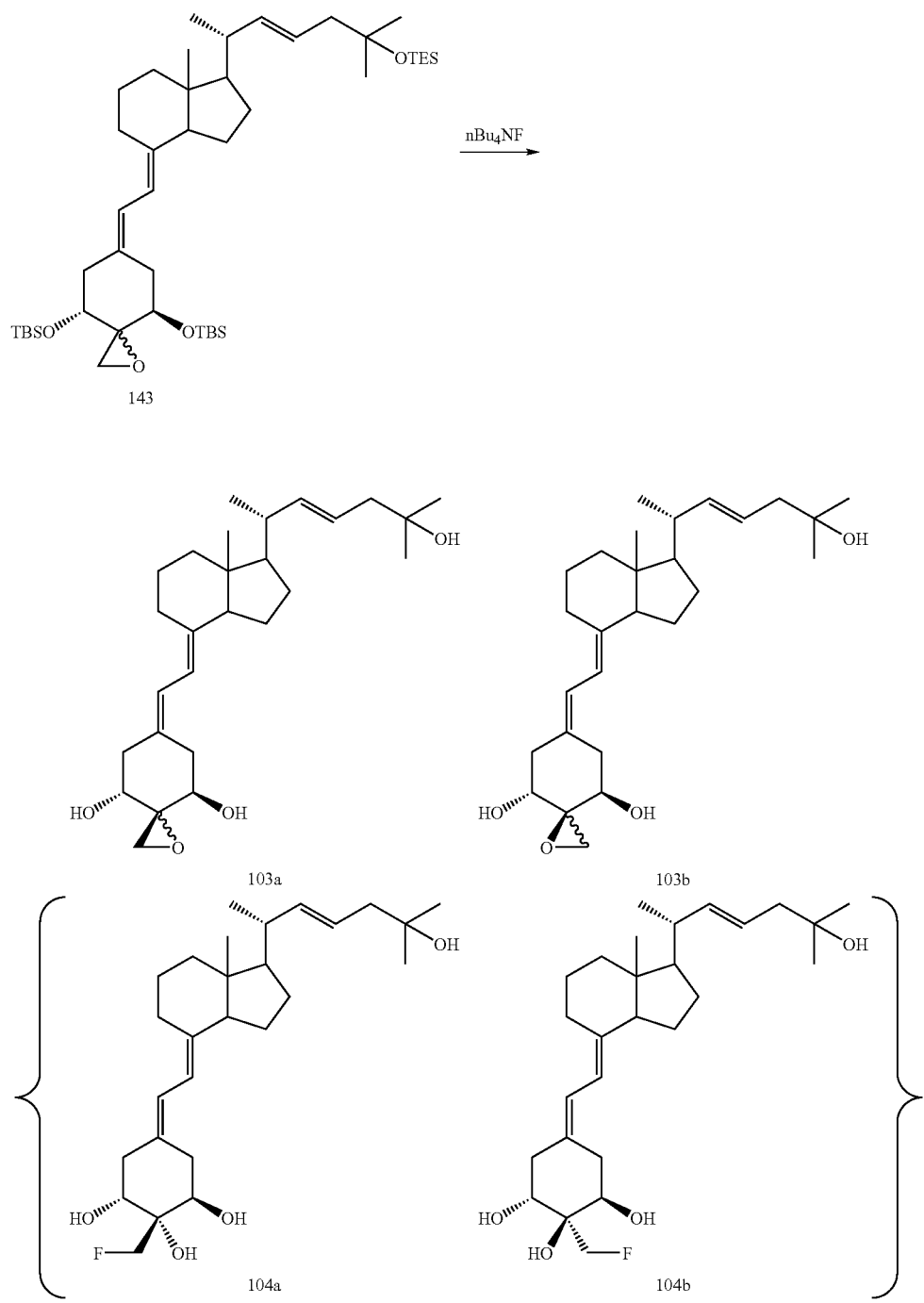

isomers 103a and 103b constituting the mixture was ca. 3:1. The compound 104 was not isolated.

The mixture (11 mg) of Compounds 103a and 103b was separated by HPLC (LiChrosorb Si 60, Hibar, 250×4 mm, hexane:CH₂Cl₂:methanol=50:50:6) to give compounds 103a (4.8 mg) and 103b (807 µg), respectively.

103a: ¹H NMR (CDCl₃) δ: 0.58 (3H, s, H-18), 1.04 (3H, d, J=6.6 Hz, H-21), 1.20 (6H, s, H-26, 27), 2.31 (1H, dd, J=13.5, 8.6 Hz, H-10), 2.40 (1H, dd, J=13.6, 6.2 Hz, H-4), 2.61 (1H, dd, J=13.6, 3.3 Hz, H-4), 2.81 (1H, m, H-9), 2.84 (1H, d, J=4.7 Hz, CH₂O), 2.94 (1H, dd, J=13.5, 4.0 Hz, H-10), 3.07 (1H, d, J=4.7 Hz, CH₂O), 3.81 (1H, m, H-3), 3.98 (1H, m, H-1), 5.39 (2H, m, H-22, 23), 5.85 (1H, d, J=11.1 Hz, H-7), 6.39 (1H, d, J=11.1 Hz, H-6).

103b: ¹H NMR (CDCl₃) δ: 0.58 (3H, s, H-18), 1.05 (3H, d, J=6.6 Hz, H-21), 1.21 (6H, s, H-26, 27), 2.31 (1H, dd, J=13.7, 6.2 Hz, H-10), 2.36 (1H, dd, J=13.7, 8.4 Hz, H-10), 2.71 (1H, dd, J=13.7, 3.6 Hz, H-4), 2.81 (1H, m, H-9), 2.86 (1H, dd, J=13.7, 4.4 Hz, H-10), 2.94, 2.99 (each 1H, dd, J=4.7 Hz, CH₂O), 3.82 (1H, m, H-3), 3.90 (1H, m, H-1), 5.40 (2H, m, H-22, 23), 5.87 (1H, d, J=11.2 Hz, H-7), 6.37 (1H, d, J=11.2 Hz, H-6).

Example 75

1α,2β,25-trihydroxy-2α-methyl-22-en-19-norvitamin D₃ (Compound 105a) and 1α,2α,25-trihydroxy-2β-methyl-22-en-19-norvitamin D₃ (Compound 105b)

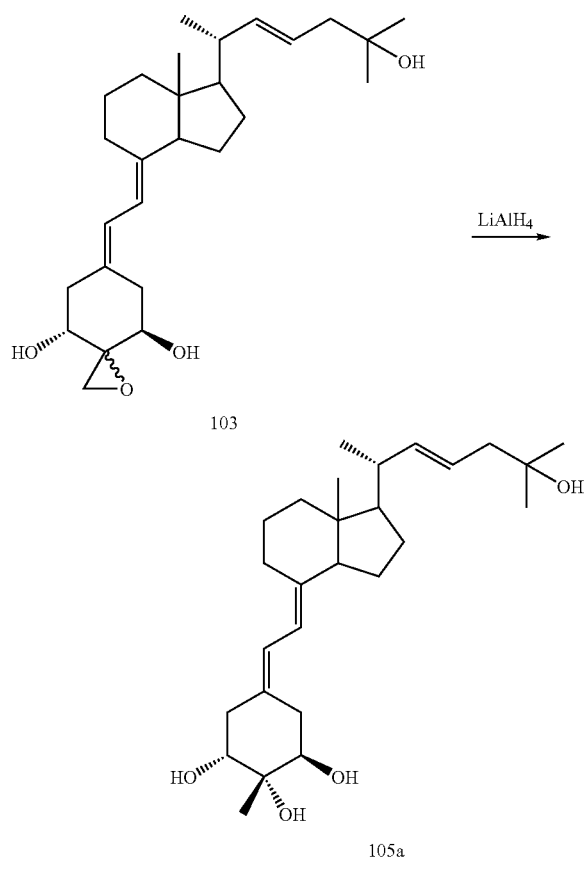

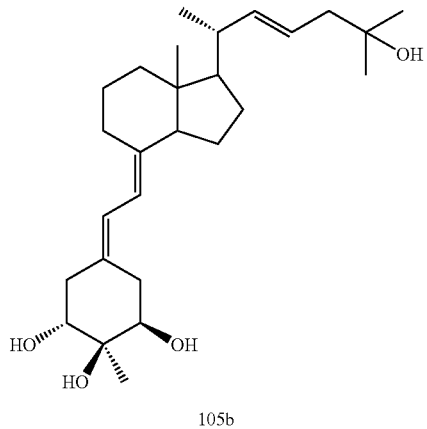

To a suspension of LiAlH₄ (1.0 mg, 0.027 mmol) in dry THF (1 mL) was added a solution of Compound 103 (11.7 mg, 0.027 mmol, a mixture of ca. 3:1), and the reaction mixture was stirred for 3 h at room temperature. An aqueous solution of potassium sodium tartrate was added to the reaction mixture, and the mixture was extracted with AcOEt. The organic phase was washed with saturated brine, dried over anhydrous MgSO₄, and distilled off. The residue was purified by silica gel column chromatography (5 g, 75% AcOEt/hexane) to obtain Compound 105 as a mixture of two kinds of stereoisomers (3.9 mg, 33%, 105a:105b=ca. 3:1). The mixture of Compounds 105a and 105b was separated and purified by HPLC (YMC-Pack ODS-AM SH-342-5, 150×20 mm, 25% H₂O/MeOH) to obtain Compound 105a (1.58 mg) and Compound 105b (261 µg).

105a: ¹H NMR (CDCl₃) δ: 0.56 (3H, s, H-18), 1.04 (3H, d, J=6.6 Hz, H-21), 1.20 (6H, s, H-26, 27), 1.24 (3H, s, 2-Me), 2.36 (1H, dd, J=14.5, 4.6 Hz, H-4), 2.54 (1H, d, J=14.5 Hz, H-4), 2.79 (1H, m, H-9), 2.93 (1H, dd, J=12.6, 4.3 Hz, H-10), 3.73 (2H, m, H-1, 3), 5.39 (2H, m, H-22, 23), 5.83 (1H, d, J=11.2 Hz, H-7), 6.29 (1H, d, J=11.2 Hz, H-6). MS m/z (%): 432 (M⁺, 37), 414 (34), 396 (11), 378 (1.2), 360 (14), 305 (21), 287 (37), 269 (37), 251 (21), 135 (100). HR-MS m/z: 432.3221 (Calcd for C₂₇H₄₄O₄: 432.3240). UV λmax (EtOH): 244, 252, 261 nm.

105b: ¹H NMR (CDCl₃) δ: 0.57 (3H, s, H-18), 1.04 (3H, d, J=6.6 Hz, H-21), 1.20 (6H, s, H-26, 27), 1.30 (3H, s, 2-Me), 2.49 (1H, dd, J=14.2, 3.4 Hz, H-4), 2.62 (1H, dd, J=14.2, 6.5 Hz, H-4), 2.67 (1H, dd, J=13.6, 4.0 Hz, H-10), 2.80 (1H, m, H-9), 3.74, 3.77 (each 1H, m, H-1, 3), 5.39 (2H, m, H-22, 23), 5.81 (1H, d, J=11.2 Hz, H-7), 6.33 (1H, d, J=11.2 Hz, H-6). MS m/z (%): 432 (M⁺, 66), 414 (31), 396 (17), 378 (20), 360 (35), 305 (29), 287 (49), 269 (48), 251 (43), 135 (100). HR-MS m/z: 432.3246 (Calcd for C₂₇H₄₄O₄: 432.3240). UV λmax (EtOH): 244, 252, 261 nm.

Example 76

20-epi-1α-[(t-butyldimethylsilyl)oxy]-2α-[(trimethylsilyl)oxy]- and 20-epi-1α-[(t-butyldimethylsilyl)oxy]-2β-[(trimethylsilyl)oxy]-22-oxa-25-[(triethylsilyl)oxy]-19-norvitamin D₃ t-butyldimethylsilyl ether (Compounds 144a, 144b)

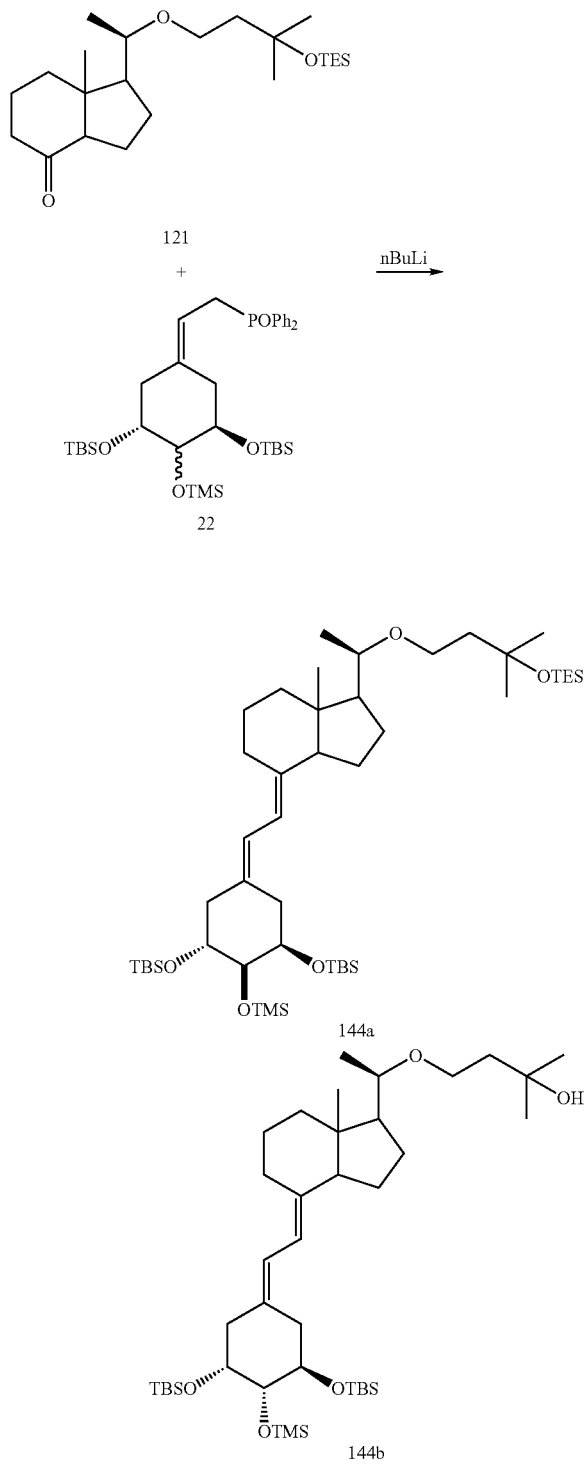

To a solution cooled to −78° C. of A-ring phosphine oxide 22 (212.0 mg, 0.321 mmol, a mixture of ca. 2:1) in dry THF (3 mL) was added n-BuLi (206 μL, 0.321 mmol, 1.56 M solution in hexane), and the resulting solution was stirred for 15 min. To this solution was added slowly a solution of C/D-ring ketone 121 (85.0 mg, 0.214 mmol) in dry THF (1 mL), and the mixture was stirred for 2 h at −78° C., saturated NH₄Cl aqueous solution was added to the mixture, and the mixture was extracted with AcOEt. The organic phase was washed with saturated brine, dried over anhydrous MgSO₄, and distilled off. The residue was purified by silica gel column chromatography (10 g) using 2% AcOEt/hexane to afford Compound 144 (158.8 mg, 88%) as a mixture of two kinds of stereoisomers. The ratio of the isomer 144a to the isomer 144b was ca. 3:2. Further, the unreacted starting material 121 (5.1 mg) was collected using 5% AcOEt/hexane.

NMR Data of the Mixture 144a (major product): $^1$H NMR (CDCl₃) δ: 0.04-0.06 (12H, Si-Me×4), 0.13 (9H, s, Si-Me×3), 0.56 (3H, s, H-18), 0.57 (6H, q, J=7.9 Hz, SiCH₂×3), 0.87, 0.88 (each 9H, s, Si-tBu×2), 0.94 (9 t, J=7.9 Hz, SiCH₂CH₃×3), 1.08 (3H, d, J=5.9 Hz, H-21), 1.21, 1.23 (each 3H, s, H-26, 27), 2.80 (1H, m, H-9), 3.26 (1H, m, H-20), 3.32, 3.69 (each 1H, m, H-23), 3.53 (1H, m, H-2), 3.80 (1H, m, H-3), 3.89 (1H, m, H-1), 5.79 (1H, d, J=11.1 Hz, H-7), 6.11 (1H, d, J=11.1 Hz, H-6).

144b (minor product): $^1$H NMR (CDCl₃) δ: 0.04-0.06 (12H, Si-Me×4), 0.12 (9H, s, Si-Me×3), 0.54 (3H, s, H-18), 0.57 (6H, q, J=7.9 Hz, SiCH₂×3), 0.86, 0.89 (each 9H, s, Si-Btu×2), 0.94 (9H, t, J=7.9 Hz, SiCH₂CH₃×3), 1.08 (3H, d, J=5.9 Hz, H-21), 1.21, 1.23 (each 3 H, s, H-26, 27), 2.80 (1H, m, H-9), 3.26 (1H, m, H-20), 3.32, 3.69 (each 1H, m, H-23), 3.59 (1H, m, H-2), 3.80 (1H, m, H-3), 3.93 (1H, m, H-1), 5.77 (1H, d, J=11.2 Hz, H-7), 6.14 (1H, d, J=11.2 Hz, H-6). MS m/z (%) of the mixture: no M⁺, 704 (10), 647 (3), 618 (7), 572 (19), 486 (20), 469 (13), 383 (17), 309 (19), 75 (100).

Example 77

20-epi-1α-[(t-butyldimethylsilyl)oxy]-2α,25-dihydroxy- and 20-epi-1α-[(t-butyldimethylsilyl)oxy]-2β,25-dihydroxy-22-oxa-19-norvitamin D₃ t-butyldimethylsilyl ether (Compounds 145a, 145b)

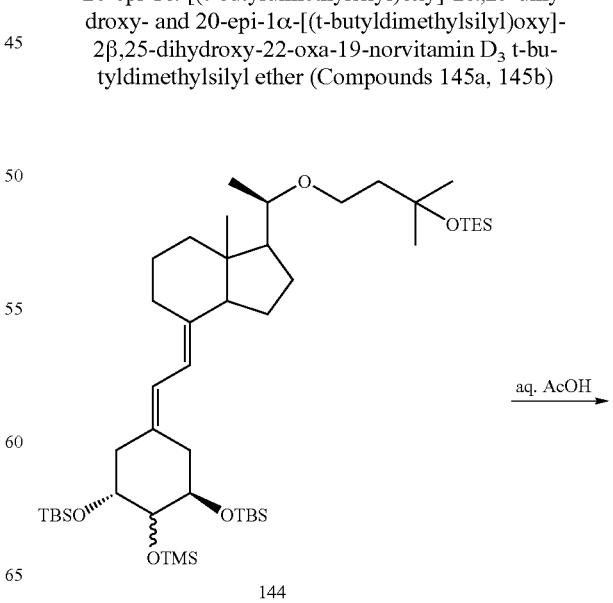

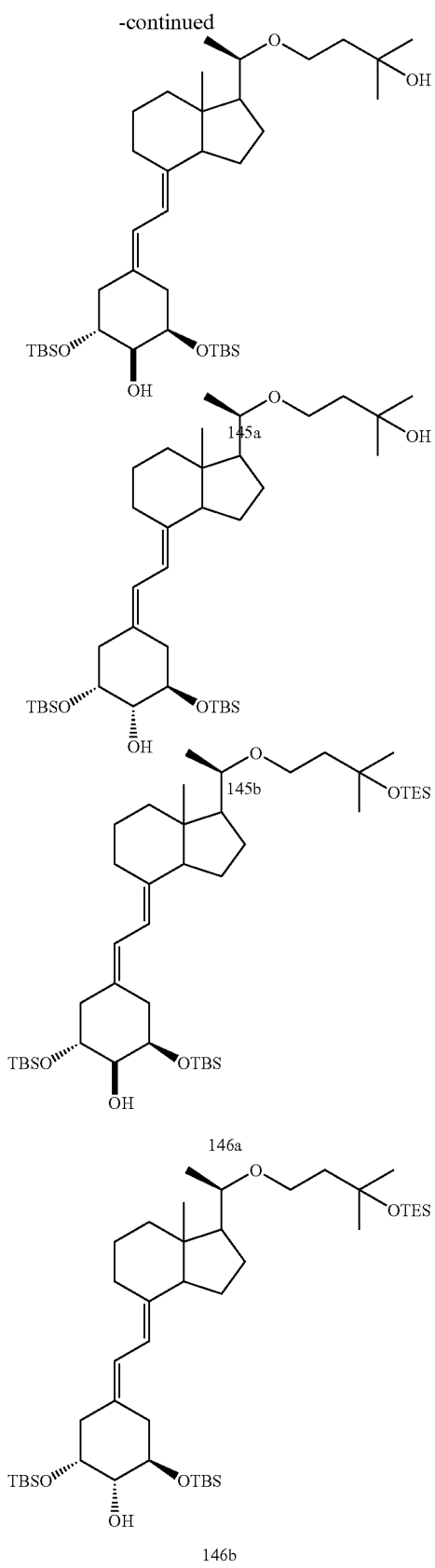

A Compound 144 (153.0 mg, 0.183 mmol, a mixture of ca. 3:2) was dissolved in THF/AcOH/H$_2$O (8:8:1, 4.25 mL), a solution was stirred at room temperature for 16 h, and diluted with AcOEt. The organic phase was successively washed with 5% NaHCO$_3$ and saturated brine, and dried over anhydrous Na$_2$SO$_4$, and distilled off. The residue was purified by silica gel column chromatography (6 g) using 5% AcOEt/hexane to afford Compound 146 (37.0 mg, 27%) as a mixture of two kinds of stereoisomers, and using 10% AcOEt/hexane to afford Compound 145 (77.1 mg, 65%) as a mixture of two kinds of stereoisomers. The ratio of the isomer 145a to the isomer 145b and the ratio of the isomer 146a to the isomer 146b was ca. 3:2, respectively.

NMR Data of the Mixture 145a (major product): $^1$H NMR (CDCl$_3$) δ: 0.06-0.10 (12H, Si-Me×4), 0.56 (3H, s, H-18), 0.87, 0.88 (each 9H, s, Si-tBu×2), 1.14 (3H, d, J=5.9 Hz, H-21), 1.22, 1.24 (each 3H, s, H-26, 27), 2.80 (1H, m, H-9), 3.28 (1H, m, H-20), 3.46, 3.85 (each 1H, m, H-23), 3.51 (1H, m, H-2), 3.59 (1H, s, OH), 3.92 (1H, m, H-3), 4.00 (1H, m, H-1), 5.78 (1H, d, J=11.1 Hz, H-7), 6.16 (1H, d, J=11.1 Hz, H-6).

145b (minor product): $^1$H NMR (CDCl$_3$) δ: 0.06-0.10 (12H, Si-Me×4), 0.54 (3H, s, H-18), 0.86, 0.89 (each 9H, s, Si-tBu×2), 1.14 (3H, d, J=5.9 Hz, H-21), 1.23, 1.24 (each 3H, s, H-26, 27), 2.80 (1H, m, H-9), 3.28 (1H, m, H-20), 3.46, 3.85 (each 1H, m, H-23), 3.59 (1H, m, H-2), 3.59 (1H, s, OH), 4.00 (2H, m, H-3, 1), 5.78 (1H, d, J=11.2 Hz, H-7), 6.19 (1H, d, J=11.2 Hz, H-6). MS m/z (%) of the mixture: 650 (M$^+$, 2), 632 (8), 546 (6), 489 (8), 443 (10), 357 (8), 265 (22), 113 (30), 75 (100).

NMR Data of the Mixture 146a (major product): $^1$H NMR (CDCl$_3$) δ: 0.06-0.10 (12H, Si-Me×4), 0.56 (3H, s, H-18), 0.56 (6H, q, J=7.9 Hz, SiCH$_2$×3), 0.87, 0.88 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.81 (1H, m, H-9), 3.26 (1H, m, H-20), 3.32, 3.70 (each 1H, m, H-23), 3.51 (1H, m, H-2), 3.91 (1H, m, H-3), 4.01 (1H, m, H-1), 5.78 (1H, d, J=11.1 Hz, H-7), 6.17 (1H, d, J=11.1 Hz, H-6).

146b (minor product): $^1$H NMR (CDCl$_3$) δ: 0.06-0.10 (12H, Si-Me×4), 0.55 (3H, s, H-18), 0.56 (6H, q, J=7.9 Hz, SiCH$_2$×3), 0.86, 0.89 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.81 (1H, m, H-9), 3.26 (1H, m, H-20), 3.32, 3.70 (each 1H, m, H-23), 3.59 (1H, m, H-2), 4.01 (2H, m, H-1, 3), 5.78 (1H, d, J=11.2 Hz, H-7), 6.20 (1H, d, J=11.2 Hz, H-6). MS m/z (%) of the mixture: 764 (M$^+$, 1), 707 (1), 632 (4), 575 (2), 546 (3), 489 (4), 443 (5), 357 (20), 265 (11), 103 (31), 75 (100).

Example 78

20-epi-1α-[(t-butyldimethylsilyl)oxy]-2α-[2-(t-butyldimethylsilyl)oxy]-ethoxy]- and 20-epi-1α-[(t-butyldimethylsilyl)oxy]-2β-[2-(t-butyldimethylsilyl)oxy)-ethoxy]-22-oxa-25-hydroxy-19-norvitamin D₃ t-butyldimethylsilyl ether (Compounds 147a, 147b)

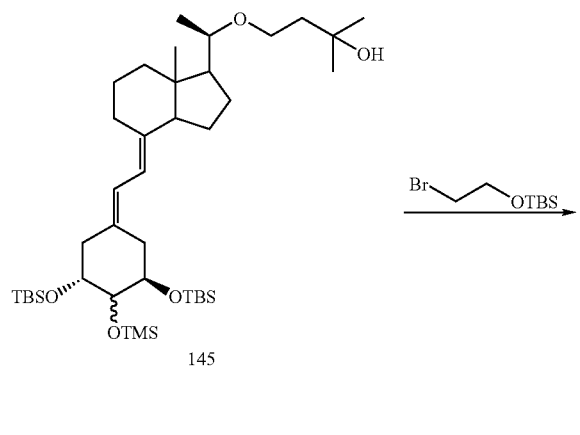

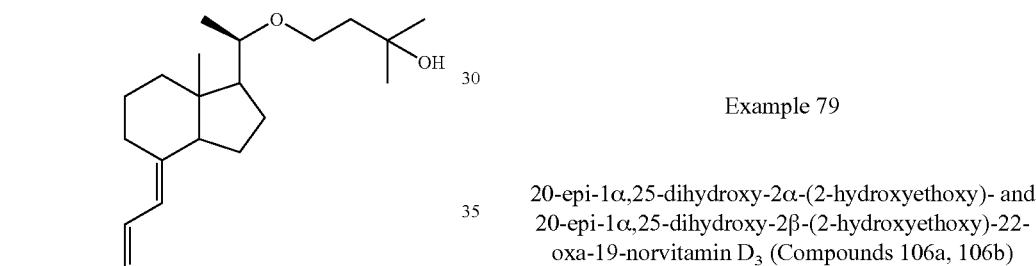

To a solution cooled to 0° C. of Compound 145 (73.5 mg, 0.113 mmol, a mixture of ca. 3:2) in dry DMF (2 mL) were added NaH (135.0 mg, 3.375 mmol, 60% paraffin liquid) and (2-bromoethoxy)-tert-butyldimethylsilane (118 μl, 0.550 mmol), and the resulting solution was stirred vigorously. After 19 h, the reaction mixture was poured into ice water, and then extracted with AcOEt/hexane (1:1). The organic phase was washed with saturated brine, dried over anhydrous MgSO₄, and distilled off. The residue was purified by silica gel column chromatography (10 g, 10-15% AcOEt/hexane) to afford Compound 147 (65.0 mg, 71%) as a mixture of two kinds of stereoisomers. The ratio of the isomer 147a to the isomer 147b was ca. 3:2.

147: ¹H NMR (CDCl₃) δ: 0.05-0.07 (18H, Si-Me×6), 0.54, 0.55 (ca. 2:3) (3H, s, H-18), 0.86-0.89 (27H, Si-tBu×3), 1.13 (3H, d, J=5.5 Hz, H-21), 1.23, 1.24 (each 3H, s, H-26, 27), 2.80 (1H, m, H-9), 3.2-4.1 (10H, m, OCH₂CH₂O, H-1, 2, 3, 20, 23), 5.77 (1H, H-7), 6.14 (1H, H-6). MS m/z (%): no M⁺, 790 (1), 676 (4), 658 (5), 572 (6), 526 (5), 397 (18), 233 (74), 75 (100).

Example 79

20-epi-1α,25-dihydroxy-2α-(2-hydroxyethoxy)- and 20-epi-1α,25-dihydroxy-2β-(2-hydroxyethoxy)-22-oxa-19-norvitamin D₃ (Compounds 106a, 106b)

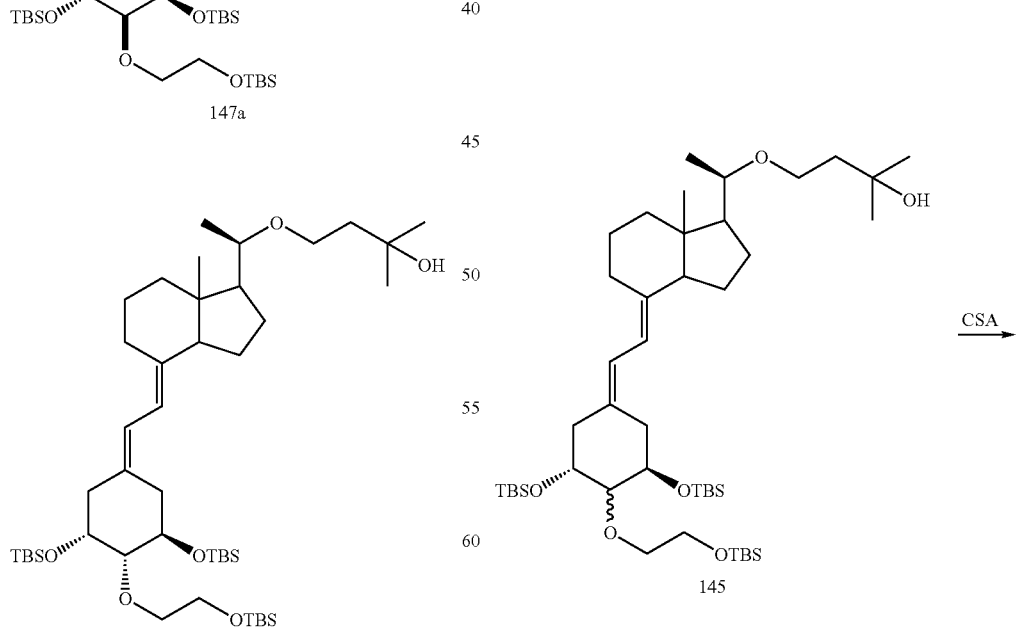

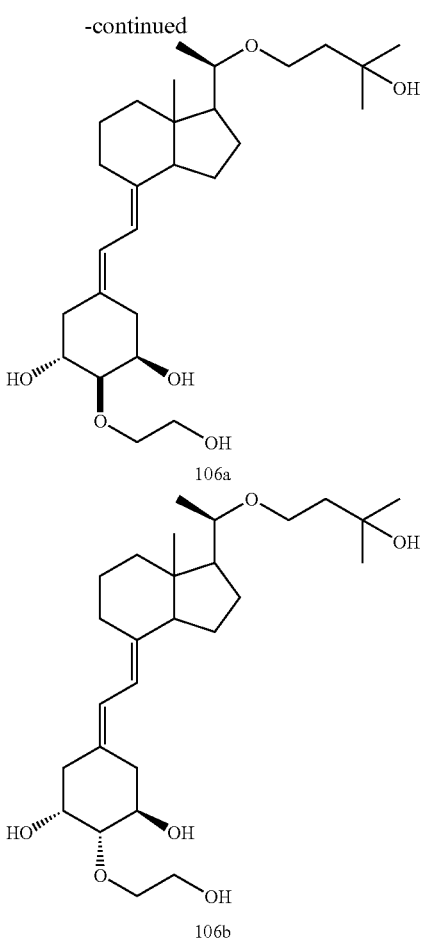

106a

106b

To a solution of Compound 147 (63.0 mg, 0.0778 mmol) in dry MeOH (1.5 mL) was added camphor sulfonic acid (108.5 mg, 0.467 mmol), and the resulting solution was stirred at room temperature for 2 h. The reaction mixture was poured into 5% $NaHCO_3$, and extracted with AcOEt. The organic phase was washed with saturated brine, dried over anhydrous $MgSO_4$, and distilled off. The residue was purified by silica gel column chromatography (5 g, 2% MeOH/AcOEt) to obtain a mixture of Compounds 106a and 106b (33.0 mg, 91%, ca. 3:2 ratio). The mixture of Compounds 106a and 106b was separated and purified by HPLC (YMC-Pack ODS-AM SH-342-5, 150×20 mm, 25% $H_2O$/MeOH) to obtain Compound 106a (13.9 mg) and Compound 106b (10.3 mg).

106a: $^1$H NMR (CDCl$_3$) δ: 0.55 (3H, s, H-18), 1.12 (3H, d, J=5.9 Hz, H-21), 1.22, 1.23 (each 3H, s, H-26, 27), 2.60 (1H, dd, J=13.4, 4.5 Hz, H-4), 2.79 (1H, m, H-9), 2.86 (1H, dd, J=14.5, 4.8 Hz, H-10), 3.26 (1H, m, H-20), 3.31 (1H, dd, J=8.1, 2.7 Hz, H-2), 3.45 (1H, m, H-23), 3.57 (1H, s, OH), 3.66-3.86 (5H, m, OCH$_2$CH$_2$O, H-23), 3.92 (1H, m, H-3), 4.14 (1H, m, H-1), 5.79 (1H, d, J=11.2 Hz, H-7), 6.33 (1H, d, J=11.2 Hz, H-6). UV λmax (EtOH): 243 (ε 29,600), 251 (ε 34,500), 261 (ε 23,200) nm. MS m/z (%): 466 (M$^+$, 39), 448 (30), 430 (13), 362 (14), 345 (12), 317 (13), 237 (9), 133 (20), 113 (50), 69 (100). HR-MS m/z: 466.3267 (Calcd for $C_{27}H_{46}O_6$: 466.3294).

106b: $^1$H NMR (CDCl$_3$) δ: 0.55 (3H, s, H-18), 1.13 (3H, d, J=5.9 Hz, H-21), 1.22, 1.24 (each 3H, s, H-26, 27), 2.34 (1H, br. d, J=14.1 Hz, H-4), 2.48 (1H, dm, J=14.1 Hz, H-4), 2.67 (1H, br. s, OH), 2.79 (1H, m, H-9), 3.07 (1H, dd, J=13.4, 3.8 Hz, H-10), 3.27.(2H, m, H-2, 20), 3.45 (1H, m, H-23), 3.56 (1H, s, OH), 3.64-3.87 (6H, m, OCH$_2$CH$_2$O, H-1, 23), 4.17 (1H, m, H-3), 5.82 (1H, d, J=11.2 Hz, H-7), 6.27 (1H, d, J=11.2 Hz, H-6). UV λmax (EtOH): 243 (ε 32,500), 251 (ε 37,900), 261 (ε 25,100) nm. MS m/z (%): 466 (M$^+$, 28), 448 (22), 430 (11), 362 (9), 345 (9), 317 (9), 237 (11), 133 (19), 113 (43), 69 (100). HR-MS m/z: 466.3300 (Calcd for $C_{27}H_{46}O_6$: 466.3294).

Example 80

20-epi-1α-[(t-butyldimethylsilyl)oxy]-2-oxo-22-oxa-25-[(triethylsilyl)oxy]-19-norvitamin D$_3$ t-butyldimethylsilyl ether (Compound 148)

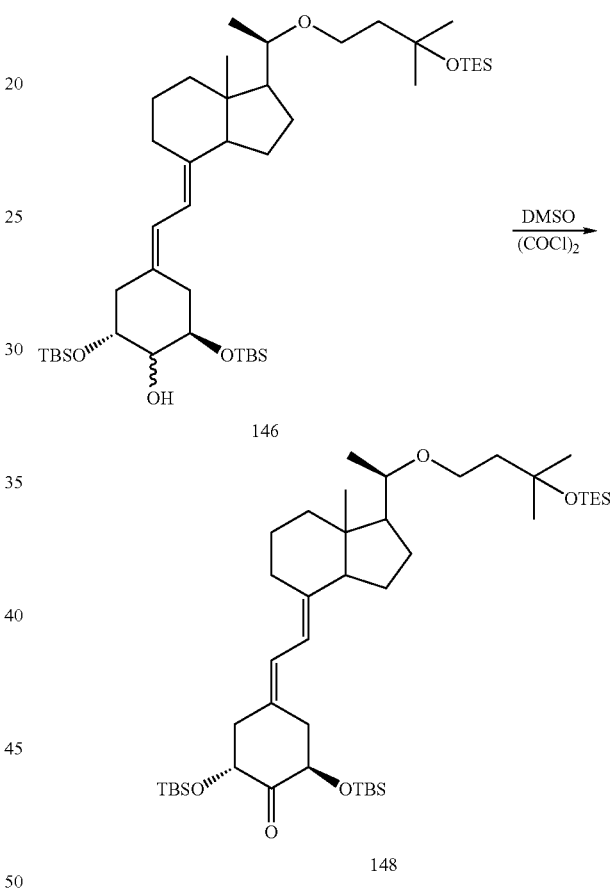

To a solution cooled to −78° C. of oxalyl chloride (8.3 μL, 0.095 mmol) in dry CH$_2$Cl$_2$ (1 mL) was added a solution of DMSO (13.5 μL, 0.190 mmol) in dry CH$_2$Cl$_2$ (0.2 mL). After being stirred for 5 min, to this mixture was added a solution of Compound 146 (60.7 mg, 0.079 mmol, a mixture of ca. 3:2) in dry CH$_2$Cl$_2$ (1.2 mL). The reaction mixture was stirred for 15 min at −78° C., and Et$_3$N (55 μL, 0.397 mmol) was added: The whole mixture was stirred at −78° C. for 30 min and at 0° C. for 10 min, quenched with ice water, and extracted with CH$_2$Cl$_2$. The organic phase was washed with saturated brine, dried over anhydrous MgSO$_4$, and distilled off. The residue was purified by silica gel column chromatography (5 g, 2% AcOEt/hexane) to afford Compound 148 (59.5 mg, 98%) as a single compound.

148: $^1$H NMR (CDCl$_3$) δ: 0.057, 0.066, 0.070, 0.097 (each 3H, s, Si-Me×4), 0.56 (3H, s, H-18), 0.57 (6H, q, J=7.9 Hz, SiCH$_2$×3), 0.87, 0.89 (each 9H, s, Si-tBu×2), 0.94 (9H, t, =7.9 Hz, SiCH$_2$CH$_3$×3), 1.09 (3H, d, J=5.9 Hz, H-21), 1.21, 1.23 (each 3H, s, H-26, 27), 2.45 (1H, dd, J=13.2, 8.7 Hz), 2.52 (1H, dd, J=14.0, 4.0 Hz), 2.70 (2H, m), 2.81 (1H, m, H-9), 3.26 (1H, m, H-20), 3.32, 3.70 (each 1H, m, H-23), 4.36 (1H, dd, J=6.3, 4.2 Hz), 4.55 (1H, dd, J=8.7, 5.5 Hz), 5.79 (1H, d, J=11.0 Hz, H-7), 6.37 (1H, d, J=11.0 Hz, H-6). MS m/z (%): no M$^+$, 705 (8), 573 (12), 487 (22), 355 (12), 103 (51), 75 (100).

Example 81

E-isomer and Z-isomer of 20-epi-1α-[(t-butyldimethylsilyl)oxy]-2-cyanomethylene-22-oxa-25-[(triethylsilyl)oxy]-19-norvitamin D$_3$ t-butyldimethylsilyl ether (Compounds 149a and 149b)

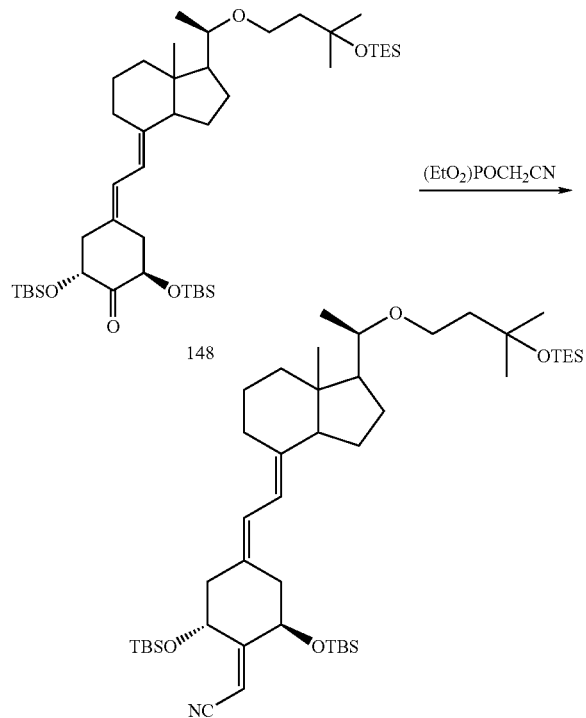

To a solution cooled to −40° C. of diethyl (cyanomethyl) phosphonate (51 μL, 0.315 mmol) in dry THF (1 mL) was added n-BuLi (202 μL, 0.315 mmol, 1.56 M solution in hexane). The mixture was stirred for 15 min, and a solution of Compound 148 (120.3 mg, 0.157 mmol) in dry THF (1.2 mL) was added slowly. The reaction mixture was stirred at −40.° C. for 1.5 h, saturated NH$_4$Cl aqueous solution was added to the mixture, and the mixture was extracted with AcOEt. The organic phase was washed with saturated brine, dried over anhydrous MgSO$_4$, and distilled off. The residue was purified by silica gel column chromatography (8 g, 1% AcOEt/hexane) to afford Compound 149 (120.6 mg, 97%) as a mixture of two kinds of stereoisomers. The ratio of the isomer 149a (E-isomer) to the isomer 149b (Z-isomer) was ca. 1:1.

NMR Data of the Mixture
149a: $^1$H NMR (CDCl$_3$) δ: 0.05, 0.07, 0.10, 0.12 (each 3H, s, Si-Me×4), 0.56 (3H, s, H-18), 0.56 (6H, q, J=7.9 Hz, SiCH$_2$×3), 0.84, 0.92 (each 9H, s, 2×Si-tBu×2), 0.93 (9H, t, J=7.9 Hz, SiCH$_2$CH$_3$×3), 1.09 (3H, d, J=5.9 Hz, H-21), 1.21, 1.23 (each 3H, s, H-26, 27), 2.31, 2.37 (each 1H, m, H-4), 2.80 (1H, m, H-9), 3.12 (1H, m, H-10), 3.26 (1H, m, H-20), 3.32, 3.69 (each 1H, m, H-23), 4.46 (1H, m, H-1), 4.99 (1H, t, J=2.8 Hz, H-3), 5.47 (1H, d, J=1.8 Hz, C=CHCN), 5.80 (1H, d, J=11.1 Hz, H-7), 6.20 (1H, d, J=11.1 Hz, H-6).

149b: $^1$H NMR (CDCl$_3$) δ: 0.06, 0.08, 0.11, 0.13 (each 3H, s, Si-Me×4), 0.56 (3H, s, H-18), 0.56 (6H, q, J=7.9 Hz, SiCH$_2$×3), 0.84, 0.92 (each 9H, s, 2×Si-tBu), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.61 (1H, m, H-4), 2.82 (1H, m, H-9), 2.99 (1H, m, H-10), 3.26 (1H, m, H-20), 3.32, 3.70 (each 1H, m, H-23), 4.58 (1H, ddd, J=1.0, 5.9, 1.9 Hz, H-3), 5.04 (1H, t, J=2.7 Hz, H-1), 5.47 (1H, d, J=1.9 Hz, C=CHCN), 5.77 (1H, d, J=11.2 Hz, H-7), 6.33 (1H, d, J=11.2 Hz, H-6). MS m/z (%) of the mixture: 785 (M$^+$, 2), 728 (8), 701 (12), 653 (6), 596 (9), 569 (16), 510 (17), 483 (11), 103 (66), 75 (100).

Example 82

E-isomer and Z-isomer of 20-epi-1α-[(t-butyldimethylsilyl)oxy]-2-[2-(formyl)-ethylidene]-22-oxa-25-[(triethylsilyl)oxy]-19-norvitamin D$_3$ t-butyldimethylsilyl ether (Compounds 150a and 150b)

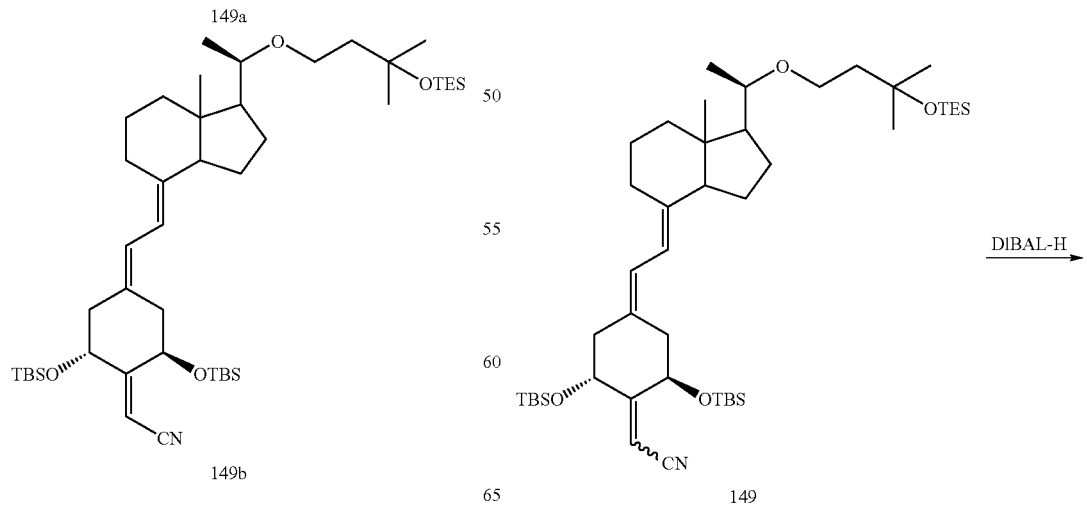

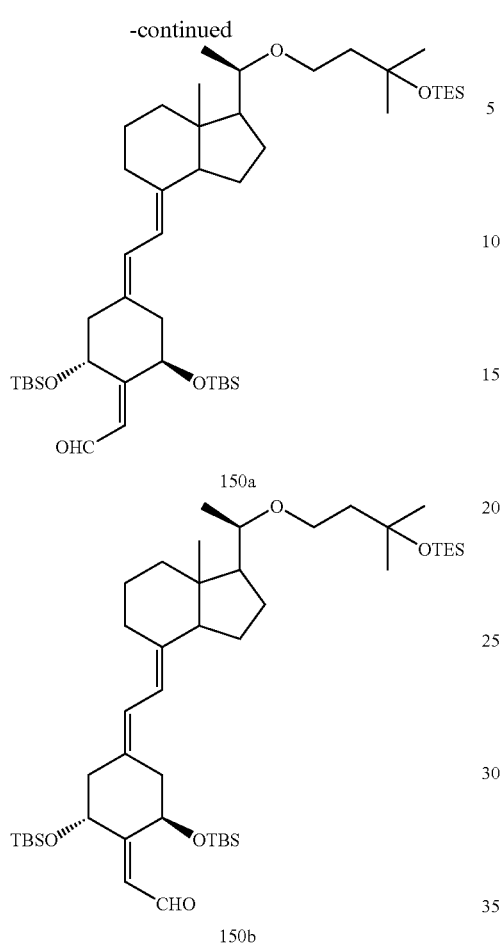

150a

150b

To a solution cooled to –78° C. of Compound 149 (77.0 m., 0.098 mmol, a mixture of ca. 1:1) in dry toluene (1 mL) was added diisobutylaluminum hydride (147 μL, 0.147 mmol, 1.0 M solution in toluene), and the mixture was stirred for 2 h. The reaction mixture was diluted with hexane, and directly purified by silica gel column chromatography (8 g, 5% AcOEt/hexane) to afford Compound 150 (66.9 mg, 87%) as a mixture of two kinds of stereoisomers. The ratio of the isomer 150a (E-isomer) to the isomer 150b (Z-isomer) was ca. 1:1.

NMR Data of the Mixture

150a: $^1$H NMR (CDCl$_3$) δ: 0.01, 0.07, 0.09, 0.10 (each 3H, s, Si-Me×4), 0.57 (3H, s, H-18), 0.56 (6H, q, J=7.9 Hz, SiCH$_2$×3), 0.84, 0.92 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.42 (2H, m, H-4), 2.80 (1H, m, H-9), 3.05 (1H, dd, J=12.8, 5.3 Hz, H-10), 3.26 (1H, m, H20), 3.32, 3.69 (each 1H, m, H-23), 4.57 (1H, m, H-1), 5.46 (1H, t, J=3.3 Hz, H-3), 5.83 (1H, d, J=11.1 Hz, H-7), 6.15 (1H, dd, J=7.9, 1.1 Hz, C=CH), 6.19 (1H, d, J=11.1 Hz, H-6), 10.18 (1H, d, J=7.9 Hz, CHO).

150b: $^1$H NMR (CDCl$_3$) δ: 0.02, 0.08, 0.10, 0.11 (each 3H, s, Si-Me×4), 0.56 (3H, s, H-18), 0.57 (6H, q, J=7.9. Hz, SiCH$_2$×3), 0.84, 0.93 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.65 (1H, m, H-4), 2.80 (1H, m, H-9), 3.00 (1H, m, H-10), 3.26 (1H, m, H-20), 3.32, 3.71 (each 1H, m, H-23), 4.69 (1H, m, H-3), 5.54 (1H, m, H-1), 5.78 (1H, d, J=11.2 Hz, H-7), 6.16 (1H, dd, J=7.9, 1.1 Hz, C=CH), 6.32 (1H, d, J=11.1 Hz, H-6), 10.16 (1H, d, J=7.9 Hz, CHO). MS m/z (%) of the mixture: 788 (M$^+$, 5), 731 (5), 656 (8), 627 (7), 599 (4), 524 (5), 495 (3), 409 (5), 103 (42), 75 (100).

Example 83

E-isomer and Z-isomer of 20-epi-1α-[(t-butyldimethylsilyl)oxy]-2-[2-(hydroxy)-ethylidene]-22-oxa-25-[(triethylsilyl)oxy]-19-norvitamin D$_3$ t-butyldimethylsilyl ether (Compounds 151a and 151b)

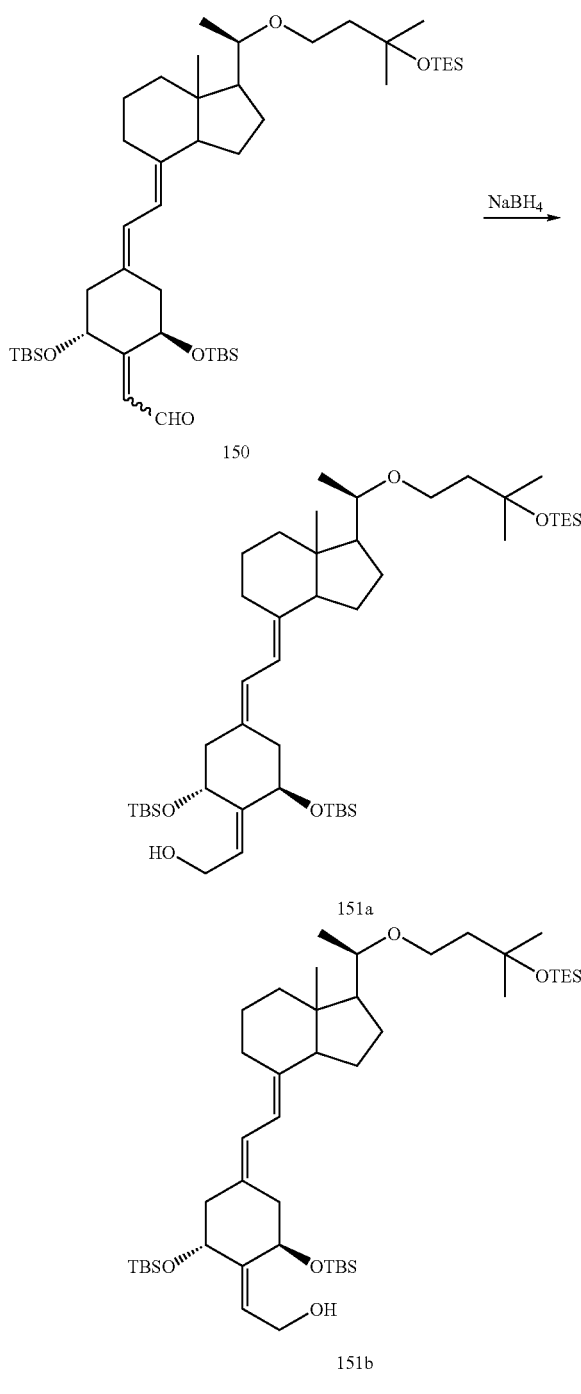

150

151a

151b

NaBH$_4$ (5.6 mg, 0.148 mmol) was added to a solution cooled to 0° C. of Compound 150 (97.0 mg, 0.123 mmol, a mixture of ca. 1:1) in MeOH/THF (2:1, 1.5 mL), and the mixture was stirred for 0.5 h. The mixture was poured into ice water, and extracted with AcOEt. The organic phase was washed with saturated brine, dried over anhydrous MgSO$_4$, and distilled off. The residue was purified by silica gel column chromatography (10 g, 7% AcOEt/hexane) to obtain Compounds 151a (43.6 mg, E-isomer) and 151b (35.5 mg, Z-isomer). The total yield was 81%.

NMR Data of the Mixture

151a: $^1$H NMR (CDCl$_3$) δ: 0.01, 0.07, 0.08 (3H, 3H, 6H, s, Si-Me'4), 0.56 (3H, s, H-18), 0.56 (6H, q, J=7.9 Hz, SiCH$_2$× 3), 0.85, 0.92 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.31 (2H, m, H-4), 2.80 (1H, m, H-9), 2.88 (1H, dd, J=12.6, 4.6 Hz, H-10), 3.26 (1H, m, H-20), 3.32, 3.70 (each 1H, m, H-23), 4.18, 4.31 (each 1H, m, CH$_2$OH), 4:37 (1H, m, H-1), 4.82 (1H, t, J=3.8 Hz, H-3), 5.72 (1H, m, C=CH), 5.83 (1H, d, J=11.0 Hz, H-7), 6.15 (1H, d, J=11.0 Hz, H-6).

151b: $^1$H NMR (CDCl$_3$) δ: 0.01, 0.07, 0.08, 0.10 (each 3H, s, Si-Me×4), 0.56 (3H, s, H-18), 0.57 (6H, q, J=7.9 Hz, SiCH$_2$×3), 0.84, 0.93 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.55 (1H, dd, J=12.5, 5.0 Hz, H-4), 2.83 (2H, m, H-9, 10), 3.26 (1H, m, H-20), 3.32, 3.70 (each 1H, m, H-23), 4.22, 4.27 (each 1H, m, CH$_2$OH), 4.48 (1H, m, H-3), 4.86 (1H, t, J=3.1 Hz, H-1), 5.72 (1H, dt, J=7.0, 1.4 Hz, C=CH), 5.79 (1H, d, J=11.1 Hz, H-7), 6.26 (1H, d, J=11.1 Hz, H-6). MS m/z (%) of the mixture: 790 (M$^+$, 1), 772 (1), 733 (1), 658 (45), 627 (11), 526 (7), 508 (7), 376 (5), 103 (33), 75 (100).

Example 84

20-epi-1α,25-dihydroxy-2-[2-(hydroxy)-ethylidene]-22-oxa-19-norvitamin D$_3$ (E-isomer) (Compound 107a)

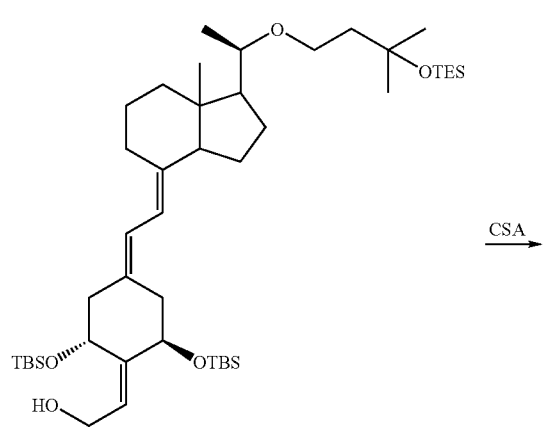

151a

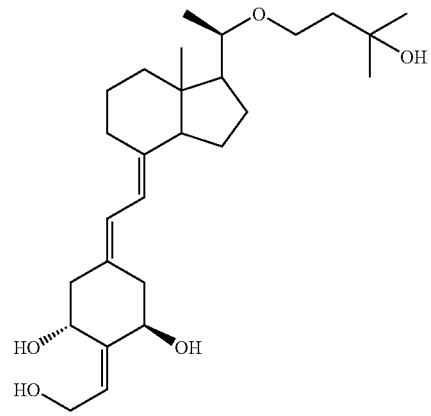

107a

To a solution of Compound 151a (43.6 mg, 0.055 mmol) in dry MeOH (1 mL) was added camphor sulfonic acid (76.8 mg, 0.331 mmol), and stirred at room temperature for 2 h. 5% NaHCO$_3$ was added to the solution, and the solution was extracted with AcOEt. The organic phase was washed with saturated brine, dried over anhydrous MgSO$_4$, and distilled off. The residue was purified by silica gel column chromatography (5 g, 2% MeOH/AcOEt) to afford Compound 107a (23.7 mg, 96%). The desired product was further purified by HPLC (YMC-Pack ODS-AM SH-342-5, 150×20 mm, 20% H$_2$O/MeOH) to obtain pure Compound 107a (20.1 mg).

107a: $^1$H NMR (CDCl$_3$) δ: 0.54 (3H, s, H-18), 1.13 (3H, d, J=5.9 Hz, H-21), 1.22, 1.23 (each 3H, s, H-26, 27), 2.33, 2.43 (each 1H, m, H-4), 2.79 (1H, m, H-9), 3.12 (1H, d, J=12.5, 4.4 Hz, H-10), 3.26 (1H, m, H-20), 3.44 (1H, m, H-23), 3.51, 3.58, 3.90 (each 1H, br. s, OH×3), 3.84 (1H, dt, J=9.4, 4.3 Hz, H-23), 4.08 (1H, dd, J=12.4, 5.2 Hz, CH$_2$OH), 4.33 (2H, m, H-1, CH$_2$OH), 4.79 (1H, m, H-3), 5.74 (1H, m, C=CH), 5.84 (1H, d, J=11.1 Hz, H-7), 6.26 (1H, d, J=11.1 Hz, H-6). UV λmax (EtOH): 246 (ε 34,600), 254 (ε 39,700), 263 (ε 26,500) nm. MS m/z (%): 448 (M$^+$, 9), 430 (8), 412 (14), 394 (26), 376 (12), 308 (13), 263 (12), 131 (20), 113 (39), 69 (100). HR-MS m/z: 448.3188 (Calcd for C$_{27}$H$_{44}$O$_5$: 448.3189).

Example 85

20-epi-1α,25-dihydroxy-2-[2-(hydroxy)-ethylidene]-22-oxa-19-norvitamin D₃ (Z-isomer) (Compound 107b)

To a solution of Compound 151b (35.5 mg, 0.045 mmol) in dry MeOH (1 mL) was added camphor sulfonic acid (62.5 mg, 0.269 mmol), and stirred at room temperature for 2 h. 5% NaHCO₃ was added to the solution, and the solution was extracted with AcOEt. The organic phase was washed with saturated brine, dried over anhydrous MgSO4, and evaporated in vacuo. The residue was purified by silica gel column chromatography (5 g, 2% MeOH/AcOEt) to afford Compound 107b (19.3 mg, 96%). The desired product was further purified by HPLC (YMC-Pack ODS-AM SH-342-5, 150×20 mm, 20% H₂O/MeOH) to obtain pure Compound 107b (17.6 mg).

107b: $^1$H NMR (CDCl$_3$) δ: 0.57 (3H, s, H-18), 1.13 (3H, d, J=5.9 Hz, H-21), 1.23, 1.24 (each 3H, s, H-26, 27), 2.68 (1H, dd, J=12.6, 4.5 Hz, H-4), 2.81 (1H, m, H-9), 2.88 (1H, d, J=14.2, 3.5 Hz, H-10), 3.28 (1H, m, H-20), 3.45, 3.84 (each 1H, m, H-23), 3.61 (1H, s, OH), 4.14 (1H, dd, J=12.5, 5.6 Hz, CH$_2$OH), 4.34 (1H, dd, J=12.5, 8.4 Hz, CH$_2$OH), 4.4 (1H, m, H-3), 4.84 (1H, m, H-1), 5.75 (1H, m, C=CH), 5.82 (1H, d, J=11.1 Hz, H-7), 6.38 (1H, d, J=11.1 Hz, H-6). UV λmax (EtOH): 246 (ε 32,300), 254 (ε 37,100), 263 (ε 24,600) nm. MS m/z (%): 448 (M$^+$, 7), 430 (7), 412 (14), 394 (25), 376 (12), 308 (13), 263 (12), 131 (21), 113 (39), 69 (100). HR-MS m/z: 448.3214 (Calcd for C$_{27}$H$_{44}$O$_5$: 448.3189).

Example 86

20-epi-1α-[(t-butyldimethylsilyl)oxy]-2β,2'-epoxy- and 1α-[(t-butyldimethyisilyl)oxy]-2α,2'-epoxy-22-oxa-25-[(triethylsilyl)oxy]-19-norvitamin D₃ t-butyldimethylsilyl ether (Compounds 152a and 152b)

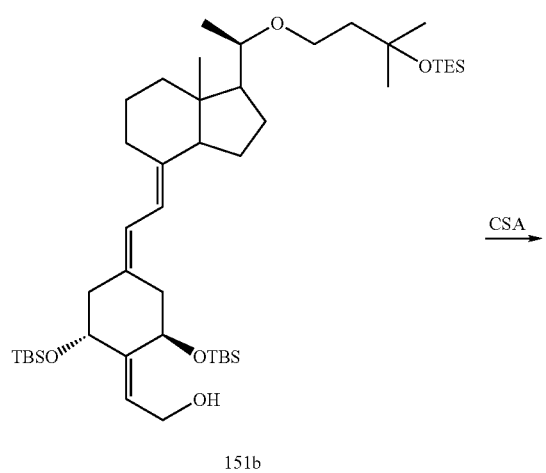

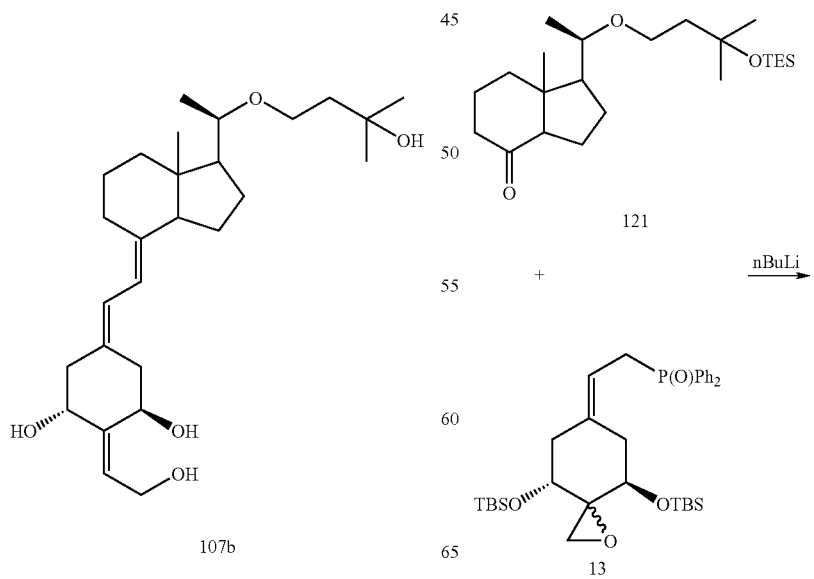

-continued

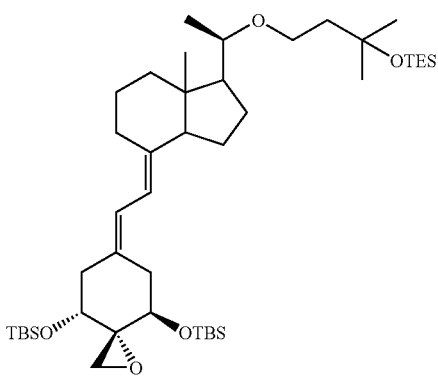

152a

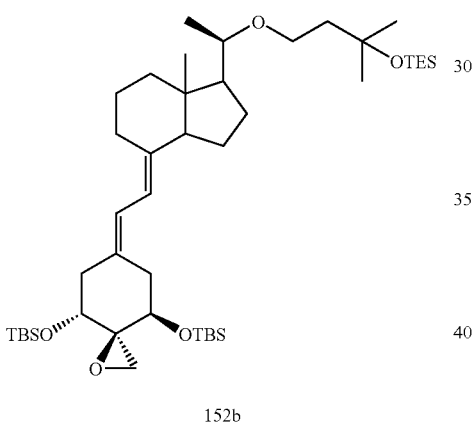

152b

To a solution cooled to −78° C. of A-ring phosphine oxide 13 (104.1 mg, 0.174 mmol, a mixture of ca. 3: 1) in dry THF (1 mL) was added n-BuLi (110.1 μL, 0.174 mmol, 1.58 M solution in hexane), and the resulting solution was stirred for 15 min. To this solution was added dropwise a solution of 22-oxa Grundmann's ketone 121 (43.6 mg, 0.110 mmol) in dry THF (1.3 mL). The mixture was stirred for 2 h with warming gradually from −78° C. to 0° C., saturated NH$_4$Cl aqueous solution was added to the mixture, and the mixture was extracted with AcOEt. The organic phase was washed with saturated brine, dried over anhydrous MgSO$_4$, and distilled off. The residue was purified by silica gel column chromatography (10 g, 2% AcOEt/hexane) to afford Compound 152 (49.8 mg, 58%) as a mixture of two kinds of stereoisomers. The ratio of the isomer 152a to the isomer 152b was ca. 5:1: Further, the unreacted starting material 121 (9.4 mg) was collected using 15% AcOEt/hexane.

N NMR Data of the Mixture 152a (major product): $^1$H NMR (CDCl$_3$) δ: 0.03-0.08 (12H, Si-Me×4), 0.56 (3H, s, H-18), 0.57 (6H, q, J=7.9 Hz, SiCH$_2$×3), 0.86, 0.88 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.73, 2.82 (each 1H, d, J=5.6 Hz, OCH$_2$), 3.25, 3.32 (each 1H, m, H-20, 23), 3.71 (1H, m, H-23), 3.82, 3.86 (each 1H, m, H-1, 3), 5.80 (1H, d, J=11.2 Hz, H-7), 6.22 (1H, d, J=11.2 Hz, H-6).

152b (minor product): $^1$H NMR (CDCl$_3$) δ: 0.03-0.08 (12H, Si-Me×4), 0.56 (3H, s, H-18), 0.57 (6H, q, J=7.9 Hz, SiCH$_2$×3), 0.86, 0.88 (each 9H, s, Si-tBu×2), 0.94 (9H, t, J=7.9 Hz, SiCH$_2$CH$_3$×3), 1.09 (3H, d, J=5.9 Hz, H-21), 1.21, 1.23 (each 3H, s, H-26, 27), 2.57, 2.92 (each 1H, d, J=5.5 Hz, OCH$_2$), 3.25, 3.32 (each 1H, m, H-20, 23), 3.71 (1H, m), 3.82 (1H, m), 4.04 (1H, m), 5.82 (1H, d, J=11.0 Hz, H-7), 6.28 (1H, d, J=11.0 Hz, H-6).

Example 87

20-epi-1α,25-dihydroxy-2β,2'-epoxy-22-oxa-19-norvitamin D$_3$ (Compound 108a), 20-epi-1α,25-dihydroxy-2α,2'-epoxy-22-oxa-19-norvitamin D$_3$ (Compound 108b), 20-epi-1α,2β,25-trihydroxy-2α-fluoromethyl-22-oxa-19-norvitamin D$_3$ (Compound 109a), and 20-epi-1α,2α,25-trihydroxy-2β-fluoromethyl-22-oxa-19-norvitamin D$_3$ (Compound 109a)

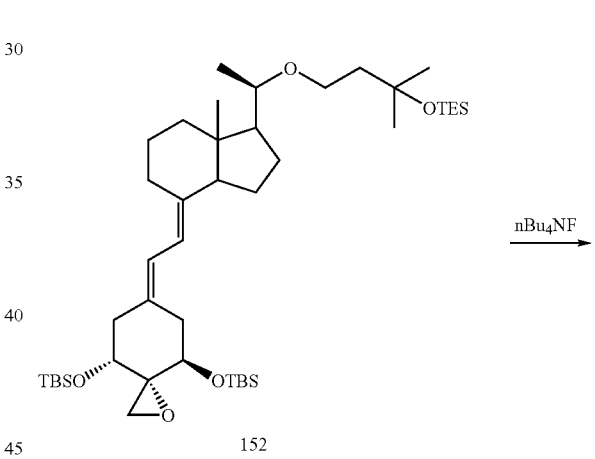

152 nBu$_4$NF

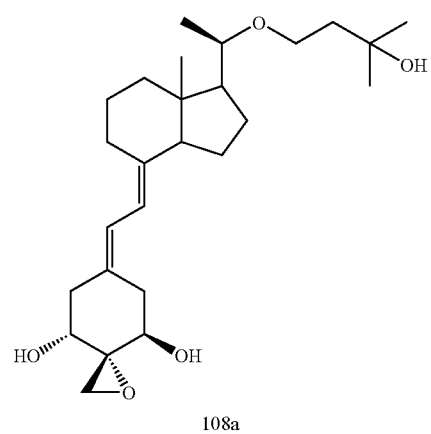

108a

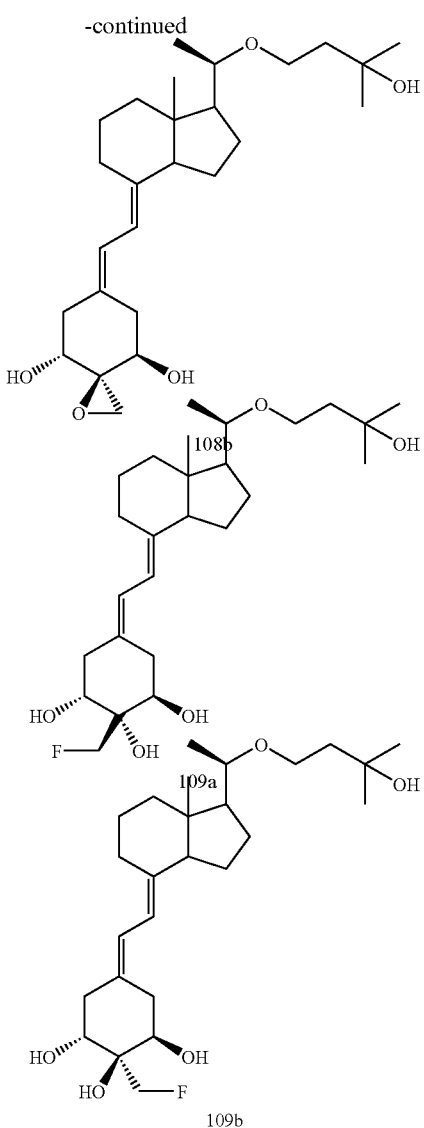

2.60 (1H, dd, J=13.7, 3.5 Hz, H-4), 2.8 (1H, m, H-9), 2.83 (1H, d, J=4.8 Hz, CH$_2$O), 2.94 (1H, dd, J=13.5, 4.3 Hz, H-10), 3.07 (1H, d, J=4.8 Hz, CH$_2$O), 3.27 (1H, m), 3.45 (1H, m), 3.82 (2H, m), 3.98 (1H, dd, J=8.6, 4.2 Hz), 5.83 (1H, d, J=11.1 Hz, H-7), 6.39 (1H, d, J=11.1 Hz, H-6). UV λmax (EtOH): 243, 251, 261 nm.

108b: $^1$H NMR (CDCl$_3$) δ: 0.56 (3H, s, H-18), 1.14 (3H, d, J=5.9 Hz, H-21), 1.23, 1.24 (each 3H, s, H-26, 27), 2.31 (1H, dd, J=13.7, 6.0 Hz, H-4), 2.36 (1H, dd, J=13.6, 8.7 Hz, H-10), 2.72 (1H, dd, J=13.7, 3.6 Hz, H-4), 2.81 (1H, m, H-9), 2.85 (1H, dd, J=13.6, 4.2 Hz, H-10), 2.94, 2.98 (each 1H, d, J=4.7 Hz, CH$_2$O), 3.27 (1H, m), 3.46 (1H, m), 3.80-3.95 (3H, m), 5.85 (1H, d, J=11.2 Hz, H-7), 6.38 (1H, d, J=11.2 Hz, H-6). UV λmax (EtOH): 243, 251, 261 nm.

109a: $^1$H NMR (CDCl$_3$) δ: 0.54 (3H, s, H-18), 1.13 (3H, d, J=5.9 Hz, H-21), 1.23, 1.24 (each 3H, s, H-26, 27), 2.48 (2H, m, H-4), 2.55 (1H, dd, J=14.4, 6.0 Hz, H-10), 2.67 (1H, br. d, J=14.4 Hz, H-10), 2.78 (1H, m, H-9), 3.27 (1H, m, H-20), 3.45 (1H, m, H-23), 3.48 (1H, s, OH), 3.85 (2H, m, H-3, 23), 3.97 (1H, m, H-1), 4.72, 4.75 (each 1H, dd, J=47.5, 9.7 Hz, CH$_2$F), 5.78 (1H, d, J=11.1 Hz, H-7), 6.40 (1H, d, J=11.1 Hz, H-6). $^{19}$F NMR (CDCl$_3$) δ: −240.3 (t, J=47.5 Hz). MS m/z (%): 454 (M$^+$, 24), 436 (9), 416 (3), 380.(1), 323 (16), 303 (4), 2.87 (3), 69 (100). UV λmax (EtOH): 243, 251, 261 nm. HR-MS m/z: 454.3087 (Calcd for C$_{26}$H$_{43}$FO$_5$: 454.3095).

109b: $^1$H NMR (CDCl$_3$) δ: 0.56 (3H, s, H-18), 1.14 (3H, d, J=6.0 Hz, H-21), 1.23, 1.24 (each 3H, s, H-26, 27), 2.75-2.90 (3H, m, H-4, 9, 10), 3.28 (1H, m, H-20), 3.45 (1H, m, H-23), 3.48 (1H, s, OH), 3.77 (1H, m, H-3), 3.84 (1H, m, H-23), 3.94 (1H, m, H-1), 4.70, 4.76 (each 1H) dd, J=48.0, 9.6 Hz, CH$_2$F), 5.83.(1H, d, J=11.3 Hz, H-7), 6.29 (1H, d, J=11.3 Hz, H-6). $^{19}$F NMR (CDCl$_3$) δ: −240.4 (t, J=48.0 Hz). MS m/Z (%): 454 (M$^+$, 30), 436 (9), 434 (10), 416 (3), 323 (16), 303 (6), 69 (100). UV λmax (EtOH): 243, 251, 261 nm. HR-MS m/z: 454.3109 (Calcd for C$_{26}$H$_{43}$FO$_5$: 454.3095).

Example 88

20-epi-1α-[(t-butyldimethylsilyl)oxy]-2β-[(trimethylsilyl)oxy]-2α-methyl- and 20-epi-1α-[(t-butyldimethylsilyl)oxy]-2α-[(trimethylsilyl)oxy]-2β-methyl-22-oxa-25-[(triethylsilyl)oxy]-19-norvitamin D$_3$ t-butyldimethylsilyl ether (Compounds 153a, 153b)

To a solution of Compound 152 (49.8 mg, 0.064 mmol, a mixture of ca. 5:1) in dry THF (1 mL) was added tetrabutylammonium fluoride (0.385 mL, 0.385 mmol, 1 M solution in THF), and the mixture was stirred at room temperature for 4 h. The mixture was poured into ice water, and extracted with AcOEt. The organic phase was washed with saturated brine, dried over anhydrous MgSO$_4$, and distilled off. The residue was purified by silica gel column chromatography (5 g) using 60% AcOEt/hexane to yield Compound 109 as a mixture of two kinds of stereoisomers (1.6 mg, 5%, 109a:109b=ca. 5:1 ratio), and using 70% AcOEt/hexane to afford Compound 108 as a mixture of two kinds of stereoisomers (23.0 mg, 83%, 108a:108b=ca. 5:1). The mixture of Compounds 108a and 108b was separated and purified by HPLC (LiChrosorb Si 60, RT 250-4, 250×10 mm, hexane:CH$_2$Cl$_2$:2-propanol=50:50:6) to obtain Compounds 108a (9.46 mg) and 108b (995 µg), respectively. The mixture of Compounds 109a and 109b was separated and purified by HPLC (YMC-Pack ODS-AM SH-342-5, 150×20.mm, 25% H$_2$O/MeOH) to-obtain Compounds 109a (813 µg) and 109b (170 µg), respectively.

108a: $^1$H NMR (CDCl$_3$) δ: 0.56 (3H, s, H-18), 1.13 (3H, d, J=5.9 Hz, H-21), 1.22, 1.24 (each 3H, s, H-26, 27), 2.29 (1H, dd, J=13.5, 8.6 Hz, H-10), 2.40 (1H, dd, J=13.7, 6.2 Hz, H-4),

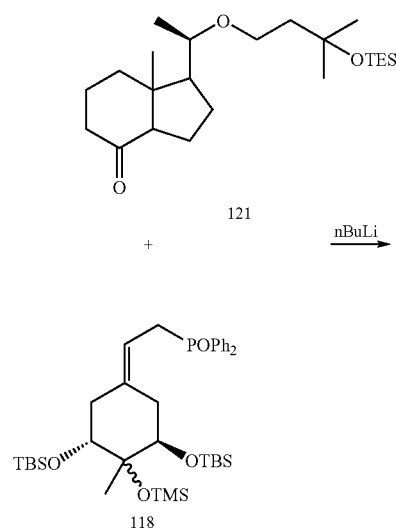

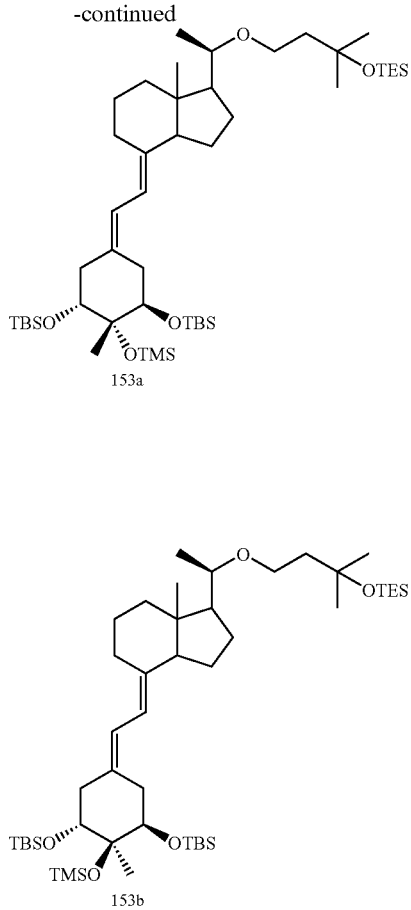

153a

153b

To a solution cooled to −78° C. of A-ring phosphine oxide 118 (214.7 mg, 0.32 mmol, a mixture of ca. 1:1) in dry THF (3 mL) was added n-BuLi (202.9 μL, 0.32 mmol, 1.58 M solution in hexane), and the resulting solution was stirred for 15 min. To this solution was added dropwise a solution of 22-oxa Grundmann's ketone 121 (54.6 mg, 0.14 mmol) in dry THF (2 mL). The mixture was stirred for 3 h with warming gradually from −78° C. to −30° C., saturated NH$_4$Cl aqueous solution was added to the mixture, and the mixture was extracted with AcOEt. The organic phase was washed with saturated brine, dried over anhydrous MgSO$_4$, and distilled off. The residue was purified by silica gel column chromatography (7 g, 3% AcOEt/hexane) to afford Compound 153 (52.1 mg, 44%) as a mixture of two kinds of stereoisomers. The ratio of the isomer 153a to the isomer 153b was ca. 3:1. Further, the unreacted starting material 121 (25.6 mg) was collected using 5% AcOEt/hexane.

153: $^1$H NMR (CDCl$_3$) δ: 0.02-0.12 (21H, Si-Me×4, Si-Me$_3$), 0.5588 (3H, s, H-18), 0.5598 (6H, q, J=7.8 Hz, Si—CH$_2$CH$_3$×3), 0.83, 0.92 (each 9H, s, Si-tBu×2), 0.94 (9H, t, J=7.8 Hz, Si—CH$_2$CH$_3$×3), 1.08 (3H, d, J=5.9 Hz, H-21), 3.20-3.30 (2H, m), 3.55-3.80 (3H, m), 5.76, 5.82 (ca. 1:3) (1H, d, J=11.1 Hz, H-7), 6.04, 6.15 (ca. 3:1) (1H, d, J=11.1 Hz, H-6). MS m/z (%): 850 (M$^+$, 3), 718 (74), 661 (5), 586 (100), 454 (3).

Example 89

1α,2β,25-trihydroxy-2α-methyl-22-oxa-19-norvitamin D$_3$ (Compound 110a) and 1α,2α,25-trihydroxy-2β-methyl-22-oxa-19-norvitamin D$_3$ (Compound 110b)

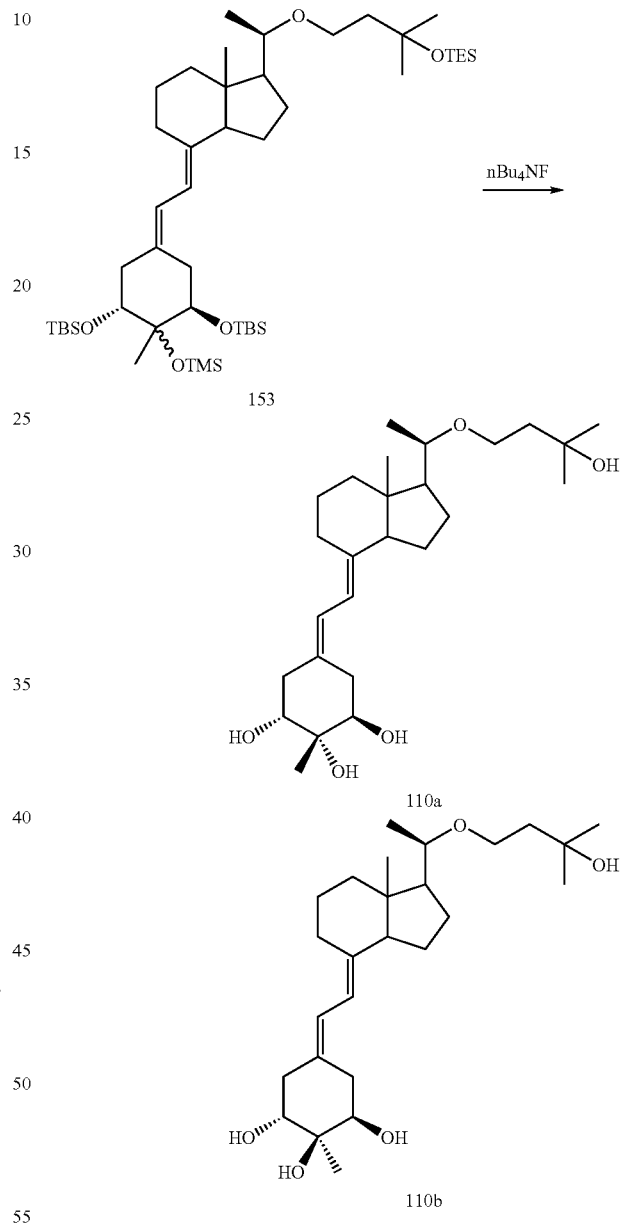

To a solution of Compound 153 (52.1 mg, 0.061 mmol, a mixture of ca. 3:1) in dry THF (1 mL) was added tetrabutylammonium fluoride (0.490 mL, 0.490 mmol, 1 M solution in THF), and the mixture was stirred at room temperature for 18 h. The mixture was poured into ice water, and extracted with AcOEt. The organic phase was washed with saturated brine, dried over anhydrous MgSO$_4$, and distilled off. The residue was purified by silica gel column chromatography (10 g) using 70%/o AcOEt/hexane to yield Compound 110 (25.7 mg, 96%) as a mixture of two kinds of stereoisomers. The ratio of the isomer 110a to the isomer 110b was ca. 3:1. The mixture of Compounds 110a and 110b was separated and purified by HPLC (YMC-Pack ODS-AM SH-342-5, 150×20 mm, 30% H$_2$O/MeOH) to obtain Compounds 110a (14.7 mg) and 110b (4.43 mg), respectively.

110a: $^1$H NMR (CDCl$_3$) δ: 0.55 (3H, s, H-18), 1.13 (3H, d, J=6.0 Hz, H-21), 1.22, 1.24 (each 3H, s, H-26, 27), 1.29 (3H, s, Me), 2.47 (1H, dd, J=14.1, 3.3 Hz, H-10), 2.64 (2H, m, H-4, 10), 2.78 (1H, m, H-9), 3.27 (1H, m, H-20), 3.45 (1H, m, H-23), 3.58 (1H, s, OH), 3.72 (2H, m, H-1, OH), 3.78 (1H, m, H-3), 3.84 (1H, m, H-23), 5.79 (1H, d, J=11.1 Hz, H-7), 6.33 (1H, d, J=11.1 Hz, H-6). MS m/z (%): 436 (M$^+$, 54), 418 (13), 400 (8), 305 (15), 69 (100). UV λmax (EtOH): 243, 251, 261 nm.

100b: $^1$H NMR (CDCl$_3$) δ: 0.54 (3H, s, H-18), 1.13 (3H, d, J=6.0 Hz, H-21), 1.23, 1.24 (each 3H, s, H-26, 27), 1.26 (3H, s, Me), 2.36 (1H, dd, J=14.4, 4.6 Hz), 2.54 (1H, br. d, J'13.8 Hz), 2.78 (1H, m, H-9), 2.92 (1H, dd, J=14.5, 4.5 Hz), 3.26 (1H, m, H-20), 3.45 (1H, m, H-23), 3.57 (1H, br. s, OH), 3.73 (3H, m, H-1, 3, OH), 3.84 (1H, m, H-23), 5.82 (1H, d, J=11.1 Hz, H-7), 6.29 (1H, d, J=11.1 Hz, H-6). UV λmax (EtOH): 243, 251, 261 nm.

Example 90

24a,26a,27a-trihomo-1α-[(t-butyldimethylsilyl)oxy]-2α-[(trimethylsilyl)oxy]- and 24a,26a,27a-trihomo-1α-[(t-butyldimethylsilyl)oxy]-2β-[(trimethylsilyl)oxy]-2β-[(trimethylsilyl)oxy]-22,24-dien-25-[(triethylsilyl)oxy]-19-norvitamin D$_3$ t-butyldimethylsilyl ether (Compounds 154a, 154b)

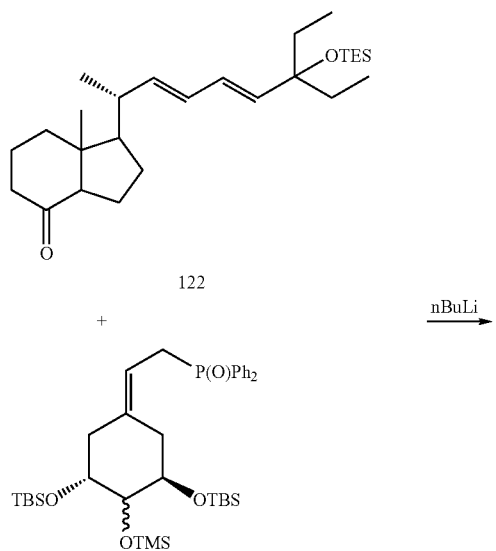

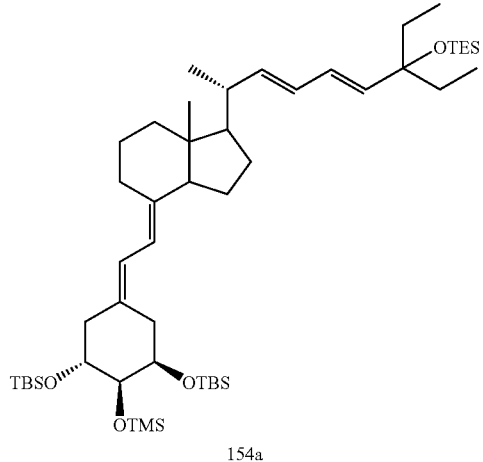

154a

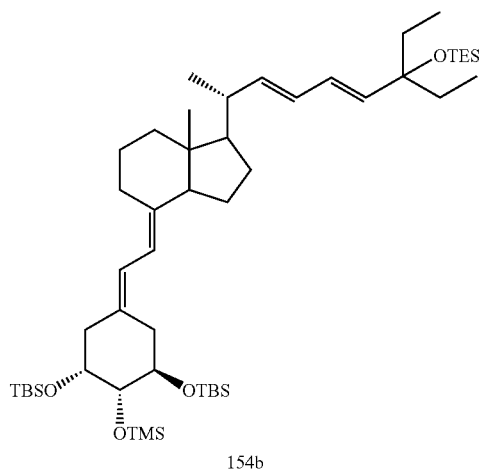

154b

To a solution cooled to −78° C. of A-ring phosphine oxide 22 (260.0 mg, 0.394 mmol, a mixture of ca. 2: 1) in dry THF (3 mL) was added n-BuLi (253 pi, 0.394 mmol, 1.56 M solution in hexane), and the resulting solution was stirred for 15 min. To this solution was added slowly a solution of C/D-ring ketone 122 (101.8 mg, 0.235 mmol) in dry THF (1 mL), and the mixture was stirred for 2 h at −78° C., saturated NH$_4$Cl aqueous solution was added to the mixture, and the mixture was extracted with AcOEt. The organic phase was washed with saturated brine, dried over anhydrous MgSO$_4$, and distilled off. The residue was purified by silica gel column chromatography (10 g) using 1% AcOEt/hexane to afford Compound 154 (106.4 mg, 52%) as a mixture of two kinds of stereoisomers. The ratio of the isomer 154a to the isomer 154b was ca. 3:2. Further, the unreacted starting material 122 (36.1 mg) was collected using 5% AcOEt/hexane.

NMR Data of the Mixture 154a (major product): ¹H NMR (CDCl₃) δ: 0.039, 0.051, 0.059, 0.064 (each 3H, s, Si-Me×4), 0.12 (9H, s, Si-Me×3), 0.56 (3H, s, H-18), 0.56 (6H, q, J=7.9 Hz, SiCH₂×3), 0.82 (6H, t, J=7.5 Hz, H-26a, 27a), 0.868, 0.874 (each 9H, s, Si-tBu×2), 0.94 (9H, t, J=7.9 Hz, SiCH₂CH₃×3), 1.06 (3H, d, J=6.6 Hz, H-21), 2.80 (1H, m, H-9), 3.53 (1H, m, H-2), 3.80 (1H, m, H-3), 3.88 (1H, m, H-1), 5.52 (1H, d, J=15.2 Hz, H-24a, overlapped with H-22), 5.81 (1H, d, J=11.1 Hz, H-7), 5.94 (1H, dd, J=14.9, 10.4 Hz, H-23), 6.05 (1H, dd, J=15.2, 10.4 Hz, H-24), 6.10 (1H, d, J=11.1 Hz, H-6).

154b (minor product): ¹H NMR (CDCl₃) δ: 0.039, 0.051, 0.059, 0.064 (each 3H, 5, Si-Me×4), 0.12 (9H, s, Si-Me×3), 0.54 (3H, s, H-18), 0.56 (6H, q, J=7.9 Hz, SiCH₂×3), 0.82 (6H, t, J=7.5 Hz, H-26a, 27a), 0.86, 0.89 (each 9H, s, Si-tBu×2), 0.94 (9H, t, J=7.9 Hz, SiCH₂CH₃×3), 1.06 (3H, d, J=6.6 Hz, H-21), 2.80 (1H, m, H-9), 3.59 (1H, m, H-2), 3.80 (1H, m, H-3), 3.94 (1H, m, H-1), 5.52 (1H, d, J=15.2 Hz, H-24a, overlapped with H-22), 5.78 (1H, d, J=11.1 Hz, H-7), 5.94 (1H, dd, J=14.9, 10.4 Hz, H-23), 6.05 (1H, dd, J=15.2, 10.4 Hz, H-24), 6.13 (1H, d, J=11.1 Hz, H-6). MS m/z (%) of the mixture: no M⁺, 740 (33), 683 (7), 608 (65), 551 (17), 505 (43), 4.59 (18), 324 (31), 149 (100), 75 (99).

Example 91

24a,26a,27a-trihomo-1α,2α,25-trihydroxy- and 24a,26a,27a-trihomo-1α,2β,25-trihydroxy-22,24-dien-19-norvitamin D₃ (Compounds 155a, 155b)

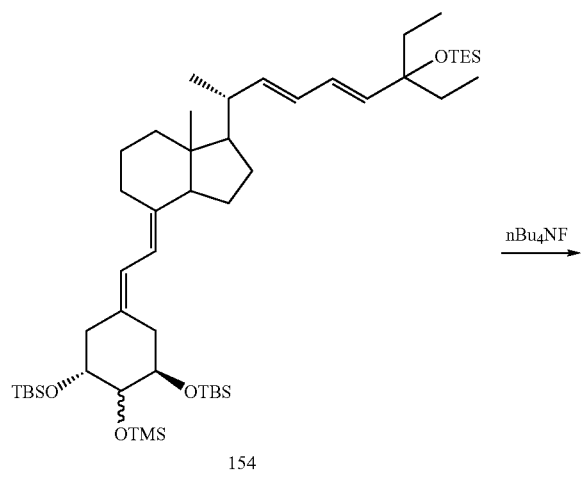

154

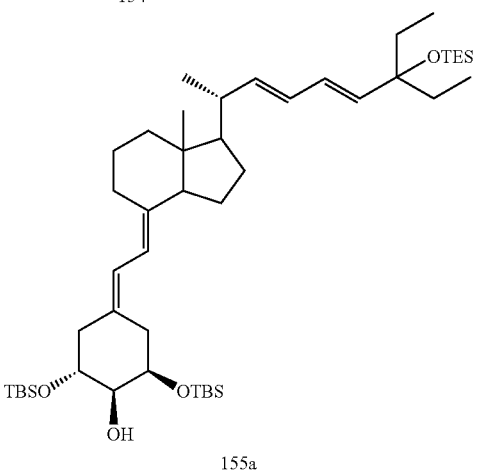

155a

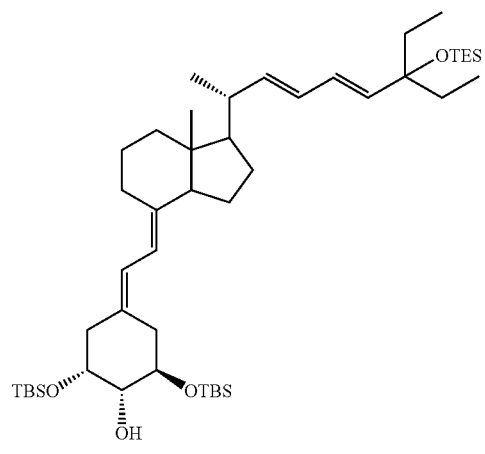

155b

To a solution of Compound 154 (55 mg, 0.063 mmol, a mixture of ca. 3:2) in dry THF (1 mL) were added Et₃N (20 μL) and tetrabutylammonium fluoride (504 μL, 0.504 mmol, 1.0 M solution in THF), and the resulting solution was stirred at room temperature for 4 h. The mixture was poured into ice water and extracted with AcOEt. The organic phase was washed with saturated brine, and dried over anhydrous MgSO₄. Removal of the solvent in vacuo afforded the residue, which was purified by silica gel column chromatography (5 g, 2% MeOH/AcOEt) to yield Compound 155 (28.0 mg, 97%) as a mixture of two kinds of stereoisomers. The ratio of the isomer 155a to the isomer 155b was ca. 3:2.

NMR Data of the mixture

155a: ¹H NMR (CDCl₃) δ: 0.57 (3H, s, H-18), 0.87 (6H, t, J=7.4 Hz, H-26a, 27a), 1.05 (3H, d, J=6.6 Hz, H-21), 1.55, 1.56 (each 2H, d, J=7.4 Hz, H-26, 27), 2.62 (1H, dd, J=12.8, 4.1 Hz, H-4), 2.80 (1H, m, H-9), 2.89 (1H, dd, J=14.7, 4.3 Hz, H-10), 3.53 (1H, d, J=8.2, 2.9 Hz, H-2), 3.79 (1H, m, H-3), 4.09 (1H, m, H-1), 5.53 (1H, d, J=15.2 Hz, H-24a, overlapped with H-22), 5.80 (1H, d, J=11.1 Hz, H-7), 5.98 (1H, dd, J=15.0, 10.3 Hz, H-23), 6.15 (1H, dd, J=15.2, 10.3 Hz, H-24), 6.37 (1H, d, J=11.1 Hz, H-6).

155b: ¹H NMR (CDCl₃) δ: 0.57 (3H, s, H-18), 0.87 (6H, t, J=7.4 Hz, H-26a, 27a), 1.05 (3H, d, J=6.6 Hz, H-21), 1.55, 1.56 (each 2H, d, J=7.4 Hz, H-26, 27), 2.43 (2H, m, H-4), 2.80 (1H, m, H-9), 3.07 (1H, dd, J=13.2, 4.9 Hz, H-10), 3.48 (1H, dd, J=8.8, 3.0 Hz, H-2), 3.67 (1H, m, H-3), 4.09 (1H, m, H-1), 5.53 (1H, d, J=15.2 Hz, H-24a, overlapped with H-22), 5.83 (1H, d, J=11.1 Hz, H-7), 5.98 (1H, dd, J=15.0, 10.3 Hz, H-23), 6.15 (1H, dd, J=15.2, 10.3 Hz, H-24), 6.29 (1H, d, J=11.1 Hz, H-6). MS m/z (%) of the mixture: 458 (M⁺, 33), 440 (95), 422 (14), 404 (16), 386 (52), 318 (40), 289 (90), 237 (44), 149 (100).

Example 92

24a,26a,27a-trihomo-1α-[(t-butyldimethylsilyl)oxy]-2α-hydroxy- and 24a,26a,27a-trihomo-1α-[(t-butyldimethylsilyl)oxy]-2β-hydroxy-22,24-dien-25-[(t-butyldimethylsilyl)oxy]-19-norvitamin D₃ t-butyldimethylsilyl ether (Compounds 156a, 156b)

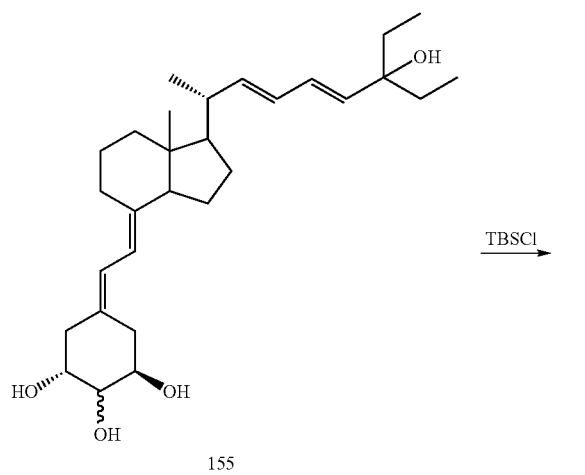

To a solution of Compound 155 (48.0 mg, 0.105 mmol, a mixture of ca. 3:2) in dry DMF (1 mL) were added Et₃N (117 μL, 0.840 mmol), tert-butyldimethylsilyl chloride (63.9 mg, 0.424 mmol) and 4,4-(dimethylamino)pyridine (6.4 mg, 0.052 mmol), and the resulting solution was stirred at room temperature for 2 h. The reaction mixture was poured into ice water, and extracted with AcOEt. The organic phase was washed with saturated brine, dried over anhydrous Na₂SO₄, and distilled off. The residue was purified by silica gel column chromatography (5 g, 5% AcOEt/hexane) to yield Compound 156 (55;3 mg, 66%) as a mixture of two kinds of stereolsomers. The ratio of the isomer 156a to the isomer 156b was ca. 3:2.

NMR Data of the Mixture 156a (major product): ¹H NMR (CDCl₃) δ: 0.06-0.10 (18H, Si-Me×6), 0.57 (3H, s, H-18), 0.87 (6H, t, J=7.5 Hz, H-26a, 27a), 0.86-0.92 (27H, Si-tBu×3), 1.06 (3H, d, J=6.6 Hz, H-21), 1.54, 1.55 (each 2H, d, J=7.5 Hz, H-26, 27), 2.80 (1H, m, H-9), 3.51 (1H, d, H-2), 3.92 (1H, m, H-3), 4.00 (1H, m, H-1), 5.53 (1H, d, J=15.3 Hz, H-24a), 5.55 (1H, dd, J=15.2, 8.5 Hz, H-22), 5.79 (1H, d, J=11.1 Hz, H-7), 5.98 (1H, dd, J=15.2, 10.4 Hz, H-23), 6.14 (2H, m, H-6, 24).

156b (minor product): ¹H NMR (CDCl₃) δ: 0.06-0.10 (18H, Si-Me×6), 0.56 (3H, s, H-18), 0.87 (6H, t, J=7.5 Hz, H-26a, 27a), 0.86-0.92 (27H, Si-tBu×3), 1.06 (3H, d, J=6.6 Hz, H-21), 1.54, 1.55 (each 2H, d, J=7.5 Hz, H-26, 27), 2.80 (1H, m, H-9), 3.59 (1H, m, H-2), 4.00 (2H, m, H-1, 3), 5.53 (1H, d, J=15.3 Hz, H-24a), 5.55 (1H, dd, J=15.2, 8.5 Hz, H-22), 5.79 (1H, d, J=11.1 Hz, H-7), 5.98 (1H, dd, J=15.2, 10.4 Hz, H-23), 6.14 (2H, m, H-6, 24). MS m/z (%) of the mixture: no M⁺, 668 (6), 611 (2), 536 (3), 479 (12), 386 (6), 149 (100), 75 (79).

Example 93

24a,26a,27a-trihomo-1α-[(t-butyldimethylsilyl)oxy]-2α-[2-(t-butyldimethylsilyl)oxy]-ethoxy- and 24a,26a,27a-trihomo-1α-[(t-butyldimethylsilyl)oxy]-2β-[2-(t-butyldimethylsilyl)oxy]-ethoxy-22,24-dien-25-[(t-butyldimethylsilyl)oxy]-19-norvitamin D₃ t-butyldimethylsilyl ether (Compounds 157a, 157b)

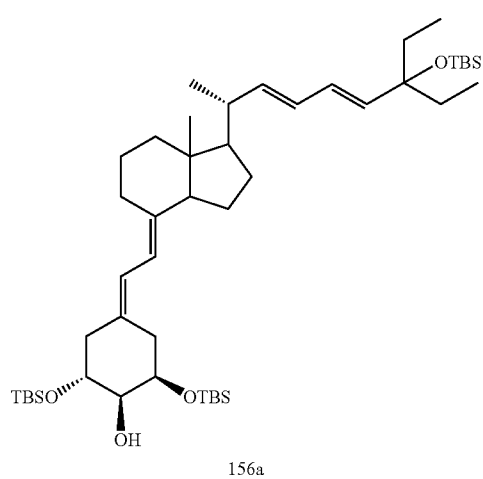

156a

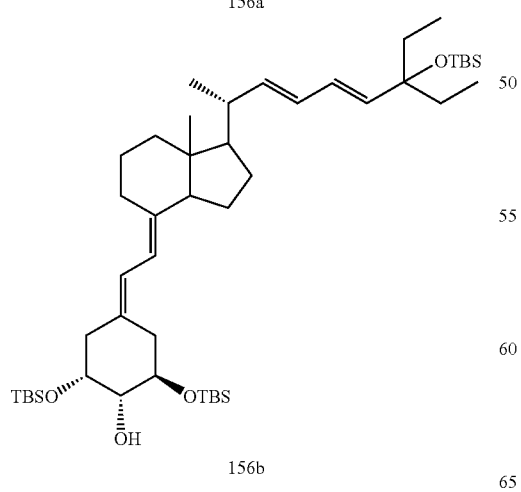

156b

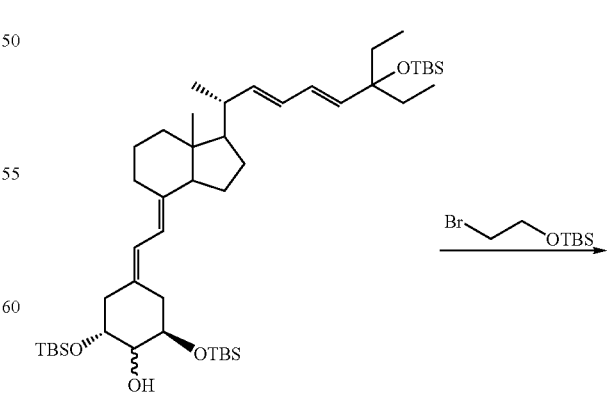

156

-continued

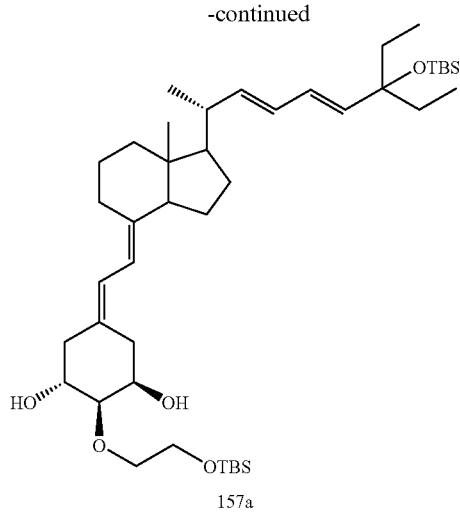

Example 94

24a,26a,27a-trihomo-1α,25-dihydroxy-2α-(2-hydroxyethoxy)- and 24a,26a,27a-trihomo-1α,25-dihydroxy-2β-(2-hydroxyethoxy)-22,24-dien-19-norvitamin D$_3$ (Compounds 111a, 111b)

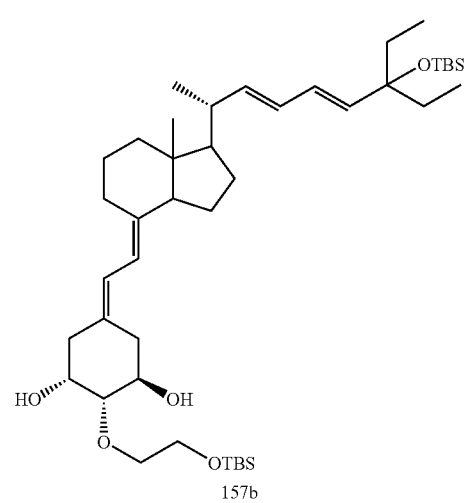

To a solution cooled to 0° C. of Compound 156 (52.4 mg, 0.065 mmol, a mixture of ca. 3:2) in dry DMF (1 mL) were added NaH (78.5 mg, 1.962 mmol, 60% paraffin liquid (dispersion in mineral oil)) and (2-bromoethoxy)-tert-butyldimethylsilane (68 μL, 0.317 mmol), and the resulting solution was stirred vigorously. After 18 h, the reaction mixture was poured into ice water, and then extracted with AcOEt/hexane (1:1). The organic phase was washed with saturated brine, dried over anhydrous MgSO$_4$, and distilled off. The residue was purified by silica gel column chromatography (10 g, 1-10% AcOEt/hexane) to afford Compound 157 (44.7 mg, 71%) as a mixture of kinds of stereoisomers. The ratio of the isomer 157a to the isomer 157b was ca. 3:2.

157: $^1$H NMR (CDCl$_3$) δ: 0.05-0.10 (24H, Si-Me×8), 0.55, 0.57 (ca. 2:3) (3H, s, H-18), 0.85-0.92 (42H, 4×Si-tBu, H-26a, 27a), 1.05 (3H, d, J=6.6 Hz, H-21), 1.54, 1.55 (each 2H, d, J=7.5 Hz, H-26, 27), 2.80 (1H, m, H-9), 3.18-4.45 (7H, m, OCH$_2$CH$_2$O, H-1, 3), 5.52 (1H, d, J=15.1 Hz, H-24a), 5.54 (1H, dd, J=15.0, 8.6 Hz, H-22), 5.79 (1H, H-7), 5.97 (1H, dd, J=15.0, 10.4 Hz, H-23), 6.15 (2H, m, H-6, 24). MS m/z (%): no M$^+$, 649 (14), 651 (11), 562 (12), 519 (24), 233 (100).

To a solution of Compound 157 (42.0 mg, 0.044 mmol, a mixture of ca. 3:2) in dry THF (1 mL) were added Et$_3$N (30 μL) and tetrabutylammonium fluoride (350 μL, 0.350 mmol, 1.0 M solution in THF), and the resulting solution was stirred at room temperature for 5 h. The mixture was poured into ice water, and extracted with AcOEt. The organic phase was washed with saturated brine, dried over anhydrous Na$_2$SO$_4$, and distilled off. The residue was purified by silica gel column chromatography (5 g, 2% MeOH/AcOEt) to yield a mixture of Compounds 111a and 111b (20.0 mg, 91%). The mixture of 111a and 111b was separated and purified by HPLC (YMC-Pack ODS-AM SH-342-5, 150×20 mm, 20% H$_2$O/MeOH) to obtain Compounds 111a (9.4 mg) and 111b (8.3 mg), respectively.

111a: $^1$H NMR (CDCl$_3$) δ: 0.57 (3H, s, H-18), 0.86 (6H, t, J=7.4 Hz, H-26a, 27a), 1.04 (3H, d, J=6.6 Hz, H-21), 1.54, 1.56 (each 2H, d, J=7.4 Hz, H-26, 27), 2.61 (1H, dd, J=13.4, 4.4 Hz, H-4), 2.80 (1H, m, H-9), 2.86 (1H, dd, J=14.4, 4.8 Hz, H-10), 3.32 (1H, dd, J=8.0, 2.5 Hz, H-2), 2.72, 3.12, 3.48 (each 1H, br. s, OH×3), 3.67-3.81 (4H, m, OCH$_2$CH$_2$O), 3.93 (1H, m, H-3), 4.15 (1H, m, H-1), 5.53 (1H, d, J=15.3 Hz, H-24a, overlapped with H-22), 5.81 (1H, d, J=11.1 Hz, H-7), 5.97 (1H, dd, J=15.0, 10.3 Hz, H-23), 6.14 (1H, dd, J=15.3, 10.3 Hz, H-24), 6.33 (1H, d, J=11.1 Hz, H-6). UV λmax (EtOH): 235 (ε 44,000), 243 (ε 44,200), 251 (ε 38,000), 261 (ε 23,800) nm. MS m/z (%): 502 (M$^+$, 11), 484 (62), 466 (33), 448 (7), 386 (17), 333 (40), 237 (29), 149 (100), 133 (43), 93 (49). HR-MS m/z: 502.3658 (Calcd for C$_{31}$H$_{50}$O$_5$: 502.3658).

111b: $^1$H NMR (CDCl$_3$) δ: 0.56 (3H, s, H-18), 0.86 (6H, t, J=7.5 Hz, H-26a, 27a), 1.05 (3H, d, J=6.6 Hz, H-21), 1.55, 1.56 (each 2H, d, J=7.5 Hz, H-26, 27), 2.34, 2.47 (each 1H, m, H-4), 2.64 (1H, br. s, OH), 2.80 (1H, m, H-9), 3.07 (1H, dd, J=13.2, 4.0 Hz, H-10), 3.27 (1H, dd, J=8.7, 2.6 Hz, H-2), 3.64-3.86 (5H, m, OCH$_2$CH$_2$O, H-1), 4.16 (1H, m, H-3), 5.35 (1H, d, J=15.3 Hz, H-24a, overlapped with H-22), 5.83 (1H, d, J=11.1 Hz, H-7), 5.97 (1H, dd, J=15.0, 10.3 Hz, H-23), 6.15 (1H, dd, J=15.3, 10.3 Hz, H-24), 6.26 (1H, d, J=11.1 Hz, H-6). UV λmax (EtOH): 235 (ε 44,000), 243 (ε 44,500), 251 (ε 38,900), 261 (ε 24,000) nm. MS m/z (%): 502 (M$^+$, 13), 484 (78), 466 (39), 448 (7), 386 (13), 333 (48), 237 (27), 149 (100), 133 (46), 93 (49). HR-MS m/z: 502.3664 (Calcd for C$_{31}$H$_{50}$O$_5$: 502.3658).

Example 95

E-isomer and Z-isomer of 24a,26a,27a-trihomo-1α-[(t-butyldimethylsilyl)oxy]-2-[2-(t-butyldimethylsilyl)oxy]-ethylidene-22,24-dien-25-[(triethylsilyl)oxy]-19-norvitamin D$_3$ t-butyldimethylsilyl ether (Compounds 15.8a, 158b)

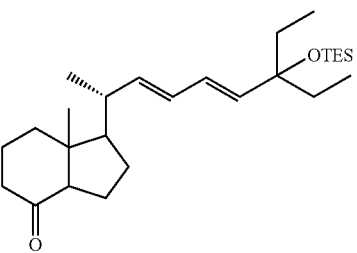

122

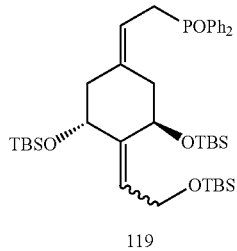

119 nBuLi →

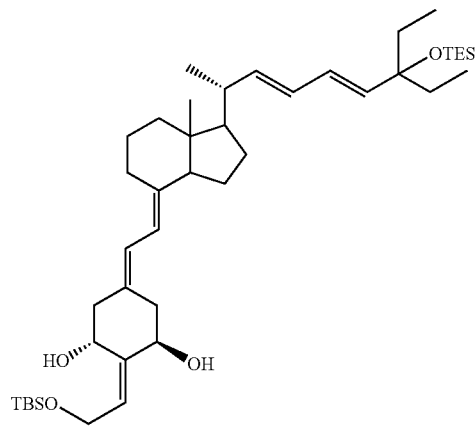

158a

+

-continued

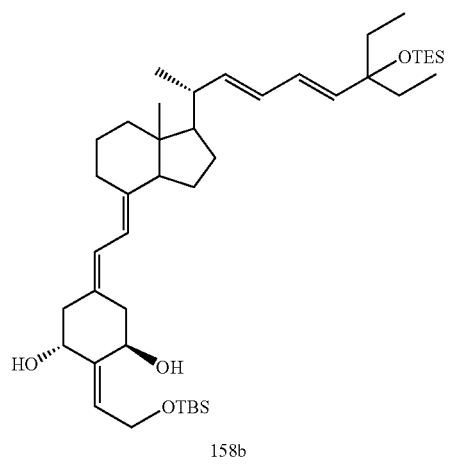

158b

Example 96

E-isomer and Z-isomer of 24a,26a,27a-trihomo-1α, 25-dihydroxy-2-[2-(hydroxy)-ethylidene]-22,24-dien-19-norvitamin $D_3$ (Compounds 112a, 112b)

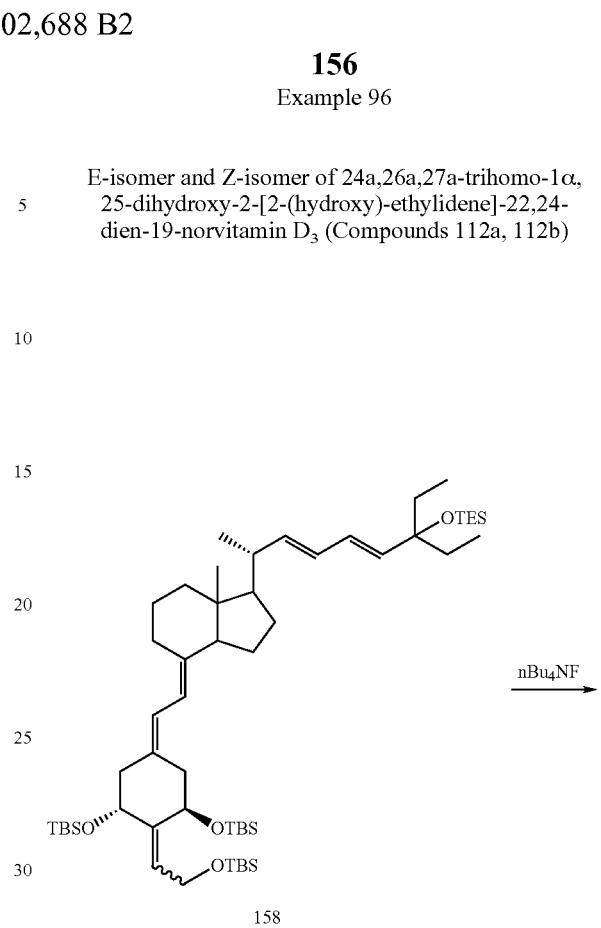

158

To a solution cooled to −78° C. of A-ring phosphine oxide 119 (119.5 mg, 0.164 mmol, a mixture of ca. 4:1) in dry THF (2 mL) was added n-BuLi (105 μL, 0.164 mmol, 1.56 M solution in hexane), and the resulting solution was stirred for 15 min. To this solution was added slowly a solution of C/D-ring ketone 122 (47.4 mg, 0.109 mmol) in dry THF (1 mL), and the mixture was stirred for 2 h at −78° C., saturated NH$_4$Cl aqueous solution was added to the mixture, and the mixture was extracted with AcOEt. The organic phase was washed with saturated brine, dried over anhydrous MgSO$_4$, and distilled off. The residue was purified by silica gel column chromatography (10 g) using 1% AcOEt/hexane to afford Compound 158 (27.7 mg, 27%) as a mixture of two kinds of stereoisomers. The ratio of the isomer 158a to the isomer 158b was ca. 6:1. Further, the unreacted starting material 122 (27 mg, 57%) was collected using 5% AcOEt/hexane.

158: $^1$H NMR (CDCl$_3$) δ: 0.01-0.08 (18H, Si-Me×6), 0.571 (3H, s, H-18), 0.569 (6H, q, J=7.9 Hz, SiCH$_2$×3), 0.83 (6H, t, J=7.5 Hz, H-26a, 27a), 0.84, 0.90, 0.92 (each 9H, s, Si-tBu×3), 0.94 (9H, t, J=7.9 Hz, SiCH$_2$CH$_3$×3), 1.06 (3H, d, J=6.6 Hz, H-21), 2.80 (1H, m, H-9), 2.97, 3.28 (ca. 6: 1) (1H, dd, J=12.5, 4.7 Hz, H-10), 4.24-4.47 (3H, m, H-1 or 3, CH$_2$OH), 4.79, 4.84 (ca. 6:1) (1H, m, H-1 or 3), 5.52 (1H, dd, J=14.9, 8.3 Hz, H-22), 5.53 (1H, d, J=15.2 Hz, H-24a), 5.61 (1H, m, C=CH), 5.87 (1H, d, J=11.1 Hz, H-7), 5.95 (1H, dd, J=14.9, 10.4 Hz, H-23), 6.06 (1H, dd, J=15.2, 10.4 Hz, H-24), 6.13 (1H, d, J=11.1 Hz, H-6).

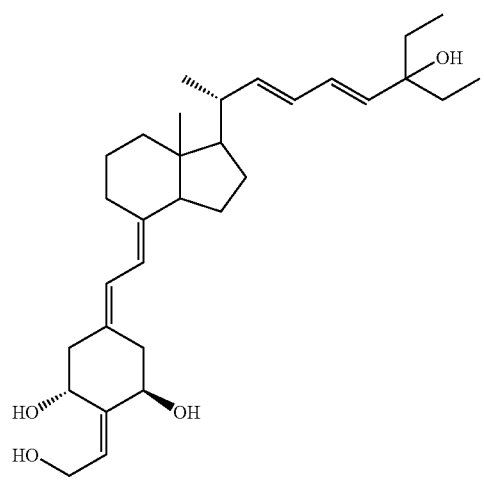

112a

-continued

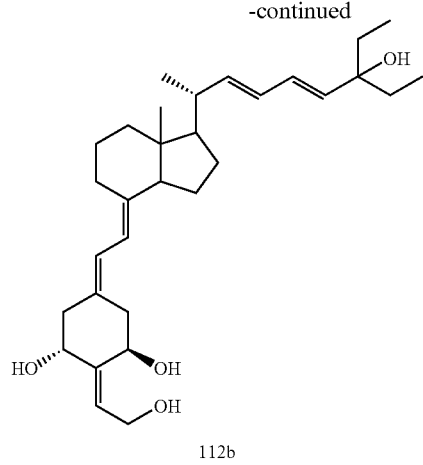

112b

To a solution of Compound 158 (56 mg, 0.0595 mmol, a mixture of ca. 6:1) in dry THF (1 mL) were added Et₃N (40 μL) and tetrabutylammonium fluoride (476 μL, 0.476 mmol, 1.0 M solution in THF), and the mixture was stirred at room temperature for 20 h. The mixture was poured into ice water, and extracted with AcOEt. The organic phase was washed with saturated brine, dried over anhydrous Na₂SO₄, and distilled off. The residue was purified by silica gel column chromatography (5 g, 2% MeOH/AcOEt) to yield a mixture of Compounds 112a and 112b (23.0 mg, 80%, ca. 10:1). The mixture of 112a and 112b was separated and purified by HPLC (LiChrosorb Si 60, Hibar RT 250-10, 250×10 mm, hexane:CH₂Cl₂:MeOH=50:50:4) to obtain Compounds 112a (17.1 mg, E-isomer) and 112b (1.9 mg, Z-isomer), respectively.

112a: $^1$H NMR (CDCl₃) δ: 0.56 (3H, s, H-18), 0.87 (6H, t, J=7.5, H-26a, 27a), 1.05 (3H, d, J=6.5 Hz, H-21), 1.55, 1.56 (each 2H, d, J=7.5 Hz, H-26, 27), 2.34, 2.44 (each 1H, m, H-4), 2.81 (1H, m, H-9), 3.14 (1H, d, J=12.5, 4.3 Hz, H-10), 3.38, 3.74 (each 1H, br. s, OH×2), 4.09 (1H, dd, J=12.3, 5.2 Hz, CH₂OH), 4.34 (2H, m, H-1, CH₂OH), 4.80 (1H, m, H-3), 5.53 (1H, d, J=15.4 Hz, H-24a, overlapped with H-22), 5.75 (1H, m, C=CH), 5.88 (1H, d, J=11.1 Hz, H-7), 5.97 (1H, dd, J=15.0, 10.4 Hz, H-23), 6.15 (1H, dd, J=15.4, 10.4 Hz, H-24), 6.27 (1H, d, J=11.1 Hz, H-6). UV λmax (EtOH): 236 (ε 47,300), 245 (ε 48,000), 254 (ε 43,200), 264 (ε 27,200) nm. MS m/z (%): 484 (M⁺, 7), 466 (15), 448 (17), 430 (44), 412 (34), 279 (33), 263 (25), 149 (100), 133 (35), 93 (38). HR-MS m/z: 484.3526 (Calcd for C₃₁H₄₈O₄: 484.3553).

112b: $^1$H NMR (CDCl₃) δ: 0.57 (3H, s, H-18), 0.87 (6H, t, J=7.5 Hz, H-26a, 27a), 1.05 (3H, d, J=6.6 Hz, H-21), 1.55, 1.56 (each 2H, d, J=7.5 Hz, H-26, 27), 2.22 (1H, m, H-4), 2.33 (1H, m, H-10), 2.70,(1H, dd, J=13.0, 4.7 Hz, H-4), 2.82 (2H, m, H-9,10), 4.25 (1H, dd, J=12.6, 6.4 Hz, CH₂OH), 4.38 (1H, dd, J=12.6, 7.3 Hz, CH₂OH), 4.46 (1H, m, H-3), 4.87 (1H, t, J=4.2 Hz, H-1), 5.54 (1H, d, J=15.3 Hz, H-24a, overlapped with H-22), 5.84 (2H, m, H-7, C=CH), 5.98 (1H, dd, J=15.0, 10.3 Hz, H-23), 6.15 (1H, dd, J=15.3, 10.3 Hz, H-24), 6.40 (1H, d, J=11.1 Hz, H-6). MS m/z (%): 484 (M⁺, 4), 466 (12), 448 (16), 430 (44), 412 (38), 279 (35), 263 (32), 149 (100), 133 (39), 93 (42). HR-MS m/z: 484.3561 (Calcd for C₃₁H₄₈O₄: 484.3553).

Example 97

24a,26a,27a-trihomo-1α-[(t-butyldimethylsilyl)oxy]-2β,2'-epoxy- and 24a,26a,27a-trihomo-1α-[(t-butyldimethylsilyl)oxy]-2α,2'-epoxy-22,24-dien-25-[(triethylsilyl)oxy]-19-norvitamin D₃ t-butyldimethylsilyl ether (Compounds 159a, 159b)

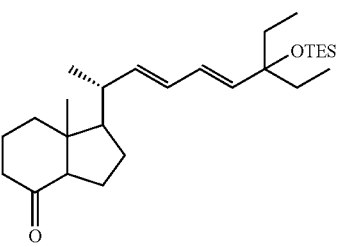

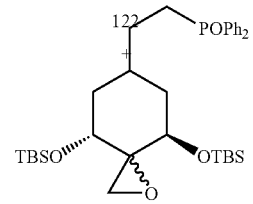

13

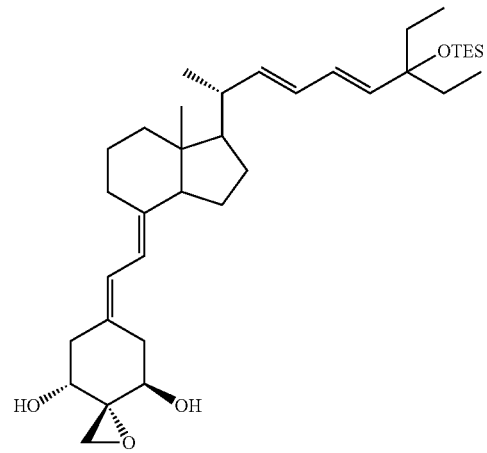

159a

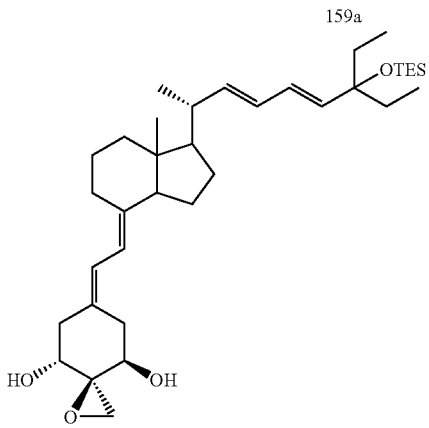

159b

To a solution cooled to −78° C. of A-ring phosphine oxide 13 (260 mg, 0.434 mmol, a mixture of ca. 3:1) in dry THF (2 mL) was added n-BuLi (276 μL, 0.436 mmol, 1.58 M solution in hexane), and the resulting solution was stirred for 15 min. To this solution was added slowly a solution of C/D-ring ketone 122 (100 mg, 0.231 mmol) in dry THF (1.5 mL). The mixture was stirred for 3 h with warming gradually from −78° C. to −20° C., saturated NH$_4$Cl aqueous solution was added to the mixture, and the mixture was extracted with AcOEt. The organic phase was washed with saturated brine, dried over anhydrous MgSO$_4$, and distilled off The residue was purified by silica gel column chromatography (10 g, 2% AcOEt/hexane) to afford Compound 159 (31.3 mg, 17%) as a mixture of two kinds of stereoisomers. The ratio of the isomer 159a to the isomer 159b was ca. 10:1. Further, the unreacted starting material 122 (48.0 mg) was collected using 5% AcOEt/hexane.

159: $^1$H NMR (CDCl$_3$) δ: 0.02, 0.05 (each 3H, s, Si-Me×2), 0.06 (6H, Si-Me×2), 0.567 (6H, q, J=7.9 Hz, SiCH$_2$×3), 0.570 (3H, s, H-18), 0.82 (6H, t, J=7.5 Hz, H-26a, 27a), 0.86, 0.87 (each 9H, s, Si-tBu×2), 0.94 (9H, t, J=7.9 Hz, SiCH$_2$CH$_3$×3), 1.06 (3H, d, J=6.6 Hz, H-21), 3.80 (1H, m), 3.87 (1H, m), 5.52 (1H, d, J=15.0 Hz, H-24a, overlapped with H-22), 5.81 (1H, d, J=11.1, H-7), 5.80–6.08 (3H, m), 6.21, 6.27 (ca. 10:1) (1H, d, J=11.1 Hz, H-7).

Example 98

24a,26a,27a-trihomo-1α,25-dihydroxy-2β,2'-epoxy- and 24a,26a,27a-trihomo-1α,25-dihydroxy-2α,2'-epoxy-22,24-dien-19-norvitamin D$_3$ (Compounds 113a, 113b), and 24a,26a,27a-trihomo-1α,2β,25-trihydroxy-2α-methyl- and 24a,26a,27a-trihomo-1α, 2α,25-trihydroxy-22,24-dien-19-norvitamin D$_3$ (Compounds 114a, 114b)

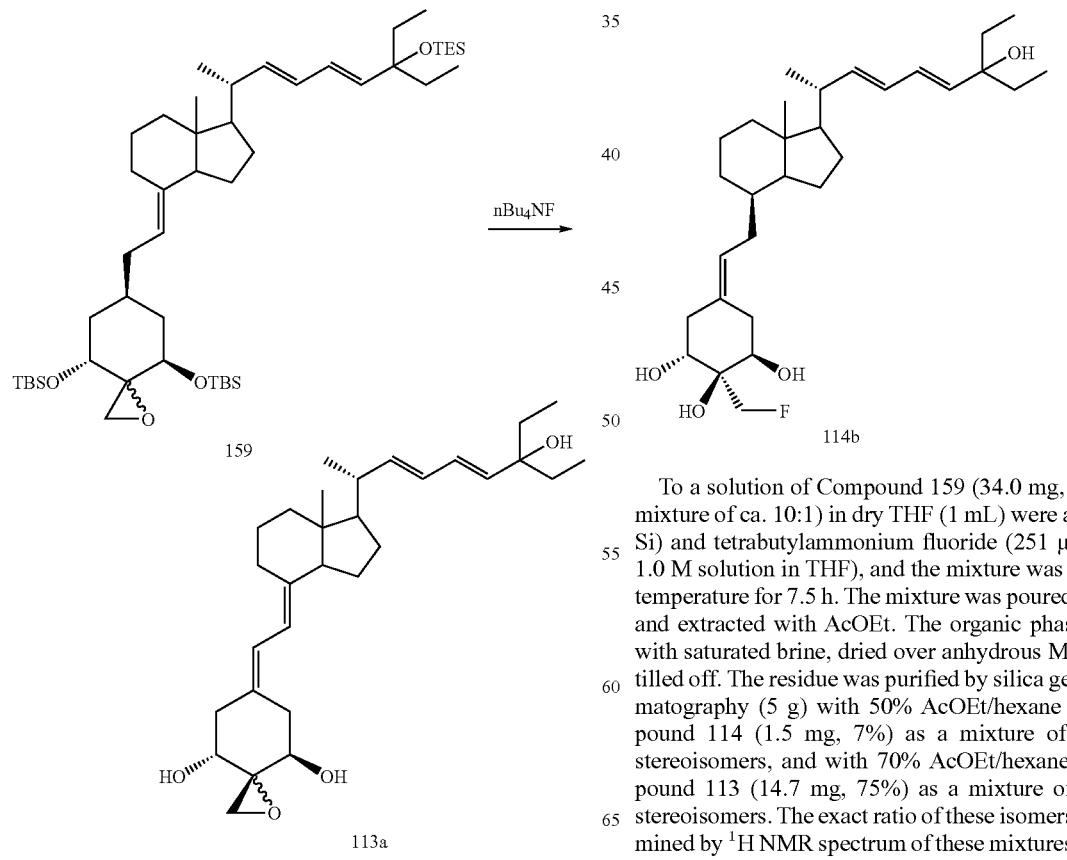

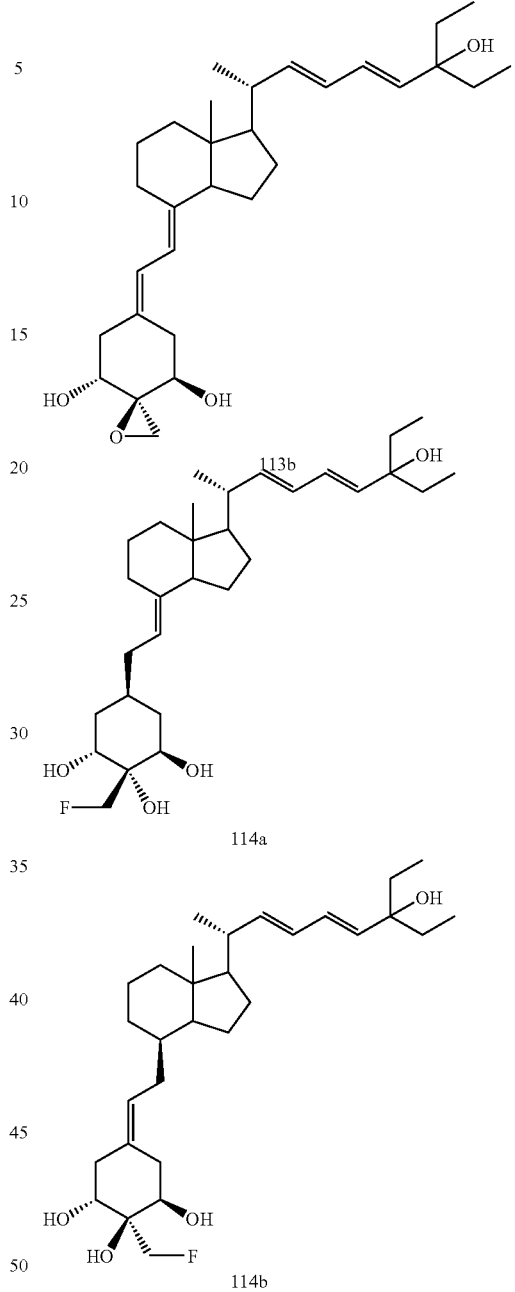

To a solution of Compound 159 (34.0 mg, 0.042 mmol, a mixture of ca. 10:1) in dry THF (1 mL) were added Et$_3$N (75 Si) and tetrabutylammonium fluoride (251 μL, 0.24 mmol, 1.0 M solution in THF), and the mixture was stirred at room temperature for 7.5 h. The mixture was poured into ice water, and extracted with AcOEt. The organic phase was washed with saturated brine, dried over anhydrous MgSO$_4$, and distilled off. The residue was purified by silica gel column chromatography (5 g) with 50% AcOEt/hexane to yield Compound 114 (1.5 mg, 7%) as a mixture of two kinds of stereoisomers, and with 70% AcOEt/hexane to give Compound 113 (14.7 mg, 75%) as a mixture of two kinds of stereoisomers. The exact ratio of these isomers was not determined by $^1$H NMR spectrum of these mixtures, since a signal derived from each isomer was overlapped. The mixture of 113a and 113b was separated and purified by HPLC (LiChrosorb Si 60, Hibar RT 250-10, 250×10 mm, hexane:$CH_2Cl_2$:MeOH=40:60:5) to obtain Compounds 113a (4.73 mg) and 113b (628 µg), respectively.

113a: $^1$H NMR ($CDCl_3$) δ: 0.57 (3H, s, H-18), 0.87 (6H, t, J=7.4 Hz, H-26a, 27a), 1.06 (3H, d, J=6.5 Hz, H-21), 2.31 (1H, dd, J=13.4, 8.6 Hz, H-10), 2.40 (1H, dd, J=13.6, 6.2 Hz, H-4), 2.61 (1H, dd, J=13.6, 3.3 Hz, H-4), 2.80 (1H, m, H-9), 2.84 (1H, d, J=4.7 Hz, OCH), 2.95 (1H, dd, J=13.4, 4.1 Hz, H-10), 3.08 (1H, d, J=4.7 Hz, OCH), 5.53 (1H, d, J=15.5 Hz, H-24a, overlapped with H-22), 5.68 (1H, d, J=11.1 Hz, H-7), 5.97 (1H, dd, J=15.0, 10.3 Hz, H-23), 6.15 (1H, dd, J=15.5, 10.3 Hz, H-24), 6.39 (1H, d, J=11.1 Hz, H-6). UV λmax (EtOH): 235, 243, 251, 261 nm.

113b: $^1$H NMR ($CDCl_3$) δ: 0.58 (3H, s, H-18), 0.87 (6H, t, J=7.6 Hz, H-26a, 27a), 1.06 (3H, d, J=6.6 Hz, H-21), 2.28-2.38 (2H, m, H-4, 10), 2.71 (1H, dd, J=13.8, 3.5 Hz, H-4), 2.80 (1H, m, H-9), 2.86 (1H, dd, J=13.2, 4.2 Hz, H-10), 2.94, 2.99 (each 1H, d, J=4.7 Hz, $OCH_2$), 5.53 (1H, d, J=15.2 Hz, H-24a, overlapped with H-22), 5.87 (1H, d, J=11.0 Hz, H-7), 5.98 (1H, dd, J=15.0, 10.3 Hz, H-23), 6.16 (1H, dd, J=15.2, 10.3 Hz, H-24), 6.38 (1H, d, J=11.0 Hz, H-6). UV λmax (EtOH): 234, 243, 251, 261 nm.

114: $^1$H NMR ($CDCl_3$) δ: 0.55 (3H, s, H-18), 0.88 (6H, t, J=7.5 Hz, H-26a, 27a), 1.05 (3H, d, J=6.6 Hz, H-21), 3.87, 3.97 (each 1H, m, H-1, 3), 4.72, 4.76 (each 1H, dd, J=48.0, 9.7 Hz, $CH_2F$), 5.53 (1H, d, J=15.1 Hz, H-24a, overlapped with H-22), 5.80 (1H, d, J=11.2 Hz, H-7), 5.97 (1H, dd, J=15.0, 10.3 Hz, H-23), 6.15 (1H, dd, J=15.1, 10.3 Hz, H-24), 6.40 (1H, d, J=11.2 Hz, H-6). $^{19}$F NMR ($CDCl_3$) δ: −240.5 (t, J=48.0 Hz).

Example 99

24a,26a,27a-trihomo-1α-[(t-butyldimethylsilyl)oxy]-2β-[(trimethylsilyl)oxy]-2α-methyl- and 24a,26a,27a-trihomo-1α-[(t-butyldimethylsilyl)oxy]-2α-[(trimethylsilyl)oxy]-2β-methyl-22,24-dien-25-[(triethylsilyl)oxy]-19-norvitamin $D_3$ t-butyldimethylsilyl ether (Compounds 160a, 160b)

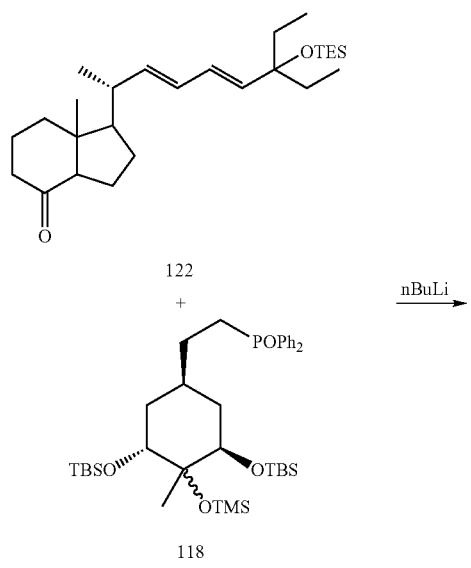

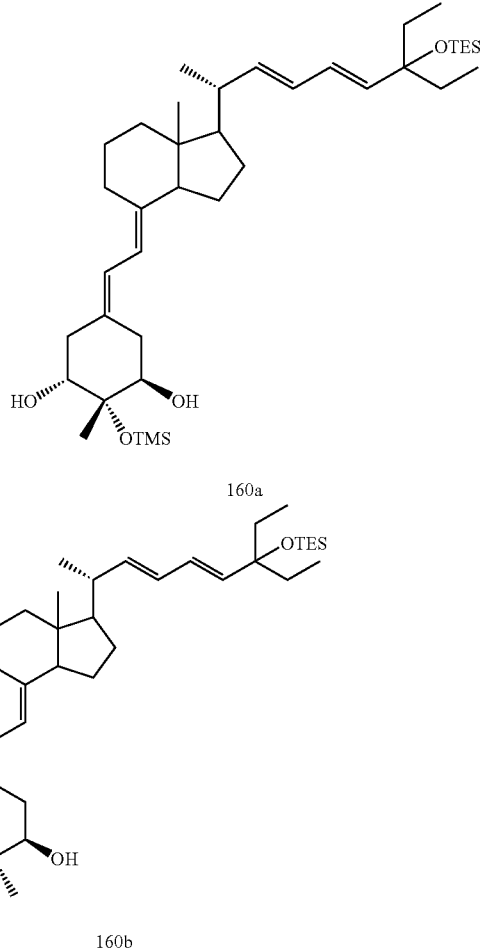

To a solution cooled to −78° C. of A-ring phosphine oxide 118 (253.9 mg, 0.377 mmol, a mixture of ca. 1:1) in dry THF (2.5 mL) was added n-BuLi (238.6 µL, 0.377 mmol, 1.58 M solution in hexane), and the resulting solution was stirred for 15 min. To this solution was added slowly a solution of C/D-ring ketone 122 (84.0 mg, 0.194 mmol) in dry THF (1.5 mL). The mixture was stirred for 3 h with warming gradually from −78° C. to −30° C., saturated $NH_4Cl$ aqueous solution was added to the mixture, and the mixture was extracted with AcOEt. The organic phase was washed with saturated brine, dried over anhydrous $MgSO_4$, and distilled off The residue was purified by silica gel column chromatography (6 g, 1% AcOEt/hexane) to afford Compound 160 (44.6 mg, 26%) as a mixture of two kinds of stereoisomers. The ratio of the isomer 160a to the isomer 160b was ca. 1:2. Further, the unreacted starting material 122 (47.0 mg) was collected using 5% AcOEt/hexane.

160: $^1$H NMR ($CDCl_3$) δ: 0.02-0.09 (12H, Si-Me×4), 0.11, 0.12 (ca. 1:2) (9H, s, Si-Me×3), 0.569 (3H, s, H-18), 0.570 (6H, q, J=7.6 Hz, Si—$CH_2CH_3$×3), 0.82 (6H, t, J=7.5 Hz, H-26a, 27a), 0.83, 0.92 (each 9H, s, Si-tBu×2), 0.94 (9H, t, J=7.6 Hz, Si—$CH_2CH_3$×3), 1.06 (3H, d, J=6.6 Hz, H-21), 3.56 (1H, m), 3.60, 3.70 (ca. 2:1) (1H, m), 5.52 (1H, d, J=15.2 Hz, H-24a, overlapped with H-22), 5.78, 5.84 (ca. 1:2) (1H, d, J=11.2 Hz, H-7), 5.90-6.15 (3H,

Example 100

24a,26a,27a-trihomo-1α,2β,25-trihydroxy-2α-methyl- and 24a,26a,27a-trihomo-1α,2β,25-trihydroxy-2β-methyl-22,24-dien-19-norvitamin $D_3$ (Compounds 115a, 115b)

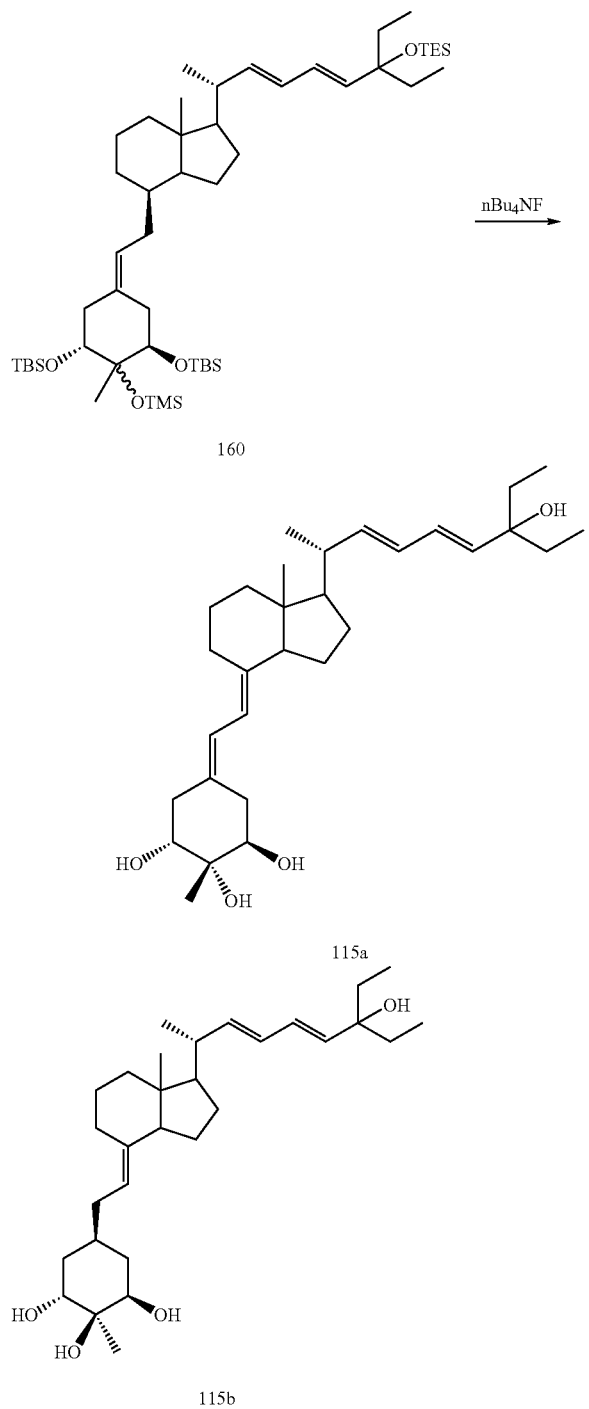

To a solution of Compound 160 (56.0 mg, 0.063 mmol, a mixture of ca. 2:1) in dry THF (1.5 mL) were added $Et_3N$ (75 μL), and tetrabutylammonium fluoride (505 μL, 0.505 mmol, 1.0 M solution in THF), and the mixture was stirred at room temperature for 24 h. The mixture was poured into ice water, and extracted with AcOEt. The organic phase was washed with saturated brine, dried over anhydrous $MgSO_4$, and evaporated in vacuo. The residue was purified by silica gel column chromatography (5 g, 60% AcOEt/hexane) to yield Compound 115 as a Mixture of Two Isomers (25.1 mg, 84%, a Mixture of ca. 5:4).

The mixture of 115a and 115b was purified by HPLC (YMC-Pack ODS-AM SH-342-5, 150×20 mm, 20% $H_2O$/MeOH) to afford Compounds 115a (5.25 mg) and 115b (6.68 mg), respectively.

115a: $^1H$ NMR ($CDCl_3$) δ: 0.56 (3H, s, H-18), 0.88 (6H, t, J=7.5 Hz, H-26a, 27a), 1.05 (3H, d, J=6.6 Hz, H-21), 2.37 (1H, dd, J=14.4, 4.4 Hz, H-4), 2.54 (1H, br. d, J=14.4 Hz, H-4), 2.80 (1H, m, H-9), 2.94 (1H, dd, J=13.5, 4.4 Hz, H-10), 3.73 (2H, m, H-1, 3), 5.53 (1H, d, J=15.4 Hz, H-24a, overlapped with H-22), 5.84 (1H, d, J=11.2 Hz, H-7), 5.97 (1H, dd, J=15.0, 10.3 Hz, H-23), 6.15 (1H, dd, J=15.4, 10.3 Hz, H-24), 6.29 (1H, d, J=11.2 Hz, H-6). MS m/z (%): 472 ($M^+$, 13), 454 (100), 436 (38), 418 (29), 400 (46). UV λmax (EtOH): 235, 243, 252, 261 nm.

115b: $^1H$ NMR ($CDCl_3$) δ: 0.57 (3H, s, H-18), 0.87 (6H, t, J=7.5 Hz, H-26a, 27a), 1.05 (3H, d, J=6.6 Hz, H-21), 2:48 (1H, dd, J=14.2, 3.2 Hz, H-10), 2.63 (1H, dd, J=14.2, 6.4 Hz, H-10), 2.66 (1H, dd, J=14.0, 4.0 Hz, H-4), 2.80 (1H, m, H-9), 3.72, 2.78 (each 1H, m, H-1, 3), 5.53 (1H, d, J=15.4 Hz, H-24a, overlapped with H-22), 5.82 (1H, d, J=11.1 Hz, H-7), 5.98 (1H, dd, J=15.0, 10.3 Hz, H-23), 6.15 (1H, dd, J=15.4, 10.3 Hz, H-24), 6.33 (1H, d, J=11.1 Hz, H-6). MS m/z (%): 472 ($M^+$, 2), 454 (100), 436 (18), 418 (10), 400 (12). UV λmax (EtOH): 235, 243, 251, 261 nm.

Example of Examination

Binding Assay for Calf Thymus Vitamin D Receptor (VDR)

The binding ability of the compounds of the present inventions described in the above Examples to vitamin D receptor (VDR) derived from calf thymus was evaluated.

The binding assay was carried out according to the manufacturer's instruction of Yamasa Shoyu Co., Ltd. as follows.

An EtOH solution (sample) containing an increasing amount of each 1α,25-dihydroxyvitamin $D_3$ (as a standard reference material), and Compounds YI-1a, YI-1b, YI-2a, YI-3a, YI-3b, YI-4a, YI-4b, YI-5a, YI-5b, 20-Epi-YI-1a, 20-Epi-YI-1b, 20-Epi-YI-2a, 20-Epi-YI-3a, 20-Epi-YI-4a, 20-Epi-YI-4b, 20-Epi-YI-5a, 20-Epi-YI-5b, 20-Epi-YI-6a, 20-Epi-YI-6b, 20-Epi-YI-7a, 20-Epi-YI-7b, 20-Epi-YI-8a, and 20-Epi-YI-8b was prepared, that is, dilution series were prepared wherein final concentrations of each compounds in a mixture, which is prepared by following step, of receptor solutions, samples, and [$^3H$]-1α,25-dihydroxyvitamin $D_3$ solutions are 100 nM, 30 nM 10 nM, 1 nM, 300 pM, 100 pM, 30 pM, 10 pM, 3 pM, and 1 pM.

Freeze-dried calf thymus vitamin D receptors (Lot. No. 111931) were purchased from Yamasa Shoyu Co., Ltd. (Choshi, Chiba, Japan) and were dissolved in 45 mL of phosphate buffer (0.3 M KCl, 0.05 M $K_2HPO_4$—$KH_2PO_4$, pH 7.4) just before use to use as a receptor solution.

50 μL of sample of Compounds YI-1a, YI-1b, YI-2a, YI-3a, YI-3b, YI-4a, YI-4b, YI-5a, YI-5b, 20-Epi-YI-1a, 20-Epi-YI-1b, 20-Epi-YI-2a, 20-Epi-YI-3a, 20-Epi-YI-4a, 20-Epi-YI-4b, 20-Epi-YI-5a, 20-Epi-YI-5b, 20-Epi-YI-6a, 20-Epi-YI-6b, 20-Epi-YI-7a, 20-EPi-YI-7b, 20-Epi-YI-8a, 20-Epi-YI-8b, or 1α,25-dihydroxyvitamin $D_3$ and 500 μL of the receptor solution were pipetted into glass culture tubes. The mixture was vortexed 2-3 times, and incubated for 1 h at room temperature. To each tubes, [$^3$H]-1α,25-dihydroxyvitamin $D_3$ (ca. 10000 dpm) in 50 μL of EtOH was added, the mixture was vortexed 2-3 times, and the whole mixture was incubated for 18 h at 4° C. (in a refrigerator). Then, 200 μL of DCC (dextran-coated charcoal; purchased from Yamasa Shoyu) was added to each tubes, and allowed to stand for 30 min at 4° C. Bound and free [$^3$]-1α,25-dihydroxyvitamin $D_3$ were separated by centrifugation at 3000 rpm for 15 min at 4° C. Aliquots (500 μL) of the supernatant were put into vial bottles from each tube, and were mixed with 10 mL of ACS-II fluid scintillator (Amersham, Buckinghamshire, U.K.) and submitted for radioactivity counting.

The relative binding affinity of the vitamin D derivatives of the present inventions to VDR was calculated regarding binding affinity of 1α,25-dihydroxyvitamin $D_3$ to VDR as 1. The following equation was used to calculate the relative VDR binding affinity:

$$X = y/x$$

X: the relative binding affinity of the compound of the present inventions to VDR y: the concentration of 1α,25-dihydroxyvitamin $D_3$ required for 50% inhibition of binding [$^3$H]-1α,25-dihydroxyvitamin $D_3$ to VDR x: the concentration of the compound of the present inventions required for 50% inhibition of binding [$^3$H]-1α,25-dihydroxyvitamin $D_3$ to VDR

TABLE 1

| Compounds | VDR affinity |
|---|---|
| YI-1a | 1/23 |
| YI-1b | 1/290 |
| YI-2a | 1/43 |
| YI-3a | 1/3 |
| YI-3b | 1/730 |
| YI-4a | 1/50 |
| YI-4b | 1/2000 |
| YI-5a | 1/26 |
| YI-5b | 1/820 |
| 20-Epi-YI-1a | 1/2 |
| 20-Epi-YI-1b | 1/5 |

TABLE 1-continued

| Compounds | VDR affinity |
|---|---|
| 20-Epi-YI-2a | 2 |
| 20-Epi-YI-3a | 1 |
| 20-Epi-YI-4a | 1/20 |
| 20-Epi-YI-4b | 1/1000 |
| 20-Epi-YI-5a | 1/5 |
| 20-Epi-YI-5b | 1/10 |
| 20-Epi-YI-6a | 1 |
| 20-Epi-YI-6b | 5 |
| 20-Epi-YI-7a | 1 |
| 20-Epi-YI-7b | 1/5 |
| 20-Epi-YI-8a | 1.6 |
| 20-Epi-YI-8b | 1/50 |

INDUSTRIAL APPLICABILITY

The compounds represented by the formulae (I) and (IV) of the present invention are a novel compound and may be useful as pharmaceutical agents for diseases accompanying with abnormal cell differentiation. Also, the compound of the present invention may be useful as reagents for studying metabolism of active vitamin $D_3$, that is, 1α,25-dihydroxyvitamin $D_3$

The invention claimed is:
1. A compound having the formula:

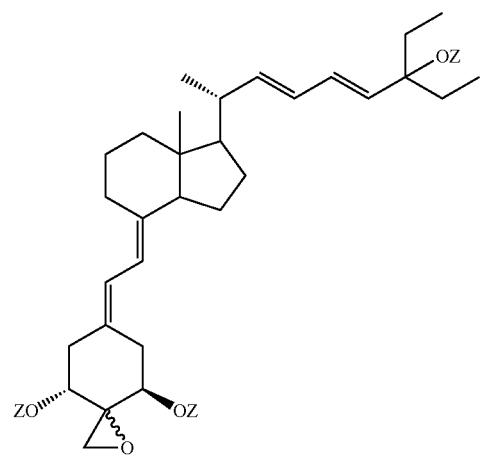

where Z may be the same or different and represents a hydrogen atom or a hydroxy protecting group.

2. 24,26,27-trihomo-1α,25-dihydroxy2β,2'-epoxy-22,24-dien-19-norvitamin $D_3$ having the formula:

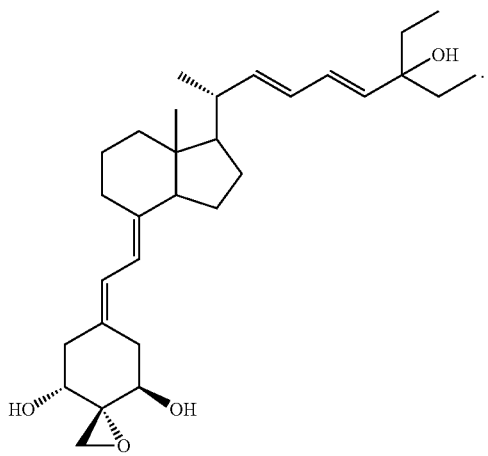

3. 24,26,27-trihomo-1α,25-dihydroxy2α,2'-epoxy-22,24-dien-19-norvitamin $D_3$ having the formula:

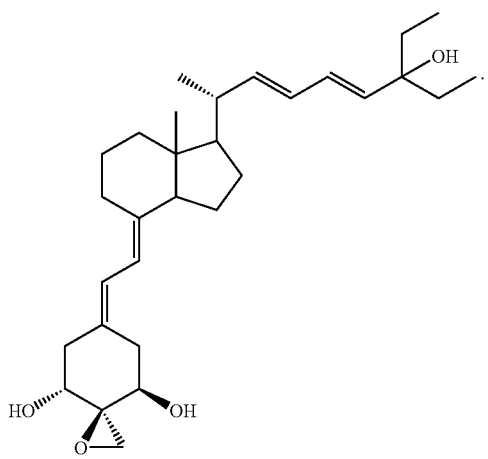

4. A method of preparing a compound of claim 1 comprising a step of obtaining a compound represented by formula III

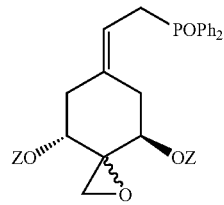
III wherein Z may be the same or different and represents a hydrogen atom or a hydroxy protecting group and Ph represents a phenyl group, from a compound represented by formula II

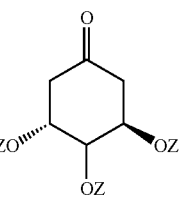
II wherein Z may be the same or different and represents a hydrogen atom or a hydroxy protecting group.

* * * * *